US006716412B2

(12) United States Patent
Unger

(10) Patent No.: US 6,716,412 B2
(45) Date of Patent: Apr. 6, 2004

(54) METHODS OF ULTRASOUND TREATMENT USING GAS OR GASEOUS PRECURSOR-FILLED COMPOSITIONS

(75) Inventor: Evan C. Unger, Tucson, AZ (US)

(73) Assignee: Imarx Therapeutics, Inc., Tuscson, AZ (US)

( * ) Notice: Subject to any disclaimer, the term of this patent is extended or adjusted under 35 U.S.C. 154(b) by 121 days.

(21) Appl. No.: 09/813,484

(22) Filed: Mar. 21, 2001

(65) Prior Publication Data

US 2001/0031243 A1 Oct. 18, 2001

Related U.S. Application Data

(62) Division of application No. 08/929,847, filed on Sep. 15, 1997, now Pat. No. 6,548,047.

(51) Int. Cl.$^7$ .............................. A61B 8/00; A61N 7/02
(52) U.S. Cl. ...................... 424/9.52; 424/9.5; 424/9.51; 424/450; 604/21; 604/52; 514/44; 600/437
(58) Field of Search ..................... 424/9.52, 9.5–9.51, 424/450; 604/21, 52; 514/44; 660/437

(56) References Cited

U.S. PATENT DOCUMENTS

| | | | |
|---|---|---|---|
| 3,015,128 A | 1/1962 | Sommerville et al. ......... 18/2.6 |
| 3,291,843 A | 12/1966 | Fritz et al. .................. 260/614 |
| 3,293,114 A | 12/1966 | Kenaga et al. .............. 162/168 |
| 3,479,811 A | 11/1969 | Walters ........................ 57/153 |
| 3,488,714 A | 1/1970 | Walters et al. .............. 161/161 |
| 3,532,500 A | 10/1970 | Priest et al. ..................... 96/91 |
| 3,557,294 A | 1/1971 | Dear et al. .................. 424/342 |
| 3,594,326 A | 7/1971 | Himmel et al. ............. 252/316 |
| 3,615,972 A | 10/1971 | Morehouse et al. .......... 156/79 |
| 3,732,172 A | 5/1973 | Herbig et al. ............... 252/316 |
| 3,873,564 A | 3/1975 | Schneider et al. ....... 260/309.6 |
| 3,945,956 A | 3/1976 | Garner .................... 260/2.5 B |
| 3,960,583 A | 6/1976 | Netting et al. .............. 106/122 |
| 4,089,801 A | 5/1978 | Schneider .................... 252/316 |
| 4,108,806 A | 8/1978 | Cohrs et al. ................... 521/54 |
| 4,138,383 A | 2/1979 | Rembaum et al. ..... 260/29.7 H |
| 4,162,282 A | 7/1979 | Fulwyler et al. ................ 264/9 |
| 4,179,546 A | 12/1979 | Garner et al. ................. 521/56 |
| 4,192,859 A | 3/1980 | Mackaness et al. ............ 424/5 |
| 4,224,179 A | 9/1980 | Schneider .................... 252/316 |
| 4,229,360 A | 10/1980 | Schneider et al. .......... 260/403 |
| 4,265,251 A | 5/1981 | Tickner ....................... 128/660 |
| 4,276,885 A | 7/1981 | Tickner et al. ............. 128/660 |
| 4,310,505 A | 1/1982 | Baldeschwieler et al. ...... 424/1 |
| 4,310,506 A | 1/1982 | Baldeschwieler et al. ...... 424/1 |
| 4,315,514 A | 2/1982 | Drewes et al. ............. 128/653 |
| 4,331,654 A | 5/1982 | Morris ........................ 424/38 |
| 4,342,826 A | 8/1982 | Cole ............................. 435/7 |
| 4,344,929 A | 8/1982 | Bonsen et al. ................ 424/15 |
| 4,420,442 A | 12/1983 | Sands ......................... 264/13 |
| 4,421,562 A | 12/1983 | Sands et al. ................. 106/75 |
| 4,426,330 A | 1/1984 | Sears ......................... 260/403 |
| 4,427,649 A | 1/1984 | Dingle et al. ................ 424/38 |
| 4,428,924 A | 1/1984 | Millington .................... 424/4 |
| 4,442,843 A | 4/1984 | Rasor et al. ................. 128/660 |
| 4,466,442 A | 8/1984 | Hilmann et al. ............ 128/653 |
| 4,485,193 A | 11/1984 | Rubens et al. ................. 521/58 |
| 4,530,360 A | 7/1985 | Duarte .................... 128/419 F |
| 4,533,254 A | 8/1985 | Cook et al. ................. 366/176 |
| 4,534,899 A | 8/1985 | Sears ......................... 260/403 |
| 4,540,629 A | 9/1985 | Sands et al. ................. 428/402 |
| 4,544,545 A | 10/1985 | Ryan et al. .................. 424/1.1 |
| 4,549,892 A | 10/1985 | Baker et al. ................. 65/21.4 |
| 4,569,836 A | 2/1986 | Gordon |
| 4,572,203 A | 2/1986 | Feinstein .................... 128/661 |
| 4,586,512 A | 5/1986 | Do-huu et al. ............. 128/660 |
| 4,603,044 A | 7/1986 | Geho et al. ..................... 424/9 |
| 4,615,879 A | 10/1986 | Runge et al. ................... 424/9 |
| 4,620,546 A | 11/1986 | Aida et al. .................. 128/660 |
| 4,621,023 A | 11/1986 | Redziniak et al. ....... 428/402.2 |
| 4,646,756 A | 3/1987 | Watmough et al. ......... 128/804 |
| 4,657,756 A | 4/1987 | Rasor et al. ..................... 424/9 |

(List continued on next page.)

FOREIGN PATENT DOCUMENTS

| | | |
|---|---|---|
| AU | B-30351/89 | 3/1993 |
| DE | 25 21 003 | 8/1976 |
| DE | 3803972 | 8/1989 |
| EP | 0 052 575 | 5/1982 |
| EP | 0 107 559 | 5/1984 |
| EP | 0 077 752 B1 | 3/1986 |
| EP | 0 224 934 | 6/1987 |
| EP | 0 231 091 | 8/1987 |
| EP | 0 272 091 | 6/1988 |
| EP | 0 324 938 | 7/1989 |
| EP | 0 338 971 | 10/1989 |
| EP | 357163 A1 | 3/1990 |

(List continued on next page.)

OTHER PUBLICATIONS

Bradbery, (Pharmacotherapy, A Pathophysiologic Approach, ed. Dipiro et al. 1992), 340–347.*
Porter, T.R., et al., "Multifold sonicated dilutions of albumin with fifty percent dextrose improve left ventricular contrast videointensity after intravenous injunction in human beings," *J. Am. Soc. Echocardiogr*, XP 000590864, Sep./Oct. 1994, 7(5), 465–471.
Porter, T.R., et al., "Noninvasive identification of acute myocardinal ischemia and reperfusion with contrast ultrasound using intravenous perfluoropropane–exposed sonicated dextrose albumin," *Am. College of Cardiology*, XP 000590865, Jul. 1995, 26(1), 33–40.

(List continued on next page.)

*Primary Examiner*—Russell Travers
*Assistant Examiner*—S Sharareh

(57) ABSTRACT

The present invention describes, among other things, the surprising discovery that gaseous precursor filled compositions are profoundly more effective as acoustically active contrast agents when they are thermally preactivated to temperatures at or above the boiling point of the instilled gaseous precursor prior to their in vivo administration to a patient. Further optimization of contrast enhancement is achieved by administering the gaseous precursor filled compositions to a patient as an infusion. Enhanced effectiveness is also achieved for ultrasound mediated targeting and drug delivery.

25 Claims, No Drawings

U.S. PATENT DOCUMENTS

| | | | |
|---|---|---|---|
| 4,658,828 A | 4/1987 | Dory | 128/660 |
| 4,663,161 A | 5/1987 | Mannino et al. | 424/89 |
| 4,675,310 A | 6/1987 | Chapman et al. | 514/6 |
| 4,681,119 A | 7/1987 | Rasor et al. | 128/660 |
| 4,684,479 A | 8/1987 | D'Arrigo | 252/307 |
| 4,689,986 A | 9/1987 | Carson et al. | 73/19 |
| 4,693,999 A | 9/1987 | Axelsson et al. | 514/174 |
| 4,718,433 A | 1/1988 | Feinstein | 128/660 |
| 4,728,575 A | 3/1988 | Gamble et al. | 428/402.2 |
| 4,728,578 A | 3/1988 | Higgins et al. | 428/462 |
| 4,731,239 A | 3/1988 | Gordon | 424/9 |
| 4,737,323 A | 4/1988 | Martin et al. | 264/4.3 |
| 4,767,610 A | 8/1988 | Long | 424/5 |
| 4,774,958 A | 10/1988 | Feinstein | 128/660.01 |
| 4,775,522 A | 10/1988 | Clark, Jr. | 424/9 |
| 4,776,991 A | 10/1988 | Farmer et al. | 264/4.3 |
| 4,781,871 A | 11/1988 | West, III et al. | 264/4.3 |
| 4,789,501 A | 12/1988 | Day et al. | 252/645 |
| 4,790,891 A | 12/1988 | Halliday et al. | 149/2 |
| 4,822,534 A | 4/1989 | Lencki et al. | 264/4.3 |
| 4,830,858 A | 5/1989 | Payne et al. | 424/450 |
| 4,834,964 A | 5/1989 | Rosen | 424/9 |
| 4,844,882 A | 7/1989 | Widder et al. | 424/9 |
| 4,863,717 A | 9/1989 | Keana | 424/9 |
| 4,865,836 A | 9/1989 | Long, Jr. | 424/5 |
| 4,866,096 A | 9/1989 | Schweighardt | 514/756 |
| 4,877,561 A | 10/1989 | Iga et al. | 264/4.3 |
| 4,893,624 A | 1/1990 | Lele | 128/399 |
| 4,895,719 A | 1/1990 | Radhakrishnan | 424/45 |
| 4,895,876 A | 1/1990 | Schweighardt et al. | 514/747 |
| 4,898,734 A | 2/1990 | Mathiowitz et al. | 424/426 |
| 4,900,540 A | 2/1990 | Ryan et al. | 424/9 |
| 4,918,065 A | 4/1990 | Stindl et al. | 514/179 |
| 4,919,895 A | 4/1990 | Heldebrant et al. | 422/129 |
| 4,921,706 A | 5/1990 | Roberts et al. | 424/450 |
| 4,927,623 A | 5/1990 | Long, Jr. | 424/5 |
| 4,933,121 A | 6/1990 | Law et al. | 264/4.3 |
| 4,938,947 A | 7/1990 | Nicolau et al. | 424/1.1 |
| 4,957,656 A | 9/1990 | Cerny et al. | 252/311 |
| 4,972,002 A | 11/1990 | Volkert | 521/120 |
| 4,984,573 A | 1/1991 | Leunbach | 128/653 |
| 4,985,550 A | 1/1991 | Charpiot et al. | 536/18.4 |
| 4,987,154 A | 1/1991 | Long, Jr. | 514/772 |
| 4,993,415 A | 2/1991 | Long | 128/653 A |
| 4,996,041 A | 2/1991 | Arai et al. | 424/9 |
| 5,000,960 A | 3/1991 | Wallach | 424/450 |
| 5,004,611 A | 4/1991 | Leigh | 424/450 |
| 5,008,050 A | 4/1991 | Cullis et al. | 264/4.3 |
| 5,008,109 A | 4/1991 | Tin | 424/422 |
| 5,013,556 A | 5/1991 | Woodle et al. | 424/450 |
| 5,019,370 A | 5/1991 | Jay et al. | 424/4 |
| 5,045,304 A | 9/1991 | Schneider et al. | 424/9 |
| 5,049,388 A | 9/1991 | Knight et al. | 424/450 |
| 4,229,360 A | 11/1991 | Schneider et al. | 260/403 |
| 5,077,036 A | 12/1991 | Long, Jr. | 424/5 |
| 5,078,994 A | 1/1992 | Nair et al. | 424/501 |
| 5,080,885 A | 1/1992 | Long, Jr. | 424/5 |
| 5,088,499 A | 2/1992 | Unger | 128/662.2 |
| 5,107,842 A | 4/1992 | Levene et al. | 128/662.02 |
| 5,114,703 A | 5/1992 | Wolf et al. | 424/5 |
| 5,123,414 A | 6/1992 | Unger | 128/654 |
| 5,135,000 A | 8/1992 | Akselrod et al. | 128/662.02 |
| 5,147,631 A | 9/1992 | Glajch et al. | 424/9 |
| 5,171,755 A | 12/1992 | Kaufman | 514/759 |
| 5,186,922 A | 2/1993 | Shell et al. | 128/654 |
| 5,190,766 A | 3/1993 | Ishihara | 424/489 |
| 5,192,549 A | 3/1993 | Barenolz et al. | 424/450 |
| 5,194,188 A | 3/1993 | Guitierrez | 264/4.1 |
| 5,194,266 A | 3/1993 | Abra et al. | 424/450 |
| 5,195,520 A | 3/1993 | Schlief et al. | 128/660.02 |
| 5,196,183 A | 3/1993 | Yudelson et al. | 424/9 |
| 5,196,348 A | 3/1993 | Schweighardt et al. | 436/173 |
| 5,198,225 A | 3/1993 | Meybeck et al. | 424/450 |
| 5,205,287 A | 4/1993 | Erbel et al. | 128/632 |
| 5,205,290 A | 4/1993 | Unger | 128/653.4 |
| 5,213,804 A | 5/1993 | Martin et al. | 424/450 |
| 5,215,680 A | 6/1993 | D'Arrigo | 252/307 |
| 5,219,538 A | 6/1993 | Henderson et al. | 428/402.2 |
| 5,247,935 A | 9/1993 | Cline et al. | 128/653.2 |
| 5,271,928 A | 12/1993 | Schneider et al. | 424/9 |
| 5,281,408 A | 1/1994 | Unger | 424/4 |
| 5,283,255 A | 2/1994 | Levy et al. | 514/410 |
| 5,305,757 A | 4/1994 | Unger et al. | 128/662.02 |
| 5,310,540 A | 5/1994 | Giddey et al. | 424/9 |
| 5,315,997 A | 5/1994 | Widder et al. | 128/653.3 |
| 5,315,998 A | 5/1994 | Tachibana et al. | 128/660.01 |
| 5,316,771 A | 5/1994 | Barenholz et al. | 424/450 |
| 5,334,381 A | 8/1994 | Unger | 424/9 |
| 5,339,814 A | 8/1994 | Lasker | 128/653.4 |
| 5,344,930 A | 9/1994 | Riess et al. | 544/84 |
| 5,350,571 A | 9/1994 | Kaufman et al. | 424/9 |
| 5,354,549 A | 10/1994 | Klaveness et al. | 424/3 |
| 5,358,702 A | 10/1994 | Unger | 424/9 |
| 5,362,477 A | 11/1994 | Moore et al. | 424/9 |
| 5,362,478 A | 11/1994 | Desai et al. | 424/9 |
| 5,380,411 A | 1/1995 | Schlief | 204/157.15 |
| 5,380,519 A | 1/1995 | Schneider et al. | 424/9 |
| 5,393,513 A | 2/1995 | Long, Jr. | 424/5 |
| 5,393,524 A | 2/1995 | Quay | 424/9 |
| 5,403,575 A | 4/1995 | Kaufman et al. | 424/1.89 |
| 5,409,688 A | 4/1995 | Quay | 424/9 |
| 5,410,516 A | 4/1995 | Uhlendorf et al. | 367/7 |
| 5,413,774 A | 5/1995 | Schneider et al. | 424/9.51 |
| 5,425,366 A | 6/1995 | Reinhardt et al. | 128/662.02 |
| 5,433,204 A | 7/1995 | Olson | 128/661.08 |
| 5,456,900 A | 10/1995 | Unger | 424/9.4 |
| 5,469,854 A | 11/1995 | Unger et al. | 128/662.02 |
| 5,470,582 A | 11/1995 | Supersaxo et al. | 424/489 |
| 5,485,839 A | 1/1996 | Aida et al. | 128/653.1 |
| 5,487,390 A | 1/1996 | Cohen et al. | 128/662.02 |
| 5,496,535 A | 3/1996 | Kirkland | 424/9.37 |
| 5,496,536 A | 3/1996 | Wolf | 424/9.322 |
| 5,498,421 A | 3/1996 | Grinstaff et al. | 424/450 |
| 5,501,863 A | 3/1996 | Rössling et al. | 424/489 |
| 5,502,094 A | 3/1996 | Moore et al. | 524/145 |
| 5,505,932 A | 4/1996 | Grinstaff et al. | 424/9.3 |
| 5,508,021 A | 4/1996 | Grinstaff et al. | 424/9.322 |
| 5,512,268 A | 4/1996 | Grinstaff et al. | 424/322 |
| 5,514,720 A | 5/1996 | Clark, Jr. et al. | 514/749 |
| 5,527,521 A | 6/1996 | Unger | 424/93 |
| 5,529,766 A | 6/1996 | Klaveness et al. | 424/9.52 |
| 5,531,980 A | 7/1996 | Schneider et al. | 424/9.52 |
| 5,536,489 A | 7/1996 | Lohrmann et al. | 424/9.52 |
| 5,536,490 A | 7/1996 | Klaveness et al. | 424/9.52 |
| 5,536,753 A | 7/1996 | Clark, Jr. | 514/749 |
| 5,540,909 A | 7/1996 | Schutt | 424/9.52 |
| 5,542,935 A | 8/1996 | Unger et al. | 604/190 |
| 5,545,396 A | 8/1996 | Albert et al. | 424/93 |
| 5,547,656 A | 8/1996 | Unger | 424/9.4 |
| 5,552,133 A | 9/1996 | Lambert et al. | 424/9.52 |
| 5,552,155 A | 9/1996 | Bailey et al. | 424/450 |
| 5,556,372 A | 9/1996 | Talish et al. | 601/2 |
| 5,556,610 A | 9/1996 | Yan et al. | 424/9.52 |
| 5,558,092 A | 9/1996 | Unger et al. | 128/660.03 |
| 5,558,094 A | 9/1996 | Quay | 128/662.02 |
| 5,558,853 A | 9/1996 | Quay | 424/9.5 |
| 5,558,854 A | 9/1996 | Quay | 424/9.52 |
| 5,558,855 A | 9/1996 | Quay | 424/9.5 |
| 5,558,856 A | 9/1996 | Klaveness et al. | 424/9.37 |
| 5,560,364 A | 10/1996 | Porter | 128/662.02 |
| 5,562,608 A | 10/1996 | Sekins et al. | 604/20 |

| | | | | | |
|---|---|---|---|---|---|
| 5,562,893 A | 10/1996 | Lohrmann ............... 424/9.52 | EP | 0 357 164 B1 | 10/1991 |
| 5,565,215 A | 10/1996 | Gref et al. ............... 424/501 | EP | 0 458 745 A1 | 11/1991 |
| 5,567,413 A | 10/1996 | Klaveness et al. ......... 424/9.51 | EP | 0 314 764 B1 | 9/1992 |
| 5,567,414 A | 10/1996 | Schneider et al. ......... 424/9.52 | EP | 0 554 213 A1 | 8/1993 |
| 5,567,415 A | 10/1996 | Porter ..................... 424/9.52 | EP | 0 586 875 | 3/1994 |
| 5,567,765 A | 10/1996 | Moore et al. .............. 524/801 | EP | 0 614 656 A1 | 9/1994 |
| 5,569,448 A | 10/1996 | Wong et al. ............... 424/9.45 | EP | 0 633 030 A1 | 1/1995 |
| 5,569,449 A | 10/1996 | Klaveness et al. ......... 424/9.51 | EP | 0 727 225 A2 | 8/1996 |
| 5,571,498 A | 11/1996 | Cacheris et al. ......... 424/9.365 | EP | 0 901 793 A1 | 3/1999 |
| 5,571,797 A | 11/1996 | Ohno et al. ............... 514/44 | FR | 2 700 952 | 8/1994 |
| 5,573,751 A | 11/1996 | Quay ..................... 424/9.52 | GB | 1044680 | 10/1966 |
| 5,578,292 A | 11/1996 | Schneider et al. ......... 424/9.51 | GB | 2193095 A | 2/1988 |
| 5,585,112 A | 12/1996 | Unger et al. .............. 424/450 | JP | 62 286534 | 12/1987 |
| 5,593,680 A | 1/1997 | Bara et al. ............... 424/401 | JP | SHO 63-60943 | 3/1988 |
| 5,595,723 A | 1/1997 | Quay ..................... 424/9.5 | WO | WO 80/02365 | 11/1980 |
| 5,605,673 A | 2/1997 | Schutt et al. .............. 424/9.51 | WO | WO 82/01642 | 5/1982 |
| 5,606,973 A | 3/1997 | Lambert et al. ......... 128/662.02 | WO | US85/01161 | 3/1985 |
| 5,612,057 A | 3/1997 | Lanza et al. .............. 424/450 | WO | WO 85/02772 | 7/1985 |
| 5,612,318 A | 3/1997 | Weichselbaum et al. ...... 514/44 | WO | WO 86/00238 | 1/1986 |
| 5,614,169 A | 3/1997 | Klaveness et al. ......... 424/9.52 | WO | WO 86/01103 | 2/1986 |
| 5,620,689 A | 4/1997 | Allen et al. .............. 424/178.1 | WO | WO 89/05040 | 6/1989 |
| 5,626,833 A | 5/1997 | Schutt et al. .............. 424/9.52 | WO | WO 90/01952 | 3/1990 |
| 5,635,539 A | 6/1997 | Clark, Jr. et al. ........... 514/759 | WO | WO 90/04384 | 5/1990 |
| 5,639,443 A | 6/1997 | Schutt et al. .............. 424/9.52 | WO | WO 90/04943 | 5/1990 |
| 5,639,473 A | 6/1997 | Grinstaff et al. ........... 424/450 | WO | WO 91/00086 | 1/1991 |
| 5,643,553 A | 7/1997 | Schneider et al. ......... 424/9.52 | WO | WO 91/03267 | 3/1991 |
| 5,648,095 A | 7/1997 | Illum et al. ................ 424/489 | WO | WO 91/09629 | 7/1991 |
| 5,648,098 A | 7/1997 | Porter ..................... 424/490 | WO | WO 91/12823 | 9/1991 |
| 5,672,585 A | 9/1997 | Pierschbacher et al. ....... 514/11 | WO | WO 91/15244 | 10/1991 |
| 5,676,928 A | 10/1997 | Klaveness et al. ......... 424/9.32 | WO | WO 92/05806 | 4/1992 |
| 5,679,459 A | 10/1997 | Riess et al. .............. 428/402.2 | WO | WO 92/10166 | 6/1992 |
| 5,686,060 A | 11/1997 | Schneider et al. ......... 424/9.52 | WO | WO 92/11873 | 7/1992 |
| 5,686,102 A | 11/1997 | Gross et al. ............... 424/450 | WO | WO 92/15284 | 9/1992 |
| 5,695,460 A | 12/1997 | Siegel et al. ................ 604/21 | WO | WO 92/17212 | 10/1992 |
| 5,707,352 A | 1/1998 | Sekins et al. ............... 604/56 | WO | WO 92/17213 | 10/1992 |
| 5,707,606 A | 1/1998 | Quay ..................... 424/9.52 | WO | WO 92/17436 | 10/1992 |
| 5,707,607 A | 1/1998 | Quay ..................... 424/9.52 | WO | WO 92/17514 | 10/1992 |
| 5,711,933 A | 1/1998 | Bichon et al. ............. 424/9.52 | WO | WO 92/21382 | 10/1992 |
| 5,716,597 A | 2/1998 | Lohrmann et al. ........... 424/9.5 | WO | WO 92/22247 | 12/1992 |
| 5,732,707 A | 3/1998 | Widder et al. ......... 128/661.08 | WO | WO 92/22249 | 12/1992 |
| 5,733,527 A | 3/1998 | Schutt ..................... 424/9.52 | WO | WO 93/00933 | 1/1993 |
| 5,740,807 A | 4/1998 | Porter ................... 128/662.02 | WO | WO 93/05819 | 1/1993 |
| 5,770,222 A | 6/1998 | Unger et al. .............. 424/450 | WO | WO 93/06869 | 4/1993 |
| 5,785,950 A | 7/1998 | Kaufman et al. ........... 424/1.89 | WO | WO 93/13809 | 7/1993 |
| 5,804,162 A | 9/1998 | Kabalnov et al. ........... 424/9.51 | WO | WO 93/17718 | 9/1993 |
| 5,830,430 A | 11/1998 | Unger et al. .............. 424/1.21 | WO | WO 93/20802 | 10/1993 |
| 5,840,023 A | 11/1998 | Oraevsky et al. ........... 600/407 | WO | WO 94/06477 | 3/1994 |
| 5,846,517 A | 12/1998 | Unger ..................... 424/9.52 | WO | WO 94/07539 | 4/1994 |
| 5,849,727 A | 12/1998 | Porter et al. ............... 514/156 | WO | WO 94/09829 | 5/1994 |
| 5,853,752 A | 12/1998 | Unger ..................... 424/450 | WO | WO 84/02909 | 8/1994 |
| 5,855,865 A | 1/1999 | Lambert et al. ........... 424/9.52 | WO | WO 94/16739 | 8/1994 |
| 5,858,399 A | 1/1999 | Lanza et al. .............. 424/450 | WO | WO 94/21302 | 9/1994 |
| 5,958,371 A | 9/1999 | Lanza et al. .............. 424/1.21 | WO | WO 94/28780 | 12/1994 |
| 5,980,936 A | 11/1999 | Krafft et al. .............. 424/450 | WO | WO 94/28873 | 12/1994 |
| 5,989,520 A | 11/1999 | Lanza et al. .............. 424/9.32 | WO | WO 95/06518 | 3/1995 |
| 5,997,898 A | 12/1999 | Unger ..................... 424/450 | WO | WO 95/07072 | 3/1995 |
| 6,056,938 A | 5/2000 | Unger et al. .............. 424/1.21 | WO | WO 95/23615 | 9/1995 |
| 6,068,857 A | 5/2000 | Weitschies et al. ......... 424/489 | WO | WO 95/24184 | 9/1995 |
| 6,159,445 A | 12/2000 | Klaveness et al. ........... 424/9.6 | WO | WO 96/36286 | 11/1996 |
| 6,258,378 B1 | 7/2001 | Schneider et al. .......... 424/450 | WO | WO 96/40281 | 12/1996 |
| 6,261,537 B1 | 7/2001 | Klaveness et al. ......... 424/9.52 | WO | WO 96/40285 | 12/1996 |
| 6,331,289 B1 | 12/2001 | Klaveness et al. ......... 424/9.52 | WO | WO 98/00172 | 1/1998 |
| | | | WO | WO 98/18501 | 5/1998 |
| | FOREIGN PATENT DOCUMENTS | | WO | WO 99/13919 | 3/1999 |
| EP | 0 359 246 | 3/1990 | WO | WO 99/39738 | 8/1999 |
| EP | 0 361 894 | 4/1990 | WO | WO 00/45856 | 8/2000 |
| EP | 0 216 730 | 1/1991 | WO | WO 01/15742 A1 | 3/2001 |
| EP | 441468 A2 | 8/1991 | WO | WO 01/15742 | 3/2001 |

OTHER PUBLICATIONS

Porter, T.R., et al., "Visually discernible myocardial echocardiographic contrast after intravenous injection of sonicated dextrose albumin microbubbles containing high molecular weight, less soluble gases," *Am. College of Cardiology*, Feb. 1995, 25(2), 509–515.

Srinivasan, S.K., et al., "Characterization of binding sites, extent of binding, and drug interactions of oligonucleotides with albumin," *Antisense Res. And Develop.*, 1995, 5, 131–139.

Xie, F., et al., "Acute myocardial ischemia and reperfusion can be visually identified non–invasively with intravenous perfluoropropane–enhanced sonicated dextrose albumin ultrasound contrast," *Circulation*, Oct. 1994, 90(4), Part 2, Abstract 2989, 1 page.

Gross, U. et al., "Phosholipid vesiculated fluorocarbons promising trend in blood substitutes" *Biomat. Art. Cells & Immob. Biotech.*, 1992, vol. 20, (2–4) pp. 831–833.

Riess, Jean G., "Fluorine in our arteries", *New J. Chem.*, 1995, vol. 19 (8–9), pp. 891–909.

Riess, Jean G., "Introducing a new element fluorine–into the liposomal membrane" *Journal of Liposome Research*, 1995, vol. 5 (3) pp. 413–430.

Trevino, L, et al., "Incorporation of a perfluoroalkylalkane (rfrh) into the phospholipid bilayer of dmpc liposomes results in greater encapsulation stability", *Journal of Liposome Research*, 1994, vol. 4 (2) pp. 1017–1028.

Zarif L. et al., "Biodistribution and excretion of a mixed flurocarbon–hydrocarbon "dowel" emulsion as determined by 19–F NMR", *Artificial Cells, Blood Substitutes, and Immobilization Biotechnology*, 1994, vol. 22,(4) pp. 1193–1198.

Fitzpatrick, et al., "Metal Ion Catalyzed Decarboxylation: Kinetics and Mechanism of the Oxidative Decarboxylation of Copper (II) Complexes of Aminomalonic Acid in Aqueous Solution", *Inorganic Chemistry*, vol. 13, No. 3, pp. 568–574 (1974).

Thanassi, "Aminomalonic Acid: Spontaneous Decarboxylation and Reaction with 5–Deoxypyridoxal", *Biochemistry*, vol. 9, No. 3, pp. 525–532 (1970).

Stelmashok et al., "Photolysis of Frozen Solutions of Malonate Complexes", *Koordinatsionnaya Khimiya*, 1977, 3(4), 524–527 (Russian and English language versions).

Mayhew et al., "High–Pressure Continuous–Flow System for Drug Entrapment in Liposomes", *Methods in Enzymology*, vol. 149, pp. 64–77 (1987).

Mayhew et al., "Characterization of Liposomes Prepared Using a Microemulsifier", *Biochimica et Biophysica Acta*, vol. 775, pp. 169–174 (1984).

Hope et al., "Production of Large Unilamellar Vesicles by a Rapid Extrusion Procedure: Characterization of Size Distribution, Trapped Volume, and Ability to Maintain a Membrane Potential", *Biochimica et Biophysica Acta*, 812:55–65 (1985).

Mayer et al., "Vesicles of Variable Size Produced by a Rapid Extrusion Procedure", *Biochimica et Biophysica Acta*, vol. 858, pp. 161–168 (1986).

Cheng, et al., "The Production and Evaluation of Contrast–Carrying Liposomes Made with an Automatic High Pressure System", *Investigative Radiology*, vol. 22, pp. 47–55 (1987).

Sigel, H., ed., Metal Ions in Biological Systems: Antibiotics and Their Complexes, vol. 19 (Marcel Dekker, N.Y. 1985).

Nayer et al., "Generation of Large Unilamellar Vesicles From Long–chain Saturated Phosphatidylcholines by Extrusion Technique", *Biochimica et Biophysica Acta*, vol. 986, pp. 200–206 (1989).

Hope et al., "Generation of Multilamellar and Unilamellar Phospholipid Vesicles", *Chemistry and Physics of Lipids*, vol. 40, pp. 89–107 (1986).

Mattrey et al., "Perfluorochemicals as US Contrast Agents for Tumor–Imaging and Hepatosplenography: Preliminary Clinical Results", *Radiology*, vol. 163, pp. 39–343 (1987).

Mattrey et al., "Perfluoroctylbromide: A Liver/Spleen–Specific and Tumor Imaging Ultrasound Contrast Material", *Radiology*, vol. 145, pp. 759–762 (1982).

Keller et al., "Successful Left Ventricular Opacification Following Peripheral Venous Injection of Sonicated Contrast Agent: An Experimental Evaluation", *LV Contrast Echocardiography*, vol. 114, No. 3, pp. 570–575 (1987).

Feinstein et al., "Two–Dimensional Contrast Echocardiography, I: In Vitro Development and Quantitative Analysis of Echo Contrast Agents", *JACC*, vol. 3, No. 1, pp. 14–20 (1984).

Ten Cate et al., "Two–Dimensional Contrast Echocardiography, II: Transpulmonary Studies", *JACC*, vol. 3, No. 1, pp. 21–27 (1984).

Unger et al., "Hepatic Metastases: Liposomal Gd–DTPA–enhanced MR Imaging", *Radiology*, vol. 171, pp. 81–85 (1989).

Gutknecht et al., "Diffusion of Carbon Dioxide Through Lipid Bilayer Membranes: Effect of Carbonic Anhydrase, Bicarbonate, and Unstirred Layers", *Chemical Abstracts*, 87:34772q (1977).

Scarpa et al., "Cation Permeability of Liposomes as a Function of the Chemical Composition of the Lipid Bilayers", *Biochimica et Biophysica Acta*, vol. 241, pp. 789–797 (1971).

MacNaughton et al., "Effects of Gaseous Anesthetics and Inert Gases on the Phase Transition in Smectic Mesophases of Dipalmitoyl Phosphatidylcholine", *Biochimica et Biophysica Acta*, vol. 597, pp. 193–198 (1980).

Tilcock et al., "Liposomal Gd–DTPA: Preparation and Characterization of Relaxivity", *Radiology*, vol. 171, pp. 77–80 (1989).

Mann et al., "Formation of Iron Oxides in Unilamellar Vesicles", *Journal of Colloid and Interface Science*, vol. 122, No. 2, pp. 326–335 (1988).

Anderson et al., "Manganese (III) Complexes in Oxidative Decarboxylation of Acids", *J. Am. Chem. Soc.*, vol. 92, No. 8, pp. 2450–2460 (1970).

Muhlradt et al., "Vitamin B6 Analogs: An Improved Synthesis of 5–Deoxypyridoxal", *New Compounds*, vol. 10, pp. 129–130 (1967).

Chapman D., "Physiochemical Properties of Phospholipids and Lipid Water Systems", *Liposome Technology*, Gregoriadis, G., ed., vol. 1, pp. 1–19 (CRC Press, Boca Raton, FL, 1984).

Violante et al., "Particulate Suspensions as Ultrasonic Contrast Agents for Liver and Spleen", *Inv. Rad.*, vol. 23, pp. S294–S297, Sep. 1988.

Fritzsch et al., "Preclinical and Clinical Results with an Ultrasonic Contrast Agent", *Inv. Rad.*, vol. 23, pp. S302–S305, Sep. 1988.

Brochure, *Experience*, Sonicator™, Heat Systems–Ultrasonics, Inc. (1987).

M. Ostro, "Liposomes", Marcel Dekker, New York, pp. 102–103 (1983).

Regen, "Polymerized Vesicles", *J. Am. Chem. Soc.*, vol. 102, pp. 6638–6640 (1989).

Rose, A. and Rose, E., "The Condensed Chemical Dictionary", Reinhold Publishing, New York, pp. 728 and 743 (1966).

A.G. Belykh, *Farmakol Toksikol. (MOSC)*, vol. 44(3), pp. 322–326 (1981) (abstract).

J. Vion–Dury et al., *J. Pharmacol. Exper. Ther.*, vol. 250(3), pp. 1113–1118 (1989) (abstract).

M.R. Zalutsky et al., *Invest. Radiol.*, vol. 2(2), pp. 141–147 (1987) (abstract).

Crowe et al., *Archives of Biochemistry and Biophysics*, vol. 242, pp. 240–247 (1985).

Crowe et al., *Archives of Biochemistry and Biophysics*, vol. 220, pp. 477–484 (1983).

Dorland's Illustrated Medical Dictionary, p. 946, 27th ed. (W.B. Saunders Company, Philadelphia 1988).

*Liposome Technology*, Gregoriadis, G., ed., vol. I, pp. 1–18, 30–35, 51–65 and 79–107 (CRC Press Inc., Bota Raton, FL, (1984).

Madden et al., "The accumulation of drugs within large unilamellar vesicles exhibiting a proton gradient: a survey", *Chemistry and Physics of Lipids*, 1990, 53, 37–46.

Sinkula et al., *J. Pharm. Sci.*, vol. 64, pp. 181–210 (1975).

Shiina et al., "Hyperthermiaby Low–frequency Synthesized Ultrasound", *IEEE Engineering*, pp. 879–880, vol. 2 (1988) (abstract).

McAvoy et al., *IEEE Engineering, Ultrasonics Symposium Proceedings*, vol. 2, pp. 677–1248 (1989) (abstract).

Chapman et al., "Biomembrane Phase Transitions", *J. Biol. Chem.*, 1974, 249:2512–2521.

Hug et al., "Liposomes for the Transformation of Eukaryotic Cells", *Biochimica et Biophysica Acta*, 1991, 1097:1–17.

Marsh, *CRC Handbook of Lipid Bilayers* (CRC Press, Boca Raton, FL 1990) pp. 139–141.

Szoka et al., "Procedure for Preparation of Liposomes With Large Internal Aqueous Space . . . ", *Proc. Natl. Acad. Sci.* 1978, 75:4194–4198.

Acoustic Imaging; AI5200; Convex Curved Linear Array Ultrasound Transducers Operator's Manual, Nov. 20, 1989, 4700–0003–1C, p. 4.

Bangham et al., "Diffusion of Univalent Ions across the Lamellae of Swollen Phospholipids", *J. Mol. Biol.*, 1965, 13:238–252.

Carson et al., "Ultrasonic Power and Intensities Produced by Diagnostic Ultrasound Equipment", *Ultrasound in Med. & Biol.*, 3, 1978, 341–350.

Kost et al., *Polymers in Medicine II: Biomedical and Pharmaceutical Applications*, "Ultrasonic Modulated Drug Delivery Systems", Chiellini et al., ed., (Plenum de Gier et al., "Relations Between Liposomes and Biomembranes", *Annals of The New York Academy of Sciences*, 1978, 308:85–99.

Felgner et al., "Lipofection: A highly efficient, lipid–mediated DNA–transfection procedure", *Proc. Natl. Acad. Sci.*, 1987, 84:7413–7417.

Gabizon et al., "Liposome formulations with prolonged circulation time in blood and enhanced uptake by tumors", *Proc. Natl. Acad. Sci.*, 1988, 85:6949–6953.

Garelli, et al., *Biochimica et Biophysica Acta*, vol. 1127:41–48 (1992).

Kawai et al., "New Procedure for DNA Transfection with Polycation and Dimethyl Sulfoxide", *Molecular and Cellular Biology*, 1984, 4:1172–1174.

Kuo et al., "Metallocene Antitumor Agents. Solution and Solid–State Molybdenocene Coordination . . . ", *J. Am. Chem. Soc.*, 1991, 113:9027–9045.

*Mammalian Cell Biotechnology: A Practical Approach*, M. Butler, 1991 (Oxford University, Press, New York), p. 57–70.

Mathiowitz et al., "Photochemical Rupture of Microcapsules: A Model System", *Journal of Applied Polymer Science*, 1981, 26:809–822.

May et al., "Cationic Liposomes Enable Bovine Herpesvirus Type 2 DNA to Infect Cells", *Acta virol.*, 1991, 35:107.

Poznansky et al., "Biologica Approaches to the Controlled Delivery of Drugs: A Critical Review", *Pharmacol, Rev.*, 1984, 36:277–336.

Sato et al., "Recent Aspects in the Use of Liposomes in Biotechnology and Medicine", *Prog. Lipid Res.* 1992, 4:345–372.

Simons et al., "Antisense c–myb oligonucleotides inhibit intimal arterial smooth muscle cell accumulation in vivo", *Nature*, 1992, 359:67–70.

Thompson, Larry, "At Age 2, Gene Therapy Enters a Growth Phase", *Science* 1992, 258:744–746.

Trubetskoy et al., "Cationic liposomes enhance targeted delivery and expression of exogenous DNA . . . ", Biochimica et Biophysica Acta 1992, 131:311–313.

Umemura et al., "Studis on Sonodynamic Cancer Therapy", *IEEE*, 1992, O–7803–0785, pp. 354–355.

Williams, "Human Gene Therapy: Searching for Better Vectors", *ASM News* [American Society for Microbology] 1992, 58:67–69.

Woodle et al., "Versatility in lipid compositions showing prolonged circulation . . . ", *Biochimica et Biophysica Acta* 1992, 1105:193–200.

Zhou et al., "Targeted delivery of DNA by liposomes and polymers", *J. of Controlled Release* 1992, 19:269–274.

Mathiowitz et al., "Polyanhydride Microspheres as Drug Carriers", *Journal of Applied Polymer Science*, vol. 35, pp. 755–774 (1988).

Sankaram et al., "Cholesterol–Induced Fluid–Phase Immiscibility in Membranes", *Proc. Natl. Acad. Sci.*, vol. 88, pp. 8686–8690 (1991).

*Scientific Apparatus Catalog* 92/93 (VWR Scientific, 1991), "Syringes", pp. 1511–1513; "Filtration, Syringe Filters", pp. 766–768; "Filtration, Membranes", pp. 750–753; "Filtration, Filter Holders", p. 744.

Gramiak et al., *Radiology*, "Detection of Intracardiac Blood Flow by Pulsed Echo–Ranging", pp. 415–418 (1971).

Feigenbaum et al., *Circulation*, "Identification of Ultrasound Echoes from the Left Ventricle by Use of Intracardiac Injections of Indocyanine Green", vol. XL1, pp. 615–621 (1970).

Santaella, et al., *FEBS 13463*, "Extended In Vivo Blood Circulation Time of Fluorinated Liposomes", vol. 336, No. 3, pp. 481–484 (1993).

Brown and Langer, *Annual Review Medicine*, 1988, 39:221 29, Annual Review, Inc., "Transdermal Delivery of Drugs", pp. 221–229.

Moseley, et al., *Microbubbles: A Novel MR Susceptibility Contrast Agent*, abstract, *1991* Napa, California Meeting of the Society for Magnetic Resonance in Medicine.

Ter–Pogossia, "Physical Principles and Instrumentation", *Computed Body Tomography*, Lee et al. (eds.), Raven Press, New York, Chapter 1, pp. 1–7 (1988.

Aronberg, "Techniques", *Computed Body Tomography*, Kee, et al., eds., Raven Press, New York, Chapter 2, pp. 9–36 (1988).

Miller, *Ultrasonics* (Sep. 1981), "Ultrasonic detection of resonant cavitation bubbles in a flow tube by their second–harmonic emissions," pp. 217–224.

Dittrich, "Cardiac Muscle Ischemia and Infarction", *The Second Annual International Symposium on Contrast Agents in Diagnostic Ultrasound*, Atlantic City, NJ (May 7, 1996) (abstract).

Pantely, "Intravenous Contrast Echocardiography–Tissue Imaging & Quantification of Coronary Blood Flow", *The Second Annual International Symposium on Contrast Agents in Diagnostic Ultrasound*, Atlantic City, NJ (May 7, 1996) (abstract).

Schutt et al., "Osmotically Stabilized Microbubble Sonographic Contrast Agents", *Acad. Radiol.*, vol. 3, Suppl. 2, pp. S188–S190 (Aug. 1996).

Frézard, et al., "Permeability and stability in buffer and in human serum of fluorinated phospholipid–based liposomes", *Biochimica et Biophysica Acta*, 1192, pp. 61–70 (1994).

Frézard, et al., "Fluorinated Phospholipid–Based Vesicles as Potential Drug Carriers: Encapsulation/Sustaining of Drugs and Stability in Human Serum", *Art, Cells, Blood Subs., and Immob. Biotech.*, 22(4), pp. 1403–1408 (1994).

Chang et al., "Semipermeable Aqueous Microcapsules", *Canadian J. Of Phys. And Pharm.*, 1996, 44, 115–128.

Chang, "Semipermeable Microcapsules", *Science*, 1964, 146, 524–525.

Deasy, *Microencapsulation and Related Drug Processes*, 1983, vol. 20, Chs. 9 and 10, 195–240 (Marcel Dekker, Inc., NY).

Yeung et al., "Preparation of Microencapsulated Liposomes", *J. Microencapsulation*, 1988, 5, 331–337.

Mattrey et al., Gas Emulsions as Ultrasound Contrast Agents; Preliminary Results in Rabbits and Dogs, *Investigative Radiology*, vol. 29, Jun. Supp. 2, pp. S139–S141, 1994.

Meltzer et al., Transmission of Ultrasonic Contrast Through the Lungs, *Ultrasound in Med. & Biol.*, vol. 7, No. 4, 377–384, 1981.

PR Newswire, Apr. 1, 1986.

Swanson et al., Chapter 22, "Enhancement Agents for Ultrasound: Fundamentals", *Pharmaceuticals In Medical Imaging*, pp. 682–687 (1990).

Ophir et al., "Contrast Agents in Diagnostic Ultrasound", *Ultrasound in Med. & Biol.*, vol. 15, No. 4, pp. 319–333 (1989).

Jacobs, "Intraocular gas measurement using A–scan ultrasound", *Current Eye Research*, vol. 5, No. 8, pp. 575–578 (1986).

Lincoff et al., "Intravitreal Expansion of Perfluorocarbon Bubbles", *Arch. Ophthalmol.*, 1980, 98, 1646.

Lincoff et al., "Intravitreal Longevity of Three in Perfluorocarbon Gases", *Arch. Ophthalmol.*, 1980, 98, 1610–1611.

Lincoff et al., "The Perfluorocarbon Gases in the Treatment of Retinal Detachment", *Ophthalmology*, 1983, 90(5), 546–551.

Gardner et al., "A Survey of Intraocular Gas Use in North America", *Arch. Ophthalmol.*, 1988, 106, 1188–1189.

Unger et al., "Liposomal MR Contrast Agents", *J. Liposome Research*, 1994, 4(2), 811–834.

Villanueva et al., "Characterization of Spatial Patters of Flow Within the Reperfused Myocardium by Myocardial Contrast Echocardiography", *Circulation*, vol. 88, No. 6, pp. 2596–2606 (Dec. 1993).

Desir et al., "Assessment of regional myocardial perfusion with myocardial contrast echocardiography in a canine model of varying degrees of coronary stenosis", *Am. Heart J.*, Jan., 1994, 127(1), 56–63.

Sekins et al., "Lung Cancer Hyperthermia via Ultrasound and PFC Liquids", *Published in Proceedings of 5th International Symposium in Hyperthermic Oncology*, Kyoto, Japan, Aug. 29–Sep. 3, 1998, 3 pages.

Nomura et al., "US Contrast Enhancement of Hepatic Tumor with Helium Gas Microbubbles: A Preliminary Report", *Jpn. J. Med. Ultrasonics*, 1991, 18(5), (Japanese with English language abstract).

Lindner et al., "Myocardial Perfusion Characteristics and Hemodynamic Profile of MRX–115, a Venous Echocardiographic Contrast Agent, During Acute Myocardial Infarction", *J. Am. Soc. Echocardiography*, 1998, 11(1), 36–46.

Regen et al., "Polymerized Phosphatidylcholine Vesicles. Synthesis and Characterization", *J. Am. Chem. Soc.*, 1982, 104(3), 191–195.

Wei et al., "Quantification of Myocardial Blood Flow with Ultrasound–Induced Destruction of Microbubbles Administered as a Constant Venous Infusion", *Circulation*, 1988, 97, 473–483.

Hynynen et al., "The Usefulness of a Contrast Agent and Gradient Recalled Acquisition in a Steady–State Imaging Sequence for Magnetic Resonance Imaging: Guided Noninvasive Ultrasound Surgery", *Investigative Radiology*, 1994, 29(10), 897–903.

Lejbkowicz et al., "The response of normal and malignant cells to ultrasound in vitro", Database *BIOSIS*, No. 1993:95122245 (abstract only).

Jackson et al., "Effect of ultrasound therapy on the repair of Achilles tendon injuries in rats", *Med. Sci. Sports Exercise*, 1991, 23(2), 171–176.

Maxwell, "Therapeutic Ultrasound: Its Effects on the Cellular and Molecular Mechanisms of Inflammation and Repair", *Physiotherapy*, 1992, 78(6), 421–426.

Tuncay et al., "Expression of Genes Associated with Tissue Remodeling Upon Ultrasound Perturbation in the Gingival Fibroblast", *J. Dental Res.*, 1996, 75, 143, (abstract only).

Wang et al., "Low Intensity Ultrasound Treatment Increases Strength in a Rat Femoral Fracture Model", *J. Orthopaedic Res.*, 1994, 12(1), 40–47.

Yang et al., "Exposure to Low–Intensity Ultrasound Increases Aggrecan Gene Expression in a Rat Femur Facture Model", *J. Orthopaedic Res.*, 1996, 14(5), 802–809.

Young et al., "Effect of therapeutic ultrasound on the healing of full–thickness excised skin lesions", *Ultrasonics*, 1990, 28(3), 175–180.

Young et al., "The Effect of Therapeutic Ultrasound on Angiogenesis", *Ultrasound Med. Biol.*, 1990, 16(3), 261–269.

Kinsler, L. E., et al., *Fundamentals of Acoustics*, $3^{rd}$ Ed., 1982, 228–331.

Meessen, H. (ed.), *Microcirculation*, Springer–Verlag, Berlin Heidelberg, New York, 1997, 44.

Ring, J., et al., "Humanalbuminunverträglichkeit: klinische und immunologische untersuchungen," *Clinical Weekly*, 1974, 52, 595–598.

Robinson, et al., F.J. Fry (ed.), "Ultrasound: its applications in medicine and biology," *Elsevier Scientific Publishing Company*, 1978, vol. 3, Chap. XI, 593–596.

Silbernagl, S., et al., "Pocket atlas of physiology," *Georg Thieme Verlag*, Stuttgart, New York, 1983, 156–157.

Wells, P.N.T., "Pulse–echo methods," *Biomedical Ultrasonics*, Academic Press, 1977, 209–220.

Porter, T. R., et al., "Thrombolytic Enhancement with Perfluorocarbon–exposed Sonicated Dextrose Albumin Microbubbles", *American Heart Journal*, Nov. 1996, vol. 132, No. 5, pp. 964–968.

Hautanen, A., et al., "Effects of modifications of the RGD sequence and its context on recognition by the fibronectin receptor," *J. Biol. Chem.*, 1989, 264(3), 1437–1442.

Takeuchi, M., et al., "Enhanced visualization of intravascular thrombus with the use of a thrombus targeting ultrasound contrast agent (MRX408): Evidence from in vivo experimental echocardiographic studies," *J. Am. College of Cardiology*, 1998, 81(12), 1 page, Abstract XP–000952675.

Unger, E.C., et al., "In vitrostudies of a new thrombus–specific ultrasound contrast agent", *J. of Cardiology*, 1998, 81(12), 58G–61G, Abstract XP–002087505.

Wu, Y., et al., "Binding and lysing of blood clots using MRX–408," *Investigate Radiology*, 1998, 33(12), 880–885.

\* cited by examiner

SEQUENCE LISTING

```
<160> NUMBER OF SEQ ID NOS: 39

<210> SEQ ID NO 1
<211> LENGTH: 5
<212> TYPE: PRT
<213> ORGANISM: Artificial Sequence
<220> FEATURE:
<223> OTHER INFORMATION: Completely synthetic sequence
<220> FEATURE:
<221> NAME/KEY: misc_feature
<222> LOCATION: (4)..(4)
<223> OTHER INFORMATION: Xaa is azetidine

<400> SEQUENCE: 1

Trp Tyr Gln Xaa Tyr
1               5

<210> SEQ ID NO 2
<211> LENGTH: 12
<212> TYPE: PRT
<213> ORGANISM: Artificial Sequence
<220> FEATURE:
<223> OTHER INFORMATION: Completely synthetic sequence
<220> FEATURE:
<221> NAME/KEY: misc_feature
<222> LOCATION: (7)..(7)
<223> OTHER INFORMATION: Xaa is azetidine

<400> SEQUENCE: 2

Trp Pro Gly Trp Tyr Gln Xaa Tyr Ala Leu Pro Leu
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Completely synthetic sequence
<220> FEATURE:
<221> NAME/KEY: misc_feature
<222> LOCATION: (9)..(9)
<223> OTHER INFORMATION: Xaa is azetidine

<400> SEQUENCE: 3

Phe Glu Trp Pro Gly Trp Tyr Gln Xaa Tyr Ala Leu Pro Leu
1               5                   10
```

```
<210> SEQ ID NO 4
<211> LENGTH: 4
<212> TYPE: PRT
<213> ORGANISM: Artificial Sequence
<220> FEATURE:
<223> OTHER INFORMATION: Completely synthetic sequence

<400> SEQUENCE: 4

Arg Gly Asp Ser
1

<210> SEQ ID NO 5
<211> LENGTH: 6
<212> TYPE: PRT
<213> ORGANISM: Artificial Sequence
<220> FEATURE:
<223> OTHER INFORMATION: Completely synthetic sequence

<400> SEQUENCE: 5

Gly Arg Gly Asp Ser Pro
1               5

<210> SEQ ID NO 6
<211> LENGTH: 4
<212> TYPE: PRT
<213> ORGANISM: Artificial Sequence
<220> FEATURE:
<223> OTHER INFORMATION: Completely synthetic sequence

<400> SEQUENCE: 6

Gly Pro Arg Pro
1

<210> SEQ ID NO 7
<211> LENGTH: 159
<212> TYPE: PRT
<213> ORGANISM: Artificial Sequence
<220> FEATURE:
<223> OTHER INFORMATION: Completely synthetic sequence

<400> SEQUENCE: 7

Asn Lys Leu Ile Val Arg Arg Gly Gln Ser Phe Tyr Val Gln Ile Asp
1               5                   10                  15

Phe Ser Arg Pro Tyr Asp Pro Arg Arg Asp Leu Phe Arg Val Glu Tyr
                20                  25                  30

Val Ile Gly Arg Tyr Pro Gln Glu Asn Lys Gly Thr Tyr Ile Pro Val
            35                  40                  45

Pro Ile Val Ser Glu Leu Gln Ser Gly Lys Trp Gly Ala Lys Ile Val
        50                  55                  60

Met Arg Glu Asp Arg Ser Val Arg Leu Ser Ile Gln Ser Ser Pro Lys
65                  70                  75                  80

Cys Ile Val Gly Lys Phe Arg Met Tyr Val Ala Val Trp Thr Pro Tyr
                85                  90                  95

Gly Val Leu Arg Thr Ser Arg Asn Pro Glu Thr Asp Thr Tyr Ile Leu
                100                 105                 110

Phe Asn Pro Trp Cys Glu Asp Asp Ala Val Tyr Leu Asp Asn Glu Lys
            115                 120                 125

Glu Arg Glu Glu Tyr Val Leu Asn Asp Ile Gly Val Ile Phe Tyr Gly
        130                 135                 140

Glu Val Asn Asp Ile Lys Thr Arg Ser Trp Ser Tyr Gly Gln Phe
145                 150                 155
```

```
<210> SEQ ID NO 8
<211> LENGTH: 26
<212> TYPE: PRT
<213> ORGANISM: Artificial Sequence
<220> FEATURE:
<223> OTHER INFORMATION: Completely synthetic sequence

<400> SEQUENCE: 8

Asn Lys Leu Ile Val Arg Arg Gly Gln Ser Phe Tyr Val Gln Ile Asp
1               5                   10                  15

Phe Ser Arg Pro Tyr Asp Pro Arg Arg Asp
            20                  25

<210> SEQ ID NO 9
<211> LENGTH: 41
<212> TYPE: PRT
<213> ORGANISM: Artificial Sequence
<220> FEATURE:
<223> OTHER INFORMATION: Completely synthetic sequence

<400> SEQUENCE: 9

Asp Asp Ala Val Tyr Leu Asp Asn Glu Lys Glu Arg Glu Glu Tyr Val
1               5                   10                  15

Leu Asn Asp Ile Gly Val Ile Phe Tyr Gly Glu Val Asn Asp Ile Lys
            20                  25                  30

Thr Arg Ser Trp Ser Tyr Gly Gln Phe
        35                  40

<210> SEQ ID NO 10
<211> LENGTH: 9
<212> TYPE: PRT
<213> ORGANISM: Artificial Sequence
<220> FEATURE:
<223> OTHER INFORMATION: Completely synthetic sequence

<400> SEQUENCE: 10

Ala Arg Arg Ser Ser Pro Ser Tyr Tyr
1               5

<210> SEQ ID NO 11
<211> LENGTH: 10
<212> TYPE: PRT
<213> ORGANISM: Artificial Sequence
<220> FEATURE:
<223> OTHER INFORMATION: Completely synthetic sequence

<400> SEQUENCE: 11

Gly Ala Gly Pro Tyr Tyr Ala Met Asp Tyr
1               5                   10

<210> SEQ ID NO 12
<211> LENGTH: 19
<212> TYPE: PRT
<213> ORGANISM: Artificial Sequence
<220> FEATURE:
<223> OTHER INFORMATION: Completely synthetic sequence

<400> SEQUENCE: 12

Arg Ser Pro Ser Tyr Tyr Arg Tyr Asp Gly Ala Gly Pro Tyr Tyr Ala
1               5                   10                  15

Met Asp Tyr

<210> SEQ ID NO 13
<211> LENGTH: 21
```

```
<212> TYPE: PRT
<213> ORGANISM: Artificial Sequence
<220> FEATURE:
<223> OTHER INFORMATION: Completely synthetic sequence

<400> SEQUENCE: 13

Ala Arg Arg Ser Pro Ser Tyr Tyr Arg Tyr Asp Gly Ala Gly Pro Tyr
1               5                   10                  15

Tyr Ala Met Asp Tyr
            20

<210> SEQ ID NO 14
<211> LENGTH: 69
<212> TYPE: PRT
<213> ORGANISM: Artificial Sequence
<220> FEATURE:
<223> OTHER INFORMATION: Completely synthetic sequence
<220> FEATURE:
<221> NAME/KEY: misc_feature
<222> LOCATION: (40)..(41)
<223> OTHER INFORMATION: Xaa is any amino acid

<400> SEQUENCE: 14

Gly Glu Glu Cys Asp Cys Gly Ser Pro Glu Asn Pro Cys Cys Asp Ala
1               5                   10                  15

Ala Thr Cys Lys Leu Arg Pro Gly Ala Gln Cys Ala Asp Gly Leu Cys
            20                  25                  30

Cys Asp Gln Cys Arg Phe Lys Xaa Xaa Arg Thr Ile Cys Arg Arg Ala
        35                  40                  45

Arg Gly Asp Asn Pro Asp Asp Arg Cys Thr Gly Gln Ser Ala Asp Cys
    50                  55                  60

Pro Arg Asn Gly Tyr
65

<210> SEQ ID NO 15
<211> LENGTH: 73
<212> TYPE: PRT
<213> ORGANISM: Artificial Sequence
<220> FEATURE:
<223> OTHER INFORMATION: Completely synthetic sequence

<400> SEQUENCE: 15

Glu Ala Gly Glu Asp Cys Asp Cys Gly Ser Pro Ala Asn Pro Cys Cys
1               5                   10                  15

Asp Ala Ala Thr Cys Lys Leu Leu Pro Gly Ala Gln Cys Gly Glu Gly
            20                  25                  30

Leu Cys Cys Asp Gln Cys Ser Phe Met Lys Lys Gly Thr Ile Cys Arg
        35                  40                  45

Arg Ala Arg Gly Asp Asp Leu Asp Asp Tyr Cys Asn Gly Ile Ser Ala
    50                  55                  60

Gly Cys Pro Arg Asn Pro Leu His Ala
65                  70

<210> SEQ ID NO 16
<211> LENGTH: 68
<212> TYPE: PRT
<213> ORGANISM: Artificial Sequence
<220> FEATURE:
<223> OTHER INFORMATION: Completely synthetic sequence

<400> SEQUENCE: 16

Glu Ala Gly Glu Glu Cys Asp Cys Gly Thr Pro Glu Asn Pro Cys Cys
1               5                   10                  15
```

```
Asp Ala Ala Thr Cys Lys Leu Arg Pro Gly Ala Gln Cys Ala Glu Gly
             20                  25                  30

Leu Cys Cys Asp Gln Cys Arg Phe Lys Gly Ala Gly Lys Ile Cys Arg
         35                  40                  45

Arg Ala Arg Gly Asp Asn Pro Asp Asp Cys Thr Gly Gln Ser Ala Asp
     50                  55                  60

Cys Pro Arg Phe
65
```

<210> SEQ ID NO 17
<211> LENGTH: 70
<212> TYPE: PRT
<213> ORGANISM: Artificial Sequence
<220> FEATURE:
<223> OTHER INFORMATION: Completely synthetic sequence
<220> FEATURE:
<221> NAME/KEY: misc_feature
<222> LOCATION: (40)..(41)
<223> OTHER INFORMATION: Xaa is any amino acid
<220> FEATURE:
<221> NAME/KEY: misc_feature
<222> LOCATION: (67)..(67)
<223> OTHER INFORMATION: Xaa is any amino acid

<400> SEQUENCE: 17

```
Gly Gly Glu Cys Asp Cys Gly Ser Pro Glu Asn Pro Cys Cys Asp Ala
1               5                  10                  15

Ala Thr Cys Lys Leu Arg Pro Gly Ala Gln Cys Ala Asp Gly Leu Cys
             20                  25                  30

Cys Asp Gln Cys Arg Phe Lys Xaa Xaa Arg Thr Ile Cys Arg Ile Ala
         35                  40                  45

Arg Gly Asp Phe Pro Asp Asp Arg Cys Thr Gly Leu Ser Ala Asp Cys
     50                  55                  60

Pro Arg Xaa Asn Asp Leu
65                  70
```

<210> SEQ ID NO 18
<211> LENGTH: 8
<212> TYPE: PRT
<213> ORGANISM: Artificial Sequence
<220> FEATURE:
<223> OTHER INFORMATION: Completely synthetic sequence

<400> SEQUENCE: 18

```
Arg Glu Tyr Val Val Met Trp Lys
1               5
```

<210> SEQ ID NO 19
<211> LENGTH: 8
<212> TYPE: PRT
<213> ORGANISM: Artificial Sequence
<220> FEATURE:
<223> OTHER INFORMATION: Completely synthetic sequence

<400> SEQUENCE: 19

```
Cys Arg Gly Asp Met Phe Gly Cys
1               5
```

<210> SEQ ID NO 20
<211> LENGTH: 8
<212> TYPE: PRT
<213> ORGANISM: Artificial Sequence
<220> FEATURE:
<223> OTHER INFORMATION: Completely synthetic sequence

```
<400> SEQUENCE: 20

Cys Arg Gly Asp Met Leu Arg Cys
1               5

<210> SEQ ID NO 21
<211> LENGTH: 8
<212> TYPE: PRT
<213> ORGANISM: Artificial Sequence
<220> FEATURE:
<223> OTHER INFORMATION: Completely synthetic sequence

<400> SEQUENCE: 21

Cys Arg Gly Asp Phe Leu Asn Cys
1               5

<210> SEQ ID NO 22
<211> LENGTH: 8
<212> TYPE: PRT
<213> ORGANISM: Artificial Sequence
<220> FEATURE:
<223> OTHER INFORMATION: Completely synthetic sequence

<400> SEQUENCE: 22

Cys Asn Thr Leu Lys Gly Asp Cys
1               5

<210> SEQ ID NO 23
<211> LENGTH: 8
<212> TYPE: PRT
<213> ORGANISM: Artificial Sequence
<220> FEATURE:
<223> OTHER INFORMATION: Completely synthetic sequence

<400> SEQUENCE: 23

Cys Asn Trp Lys Arg Gly Asp Cys
1               5

<210> SEQ ID NO 24
<211> LENGTH: 5
<212> TYPE: PRT
<213> ORGANISM: Artificial Sequence
<220> FEATURE:
<223> OTHER INFORMATION: Completely synthetic sequence
<220> FEATURE:
<221> NAME/KEY: misc_feature
<222> LOCATION: (1)..(2)
<223> OTHER INFORMATION: N-methyl linkage
<220> FEATURE:
<221> NAME/KEY: misc_feature
<222> LOCATION: (5)..(5)
<223> OTHER INFORMATION: Xaa is penicillamine

<400> SEQUENCE: 24

Cys Arg Gly Asp Xaa
1               5

<210> SEQ ID NO 25
<211> LENGTH: 7
<212> TYPE: PRT
<213> ORGANISM: Artificial Sequence
<220> FEATURE:
<223> OTHER INFORMATION: Completely synthetic sequence
<220> FEATURE:
<221> NAME/KEY: misc_feature
<222> LOCATION: (1)..(2)
<223> OTHER INFORMATION: Xaa= any amino acid
<220> FEATURE:
<221> NAME/KEY: misc_feature
```

```
<222> LOCATION: (6)..(7)
<223> OTHER INFORMATION: Xaa= any amino acid

<400> SEQUENCE: 25

Xaa Xaa Arg Gly Asp Xaa Xaa
1               5

<210> SEQ ID NO 26
<211> LENGTH: 8
<212> TYPE: PRT
<213> ORGANISM: Artificial Sequence
<220> FEATURE:
<223> OTHER INFORMATION: Completely synthetic sequence

<400> SEQUENCE: 26

Leu Ser Pro Phe Pro Phe Asp Leu
1               5

<210> SEQ ID NO 27
<211> LENGTH: 8
<212> TYPE: PRT
<213> ORGANISM: Artificial Sequence
<220> FEATURE:
<223> OTHER INFORMATION: Completely synthetic sequence

<400> SEQUENCE: 27

Leu Ser Pro Phe Ala Phe Asp Leu
1               5

<210> SEQ ID NO 28
<211> LENGTH: 8
<212> TYPE: PRT
<213> ORGANISM: Artificial Sequence
<220> FEATURE:
<223> OTHER INFORMATION: Completely synthetic sequence

<400> SEQUENCE: 28

Leu Ser Ala Phe Pro Phe Asp Leu
1               5

<210> SEQ ID NO 29
<211> LENGTH: 8
<212> TYPE: PRT
<213> ORGANISM: Artificial Sequence
<220> FEATURE:
<223> OTHER INFORMATION: Completely synthetic sequence

<400> SEQUENCE: 29

Leu Ser Pro Phe Pro Phe Asp Ala
1               5

<210> SEQ ID NO 30
<211> LENGTH: 9
<212> TYPE: PRT
<213> ORGANISM: Artificial Sequence
<220> FEATURE:
<223> OTHER INFORMATION: Completely synthetic sequence

<400> SEQUENCE: 30

Ser Pro Phe Pro Phe Asp Leu Leu Leu
1               5

<210> SEQ ID NO 31
<211> LENGTH: 8
<212> TYPE: PRT
<213> ORGANISM: Artificial Sequence
<220> FEATURE:
```

-continued

<223> OTHER INFORMATION: Completely synthetic sequence

<400> SEQUENCE: 31

Gln Leu Ser Pro Ser Pro Asp Leu
1               5

<210> SEQ ID NO 32
<211> LENGTH: 8
<212> TYPE: PRT
<213> ORGANISM: Artificial Sequence
<220> FEATURE:
<223> OTHER INFORMATION: Completely synthetic sequence

<400> SEQUENCE: 32

Ser Ile Ile Asn Phe Glu Lys Leu
1               5

<210> SEQ ID NO 33
<211> LENGTH: 8
<212> TYPE: PRT
<213> ORGANISM: Artificial Sequence
<220> FEATURE:
<223> OTHER INFORMATION: Completely synthetic sequence

<400> SEQUENCE: 33

Leu Ser Pro Tyr Pro Phe Asp Leu
1               5

<210> SEQ ID NO 34
<211> LENGTH: 8
<212> TYPE: PRT
<213> ORGANISM: Artificial Sequence
<220> FEATURE:
<223> OTHER INFORMATION: Completely synthetic sequence

<400> SEQUENCE: 34

Ala Ser Pro Phe Pro Phe Asp Leu
1               5

<210> SEQ ID NO 35
<211> LENGTH: 11
<212> TYPE: PRT
<213> ORGANISM: Artificial Sequence
<220> FEATURE:
<223> OTHER INFORMATION: Completely synthetic sequence

<400> SEQUENCE: 35

Ser Ser Phe Gly Ala Phe Gly Ile Phe Pro Lys
1               5                   10

<210> SEQ ID NO 36
<211> LENGTH: 16
<212> TYPE: PRT
<213> ORGANISM: Artificial Sequence
<220> FEATURE:
<223> OTHER INFORMATION: Completely synthetic sequence

<400> SEQUENCE: 36

Ala Asn Glu Arg Ala Asp Leu Ile Ala Tyr Leu Lys Gln Ala Thr Lys
1               5                   10                  15

<210> SEQ ID NO 37
<211> LENGTH: 17
<212> TYPE: PRT
<213> ORGANISM: Artificial Sequence
<220> FEATURE:
<223> OTHER INFORMATION: Completely synthetic sequence -continued

```
<400> SEQUENCE: 37

Ala Asn Glu Arg Ala Asp Leu Ile Ala Tyr Leu Lys Gln Ala Thr Ala
1               5                   10                  15

Lys

<210> SEQ ID NO 38
<211> LENGTH: 16
<212> TYPE: PRT
<213> ORGANISM: Artificial Sequence
<220> FEATURE:
<223> OTHER INFORMATION: Completely synthetic sequence

<400> SEQUENCE: 38

Ala Asn Glu Arg Ala Asp Leu Ile Ala Tyr Leu Lys Gln Ala Ser Lys
1               5                   10                  15

<210> SEQ ID NO 39
<211> LENGTH: 6
<212> TYPE: PRT
<213> ORGANISM: Artificial Sequence
<220> FEATURE:
<223> OTHER INFORMATION: Completely synthetic sequence

<400> SEQUENCE: 39

Lys Gln Ala Gly Asp Val
1               5
```

METHODS OF ULTRASOUND TREATMENT USING GAS OR GASEOUS PRECURSOR-FILLED COMPOSITIONS

CROSS-REFERENCE TO RELATED APPLICATIONS

This application is a divisional of U.S. patent application Ser. No. 08/929,847, filed Sep. 15, 1997, now U.S. Pat. No. 6,548,047 which is incorporated herein by reference in its entirety.

FIELD OF THE INVENTION

The present invention describes, among other things, the surprising discovery that gaseous precursor filled compositions are profoundly more effective as acoustically active contrast agents when the compositions are thermally preactivated to temperatures at or above the boiling point of the instilled gaseous precursor prior to their in vivo administration to a patient. Further optimization of contrast enhancement is achieved by administering the gaseous precursor filled compositions to a patient as an infusion. Enhanced effectiveness is also achieved for ultrasound mediated targeting and drug delivery.

BACKGROUND OF THE INVENTION

Previously, gaseous precursor filled contrast agents had limited effectiveness because high doses of gaseous precursor materials were required to be intravascularly injected into a patient to produce contrast enhancement. Even after IV injection into a patient, not all of the gaseous precursor materials converted into stable gaseous vesicles. Gaseous precursor materials that did not convert to a gas were much less effective as a contrast agent. Sonication, agitation and hypobaric activation were developed to activate gaseous precursor filled contrast agents; however, these methods were incompletely effective and ineffective for sustained infusions of the contrast agents.

More effective methods of converting gaseous precursor materials to a gas are necessary to overcome the problems associated with the prior art. The invention is directed to these, as well as other, important ends.

SUMMARY OF THE INVENTION

The present invention describes methods of providing images of regions of a patient comprising heating a composition comprising a gaseous precursor to a temperature at or above the boiling point of the gaseous precursor; administering the composition to the patient; and scanning the patient using diagnostic imaging to obtain visible images of regions of the patient. Preferably, the gaseous precursor is a fluorinated compound. If desired, the composition may be administered to the patient as an infusion. The compositions may comprise a wide variety of additional components, including, for example, one or more of gases, gaseous precursors, liquids, oils, stabilizing materials, diagnostic agents, targeting ligands and/or bioactive agents.

The present invention also describes methods of diagnosing the presence of diseased tissues in a patient comprising heating a composition comprising a gaseous precursor to a temperature at or above the boiling point of the gaseous precursor; administering the composition to the patient; and scanning the patient using diagnostic imaging to obtain visible images of any diseased tissues in the patient. Preferably, the gaseous precursor is a fluorinated compound. If desired, the composition may be administered to the patient as an infusion. The composition may comprise a wide variety of additional components, including, for example, one or more of gases, gaseous precursors, liquids, oils, stabilizing materials, diagnostic agents, targeting ligands and/or bioactive agents.

The present invention also describes methods of delivering bioactive agents to a patient comprising heating a composition comprising a bioactive agent and a gaseous precursor to a temperature at or above the boiling point of the gaseous precursor; and administering the composition to the patient. If desired, the methods may further comprise imaging the patient to monitor the location of the composition and/or conducting ultrasound imaging on the patient to facilitate delivery of the bioactive agents. Preferably, the gaseous precursor is a fluorinated compound. The composition may be administered to the patient as an infusion, if desired. The composition may comprise a wide variety of additional components, including, for example, one or more of gases, gaseous precursors, liquids, oils, stabilizing materials, diagnostic agents, targeting ligands and/or bioactive agents.

These and other aspects of the invention will become more apparent from the following detailed description.

DETAILED DESCRIPTION OF THE INVENTION

As employed above and throughout the disclosure, the following terms, unless otherwise indicated, shall be understood to have the following meanings.

"Lipid" refers to a naturally-occurring, synthetic or semi-synthetic (i.e., modified natural) compound which is generally amphipathic. The lipids typically comprise a hydrophilic component and a hydrophobic component. Exemplary lipids include, for example, fatty acids, neutral fats, fluorinated lipids, phosphatides, oils, fluorinated oils, glycolipids, surface active agents (surfactants and fluorosurfactants), aliphatic alcohols, waxes, terpenes and steroids. The phrase semi-synthetic (or modified natural) denotes a natural compound that has been chemically modified in some fashion.

"Surfactant" refers to a surface active agent, which is a compound that alters surface tension. Surface active agents include, for example, detergents, wetting agents and emulsifiers. "Fluorosurfactant" refers to a surfactant in which at least one hydrogen atom of the surfactant is replaced with a fluorine atom.

"Polymer" or "polymeric" refers to molecules formed from the chemical union of two or more repeating units. Accordingly, included within the term "polymer" may be, for example, dimers, trimers and oligomers. The polymer may be synthetic, naturally-occurring or semisynthetic. In a preferred form, "polymer" refers to molecules which comprise 10 or more repeating units.

"Protein" refers to molecules comprising, and preferably consisting essentially of, α-amino acids in peptide linkages. Included within the term "protein" are globular proteins such as albumins, globulins and histones, and fibrous proteins such as collagens, elastins and keratins. Also included within the term "protein" are "compound proteins," wherein a protein molecule is united with a nonprotein molecule, such as nucleoproteins, mucoproteins, lipoproteins and metalloproteins. The proteins may be naturally-occurring, synthetic or semi-synthetic.

"Amphiphilic moiety" or "amphiphile" refers to a synthetic, semi-synthetic (modified natural) or naturally-occurring compound having a water-soluble, hydrophilic portion and a water-insoluble, hydrophobic portion. Preferred amphiphilic compounds are characterized by a polar head group, for example, a phosphatidylcholine group, and one or more nonpolar, aliphatic chains, for example, palmitoyl groups. "Fluorinated amphiphilic moiety" refers to an amphiphilic compound in which at least one hydrogen atom of the amphiphilic compound is replaced with a fluorine atom. In a preferred form, the fluorinated amphiphilic compounds are polyfluorinated. "Polyfluorinated amphiphilic moiety" refers to amphiphilic compounds which contain two or more fluorine atoms. "Perfluorinated amphiphilic moiety" refers to amphiphilic compounds in which all the hydrogen atoms have been replaced with a fluorine atom. "Amphipathy" refers to the simultaneous attraction and repulsion in a single molecule or ion containing one or more groups having an affinity for the phase or medium in which they are dissolved, emulsified and/or suspended, together with one or more groups that tend to be expelled from the involved phase or medium.

"Vesicle" refers to an entity which is generally characterized by the presence of one or more walls or membranes which form one or more internal voids. Vesicles may be formulated, for example, from a stabilizing material such as a lipid, including the various lipids described herein, a proteinaceous material, including the various proteins described herein, and a polymeric material, including the various polymeric materials described herein. Vesicles may also be formulated from carbohydrates, surfactants, and other stabilizing materials, as desired. The lipids, proteins, polymers, surfactants and/or other vesicle forming stabilizing materials may be natural, synthetic or semi-synthetic. Preferred vesicles are those which comprise walls or membranes formulated from lipids. The walls or membranes may be concentric or otherwise. The stabilizing compounds may be in the form of one or more monolayers or bilayers. In the case of more than one monolayer or bilayer, the monolayers or bilayers may be concentric. Stabilizing compounds may be used to form a unilamellar vesicle (comprised of one monolayer or bilayer), an oligolamellar vesicle (comprised of about two or about three monolayers or bilayers) or a multilamellar vesicle (comprised of more than about three monolayers or bilayers). The walls or membranes of vesicles may be substantially solid (uniform), or they may be porous or semi-porous. The vesicles described herein include such entities commonly referred to as, for example, liposomes, micelles, bubbles, microbubbles, microspheres, lipid-coated bubbles, polymer-coated bubbles, protein-coated bubbles, nanospheres, microballoons, microcapsules, aerogels, clathrate bound vesicles, hexagonal H II phase structures, cochleates and the like. The internal void of the vesicles may be filled with a wide variety of materials including, for example, water, oil, gases, gaseous precursors, liquids, fluorinated liquids, liquid perfluorocarbons, liquid perfluoroethers, and bioactive agents, if desired, and/or other materials. The vesicles may also comprise a targeting ligand, if desired.

"Liposome" refers to a generally spherical or spheroidal cluster or aggregate of amphipathic compounds, including lipid compounds, typically in the form of one or more concentric layers, for example, bilayers. They may also be referred to herein as lipid vesicles. The liposomes may be formulated, for example, from ionic lipids and/or non-ionic lipids. Liposomes formulated from non-ionic lipids may be referred to as niosomes. Liposomes formulated, at least in part, from ionic lipids may be referred to as cochleates.

"Micelle" refers to colloidal entities formulated from lipids. In preferred embodiments, the micelles comprise a monolayer, bilayer, or hexagonal H II phase structure.

"Aerogel" refers to generally spherical or spheroidal entities which are characterized by a plurality of small internal voids. The aerogels may be formulated from synthetic materials (for example, a foam prepared from baking resorcinol and formaldehyde), as well as natural materials, such as carbohydrates (polysaccharides) or proteins.

"Clathrate" refers to a solid, semi-porous or porous particle which may be associated with vesicles. In a preferred form, the clathrates may form a cage-like structure containing cavities which comprise one or more vesicles bound to the clathrate, if desired. A stabilizing material may, if desired, be associated with the clathrate to promote the association of the vesicle with the clathrate. Clathrates may be formulated from, for example, porous apatites, such as calcium hydroxyapatite, and precipitates of polymers and metal ions, such as alginic acid precipitated with calcium salts.

A "fluorinated compound" refers to a compound that contains at least one fluorine atom. More preferably, the fluorinated compound is a "polyfluorinated compound," which refers to a compound that contains at least two fluorine atoms. Even more preferably, the fluorinated compound is "perfluorinated," which means fully fluorinated, such as a compound where all hydrogen atoms have been replaced by fluorine atoms. The fluorinated compound may be in the form of a gas or a liquid (including a gaseous precursor). Preferably, the liquid is a gaseous precursor that can convert to a gas. A variety of fluorinated compounds may be employed in this invention. Where the fluorinated compound is a carbon based compound, the fluorinated compound preferably contains from 1 to about 30 carbon atoms, more preferably 1 to about 24 carbon atoms, even more preferably 1 to about 12 carbon atoms, still even more preferably about 5 to about 12 carbon atoms, and most preferably about 6 to about 10 carbon atoms. Thus, the number of carbon atoms in the fluorinated compound may be 1, 2, 3, 4, 5, 6, 7, 8, 9, 10, 11, 12, 13, 14, 15, 16, 17, 18, 19, 20, 21, 22, 23, 24, carbon atoms, and upwards. Alternatively, the fluorinated compound may be a sulfur or selenium based fluorinated compound, such as sulfur hexafluoride or selenium hexafluoride. The fluorinated compound may also, for example, have carbon atoms interrupted by one or more heteroatoms, such as —O— bonds (as in ether compounds) or have other substituents such as amines. Preferred fluorinated compounds of the present invention are fluorinated organic compounds, more preferably, perfluorocarbons and perfluoroethers.

"Gas filled vesicle" refers to a vesicle having a gas encapsulated therein. "Gaseous precursor filled vesicle" refers to a vesicle having a gaseous precursor encapsulated therein. The vesicles may be minimally, partially, substantially, or completely filled with the gas and/or gaseous precursor. The term "substantially" as used in reference to the gas and/or gaseous precursor filled vesicles means that greater than about 30% of the internal void of the substantially filled vesicles comprises a gas and/or gaseous precursor. Preferably, greater than about 40% of the internal void of the substantially filled vesicles comprises a gas and/or gaseous precursor, with greater than about 50% being more preferred. More preferably, greater than about 60% of the internal void of the substantially filled vesicles comprises a gas and/or gaseous precursor, with greater than about 70% or about 75% being more preferred. Even more preferably, greater than about 80% of the internal void of the substantially filled vesicles comprises a gas and/or gaseous precursor, with greater than about 85% or about 90% being still more preferred. In particularly preferred embodiments, greater than about 95% of the internal void of the vesicles comprises a gas and/or gaseous precursor, with about 100% being especially preferred. Alternatively, the vesicles may contain no or substantially no gas or gaseous precursor.

"Emulsion" refers to a mixture of two or more generally immiscible liquids, and is generally in the form of a colloid. The mixture may be of lipids, for example, which may be homogeneously or heterogeneously dispersed throughout the emulsion. Alternatively, the lipids may be aggregated in the form of, for example, clusters or layers, including monolayers or bilayers.

"Suspension" or "dispersion" refers to a mixture, preferably finely divided, of two or more phases (solid, liquid or gas), such as, for example, liquid in liquid, solid in solid, gas in liquid, and the like which preferably can remain stable for extended periods of time.

"Hexagonal H II phase structure" refers to a generally tubular aggregation of lipids in liquid media, for example, aqueous media, in which the hydrophilic portion(s) of the lipids generally face inwardly in association with an aqueous liquid environment inside the tube. The hydrophobic portion(s) of the lipids generally radiate outwardly and the complex assumes the shape of a hexagonal tube. A plurality of tubes is generally packed together in the hexagonal phase structure.

"Patient" refers to animals, including mammals, preferably humans.

"Region of a patient" refers to a particular area or portion of the patient and in some instances to regions throughout the entire patient. Exemplary of such regions are the pulmonary region, the gastrointestinal region, the cardiovascular region (including myocardial tissue), the renal region as well as other bodily regions, tissues, lymphocytes, receptors, organs and the like, including the vasculature and circulatory system, and as well as diseased tissue, including cancerous tissue. "Region of a patient" includes, for example, regions to be imaged with diagnostic imaging, regions to be treated with a bioactive agent, regions to be targeted for the delivery of a bioactive agent, and regions of elevated temperature. The "region of a patient" is preferably internal, although it may be external. The phrase "vasculature" denotes blood vessels (including arteries, veins and the like). The phrase "gastrointestinal region" includes the region defined by the esophagus, stomach, small and large intestines, and rectum. The phrase "renal region" denotes the region defined by the kidney and the vasculature that leads directly to and from the kidney, and includes the abdominal aorta. "Region to be targeted" or "targeted region" refer to a region of a patient where delivery of a bioactive agent is desired. "Region to be imaged" or "imaging region" denotes a region of a patient where diagnostic imaging is desired.

"Delivery vehicle" or "vehicle" refers to a composition, substance or material that can transport or carry in vivo or in vitro a bioactive agent. Suitable delivery vehicles include, for example, stabilizing materials, vesicles, liposomes, micelles, aerogels, clathrates, gas filled vesicles, gaseous precursor filled vesicles, gas and gaseous precursor filled vesicles, gas and liquid filled vesicles, gaseous precursor and liquid filled vesicles, gas, gaseous precursor and liquid filled vesicles, emulsions, suspensions, dispersions, hexagonal H II phase structures, cochleates and the like.

"Bioactive agent" refers to a substance which may be used in connection with an application that is therapeutic or diagnostic, such as, for example, in methods for diagnosing the presence or absence of a disease in a patient and/or methods for the treatment of a disease in a patient. "Bioactive agent" refers to substances which are capable of exerting a biological effect in vitro and/or in vivo. The bioactive agents may be neutral, positively or negatively charged. Suitable bioactive agents include, for example, prodrugs, diagnostic agents, therapeutic agents, pharmaceutical agents, drugs, oxygen delivery agents, blood substitutes, synthetic organic molecules, proteins, peptides, vitamins, steroids, steroid analogs and genetic material, including nucleosides, nucleotides and polynucleotides.

"Diagnostic agent" refers to any substance which may be used in connection with methods for imaging an internal region of a patient and/or diagnosing the presence or absence of a disease or diseased tissue in a patient. Diagnostic agents include, for example, contrast agents for use in connection with ultrasound imaging, magnetic resonance imaging (MRI), nuclear magnetic resonance (NMR), computed tomography (CT), electron spin resonance (ESR), nuclear medical imaging, optical imaging, elastography, radiofrequency (RF), microwave laser and the like. Diagnostic agents may also include any other agents useful in facilitating diagnosis of a disease or other condition in a patient, whether or not imaging methodology is employed.

"Therapeutic agent," "pharmaceutical agent" or "drug" refers to any therapeutic or prophylactic agent which may be used in the treatment (including the prevention, diagnosis, alleviation, or cure) of a malady, affliction, condition, disease or injury in a patient. Therapeutically useful peptides, polypeptides and polynucleotides may be included within the meaning of the term pharmaceutical or drug.

"Targeting ligand" refers to any material or substance which may promote targeting of tissues and/or receptors in vivo and/or in vitro with the compositions of the present invention. The targeting ligand may be synthetic, semi-synthetic, or naturally-occurring. Materials or substances which may serve as targeting ligands include, for example, proteins, including antibodies, antibody fragments, hormones, hormone analogues, glycoproteins and lectins, peptides, polypeptides, amino acids, sugars, saccharides, including monosaccharides and polysaccharides, carbohydrates, vitamins, steroids, steroid analogs, hormones, cofactors, and genetic material, including nucleosides, nucleotides, nucleotide acid constructs and polynucleotides. A "precursor" to a targeting ligand refers to any material or substance which may be converted to a targeting ligand. Such conversion may involve, for example, anchoring a precursor to a targeting ligand. Exemplary targeting precursor moieties include maleimide groups, disulfide groups, such as ortho-pyridyl disulfide, vinylsulfone groups, azide groups, and α-iodo acetyl groups.

"Genetic material" refers generally to nucleotides and polynucleotides, including deoxyribonucleic acid (DNA) and ribonucleic acid (RNA). The genetic material may be made by synthetic chemical methodology known to one of ordinary skill in the art, or by the use of recombinant technology, or by a combination thereof. The DNA and RNA may optionally comprise unnatural nucleotides and may be single or double stranded. "Genetic material" also refers to sense and anti-sense DNA and RNA, that is, a nucleotide sequence which is complementary to a specific sequence of nucleotides in DNA and/or RNA.

"Stabilizing material" or "stabilizing compound" refers to any material which can improve the stability of compositions containing the gases, gaseous precursors, liquids, targeting ligands and/or other bioactive agents described herein, including, for example, mixtures, suspensions, emulsions, dispersions, vesicles, or the like. Encompassed in the definition of "stabilizing material" are certain of the present bioactive agents. The improved stability involves, for example, the maintenance of a relatively balanced condition, and may be exemplified, for example, by increased resistance of the composition against destruction, decomposition, degradation, and the like. In the case of preferred embodiments involving vesicles filled with gases, gaseous precursors, liquids, targeting ligands and/or bioactive agents, the stabilizing compounds may serve to either form the vesicles or stabilize the vesicles, in either way serving to minimize or substantially (including completely) prevent the escape of gases, gaseous precursors and/or bioactive agents from the vesicles until release is desired. The term "substantially," as used in the context of preventing escape of gases, gaseous precursors and/or bioactive agents from the vesicles, means greater than about 50% is maintained entrapped in the vesicles until release is desired, and preferably greater than about 60%, more preferably greater than about 70%, even more preferably greater than about 80% or about 85%, still even more preferably greater than about 90% is maintained entrapped in the vesicles until release is desired. In particularly preferred embodiments, greater than about 95% of the gases, gaseous precursors and/or bioactive agents are maintained entrapped until release is desired. The gases, gaseous precursors, liquids and/or bioactive agents may also be completely maintained entrapped (i.e., about 100% is maintained entrapped), until release is desired. Exemplary stabilizing materials include, for example, lipids, proteins, polymers, carbohydrates and surfactants. The resulting mixture, suspension, emulsion or the like may comprise walls (i.e., films, membranes and the like) around the bioactive agent, gases and/or gaseous precursors, or may be substantially devoid of walls or membranes, if desired. The stabilizing may, if desired, form droplets. The stabilizing material may also comprise salts and/or sugars. In certain embodiments, the stabilizing materials may be substantially (including completely) cross-linked. The stabilizing material may be neutral, positively or negatively charged.

"Droplet" refers to a spherical or spheroidal entity which may be substantially liquid or which may comprise liquid and solid, solid and gas, liquid and gas, or liquid, solid and gas. Solid materials within a droplet may be, for example, particles, polymers, lipids, proteins, or surfactants.

"Cross-link," "cross-linked" and "cross-linking" generally refer to the linking of two or more stabilizing materials, including lipid, protein, polymer, carbohydrate, surfactant stabilizing materials and/or bioactive agents, by one ore more bridges. The bridges may be composed of one or more elements, groups, or compounds, and generally serve to join an atom from a first stabilizing material molecule to an atom of a second stabilizing material molecule. The cross-link bridges may involve covalent and/or non-covalent associations. Any of a variety of elements, groups, and/or compounds may form the bridges in the cross-links, and the stabilizing materials may be cross-linked naturally or through synthetic means. For example, cross-linking may occur in nature in material formulated from peptide chains which are joined by disulfide bonds of cystine residues, as in keratins, insulins and other proteins. Alternatively, cross-linking may be effected by suitable chemical modification, such as, for example, by combining a compound, such as a stabilizing material, and a chemical substance that may serve as a cross-linking agent, which may cause to react by, for example, exposure to heat, high-energy radiation, ultrasonic radiation and the like. Examples include cross-linking by sulfur to form disulfide linkages, cross-linking using organic peroxides, cross-linking of unsaturated materials by means of high-energy radiation, cross-linking with dimethylol carbamate, and the like. If desired, the stabilizing compounds and/or bioactive agents may be substantially cross-linked. The term "substantially" means that greater than about 50% of the stabilizing compounds contain cross-linking bridges. If desired, greater than about 60%, 70%, 80%, 90%, 95% or even 100% of the stabilizing compounds contain such cross-linking bridges. Alternatively, the stabilizing materials may be non-cross-linked, i.e., such that greater than about 50% of the stabilizing compounds are devoid of cross-linking bridges, and if desired, greater than about 60%, 70%, 80%, 90%, 95% or even 100% of the stabilizing compounds are devoid of cross-linking bridges.

"Vesicle stability" refers to the ability of vesicles to retain the gas, gaseous precursor and/or other bioactive agents entrapped therein after being exposed, for about one minute, to a pressure of about 100 millimeters (mm) of mercury (Hg). Vesicle stability is measured in percent (%), this being the fraction of the amount of gas which is originally entrapped in the vesicle and which is retained after release of the pressure. Vesicle stability also includes "vesicle resilience" which is the ability of a vesicle to return to its original size after release of the pressure.

"Covalent association" refers to an intermolecular association or bond which involves the sharing of electrons in the bonding orbitals of two atoms.

"Non-covalent association" refers to intermolecular interaction among two or more separate molecules which does not involve a covalent bond. Intermolecular interaction is dependent upon a variety of factors, including, for example, the polarity of the involved molecules, and the charge (positive or negative), if any, of the involved molecules. Non-covalent associations include ionic interactions, electrostatic interactions, dipole-dipole interactions, van der Waal's forces, and combinations thereof.

"Ionic interaction" or "electrostatic interaction" refers to intermolecular interaction among two or more molecules, each of which is positively or negatively charged. Thus, for example, "ionic interaction" or "electrostatic interaction" refers to the attraction between a first, positively charged molecule and a second, negatively charged molecule. Ionic or electrostatic interactions include, for example, the attraction between a negatively charged bioactive agent, for example, genetic material, and a positively charged lipid, for example, a cationic lipid, such as lauryltrimethylammonium bromide.

"Dipole-dipole interaction" refers generally to the attraction which can occur among two or more polar molecules. Thus, "dipole-dipole interaction" refers to the attraction of the uncharged, partial positive end of a first polar molecule, commonly designated as $\delta^+$, to the uncharged, partial negative end of a second polar molecule, commonly designated as $\delta^-$. Dipole-dipole interactions are exemplified by the attraction between the electropositive head group, for example, the choline head group, of phosphatidylcholine and an electronegative atom, for example, a heteroatom, such as oxygen, nitrogen or sulphur, which is present in a stabilizing material, such as a polysaccharide. "Dipole-dipole interaction" also refers to intermolecular hydrogen bonding in which a hydrogen atom serves as a bridge between electronegative atoms on separate molecules and in which a hydrogen atom is held to a first molecule by a covalent bond and to a second molecule by electrostatic forces.

"Van der Waal's forces" refers to the attractive forces between non-polar molecules that are accounted for by quantum mechanics. Van der Waal's forces are generally associated with momentary dipole moments which are induced by neighboring molecules and which involve changes in electron distribution.

"Hydrogen bond" refers to an attractive force, or bridge, which may occur between a hydrogen atom which is bonded covalently to an electronegative atom, for example, oxygen, sulfur, or nitrogen, and another electronegative atom. The hydrogen bond may occur between a hydrogen atom in a first molecule and an electronegative atom in a second molecule (intermolecular hydrogen bonding). Also, the hydrogen bond may occur between a hydrogen atom and an electronegative atom which are both contained in a single molecule (intramolecular hydrogen bonding).

"Hydrophilic interaction" refers to molecules or portions of molecules which may substantially bind with, absorb and/or dissolve in water. This may result in swelling and/or the formation of reversible gels.

"Hydrophobic interaction" refers to molecules or portions of molecules which do not substantially bind with, absorb and/or dissolve in water.

"Biocompatible" refers to materials which are generally not injurious to biological functions and which will not result in any degree of unacceptable toxicity, including allergenic responses and disease states. Generally, the compositions described herein that are administered to patients are biocompatible.

"In combination with" refers to the incorporation of bioactive agents and/or targeting ligands in a stabilizing composition of the present invention, including emulsions, suspensions and vesicles. The bioactive agent and/or targeting ligand can be combined with the stabilizing compositions in any of a variety of ways. For example, the bioactive agent and/or targeting ligand may be associated covalently and/or non-covalently with the compounds or stabilizing materials. In the case of vesicles, the bioactive agent may be entrapped within the internal void of the vesicle. The bioactive agent and/or targeting ligand may also be integrated within the layer(s) or wall(s) of the vesicle, for example, by being interspersed among stabilizing materials which form or are contained within the vesicle layer(s) or wall(s). In addition, the bioactive agent and/or targeting ligand may be located on the surface of a vesicle or non-vesicular stabilizing material. The bioactive agent and/or targeting ligand may be concurrently entrapped within the internal void of the vesicle and/or integrated within the layer(s) or wall(s) of the vesicles and/or located on the surface of a vesicle or non-vesicular stabilizing material. Preferably, the targeting ligand is located on the surface of a vesicle or non-vesicular stabilizing material. In any case, the bioactive agent and/or targeting ligand may interact chemically with the walls of the vesicles, including, for example, the inner and/or outer surfaces of the vesicle and may remain substantially adhered thereto. Such interaction may take the form of, for example, non-covalent association or bonding, ionic interactions, electrostatic interactions, dipole-dipole interactions, hydrogen bonding, van der Waal's forces, covalent association or bonding, cross-linking or any other interaction, as will be apparent to one skilled in the art in view of the present disclosure. In some embodiments, the interaction may result in the stabilization of the vesicle. The bioactive agent and/or targeting ligand may also interact with the inner or outer surface of the vesicle or the non-vesicular stabilizing material in a limited manner. Such limited interaction would permit migration of the bioactive agent and/or targeting ligand, for example, from the surface of a first vesicle to the surface of a second vesicle, or from the surface of a first non-vesicular stabilizing material to a second non-vesicular stabilizing material. Alternatively, such limited interaction may permit migration of the bioactive agent and/or targeting ligand, for example, from within the walls of a vesicle and/or non-vesicular stabilizing material to the surface of a vesicle and/or non-vesicular stabilizing material, and vice versa, or from inside a vesicle or non-vesicular stabilizing material to within the walls of a vesicle or non-vesicular stabilizing material and vice versa.

"Tissue" refers generally to specialized cells which may perform a particular function. The term "tissue" may refer to an individual cell or a plurality or aggregate of cells, for example, membranes, blood or organs. The term "tissue" also includes reference to an abnormal cell or a plurality of abnormal cells. Exemplary tissues include myocardial tissue, including myocardial cells and cardiomyocites, membranous tissues, including endothelium and epithelium, laminae, connective tissue, including interstitial tissue, and tumors.

"Intracellular" or "intracellularly" refers to the area within the plasma membrane of a cell, including the protoplasm, cytoplasm and/or nucleoplasm. "Intracellular delivery" refers to the delivery of a bioactive agent and/or targeting ligand into the area within the plasma membrane of a cell. "Cell" refers to any one of the minute protoplasmic masses which make up organized tissue, comprising a mass of protoplasm surrounded by a membrane, including nucleated and unnucleated cells and organelles. "Receptor" refers to a molecular structure within a cell or on the surface of a cell which is generally characterized by the selective binding of a specific substance. Exemplary receptors include cell-surface receptors for peptide hormones, neurotransmitters, antigens, complement fragments, immunoglobulins and cytoplasmic receptors.

"Alkyl" refers to linear, branched or cyclic hydrocarbon groups. Preferably, the alkyl is a linear or branched hydrocarbon group, more preferably a linear hydrocarbon group. Linear and branched alkyl groups include, for example, methyl, ethyl, n-propyl, i-propyl, n-butyl, t-butyl, n-pentyl, hexyl, heptyl, octyl, nonyl, and decyl groups. Cyclic hydrocarbon groups (cycloalkyl groups) include, for example, cyclopentyl, cyclohexyl and cycloheptyl groups. "Fluoroalkyl" refers to an alkyl which is substituted with one or more fluorine atoms, including, for example, fluoroalkyl groups of the formula $CF_3(CF_2)_n(CH_2)_m$—, wherein each of m and n is independently an integer from 0 to about 22. Exemplary fluoroalkyl groups include perfluoromethyl, perfluoroethyl, perfluoropropyl, perfluorobutyl, perfluorocyclobutyl, perfluoropentyl, perfluorohexyl, perfluoroheptyl, perfluorooctyl, perfluorononyl, perfluorodecyl, perfluoroundecyl and perfluorododecyl.

"Acyl" refers to an alkyl-CO— group wherein alkyl is as previously described. Preferred acyl groups comprise alkyl of 1 to about 30 carbon atoms. Exemplary acyl groups include acetyl, propanoyl, 2-methylpropanoyl, butanoyl and palmitoyl. "Fluoroacyl" refers to an acyl group that is substituted with one or more fluorine atoms, up to and including perfluorinated acyl groups.

"Aryl" refers to an aromatic carbocyclic radical containing about 6 to about 10 carbon atoms. The aryl group may be optionally substituted with one or more aryl group substituents which may be the same or different, where "aryl group substituent" includes alkyl, alkenyl, alkynyl, aryl, aralkyl, hydroxy, alkoxy, aryloxy, aralkoxy, carboxy, aroyl, halo, nitro, trihalomethyl, cyano, alkoxycarbonyl, aryloxycarbonyl, aralkoxycarbonyl, acyloxy, acylamino, aroylamino, carbamoyl, alkylcarbamoyl, dialkylcarbamoyl, arylthio, alkylthio, alkylene and —NRR', where R and R' are each independently hydrogen, alkyl, aryl and aralkyl. Exemplary aryl groups include substituted or unsubstituted phenyl and substituted or unsubstituted naphthyl.

"Alkylaryl" refers to alkyl-aryl-groups (e.g., $CH_3$—$(C_6H_4)$—) and aryl-alkyl-groups (e.g., $(C_6H_5)$—$CH_2$—) where aryl and alkyl are as previously described. Exemplary alkylaryl groups include benzyl, phenylethyl and naphthylmethyl. "Fluoroalkylaryl" refers to an alkylaryl group that is substituted with one or more fluorine atoms, up to and including perfluorinated alkylaryl groups.

"Alkylene" refers to a straight or branched bivalent aliphatic hydrocarbon group having from 1 to about 30 carbon atoms. The alkylene group may be straight, branched or cyclic. The alkylene group may be also optionally unsaturated and/or substituted with one or more "alkyl group substituents," including halogen atoms, such as fluorine atoms. There may be optionally inserted along the alkylene group one or more oxygen, sulphur or substituted or unsubstituted nitrogen atoms, wherein the nitrogen substituent is alkyl as previously described. Exemplary alkylene groups include methylene (—$CH_2$—), ethylene (—$CH_2CH_2$—), propylene (—$(CH_2)_3$—), cyclohexylene (—$C_6HRO$—), —CH=CH—CH=CH—, —CH=CH—$CH_2$—, —$(CF_2)_n$$(CH_2)_m$—, where n is an integer from about 1 to about 22 and m is an integer from 0 to about 22, —$(CH_2)_n$—N(R)—$(CH_2)_m$—, wherein each of m and n is independently an integer from 0 to about 30 and R is hydrogen or alkyl, methylenedioxy (—O—$CH_2$—O—) and ethylenedioxy (—O—$(CH_2)_2$—O—). It is preferred that the alkylene group has about 2 to about 3 carbon atoms.

The present invention is based on the surprising discovery that thermally preactivating gaseous precursor filled compositions prior to in vivo administration of the compositions to a patient profoundly enhances the acoustic activity of the compositions when diagnostic imaging, such as ultrasound, is applied. It is unexpected that thermally preactivating gaseous precursor filled compositions would enhance the acoustic activity of the compositions, in part, because normal body temperatures (e.g., about 37° C.) are often greater than the boiling points of many of the gaseous precursors used in the compositions. Yet the usefulness of such compositions is significantly enhanced with thermal preactivation. The methods of the present invention are particularly useful when the compositions are administered as an infusion. Such infusion enhances the lifetime of acoustic activity of the compositions.

Although not intending to be bound by any theory of operation, for applications in which the ultimate purpose for administration of the compositions is the delivery of bioactive agents, thermally preactivating the gaseous precursor filled compositions may increase the efficacy of ultrasound-induced rupture or cavitation, which facilitates release of the bioactive agent in a desired region of the patient. When the composition further comprises a targeting moiety, such as a targeting ligand, thermal preactivation allows more effective imaging of the acoustically active composition at the in vivo site of binding as a means for monitoring the efficacy of targeted drug release. The thermally preactivated compositions have a wide variety of uses including, for example, diagnostic imaging, targeted therapeutic administration and gene delivery.

Thermal preactivation changes liquid gaseous precursors in the compositions into gases prior to their in vivo administration to a patient. Generally, the gaseous precursor filled compositions are thermally preactivated by being heated to a temperature at or above the boiling point of the gaseous precursor, preferably to a temperature above the boiling point of the gaseous precursor, prior to in vivo administration of the compositions to a patient. Preferably the compositions are heated to a temperature that is at least about 1° C. above the boiling point of the gaseous precursor, more preferably the temperature is at least about 2° C. or about 3° C. above the boiling point of the gaseous precursor, even more preferably the temperature is at least about 4° C., about 5° C. or about 6° C. about the boiling point of the gaseous precursor. Alternatively, the compositions may be heated to a temperature that is at least about 7° C., about 8° C., about 9° C., about 10° C., about 15° C., about 20° C. or about 25° C. or more above the boiling point of the gaseous precursor. In other words, the gaseous precursor filled compositions may be thermally preactivated by being heated to a temperature at or above the boiling point of the gaseous precursor, preferably by being heated to a temperature that is at least about 1° C. to about 25° C., more preferably about 1° C. to about 20° C., even more preferably about 1° C. to about 15° C., above the boiling point of the gaseous precursor, prior to in vivo administration of the compositions to a patient. In preferred embodiments, the gaseous precursors have a boiling point up to about 40° C., more preferably from about 37° C. to less than about 40° C.

Thermal preactivation of gaseous precursor filled compositions also means that the compositions are heated to a temperature where substantially all of the liquid gaseous precursor in the composition is converted to a gas prior to in vivo administration of the composition to a patient. In this context, "substantially" means that at least about 25% of the liquid gaseous precursor is converted to a gas, preferably about 50% or about 60%, more preferably about 70%, about 80% or about 85%, even more preferably about 90% or about 95%, still more preferably about 99%, most preferably about 100% of the liquid gaseous precursor in the composition is converted to a gas prior to in vivo administration of the composition to a patient.

For activation, the gaseous precursor filled compositions may be heated via a syringe or jacketed power injector with a heating blanket, a fluid heating jacket, an immersion heater, an ultrasonic pressure wave generating device, a mechanical agitation device, light (e.g., UV or IR), sonication, microwave or by any other means that induces heating, as will be apparent to one skilled in the art, prior to administration to a patient.

The gaseous precursor filled compositions that are thermally preactivated may be in a vesicular or non-vesicular form, preferably a vesicular form. The compositions that are thermally preactivated preferably comprise a stabilizing material, as described herein. Preferably the stabilizing material is a lipid, a polymer, a protein, a carbohydrate or a surfactant. The gaseous precursor filled compositions of the present invention may be in the form of, for example, vesicles, microspheres, liposomes, micelles, aerogels, clathrates, cochleates, hexagonal H II phase structures, emulsions, suspensions, dispersions and the like. The gaseous precursor filled compositions of the present invention may also be referred to as contrast agents, delivery vehicles and the like. As one skilled in the art will recognize in view of the present disclosure, after the gaseous precursor filled compositions are thermally preactivated, the compositions will then be gas filled compositions.

A wide variety of lipids may be used as stabilizing materials and vesicles in the present invention. The lipids may be of either natural, synthetic or semi-synthetic origin, including for example, fatty acids, fluorinated lipids, neutral fats, phosphatides, oils, fluorinated oils, glycolipids, surface active agents (surfactants and fluorosurfactants), aliphatic alcohols, waxes, terpenes and steroids. Suitable lipids which may be used to prepare the stabilizing materials of the present invention include, for example, fatty acids, lysolipids, fluorinated lipids, phosphocholines, such as those associated with platelet activation factors (PAF) (Avanti Polar Lipids, Alabaster, Ala.), including 1-alkyl-2-acetoyl-sn-glycero 3-phosphocholines, and 1-alkyl-2-hydroxy-sn-glycero 3-phosphocholines, which target blood clots; phosphatidylcholine with both saturated and unsaturated lipids, including dioleoylphosphatidylcholine; dimyristoylphosphatidylcholine; dipentadecanoylphosphatidylcholine; dilauroylphosphatidylcholine; dipalmitoylphosphatidylcholine (DPPC); distearoylphosphatidylcholine (DSPC); and diarachidonylphosphatidylcholine (DAPC); phosphatidylethanolamines, such as dioleoylphosphatidylethanolamine, dipalmitoylphosphatidylethanolamine (DPPE) and distearoylphosphatidylethanolamine (DSPE); phosphatidylserine; phosphatidylglycerols, including distearoylphosphatidylglycerol (DSPG); phosphatidylinositol; sphingolipids such as sphingomyelin; glycolipids such as ganglioside GM1 and GM2; glucolipids; sulfatides; glycosphingolipids; phosphatidic acids, such as dipalmitoylphosphatidic acid (DPPA) and distearoylphosphatidic acid (DSPA); palmitic acid; stearic acid; arachidonic acid; oleic acid; lipids bearing polymers, such as chitin, hyaluronic acid, polyvinylpyrrolidone or polyethylene glycol (PEG), also referred to herein as "pegylated lipids" with preferred lipid bearing polymers including DPPE-PEG (DPPE-PEG), which refers to the lipid DPPE having a PEG polymer attached thereto, including, for example, DPPE-PEG5000, which refers to DPPE having attached thereto a PEG polymer having a mean average molecular weight of about 5000; lipids bearing sulfonated mono-, di-, oligo- or polysaccharides; cholesterol, cholesterol sulfate and cholesterol hemisuccinate; tocopherol hemisuccinate; lipids with ether and ester-linked fatty acids; polymerized lipids (a wide variety of which are well known in the art); diacetyl phosphate; dicetyl phosphate; stearylaamine; cardiolipin; phospholipids with short chain fatty acids of about 6 to about 8 carbons in length; synthetic phospholipids with asymmetric acyl chains, such as, for example, one acyl chain of about 6 carbons and another acyl chain of about 12 carbons; ceramides; non-ionic liposomes including niosomes such as polyoxyalkylene (e.g., polyoxyethylene) fatty acid esters, polyoxyalkylene (e.g., polyoxyethylene) fatty alcohols, polyoxyalkylene (e.g., polyoxyethylene) fatty alcohol ethers, polyoxyalkylene (e.g., polyoxyethylene) sorbitan fatty acid esters (such as, for example, the class of compounds referred to as TWEEN®, including, for example, TWEEN® 20, TWEEN® 40 and TWEEN® 80, commercially available from ICI Americas, Inc., Wilmington, Del.), glycerol polyethylene glycol oxystearate, glycerol polyethylene glycol ricinoleate, alkyloxylated (e.g., ethoxylated) soybean sterols, alkyloxylated (e.g., ethoxylated) castor oil, polyoxyethylene-polyoxypropylene polymers, and polyoxy-alkylene (e.g., polyoxyethylene) fatty acid stearates; sterol aliphatic acid esters including cholesterol sulfate, cholesterol butyrate, cholesterol isobutyrate, cholesterol palmitate, cholesterol stearate, lanosterol acetate, ergosterol palmitate, and phytosterol n-butyrate; sterol esters of sugar acids including cholesterol glucuronide, lanosterol glucuronide, 7-dehydrocholesterol glucuronide, ergosterol glucuronide, cholesterol gluconate, lanosterol gluconate, and ergosterol gluconate; esters of sugar acids and alcohols including lauryl glucuronide, stearoyl glucuronide, myristoyl glucuronide, lauryl gluconate, myristoyl gluconate, and stearoyl gluconate; esters of sugars and aliphatic acids including sucrose laurate, fructose laurate, sucrose palmitate, sucrose stearate, glucuronic acid, gluconic acid and polyuronic acid; saponins including sarsasapogenin, smilagenin, hederagenin, oleanolic acid, and digitoxigenin; glycerol dilaurate, glycerol trilaurate, glycerol dipalmitate, glycerol and glycerol esters including glycerol tripalmitate, glycerol distearate, glycerol tristearate, glycerol dimyristate, glycerol trimyristate; long chain alcohols including n-decyl alcohol, lauryl alcohol, myristyl alcohol, cetyl alcohol, and n-octadecyl alcohol; 6-(5-cholesten-3β-yloxy)-1-thio-β-D-galactopyranoside; digalactosyldiglyceride; 6-(5-cholesten-3β-yloxy)hexyl-6-amino-6-deoxy-1-thio-β-D-galactopyranoside; 6-(5-cholesten-3β-yloxy)hexyl-6-amino-6-deoxyl-1-thio-α-D-mannopyranoside; 12-(((7'-diethylaminocoumarin-3-yl)carbonyl)methylamino)octadecanoic acid; N-[12-(((7'-diethylaminocoumarin-3-yl)carbonyl)methylamino)octadecanoyl]-2-aminopalmitic acid; cholesteryl(4'-trimethylammonio)butanoate; N-succinyldioleoylphosphatidylethanolamine; 1,2-dioleoyl-sn-glycerol; 1,2-dipalmitoyl-sn-3-succinylglycerol; 1,3-dipalmitoyl-2-succinylglycerol; 1-hexadecyl-2-palmitoylglycerophosphoethanolamine and palmitoylhomocysteine, and/or any combinations thereof. In preferred embodiments, the stabilizing materials comprise phospholipids, including one or more of DPPC, DPPE, DPPA, DSPC, DSPE, DSPG and DAPC.

Examples of polymerized lipids include unsaturated lipophilic chains such as alkenyl or alkynyl, containing up to about 50 carbon atoms; phospholipids such as phosphoglycerides and sphingolipids carrying polymerizable groups; and saturated and unsaturated fatty acid derivatives with hydroxyl groups, such as triglycerides of d-12-hydroxyoleic acid, including castor oil and ergot oil. Polymerization may be designed to include hydrophilic substituents such as carboxyl or hydroxyl groups, to enhance dispersability so that the backbone residue resulting from biodegradation is water soluble. Suitable polymerizable lipids are also described, for example, by Klaveness et al, U.S. Pat. No. 5,536,490, the disclosure of which is hereby incorporated by reference herein in its entirety.

Suitable fluorinated lipids include, for example, compounds of the formula:

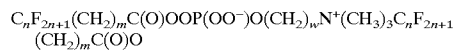

$C_nF_{2n+1}(CH_2)_mC(O)OOP(OO^-)O(CH_2)_wN^+(CH_3)_3C_nF_{2n+1}(CH_2)_mC(O)O$ where m is 0 to about 18, n is 1 to about 12; and w is 1 to about 8. Examples of and methods for the synthesis of these, as well as other fluorinated lipids useful in the present invention, are set forth in U.S. application Ser. No. 08/465,868, filed Jun. 6, 1995, Reiss et al, U.S. Pat. No. 5,344,930, Frezard et al., *Biochem Biophys Acta*, 1192:61–70 (1994), and Frezard et al, *Art. Cells Blood Subs and Immob Biotech.*, 22:1403–1408 (1994), the disclosures of each of which are incorporated herein by reference in their entirety. One specific example of a difluoroacyl glycerylphosphatidylcholine, nonafluorinated diacyl glycerylphosphatidylcholine, is represented by compound A, below. One skilled in the art will appreciate that analogous fluorinated derivatives of other common phospholipids (diacylphosphatidyl serine, diacylphosphatidyl ethanolamine, diacylphosphatidyl glycerol, diacylphosphatidyl glycerol, and the like) as well as fluorinated derivatives of fatty acyl esters and free fatty acids may also function in accordance with the scope of the invention. Additionally lipid based and fluorinated (including perfluorinated) surfactants may be used as stabilizing materials in the present invention.

Exemplary polymerizable and/or fluorinated lipid compounds which may be utilized in the compositions of the present invention are illustrated below.

A

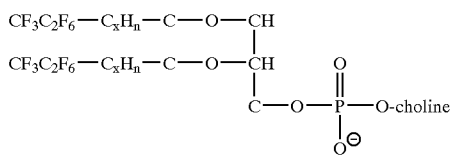

B

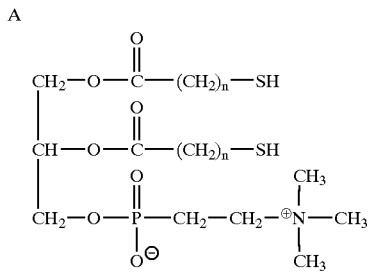

C

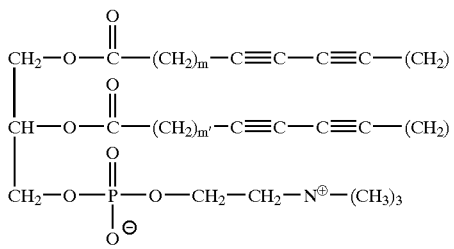

D

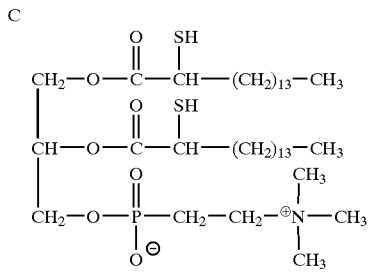

E

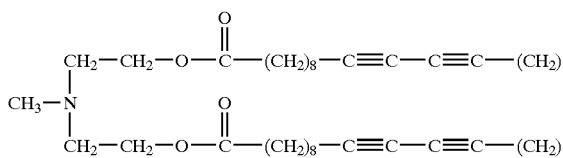

F

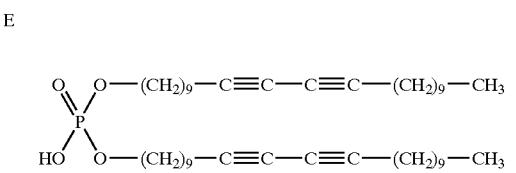

G

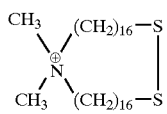

H

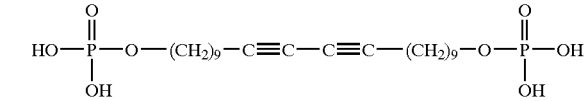

I

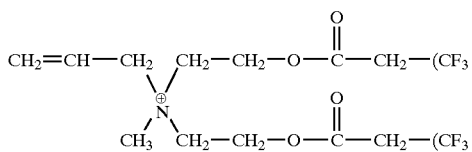

J

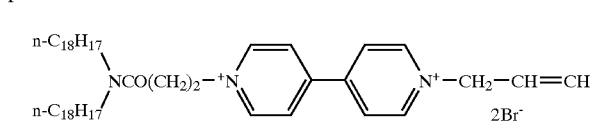

K

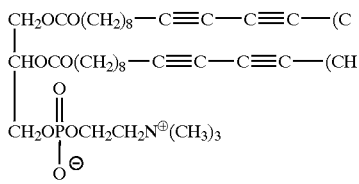

L

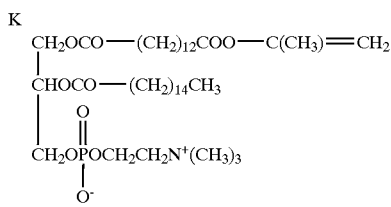

M

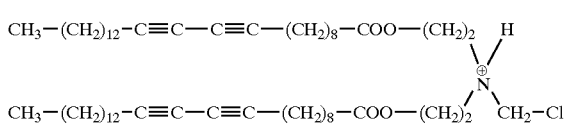

N

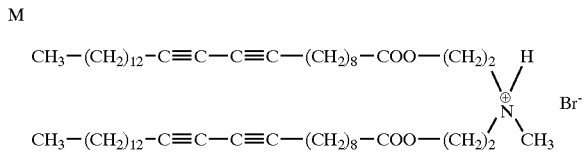

O

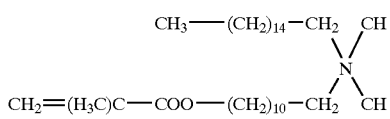

P

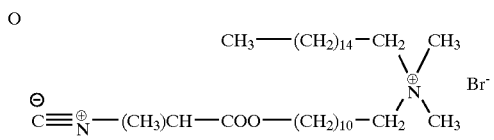

-continued

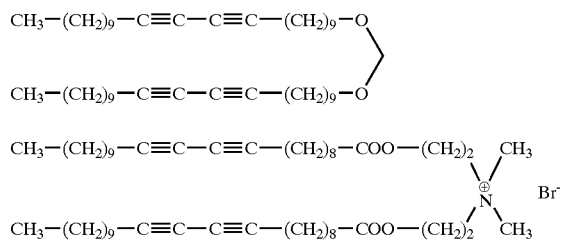
Q

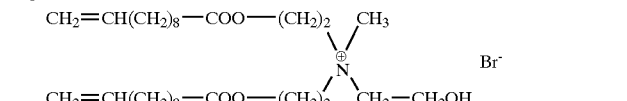
R

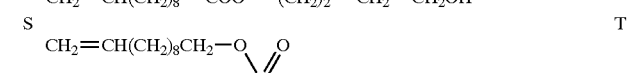

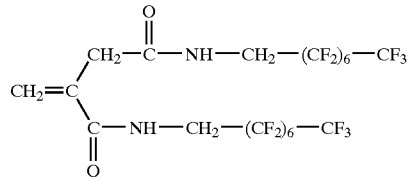
S

T

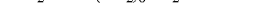

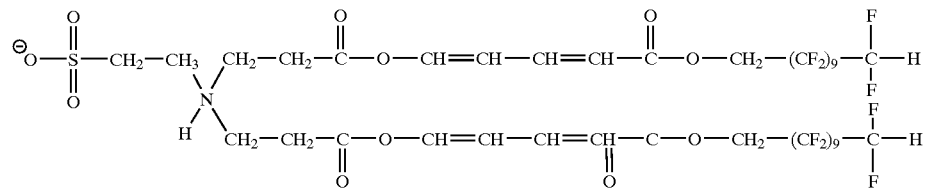
U

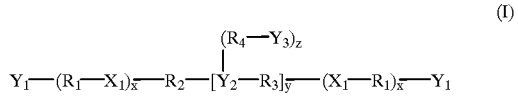
V

In formula A, above, x is an integer from about 8 to about 18, and n is 2x. Most preferably x is 12 and n is 24. In formulas B, C, K and L, above, m, n, m' and n' are, independently, an integer of from about 8 to about 18, preferably about 10 to about 14.

If desired, the stabilizing material may comprise a cationic lipid, such as, for example, N-[1-(2,3-dioleoyloxy) propyl]-N,N,N-trimethylammonium chloride (DOTMA), 1,2-dioleoyloxy-3-(trimethylammonio)propane (DOTAP); and 1,2-dioleoyl-3-(4'-trimethylammonio)butanoyl-sn-glycerol (DOTB). If a cationic lipid is employed in the stabilizing materials, the molar ratio of cationic lipid to non-cationic lipid may be, for example, from about 1:1000 to about 1:100. Preferably, the molar ratio of cationic lipid to non-cationic lipid may be from about 1:2 to about 1:10, with a ratio of from about 1:1 to about 1:2.5 being preferred. Even more preferably, the molar ratio of cationic lipid to non-cationic lipid may be about 1:1.

Suitable cationic lipids include compounds having the formula (I):

$$Y_1-(R_1-X_1)_{\overline{x}}-R_2-[Y_2-R_3]_{\overline{y}}-(X_1-R_1)_{\overline{x}}-Y_1 \quad \overset{(R_4-Y_3)_z}{|}$$

(I)

where each of x, y and z is independently an integer from 0 to about 100; each $X_1$ is independently —O—, —S—, —$NR_5$—, —C(=$X_2$)—, —C(=$X_2$)—N($R_5$)—, —N($R_5$)—C(=$X_2$)—, —C(=$X_2$)—O—, —O—C(=$X_2$)— or —$X_2$—($R_5X_2$)P(=$X_2$)—$X_2$—; each $X_2$ is independently O or S; each $Y_1$ is independently a phosphate residue, N($R_6$)$_a$—, S($R_6$)$_a$—, P($R_6$)$_a$— or —$CO_2R_6$, wherein a is an integer from 1 to 3; each $Y_2$ is independently —N($R_6$)$_b$—, —S($R_6$)$_b$— or —P($R_6$)$_b$—, wherein b is an integer from 0 to 2; each $Y_3$ is independently a phosphate residue, N($R_6$)$_a$—, S($R_6$)$_a$—, P($R_6$)$_a$— or —$CO_2R_6$, wherein a is an integer from 1 to 3; each of $R_1$, $R_2$, $R_3$ and $R_4$ is independently alkylene of 1 to about 20 carbons; each $R_5$ is independently hydrogen or alkyl of 1 to about 10 carbons; and each $R_6$ is independently —[$R_7$—$X_3$]$_c$—$R_8$ or —$R_9$—[$X_4$—$R_{10}$]$_d$—Q, wherein: each of c and d is independently an integer from 0 to about 100; each Q is independently a phosphate residue, —N($R_{11}$)$_q$, —S($R_{11}$)$_q$, —P($R_{11}$)$_q$ or —$CO_2R_6$, wherein q is an integer from 1 to 3; each of $X_3$ and $X_4$ is independently —O—, —S—, —$NR_5$—, —C(=$X_2$)—, —C(=$X_2$)—N($R_5$)—, —N($R_5$)—C(=$X_2$)—, —C(=$X_2$)—O—, —O—C(=$X_2$)—($R_5X_2$)P(=$X_2$)—$X_2$—; each $R_7$ is independently alkylene of 1 to about 20 carbons; each $R_8$ is independently hydrogen or alkyl of 1 to about 60 carbons; each of $R_9$ and $R_{10}$ is independently alkylene of 1 to about 20 carbons; and each $R_{11}$ is independently —[$R_7$—$X_3$]$_c$—$R_8$ or —$R_9$—[$X_4$—$R_{10}$]$_d$—W, wherein: each W is independently a phosphate residue, —N($R_{12}$)$_w$, —S($R_{12}$)$_w$, —P($R_{12}$)$_w$ or —$CO_2R_6$, wherein w is an integer from 1 to 3; and $R_{12}$ is —[$R_7$—$X_3$]$_c$—$R_8$, with the proviso that the compound of formula (I) comprises at least one, and preferably at least two, quaternary salts.

In the above formula (I), each of x, y and z is independently an integer from 0 to about 100. Preferably, each of x, y and z is independently an integer of from 0 to about 50, with integers from 0 to about 20 being more preferred. Even more preferably, each of x, y and z is independently an integer from 0 to about 10, with integers from 0 to about 5 being still more preferred. In certain particularly preferred embodiments, x is 1, y is 2 or 3 and z is 0 or 1.

In the above formula (I), each $X_1$ is independently —O—, —S—, —$NR_5$—, —C(=$X_2$)—, —C(=$X_2$)—N($R_5$)—, —N($R_5$)—C(=$X_2$)—, —C(=$X_2$)—O—, —O—C(=$X_2$)— or —$X_2$—($R_5X_2$)P(=$X_2$)—$X_2$—, Preferably, each $X_1$ is independently —C(=O)—$NR_5$—, —$NR_5$—C(=O)—, —C(=O)—O— or —O—C(=O)—.

Each $X_2$ in the definitions of $X_1$, $X_3$ and $X_4$ above is independently O or S. Preferably, $X_2$ is O.

In the above formula (I), each $Y_1$ is independently a phosphate residue, N($R_6$)$_a$—, S($R_6$)$_a$—, P($R_6$)$_a$— or —CO$_2$R$_6$, wherein a is an integer from 1 to 3. Preferably, each Y$_1$ is independently a phosphate residue, N(R$_6$)$_a$— or —CO$_2$R$_6$, wherein a is 2 or 3. Preferably, a is 3.

Each Y$_2$ in formula (I) above is independently —N(R$_6$)$_b$—, —S(R$_6$)$_b$— or —P(R$_6$)$_b$—, wherein b is an integer from 0 to 2. Preferably, Y$_2$ is —N(R$_6$)$_b$—, wherein b is 1 or 2.

In the above formula (I), each Y$_3$ is independently a phosphate residue, N(R$_6$)$_a$—, S(R$_6$)$_a$—, P(R$_6$)$_a$— or —CO$_2$R$_6$, wherein a is an integer from 1 to 3. Preferably, each Y$_3$ is independently a phosphate residue, N(R$_6$)$_a$— or —CO$_2$R$_6$, wherein a is 2 or 3. Preferably, a is 3.

In the above formula (I), each of R$_1$, R$_2$, R$_3$ and R$_4$ is independently alkylene of 1 to about 20 carbons. Preferably, each of R$_1$, R$_2$, R$_3$ and R$_4$ is independently straight chain alkylene of 1 to about 10 carbons or cycloalkylene of about 4 to about 10 carbons. More preferably, each of R$_1$, R$_2$, R$_3$ and R$_4$ is independently straight chain alkylene of 1 to about 4 carbons or cycloalkylene of about 5 to about 7 carbons. Even more preferably, each of R$_1$, R$_2$, R$_3$ and R$_4$ is independently methylene, ethylene or cyclohexylene.

In the above definitions of X$_1$, X$_3$ and X$_4$, each R$_5$ is independently hydrogen or alkyl of 1 to about 10 carbons. Preferably, each R$_5$ is independently hydrogen or alkyl of 1 to about 4 carbons. More preferably, R$_5$ is hydrogen.

In the above definitions of Y$_1$, Y$_2$ and Y$_3$, each R$_6$ is independently —[R$_7$—X$_3$]$_c$—R$_8$ or —R$_9$—[X$_4$—R$_{10}$]$_d$—Q, wherein each of c and d is independently an integer from 0 to about 100. Preferably, each of c and d is independently an integer from 0 to about 50, with integers from 0 to about 20 being more preferred. Even more preferably, each of c and d is independently an integer from 0 to about 10, with integers from 0 to about 5 being still more preferred. In certain particularly preferred embodiments, c is 0 or 1 and d is 1.

Each Q in R$_6$ above is independently a phosphate residue, —N(R$_{11}$)$_q$, —S(R$_{11}$)$_q$, —P(R$_{11}$)$_q$ or —CO$_2$R$_{11}$, wherein q is an integer from 1 to 3. Preferably, each Q is independently a phosphate residue, —N(R$_{11}$)$_q$ or —CO$_2$R$_{11}$, wherein q is 2 or 3. Preferably, q is 3.

Also in the above definition of R$_6$, each of X$_3$ and X$_4$ is independently —O—, —S—, —NR$_5$—, —C(=X$_2$)—, —C(=X$_2$)—N(R$_5$)—, —N(R$_5$)—C(=X$_2$)—, —C(=X$_2$)—O—, —O—C(=X$_2$)— or —X$_2$—(R$_5$X$_2$)P(=X$_2$)—X$_2$—, wherein each of X$_2$ and R$_5$ is independently as previously described. Preferably, each of X$_3$ and X$_4$ is independently —C(=O)—NR$_5$—, —NR$_5$—C(=O)—, —C(=O)—O— or —O—C(=O)—.

In the definitions of R$_6$, R$_{11}$ and R$_{12}$ above, each R$_7$ is independently alkylene of 1 to about 20 carbons. Preferably, each R$_7$ is independently alkylene of 1 to about 10 carbons, with alkylene of 1 to about 4 carbons being preferred. More preferably, each R$_7$ is independently methylene or ethylene.

Also in the definitions of R$_6$, R$_{11}$ and R$_{12}$ above, each R$_8$ is independently hydrogen or alkyl of 1 to about 60 carbons. Preferably, each R$_8$ is independently hydrogen or alkyl of 1 to about 40 carbons, with hydrogen or alkyl of 1 to about 20 carbons being more preferred. Even more preferred, each R$_8$ is independently hydrogen or alkyl of 1 to about 16 carbons. In certain particularly preferred embodiments, each R$_8$ is independently hydrogen, methyl, dodecyl or hexadecyl.

Each of R$_9$ and R$_{10}$ in the definitions of R$_6$ and R$_{11}$ above is independently alkylene of 1 to about 20 carbons. Preferably, each of R$_9$ and R$_{10}$ is independently alkylene of 1 to about 10 carbons. More preferably, each of R$_9$ and R$_{10}$ is independently alkylene of 1 to about 4 carbons. Even more preferably, each of R$_9$ and R$_{10}$ is independently methylene or ethylene.

Each R$_{11}$ in Q above is independently —[R$_7$—X$_3$]$_c$—R$_8$ or —R$_9$—[X$_4$—R$_{10}$]$_d$—W, wherein each of c, d, X$_3$, X$_4$, R$_7$, R$_8$, R$_9$ and R$_{10}$ is independently as previously described.

Each W in R$_{11}$ above is independently a phosphate residue, —N(R$_{12}$)$_w$, —S(R$_{12}$)$_w$, —P(R$_{12}$)$_w$ or —CO$_2$R$_{12}$, wherein w is an integer from 1 to 3. Preferably, W is a phosphate residue, —N(R$_{12}$)$_w$ or —CO$_2$R$_{12}$, wherein w is 2 or 3. Preferably, w is 3.

In the above definition of W, R$_{12}$ is —[R$_7$—X$_3$]$_c$—R$_8$, wherein each of c, X$_3$, R$_7$ and R$_8$ is independently as previously described.

Another cationic lipid compound which may be incorporated in the compositions of the present invention is a compound of the formula (II):

$$Y_1—R_1—Y_1 \quad (II)$$

where each Y$_1$ is independently a phosphate residue, N(R$_2$)$_a$—, S(R$_2$)$_a$—, P(R$_2$)$_a$— or —CO$_2$R$_2$, wherein a is an integer from 1 to 3; R$_1$ is alkylene of 1 to about 60 carbons containing 0 to about 30 —O—, S—, —NR$_3$— or —X$_2$—(R$_3$X$_2$)P(=X$_2$)—X$_2$— heteroatoms or heteroatom groups; R$_2$ is a residue of the formula —R$_4$—[(X$_1$—R$_5$)$_x$—Y$_2$]$_y$—R$_6$, wherein each of x and y is independently an integer from 0 to about 100; each X$_1$ is independently a direct bond, —O—, —S—, —NR$_3$—, —C(=X$_2$)—, —C(=X$_2$)—N(R$_3$)—, —N(R$_3$)—C(=X$_2$)—, —C(=X$_2$)—O—, —O—C(=X$_2$)— or —X$_2$—(R$_3$X$_2$)P(=X$_2$)—X$_2$—; each or S; each Y$_2$ is independently —S(R$_2$)$_b$—, —N(R$_2$)$_b$— or —P(R$_2$)$_b$—, wherein b is an integer from 0 to 2; each R$_3$ is independently hydrogen or alkyl of 1 to about 10 carbons; each of R$_4$ and R$_5$ is independently a direct bond or alkylene of 1 to about 30 carbons containing 0 to about 15 —O—, —S—, —NR$_3$— or —X$_2$—(R$_3$X$_2$)P(=X$_2$)—X$_2$— heteroatoms or heteroatom groups; and each R$_6$ is independently hydrogen or alkyl of 1 to about 60 carbons containing 0 to about 30—O—, —S—, —NR$_3$— or —X$_2$—(R$_3$X$_2$)P(=X$_2$)—X$_2$— heteroatoms or heteroatom groups; with the proviso that the compound of formula (II) comprises at least one, and preferably at least two, quaternary salts.

In the above formula (II), each Y$_1$ is independently a phosphate residue, N(R$_2$)$_a$—, S(R$_2$)$_a$—, P(R$_2$)$_a$— or —CO$_2$R$_2$, wherein a is an integer from 1 to 3. Preferably, each Y$_1$ is independently a phosphate residue, —N(R$_2$)$_a$— or —CO$_2$R$_2$, wherein a is 2 or 3. Preferably, a is 3.

Also in the above formula (II), R$_1$ is alkylene of 1 to about 60 carbons containing 0 to about 30 —O—, —S—, —NR$_3$— or —X$_2$—(R$_3$X$_2$)P(=X$_2$)—X$_2$— heteroatoms or heteroatom groups. Preferably, R$_1$ is alkylene of 1 to about 40 carbons, with alkylene of 1 to about 20 carbons being preferred. More preferably, R$_1$ is straight chain alkylene of 1 to about 10 carbons or cycloalkylene of about 4 to about 10 carbons. Even more preferably, R$_1$ is straight chain alkylene of 1 to about 4 carbons or cycloalkylene of about 5 to about 7 carbons.

In the above definition of Y$_1$, R$_2$ is a residue of the formula —R$_4$—[(X$_1$—R$_5$)$_x$—Y$_2$]$_y$—R$_6$, wherein each of x and y is independently an integer from 0 to about 100. Preferably, each of x and y is independently an integer from 0 to about 50, with integers from 0 to about 20 being more preferred. Even more preferably, each of x and y is independently an integer from 0 to about 10.

In the above definition of R$_2$, each X$_1$ is independently a direct bond, —O—, —S—, —NR$_3$—, —C(=X$_2$)—, —C(=X$_2$)—N(R$_3$)—, —N(R$_3$)—C(=X$_2$)—, —C(=X$_2$)—O—, —O—C(=X$_2$)— or —X$_2$—(R$_3$X$_2$)P(=X$_2$)—X$_2$—. Preferably, X$_1$ is a direct bond, —C(=X$_2$)—N(R$_3$)—, —N(R$_3$)—C(=X$_2$)—, —C(=X$_2$)—O— or —O—C(=X$_2$)—.

Each $X_2$ in the above definitions of $X_1$, $R_1$, $R_4$, $R_5$ and $R_6$ is independently O or S. Preferably, $X_2$ is O.

Each $Y_2$ in the above definition of $R_2$ is independently —$S(R_2)_b$—, —$N(R_2)_b$— or —$P(R_2)_b$—, wherein b is an integer of from 0 to 2. Preferably, $Y_2$ is —$N(R_2)_b$— and b is 1 or 2.

In the above definitions of $X_1$, $R_1$, $R_4$, $R_5$ and $R_6$, each $R_3$ is independently hydrogen or alkyl of 1 to about 10 carbons. Preferably, each $R_3$ is independently hydrogen or alkyl of 1 to about 4 carbons. More preferably, $R_3$ is hydrogen.

In the above definition of $R_2$, each of $R_4$ and $R_5$ is independently a direct bond or alkylene of 1 to about 30 carbons containing 0 to about 15 —O—, —S—, —$NR_3$— or —$X_2$—$(R_3X_2)P(=X_2)$—$X_2$— heteroatoms or heteroatom groups. Preferably, each of $R_4$ and $R_5$ is independently a direct bond or alkylene of 1 to about 20 carbons. More preferably, each of $R_4$ and $R_5$ is independently a direct bond, straight chain alkylene of 1 to about 10 carbons or cycloalkylene of 4 to about 10 carbons. Even more preferably, each of $R_4$ and $R_5$ is independently a direct bond, straight chain alkylene of 1 to about 4 carbons or cycloalkylene of about 5 to about 7 carbons.

Each $R_6$ in $R_2$ above is independently hydrogen or alkyl of 1 to about 60 carbons containing 0 to about 30 —O—, —S—, —$NR_3$— or —$X_2$—$(R_3X_2)P(=X_2)$—$X_2$— heteroatoms or heteroatom groups. Preferably, each $R_6$ is independently hydrogen or alkyl of 1 to about 40 carbons. More preferably, each $R_6$ is independently hydrogen or alkyl of 1 to about 20 carbons.

The cationic lipid may also be a compound of the formula (III):

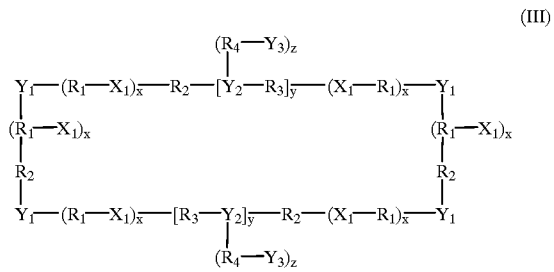

where each of x, y and z is independently an integer from 0 to about 100; each $X_1$ is independently —O—, —S—, —$NR_5$—, —$C(=X_2)$—, —$C(=X_2)$—$N(R_5)$—, —$N(R_5)$—$C(=X_2)$—, —$C(=X_2)$—O—, —O—$C(=X_2)$— or —$X_2$—$(R_5X_2)P(=X_2)$—$X_2$—; each $X_2$ is independently O or S; each $Y_1$ is independently —O—, —$N(R_6)_a$—, —$S(R_6)_a$— or —$P(R_6)_a$—, wherein a is an integer from 0 to 2; each $Y_2$ is independently —$N(R_6)_a$—, —$S(R_6)_a$— or —$P(R_6)_a$—, wherein a is an integer from 0 to 2; each $Y_3$ is independently a phosphate residue, $N(R_6)_b$—, $S(R_6)_b$—, $P(R_6)_b$— or —$CO_2R_6$, wherein b is an integer from 1 to 3; each of $R_1$, $R_2$, $R_3$ and $R_4$ is independently alkylene of 1 to about 20 carbons; each $R_5$ is independently hydrogen or alkyl of 1 to about 10 carbons; and each $R_6$ is independently —$[R_7$—$X_3]_c$—$R_8$ or —$R_9$—$[X_4$—$R_{10}]_d$—Q, where each of c and d is independently an integer from 0 to about 100; each Q is independently a phosphate residue, —$N(R_{11})_q$, —$S(R_{11})_q$, —$P(R_{11})_q$ or —$CO_2R$, , wherein q is an integer from 1 to 3; each of $X_3$ and $X_4$ is independently —O—, —S—, —$NR_5$—, —$C(=X_2)$—, —$C(=X_2)$—$N(R_5)$—, —$N(R_5)$—$C(=X_2)$—, —$C(=X_2)$—O—, —O—C$(=X_2)$— or —$X_2$—$(R_5X_2)P(=X_2)$—$X_2$—; each $R_7$ is independently alkylene of 1 to about 20 carbons; each $R_8$ is independently hydrogen or alkyl of 1 to about 60 carbons; each of $R_9$ and $R_{10}$ is independently alkylene of 1 to about 20 carbons; and each $R_{11}$ is independently —$[R_7$—$X_3]_c$—$R_8$ or —$R_9$—$[X_4$—$R_{10}]_d$—W, where each W is independently a phosphate residue, —$N(R_{12})$, —$S(R_{12})$, —$P(R_{12})$, or —$CO_2R_{12}$, wherein w is an integer from 1 to 3; and $R_{12}$ is —$[R_7$—$X_3]_c$—$R_8$; with the proviso that the compound of formula (III) comprises at least one, and preferably at least two, quaternary salts.

In the above formula (III), each of x, y and z is independently an integer from 0 to about 100. Preferably, each of x, y and z is independently an integer from 0 to about 50, with integers from 0 to about 20 being more preferred. Even more preferably, each of x, y and z is independently an integer from 0 to about 10. Still more preferably, each of x, y and z is independently an integer from 0 to about 5. In certain particularly preferred embodiments, x is 1, y is 2 or 3 and z is 0 or 1.

In the above formula (III), each $X_1$ is independently —O—, —S—, —$NR_5$—, —$C(=X_2)$—, —$C(=X_2)$—$N(R_5)$—, —$N(R_5)$—$C(=X_2)$—, —$C(=X_2)$—O—, —O—C$(=X_2)$— or —$X_2$—Preferably, each $X_1$ is independently —$C(=O)$—$NR_5$—, —$NR_5$—$C(=O)$—, —$C(=O)$—O— or —O—$C(=O)$—.

In the above definitions of $X_1$, $X_3$ and $X_4$, each $X_2$ is independently O or S. Preferably, $X_2$ is O.

Each $Y_1$ in formula (III) above is independently —O—, —$N(R_6)_a$—, —$S(R_6)_a$— or —$P(R_6)_a$—, wherein a is an integer from 0 to 2. Preferably, $Y_1$ is —$N(R_6)_a$—, wherein a is 1 or 2.

Each $Y_2$ in formula (III) above is independently —$N(R_6)_a$—, —$S(R_6)_a$— or —$P(R_6)_a$—, wherein a is an integer from 0 to 2. Preferably, $Y_2$ is —$N(R_6)_a$—.

In the above formula (III), each $Y_3$ is independently a phosphate residue, $N(R_6)_b$—, $S(R_6)_b$—, $P(R_6)_b$— or —$CO_2R_6$, wherein b is an integer from 1 to 3. Preferably, each $Y_3$ is independently a phosphate residue or $N(R_6)_b$—, wherein b is 2 or 3. Preferably, b is 3.

In the above formula (III), each of $R_1$, $R_2$, $R_3$ and $R_4$ is independently alkylene of 1 to about 20 carbons. Preferably, each of $R_1$, $R_2$, $R_3$ and $R_4$ is independently straight chain alkylene of 1 to about 10 carbons or cycloalkylene of about 4 to about 10 carbons. More preferably, each of $R_1$, $R_2$, $R_3$ and $R_4$ is independently straight chain alkylene of 1 to about 4 carbons or cycloalkylene of about 5 to about 7 carbons. Even more preferably, each of $R_1$, $R_2$, $R_3$ and $R_4$ is independently methylene, ethylene or cyclohexylene.

In the above definitions of $X_1$, $X_3$ and $X_4$, each $R_5$ is independently hydrogen or alkyl of 1 to about 10 carbons. Preferably, each $R_5$ is independently hydrogen or alkyl of 1 to about 4 carbons. More preferably, $R_5$ is hydrogen.

In the above definitions of $Y_1$, $Y_2$ and $Y_3$, each $R_6$ is independently —$[R_7$—$X_3]_c$—$R_8$ or —$R_9$—$[X_4$—$R_{10}]_d$—Q, wherein each of c and d is independently an integer from 0 to about 100. Preferably, each of c and d is independently an integer from 0 to about 50, with integers from 0 to about 20 being more preferred. Even more preferably, each of c and d is independently an integer from 0 to about 10, with integers from 0 to about 5 being still more preferred. In certain particularly preferred embodiments, c is 0 or I and d is 1.

Each Q in $R_6$ above is independently a phosphate residue, —$N(R_{11})_q$, —$S(R_{11})_q$, —$P(R_{11})_q$ or —$CO_2R_{11}$, wherein q is an integer from 1 to 3. Preferably, each Q is independently a phosphate residue, —$N(R_{11})_q$ or —$CO_2R_{11}$, wherein q is 2 or 3. Preferably, q is 3.

Also in the above definition of $R_6$, each of $X_3$ and $X_4$ is independently —O—, —S—, —$NR_5$—, —$C(=X_2)$—, —C(=$X_2$)—N($R_5$)—, —N($R_5$)—C(=$X_2$)—, —C(=$X_2$)—O—, —O—C(=$X_2$)— or —$X_2$—($R_5X_2$)P(=$X_2$)—$X_2$—, wherein $X_2$ and $R_5$ are as previously described. Preferably, each of $X_3$ and $X_4$ is independently —C(=O)—$NR_5$—, —$NR_5$—C(=O)—, —C(=O)—O— or —O—C(=O)—.

In the definitions of $R_6$, $R_{11}$ and $R_{12}$ above, each $R_7$ is independently alkylene of 1 to about 20 carbons. Preferably, each $R_7$ is independently alkylene of 1 to about 10 carbons, with alkylene of 1 to about 4 carbons being preferred. More preferably, each $R_7$ is independently methylene or ethylene.

Also in the definitions of $R_6$, $R_{11}$ and $R_{12}$ above, each $R_8$ is independently hydrogen or alkyl of 1 to about 60 carbons. Preferably, each $R_8$ is independently hydrogen or alkyl of 1 to about 40 carbons, with hydrogen or alkyl of 1 to about 20 carbons being more preferred. In certain particularly preferred embodiments, each $R_8$ is independently hydrogen, methyl, dodecyl or hexadecyl.

Each of $R_9$ and $R_{10}$ in the definitions of $R_6$ and $R_{11}$ above is independently alkylene of 1 to about 20 carbons. Preferably, each of $R_9$ and $R_{10}$ is independently alkylene of 1 to about 10 carbons. More preferably, each of $R_9$ and $R_{10}$ is independently alkylene of 1 to about 4 carbons. Even more preferably, each of $R_9$ and $R_{10}$ is independently methylene or ethylene.

In Q above, each $R_{11}$ is independently -[$R_7$—$X_3$]$_c$—$R_8$ or —$R_9$—[$X_4$—$R_{10}$]$_d$W, wherein each of c, d, $X_3$, $X_4$, $R_7$, $R_8$, $R_9$ and $R_{10}$ is independently as previously described.

Each W in $R_{11}$ above is independently a phosphate residue, —N($R_{12}$)$_w$, —S($R_{12}$)$_w$, —P($R_{12}$)$_w$ or —$CO_2R_{12}$, wherein w is an integer from 1 to 3. Preferably, each W is independently a phosphate residue, —N($R_{12}$), or —$CO_2R_{12}$, wherein w is 2 or 3. Preferably, w is 3.

In W above, $R_{12}$ is —[$R_7$—$X_3$]$_c$—$R_8$, wherein each of c, $X_3$, $R_7$ and $R_8$ is independently as previously described.

In the above formulas (I), (II) and (III), it is intended that when any symbol appears more than once in a particular formula or substituent, its meaning in each instance is independent of the other. Also in the above formulas (I), (II) and (III), it is intended that when each of two or more adjacent symbols is defined as being "a direct bond" to provide multiple, adjacent direct bonds, the multiple and adjacent direct bonds devolve into a single direct bond.

The cationic lipid compounds of formula (I), formula (II) and formula (III) which are described above are set forth in U.S. application Ser. No. 08/391,938, filed Feb. 21, 1995, the disclosure of which is hereby incorporated by reference herein in its entirety.

If desired, aggregates or cochleates may be constructed of one or more charged lipids in association with one or more polymer bearing lipids, optionally in association with one or more neutral lipids. The charged lipids may either be anionic (i.e., negatively charged, that is, carrying a net negative charge) or cationic (i.e., positively charged, that is, carrying a net positive charge). Typically, the lipids are aggregated in the presence of a multivalent species, such as a counter ion, opposite in charge to the charged lipid. For the delivery of bioactive agents to selective sites in vivo, aggregates of preferably under 2 μm, more preferably under 0.5 μm, and even more preferably under 200 nm are desired. Most preferably the lipid aggregates are under 200 nm in size and may be as small as 5–10 nm in size.

Exemplary anionic lipids include phosphatidic acid and phosphatidyl glycerol and fatty acid esters thereof, amides of phosphatidyl ethanolamine such as anandamides and methanandamides, phosphatidyl serine, phosphatidyl inositol and fatty acid esters thereof, cardiolipin, phosphatidyl ethylene glycol, acidic lysolipids, sulfolipids, and sulfatides, free fatty acids, both saturated and unsaturated, and negatively charged derivatives thereof. Phosphatidic acid and phosphatidyl glycerol and fatty acid esters thereof are preferred anionic lipids.

When the charged lipid is anionic, a multivalent (divalent, trivalent, etc.) cationic material may be used to form aggregates. Useful cations include, for example, cations derived from alkaline earth metals, such as beryllium ($Be^{+2}$), magnesium ($Mg^{+2}$), calcium ($Ca^{+2}$), strontium ($Sr^{+2}$), and barium ($Ba^{+2}$); amphoteric ions such as aluminum ($Al^{+3}$), gallium ($Ga^{+3}$), germanium ($Ge^{+3}$), tin ($Sn^{+4}$), and lead ($Pb^{+2}$ and $Pb^{+4}$); transition metals such as titanium ($Ti^{+3}$ and $Ti^{+4}$), vanadium ($V^{+2}$ and $V^{+3}$), chromium ($Cr^{+2}$ and $Cr^{+3}$), manganese ($Mn^{+2}$ and $Mn^{+3}$), iron ($Fe^{+2}$ and $Fe^{+3}$), cobalt ($Co^{+2}$ and $Co^{+3}$), nickel ($Ni^{+2}$ and $Ni^{+3}$), copper ($Cu^{+2}$), zinc ($Zn^{+2}$), zirconium ($Zr^{+4}$), niobium ($Nb^{+3}$), molybdenum ($Mo^{+2}$ and $Mo^{+3}$), cadmium ($Cd^{+2}$), indium ($In^{+3}$), tungsten ($W^{+2}$ and $W^{+4}$), osmium ($Os^{+2}$, $Os^{+3}$ and $Os^{+4}$), iridium ($Ir^{+2}$, $Ir^{+3}$ and $Ir^{+4}$), mercury ($Hg^{+2}$), and bismuth ($Bi^{+3}$); and rare earth lanthanides, such as lanthanum ($La^{+3}$), and gadolinium ($Gd^{+3}$). Cations in all of their ordinary valence states will be suitable for forming aggregates and cross-linked lipids. Preferred cations include calcium ($Ca^{+2}$), magnesium ($Mg^{+2}$), and zinc ($Zn^{+2}$) and paramagnetic cations such as manganese (preferably $Mn^{+2}$) and gadolinium ($Gd^{+3}$). Particularly preferred is calcium ($Ca^{+2}$). As will be apparent to one skilled in the art, some of the above ions (notably lead and nickel) may have associated toxicity and thus may be inappropriate for in vivo use.

When the charged lipid is cationic, an anionic material, for example, may be used to form aggregates. Preferably, the anionic material is multivalent, such as, for example, divalent. Examples of useful anionic materials include monatomic and polyatomic anions such as carboxylate ions, sulfide ion, sulfite ions, sulfate ions, oxide ions, nitride ions, carbonate ions, and phosphate ions. Anions of ethylene diamine tetraacetic acid (EDTA), diethylene triamine pentaacetic acid (DTPA), and 1,4,7,10-tetraazocyclododecane-N',N',N",N"-tetraacetic acid (DOTA) may also be used. Further examples of useful anionic materials include anions of polymers and copolymers of acrylic acid, methacrylic acid, other polyacrylates and methacrylates, polymers with pendant $SO_3H$ groups, such as sulfonated polystyrene, and polystyrenes containing carboxylic acid groups.

Examples of cationic lipids include those listed hereinabove. A preferred cationic lipid for formation of aggregates is N-[1-(2,3-dioleoyloxy)propyl]-N,N,N-trimethyl-ammonium chloride ("DOTMA"). Synthetic cationic lipids may also be used. These include common natural lipids derivatized to contain one or more basic functional groups. Examples of lipids which can be so modified include dimethyldioctadecyl-ammonium bromide, sphingolipids, sphingomyelin, lysolipids, glycolipids such as ganglioside GM1, sulfatides, glycosphingolipids, cholesterol and cholesterol esters and salts, N-succinyldioleoylphosphatidylethanolamine, 1,2,-dioleoyl-sn-glycerol, 1,3-dipalmitoyl-2-succinylglycerol, 1,2-dipalmitoyl-sn-3-succinylglycerol, 1-hexadecyl-2-palmitoylglycerophosphatidylethanolamine and palmitoyl-homocystiene.

Specially synthesized cationic lipids also function in the embodiments of the invention, such as those disclosed in U.S. patent application Ser. No. 08/391,938, filed Feb. 21, 1995, the disclosure of which is hereby incorporated herein by reference in its entirety, and include, for example, N,N'-bis(dodecyaminocarbonyl-methylene)-N,N'-bis (β-N,N,N- trimethylammoniumethylami-
nocarbonylmethyleneethylenediamine tetraiodide; N,N''-
bishexadecylaminocarbonylmethylene)-N,N',N''-tris (β-N, N,N-trimethylammoniumethylaminocarbonylmethylenediethylenetriamine hexaiodide; N,N'-Bis (dodecylaminocarbonylmethylene)-N,N''-bis(β-N,N,N-trimethylammoniumethylaminocarbonylmethylene) cyclohexylene-1,4-diamine tetraiodide; 1,1,7,7-tetra-(β-N, N,N,N-tetramethylammoniumethylaminocarbonylmethylene)-3-hexadecylaminocarbonylmethylene-1,3,7-triaazaheptane heptaiodide; and N,N,N'N'-tetraphosphoethanolaminocarbonylmethylene) diethylenetriamine tetraiodide.

In the case of stabilizing materials which contain both cationic and non-cationic lipids, a wide variety of lipids, as described above, may be employed as the non-cationic lipid. Preferably, the non-cationic lipid comprises one or more of DPPC, DPPE and dioleoylphosphatidylethanolamine. In lieu of the cationic lipids listed above, lipids bearing cationic polymers, such as polylysine or polyarginine, as well as alkyl phosphonates, alkyl phosphinates, and alkyl phosphites, may also be used in the stabilizing materials.

Saturated and unsaturated fatty acids which may be employed in the present stabilizing materials include molecules that preferably contain from about 12 carbon atoms to about 22 carbon atoms, in linear or branched form. Hydrocarbon groups consisting of isoprenoid units and/or prenyl groups can be used. Suitable saturated fatty acids include, for example, lauric, myristic, palmitic, and stearic acids. Suitable unsaturated fatty acids include, for example, lauroleic, physeteric, myristoleic, palmitoleic, petroselinic, and oleic acids. Suitable branched fatty acids include, for example, isolauric, isomyristic, isopalmitic, and isostearic acids.

Other useful lipids or combinations thereof apparent to one skilled in the art which are in keeping with the spirit of the present invention are also encompassed by the present invention. For example, carbohydrate-bearing lipids may be employed, as described in U.S. Pat. No. 4,310,505, the disclosure of which is hereby incorporated herein by reference in its entirety.

In addition to stabilizing materials and/or vesicles formulated from lipids, embodiments of the present invention may involve vesicles formulated, in whole or in part, from proteins or derivatives thereof. Suitable proteins for use in the present invention include, for example, albumin, hemoglobin, α-1-antitrypsin, α-fetoprotein, aminotransferases, amylase, C-reactive protein, carcinoembryonic antigen, ceruloplasmin, complement, creatine phosphokinase, ferritin, fibrinogen, fibrin, transpeptidase, gastrin, serum globulins, myoglobin, immunoglobulins, lactate dehydrogenase, lipase, lipoproteins, acid phosphatase, alkaline phosphatase, α-1-serum protein fraction, α-2-serum protein fraction, β-protein fraction, γ-protein fraction and γ-glutamyl transferase. Other stabilizing materials and vesicles formulated from proteins that may be used in the present invention are described, for example, in U.S. Pat. Nos. 4,572,203, 4,718,433, 4,774,958, and 4,957,656, the disclosures of which are hereby incorporated herein by reference in their entirety. Other protein-based stabilizing materials and vesicles, in addition to those described above and in the aforementioned patents, would be apparent to one of ordinary skill in the art in view of the present disclosure.

In addition to stabilizing materials and/or vesicles formulated from lipids and/or proteins, embodiments of the present invention may also involve stabilizing materials or vesicles formulated from polymers which may be of natural, semi-synthetic (modified natural) or synthetic origin. Polymer denotes a compound comprised of two or more repeating monomeric units, and preferably 10 or more repeating monomeric units. Semi-synthetic polymer (or modified natural polymer) denotes a natural polymer that has been chemically modified in some fashion. Suitable natural polymers include naturally occurring polysaccharides, such as, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dermatan, hyaluronic acid, alginic acid, xanthin gum, starch and various other natural homopolymer or heteropolymers, such as those containing one or more of the following aldoses, ketoses, acids or amines: erythrose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Accordingly, suitable polymers include, for example, proteins, such as albumin. Exemplary semi-synthetic polymers include carboxymethylcellulose, hydroxymethylcellulose, hydroxypropylmethylcellulose, methyl-cellulose, and methoxycellulose. Exemplary synthetic polymers suitable for use in the present invention include polyphosphazenes, polyalkylenes (e.g., polyethylene), such as, for example, polyethylene glycol (including, for example, the class of compounds referred to as Pluronics®, commercially available from BASF, Parsippany, N.J.), polyoxyalkylenes (e.g., polyoxyethylene), and polyethylene terephthlate, polypropylenes (such as, for example, polypropylene glycol), polyurethanes (such as, for example, polyvinyl alcohol (PVA), polyvinyl chloride and polyvinylpyrrolidone), polyamides including nylon, polystyrene, polylactic acids, fluorinated hydrocarbon polymers, fluorinated carbon polymers (such as, for example, polytetrafluoro-ethylene), acrylate, methacrylate, and polymethylmethacrylate, and derivatives thereof. Preferred are synthetic polymers or copolymers prepared from monomers, such as acrylic acid, methacrylic acid, ethyleneimine, crotonic acid, acrylamide, ethyl acrylate, methyl methacrylate, 2-hydroxyethyl methacrylate (HEMA), lactic acid, glycolic acid, ε-caprolactone, acrolein, cyanoacrylate, bisphenol A, epichlorhydrin, hydroxyalkyl-acrylates, siloxane, dimethylsiloxane, ethylene oxide, ethylene glycol, hydroxyalkyl-methacrylates, N-substituted acrylamides, N-substituted methacrylamides, N-vinyl-2-pyrrolidone, 2,4-pentadiene-1-ol, vinyl acetate, acrylonitrile, styrene, p-amino-styrene, p-amino-benzyl-styrene, sodium styrene sulfonate, sodium 2-sulfoxyethyl-methacrylate, vinyl pyridine, aminoethyl methacrylates, 2-methacryl-oyloxytrimethylammonium chloride, and polyvinylidene, as well polyfunctional crosslinking monomers such as N,N'-methylenebisacrylamide, ethylene glycol dimethacrylates, 2,2'-(p-phenylenedioxy)diethyl dimethacrylate, divinylbenzene, triallylamine and methylenebis(4-phenylisocyanate), including combinations thereof. Preferable polymers include polyacrylic acid, polyethyleneimine, polymethacrylic acid, polymethylmethacrylate, polysiloxane, polydimethylsiloxane, polylactic acid, poly(ε-caprolactone), epoxy resin, poly(ethylene oxide), poly(ethylene glycol), and polyamide (nylon) polymers. Preferable copolymers include the following: polyvinylidene-polyacrylonitrile, polyvinylidene-polyacrylonitrile-polymethyl-methacrylate, polystyrene-polyacrylonitrile and poly d-l, lactide co-glycolide polymers. A preferred copolymer is polyvinylidene-polyacrylonitrile. Other suitable monomers and polymers will be apparent to one skilled in the art in view of the present disclosure.

Stabilizing materials and vesicles may be prepared from other materials. The materials may be basic and fundamental, and may form the primary basis for creating or establishing the stabilized materials, such as gas and gaseous precursor filled vesicles. For example, surfactants and fluorosurfactants may be basic and fundamental materials for preparing stabilizing materials and vesicles. On the other hand, the materials may be auxiliary, and act as subsidiary or supplementary agents which may enhance the functioning of the basic stabilizing material(s), or contribute some desired property in addition to that afforded by the basic stabilizing material(s).

It is not always possible to determine whether a given material is a basic or an auxiliary agent, since the functioning of the material is determined empirically, for example, by the results produced with respect to producing stabilized materials or vesicles. As an example of how the basic and auxiliary materials may function, it has been observed that the simple combination of a lipid and water or saline when shaken will often give a cloudy solution subsequent to autoclaving for sterilization. Such a cloudy solution may function as a contrast agent, but is aesthetically objectionable and may imply instability in the form of undissolved or undispersed lipid particles. Cloudy solutions may also be undesirable where the undissolved particulate matter has a diameter of greater than about 7 μm, and especially greater than about 10 μm. Manufacturing steps, such as sterile filtration, may also be problematic with solutions which contain undissolved particulate matter. Thus, propylene glycol may be added to remove this cloudiness by facilitating dispersion or dissolution of the lipid particles. Propylene glycol may also function as a wetting agent which can improve vesicle formation and stabilization by increasing the surface tension on the vesicle membrane or skin. It is possible that propylene glycol can also function as an additional layer that may coat the membrane or skin of the vesicle, thus providing additional stabilization. The conventional surfactants described by D'Arrigo, U.S. Pat. Nos. 4,684,479 and 5,215,680, the disclosures of each of which are hereby incorporated by reference herein in their entireties, may be used as basic or auxiliary stabilizing materials in the present invention.

Oils and fluorinated oils are auxiliary and basic stabilizing materials that may be used in the present invention. Suitable oils include, for example, soybean oil, peanut oil, canola oil, olive oil, safflower oil, corn oil, almond oil, cottonseed oil, ethyl oleate, isopropyl myristate, isopropyl palmitate, mineral oil, myristyl alcohol, octyldodecanol, persic oil, sesame oil, squalene, myristyl oleate, cetyl oleate, myristyl palmitate, or any other oil commonly known to be ingestible which is suitable for use as a stabilizing compound in accordance with the teachings herein. The oils described herein may be fluorinated, such as triolein with a fluorine ($F_2$) gas. A "fluorinated oil" refers to an oil in which at least one hydrogen atom of the oil is replaced with a fluorine atom. Preferably, at least two or more of the hydrogen atoms in the oil are replaced with fluorine atoms. Other suitable fluorinated oils are described, for example, in U.S. Pat. No. 5,344,930, the disclosure of which is hereby incorporated by reference herein in its entirety. Optionally, any of the oils described herein may be used in a composition with a bioactive agent or added to the stabilizing material in order to dissolve the bioactive agent.

Additional auxiliary and basic stabilizing materials which may be used in the present invention are described, for example, in U.S. application Ser. No. 08/444,754, filed May 15, 1995, the disclosure of which is hereby incorporated herein by reference in its entirety.

Compounds used to make mixed micelle systems may be used as basic or auxiliary stabilizing materials, and include, for example, lauryltrimethylammonium bromide (dodecyl-), cetyltrimethylammonium bromide (hexadecyl-), myristyltrimethylammonium bromide (tetradecyl-), alkyldimethyl-benzylammonium chloride (where alkyl is $C_{12}$, $C_{14}$ or $C_{16}$), benzyldimethyldodecylammonium bromide/chloride, benzyldimethyl hexadecyl-ammonium bromide/chloride, benzyldimethyl tetradecylammonium bromide/chloride, cetyldimethylethylammonium bromide/chloride, or cetylpyridinium bromide/chloride.

It may be possible to enhance the stability of stabilizing materials or vesicles by incorporating in the stabilizing materials and/or vesicles at least a minor amount, for example, about 1 to about 10 mole percent, based on the total amount of lipid employed, of a negatively charged lipid. Suitable negatively charged lipids include, for example, phosphatidylserine, phosphatidic acid, and fatty acids. Without intending to be bound by any theory or theories of operation, it is contemplated that such negatively charged lipids provide added stability by counteracting the tendency of vesicles to rupture by fusing together. Thus, the negatively charged lipids may act to establish a uniform negatively charged layer on the outer surface of the vesicle, which will be repulsed by a similarly charged outer layer on other vesicles which are proximate thereto. In this way, the vesicles may be less prone to come into touching proximity with each other, which may lead to a rupture of the membrane or skin of the respective vesicles and consolidation of the contacting vesicles into a single, larger vesicle. A continuation of this process of consolidation will, of course, lead to significant degradation of the vesicles.

The lipids used, especially in connection with vesicles, are preferably flexible. This means, in the context of the present invention, that the vesicles can alter their shape, for example, to pass through an opening having a diameter that is smaller than the diameter of the vesicle.

In preferred embodiments, the stabilizing material and/or vesicle composition may contain, in whole or in part, a fluorinated (including perfluorinated) compound. Suitable fluorinated compounds include, for example, fluorinated surfactants, including alkyl surfactants, and fluorinated amphiphilic compounds. A wide variety of such compounds may be employed, including, for example, the class of compounds which are commercially available as ZONYL® fluorosurfactants (the DuPont Company, Wilmington, Del.), including the ZONYL® phosphate salts (e.g., $[F(CF_2CF_2)_{3-8}CH_2CH_2O]_{1,2}P(O)(O^-NH_4^+)_{2,1}$) which have terminal phosphate groups and ZONYL® sulfate salts which have terminal sulfate groups (e.g., $F(CF_2CF_2)_{3-8}CH_2CH_2SCH_2CH_2N^+(CH_3)_3{}^-OSO_2OCH_3$). Suitable ZONYL® surfactants also include, for example, ZONYL® fluorosurfactants identified as Telomer B, including Telomer B fluorosurfactants which are pegylated (i.e., have at least one polyethylene glycol group attached thereto), also known as PEG-Telomer B, available from the DuPont Company. Other suitable fluorosurfactants are described in U.S. Pat. Nos. 5,276,146, 5,344,930 and 5,562,893, and U.S. application Ser. No. 08/465,868, filed Jun. 6, 1995, the disclosures of each of which are hereby incorporated by reference herein in their entirety.

Other suitable fluorinated surfactants and fluorinated lipid compounds for use as the stabilizing material in the present invention are described in U.S. application Ser. No. 08/887, 215, filed Jul. 2, 1997, the disclosure of which is hereby incorporated by reference herein in its entirety. Suitable fluorinated surfactants and fluorinated lipids include the compounds of formulas (IV), (V), (VI), (VII), (VIIa), (VIII), (VIIIa), (IX), and (X).

The stabilizing material may be a fluorinated fatty acyl derivative, such as, for example, that of formula (IV):

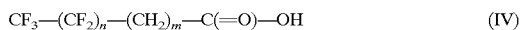

$$CF_3-(CF_2)_n-(CH_2)_m-C(=O)-OH \qquad (IV)$$

where n is an integer of from about 7 to about 13, preferably from about 9 to about 11; and m is an integer of from 1 to about 4, preferably 1 to about 2.

The stabilizing material may be a PEG Telomer compound of formula (V):

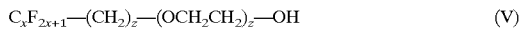

$$C_xF_{2x+1}-(CH_2)_z-(OCH_2CH_2)_z-OH \qquad (V)$$

where x is an integer of from about 6 to about 12, preferably from about 8 to about 10, more preferably about 9; and z is an integer of from about 8 to about 20; preferably from about 8 to about 16; still more preferably from about 8 to about 12; even more preferably about 8 to about 10; most preferably about 9.

The stabilizing material may be a fluorinated carbohydrate derivative, such as, for example, that of formula (VI):

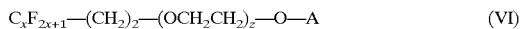

$$C_xF_{2x+1}-(CH_2)_2-(OCH_2CH_2)_z-O-A \qquad (VI)$$

where x is an integer of from about 6 to about 12; preferably from about 8 to about 10; more preferably 9; z is an integer of from about 8 to about 20; preferably from about 8 to about 16; more preferably from about 8 to about 12; still more preferably from about 8 to about 10; most preferably about 9; and A is a monosaccharide or a disaccharide. Suitable monosaccharides and disaccharides include, for example, allose, altrose, glucose, dextrose, mannose, glycerose, gulose, idose, galactose, talose, fructose, psicose, sorbose, rhamnose, tagatose, ribose, arabinose, xylose, lyxose, ribulose, xylulose, erythrose, threose, erythrulose, fucose, sucrose, lactose, maltose, isomaltose, trehalose, cellobiose and the like. Preferably, the monosaccharide or disaccharide is glucose, dextrose, fructose, mannose, galactose, glucosamine, galactosamine, maltose, sucrose or lactose.

The stabilizing material may also be a fluorinated lipophilic derivative, such as, for example, that of formula (VII), which includes the compounds described in U.S. application Ser. No. 08/465,868, filed Jun. 6, 1995, the disclosure of which is hereby incorporated by reference herein in its entirety:

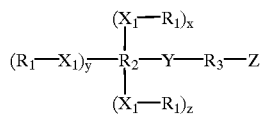

(VII)

where each of x, y and z is independently 0 or 1; each $X_1$ is independently $-O-$, $-S-$, $-SO-$, $-SO_2-$, $-NR_4-$, $-C(=X_2)-$, $-C(=X_2)-O-$, $-O-C(=X_2)-$, $-C(=X_2)-NR_4-$ or $-NR_4-C(=X_2)-$; $X_2$ is O or S; T is a direct bond or $-X_3-M(=O)(ORS)_q-O-$, where q is 1 or 2; $X_3$ is a direct bond or $-O-$; M is P or S; Z is hydrogen, the residue of a hydrophilic polymer, a saccharide residue or $-N(R_6)_r$ where r is 2 or 3; each $R_1$ is independently an alkyl group of 1 to about 30 carbon atoms or a fluorinated alkyl group of 1 to about 30 carbon atoms; $R_2$ is a direct bond or an alkylene linking group of 1 to about 10 carbon atoms; $R_3$ is a direct bond or an alkylene diradical of 1 to about 10 carbon atoms; each of $R_4$ and $R_5$ is independently hydrogen or an alkyl group of 1 to about 8 carbon atoms; and each $R_6$ is independently hydrogen, an alkyl group of 1 to about 8 carbon atoms or a residue of a hydrophilic polymer; provided that at least one of x, y and z is 1, at least one of $R_1$ is a fluorinated alkyl group of 1 to about 30 carbon atoms; provided that when $R_2$ is a direct bond, two of x, y and z are each 0.

In formula (VII), each of x, y and z is independently 0 or 1, provided that at least one of x, y and z is 1. In some embodiments, two of x, y and z are each 0. In other embodiments, one of x, y and z is 0 or 1 and the other two of x, y and z are each 1, with one of x, y and z being 0 and the other two of x, y and z being 1 being more preferred. In other embodiments, each of x, y and z is 1.

Each $X_1$ is independently $-O-$, $-S-$, $-SO-$, $-SO_2-$, $-NR_4-$, $-C(=X_2)-$, $-C(=X_2)-O-$, $-O-C(=X_2)-$, $-C(=X_2)-NR_4-$ or $-NR_4-C(=X_2)-$. Preferably, each $X_1$ is independent $-O-$, $-S-$, $-C(=X_2)-$, $-C(=X_2)-O-$, $-O-C(=X_2)-$, $-C(=X_2)-NR_4-$ or $-NR_4-C(=X_2)-$. More preferably, each $X_1$ is independently $-C(=X_2)-O-$ or $-O-C(=X_2)-$, most preferably $-C(=X_2)-O-$.

Each $X_2$ is O or S, preferably O.

Y is a direct bond or $-X_3-M(=O)(OR_5)_q-O-$, where q is 1 or 2. Preferably, Y is $-X_3-M(=O)(OR_5)_q-O-$. M is P or S, preferably P. $X_3$ is a direct bond or $-O-$, preferably, a direct bond.

Z is hydrogen atom, the residue of a hydrophilic polymer, a saccharide residue or $-N(R_6)_r$, where r is 2 or 3. In preferred embodiments, Z is $-N(R_6)_r$.

Each $R_1$ is independently an alkyl group of 1 to about 30 carbon atoms or a fluorinated alkyl group of 1 to about 30 carbon atoms, provided that at least one of $R_1$ is a fluorinated alkyl group of 1 to about 30 carbon atoms. Thus, when only one of x, y and z is 1, $R_1$ is necessarily a fluorinated alkyl group of 1 to about 30 carbon atoms. In preferred embodiments, where one or none of x, y and z is 0, and preferably where one of x, y and z is 0 and the other two of x, y and z are each 1, at least one of $R_1$ is an alkyl group of 1 to about 30 carbon atoms and at least one of $R_1$ is a fluorinated alkyl group of 1 to about 30 carbon atoms. In other embodiments, each $R_1$ is independently a fluorinated alkyl group of 1 to about 30 carbon atoms. When a fluorinated alkyl group of 1 to about 30 carbon atoms, $R_1$ is preferably a polyfluorinated alkyl group of 1 to about 30 carbon atoms, with a perfluorinated alkyl group of 1 to about 30 carbon atoms being more preferred. When a fluorinated alkyl group of 1 to about 30 carbon atoms, $R_1$ is preferably $C_nF_{2n+1}$—$(CH_2)_m$—, where n is 1 to about 16, preferably about 9 to about 14, and m is 0 to about 18, preferably 1 to about 10, more preferably 1 to about 4.

$R_2$ is a direct bond or an alkylene linking group of 1 to about 10 carbon atoms, provided that when $R_2$ is a direct bond, two of x, y and z are each 0. Preferably, $R_2$ is a direct bond or an alkylene linking group of 1 to about 4 carbon atoms. More preferably, $R_2$ is an alkylene linking group of about 3 carbons. Even more preferably, $R_2$ is —$CH_2$—$CH_2$—$CH_2$—.

$R_3$ is a direct bond or an alkylene diradical of 1 to about 10 carbons. Preferably, $R_3$ is a direct bond or an alkylene diradical of 1 to about 4 carbon atoms. More preferably, $R_3$ is an alkylene diradical of about 2 carbon atoms. Even more preferably, $R_3$ is —$CH_2CH_2$—.

Each of $R_4$ and $R_5$ is independently a hydrogen atom or an alkyl group of 1 to about 8 carbon atoms, preferably of 1 to about 4 carbon atoms. More preferably, each of $R_4$ and $R_5$ is a hydrogen atom.

$R_6$ is a hydrogen atom, an alkyl group of 1 to about 8 carbon atoms or a residue of a hydrophilic polymer. Preferably, $R_6$ is a hydrogen atom or an alkyl group of 1 to about 4 carbon atoms. More preferably, $R_6$ is a hydrogen atom or a methyl group, with a methyl group being even more preferred.

When any symbol appears more than once in a particular formula or substituent, such as, for example, in formula (VII), its meaning in each instance is independent of the other, unless otherwise indicated. This independence of meaning is subject to any of the stated provisos. Also, when each of two or more adjacent symbols is defined as being "a direct bond" to provide multiple, adjacent direct bonds, the multiple and adjacent direct bonds devolve into a single direct bond.

Z and $R_6$ in the definition of Z in formula (VII), can be the residue of a hydrophilic polymer. Exemplary polymers from which Z and/or $R_6$ can be derived include polymers in which the repeating units contain one or more hydroxy groups (polyhydroxy polymers), including, for example, poly(vinyl alcohol); polymers in which the repeating units contain one or more amino groups (polyamine polymers), including, for example, peptides, polypeptides, proteins and lipoproteins, such as albumin and natural lipoproteins; polymers in which the repeating units contain one or more carboxy groups (polycarboxy polymers), including, for example, carboxymethylcellulose, alginic acid and salts thereof, such as sodium and calcium alginate, glycosaminoglycans and salts thereof, including salts of hyaluronic acid, phosphorylated and sulfonated derivatives of carbohydrates, genetic material, such as interleukin-2 and interferon, and phosphorothioate oligomers; and polymers in which the repeating units contain one or more saccharide moieties (polysaccharide polymers), including, for example, carbohydrates. The molecular weight of the polymers from which Z and/or $R_6$ are derived may vary, and is generally about 50 to about 5,000,000, with polymers having a molecular weight of about 100 to about 50,000 being preferred. More preferred polymers have a molecular weight of about 150 to about 10,000, with molecular weights of 200 to about 8,000 being even more preferred.

Preferred polymers from which Z and/or $R_6$ are derived include, for example, poly(ethylene glycol) (PEG), poly(vinylpyrrolidine), polyoxomers, polysorbate and poly(vinyl alcohol), with PEG polymers being particularly preferred. Preferred among the PEG polymers are PEG polymers having a molecular weight of from about 100 to about 10,000. More preferably, the PEG polymers have a molecular weight of from about 200 to about 8,000, with PEG 2,000, PEG 5,000 and PEG 8,000, which have molecular weights of 2,000, 5,000 and 8,000, respectively, being even more preferred. Other suitable hydrophilic polymers, in addition to those exemplified above, will be readily apparent to one skilled in the art based on the present disclosure. Generally, polymers from which Z and/or $R_6$ are derived include polymers that can be incorporated in the fluorinated amphiphilic compounds via alkylation or acylation reactions.

As with the various polymers exemplified above, the polymeric residues can contain functional groups in addition, for example, to those typically involved in linking the polymeric residues to the fluorinated amphiphilic compounds. Such functionalities include, for example, carboxyl, amine, hydroxy and thiol groups. These functional groups on the polymeric residues can be further reacted, if desired, with materials which are generally reactive with such functional groups and which can assist in targeting specific tissues in the body including, for example, diseased tissue. Exemplary materials which can be reacted with the additional functional groups include, for example, proteins, including antibodies, carbohydrates, peptides, glycopeptides, glycolipids, lectins and nucleosides.

In addition to residues of hydrophilic polymers, Z in formula (VII) can be a saccharide residue. Exemplary saccharides from which Z can be derived include, for example, monosaccharides or sugar alcohols, such as erythrose, threose, ribose, arabinose, xylose, lyxose, fructose, sorbitol, mannitol and sedoheptulose, with preferred monosaccharides being fructose, mannose, xylose, arabinose, mannitol and sorbitol; and disaccharides, such as lactose, sucrose, maltose and cellobiose. Other saccharides include, for example, inositol and ganglioside head groups. Other suitable saccharides, in addition to those exemplified above, will be readily apparent to one skilled in the art based on the present disclosure. Generally, saccharides from which Z is derived include saccharides that can be incorporated in the fluorinated amphiphilic compounds via alkylation or acylation reactions.

Preferred fluorinated compounds that are within the scope of formula (VII) are the fluorinated compounds of the formula (VIIa):

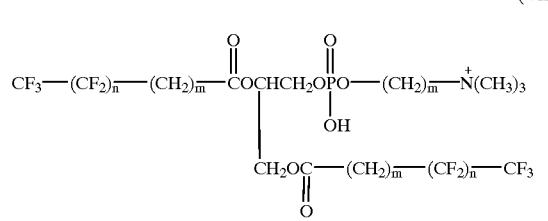

(VIIa)

where n is an integer of from about 7 to about 13, preferably from about 9 to about 11; and m is an integer of from about 1 to about 4, preferably 1 to about 2.

The stabilizing material may also be a fluorinated amphiphilic moiety of formula (VIII):

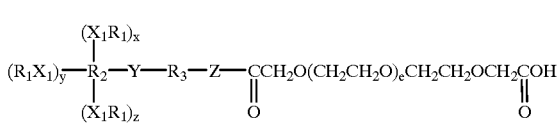

(VIII)

where $R_1$, $R_2$, $R_3$, $X_1$, Y, Z, x, y and z are as defined in formula (VII), including the preferred embodiments thereof; and where e is an integer of from 1 to about 30, preferably about 3 to about 20, more preferably about 4 to about 16, still more preferably about 4 to about 12, most preferably about 7 to about 9.

In a more preferred embodiment, the compound of formula (VIII) may be a compound of the formula (VIIIa):

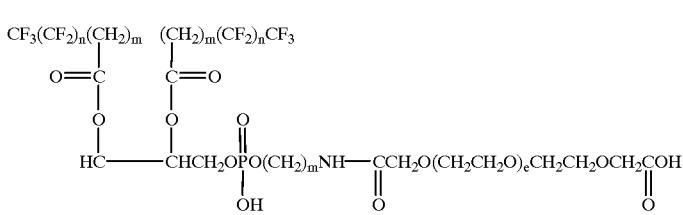

(VIIIa)

where n and m are as defined above in formula (VIIa) and where e is as defined above in formula (VIII).

The stabilizing material may also be a fluorinated fatty acyl derivative, such as, for example, that of formula (IX):

(IX)

Still further, the stabilizing material may be a fluorinated lipophilic derivative, such as, for example, that of formula (X):

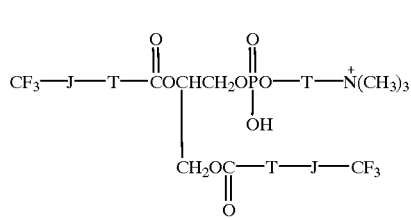

(X)

In the above formulas (IX) and (X), J is (—(C=C)$_{p1}$—(CF$_2$)$_{p2}$—(C=C)$_{p3}$—(CF$_2$)$_{p4}$—(C=C)$_{p5}$—(CF$_2$)$_{p6}$—(C=C)$_{p7}$—(CF$_2$)$_{p8}$—(C=C)$_{p9}$—(CF$_2$)$_{p10}$—(C=C)$_{p11}$—(CF$_2$)$_{p12}$—(C=C)$_{p13}$—,) where p1, p2, p3, p4, p5, p6, p7, p8, p9, p10, p11, p12 and p13 are independently an integer of 0, 1 or 2; provided that the sum of (p1+p2+p3+p4+p5+p6+p7+p8+p9+p10+p11+p12+p13) is an integer of from about 7 to about 13, and provided that at least one of p2, p4, p6, p8, p10 or p12 is an integer of at least 1; and where T is (—(C=C)$_{t1}$—(CH$_2$)$_{t2}$—(C=C)$_{t3}$—(CH$_2$)$_{t4}$—), where t1, t2, t3, and t4 are independently an integer of 0, 1 or 2; provided that the sum of (t1+t2+t3+t4) is an integer of from 1 to about 4.

Other suitable fluorinated compounds that may be used as stabilizing materials and/or vesicles are described in U.S. Pat. No. 5,562,893, the disclosure of which is hereby incorporated herein by reference in its entirety. For example, synthetic organic monomeric repeating units may be used to form polymers suitable as stabilizing materials, including hydroxyacids, lactones, lactides, glycolides, acryl containing compounds, aminotriazol, orthoesters, anyhdrides, ester imides, imides, acetals, urethanes, vinyl alcohols, enolketones, and organosiloxanes.

The method of introducing fluorine into any of these materials is known in the art. For example, the introduction of perfluoro-t-butyl moieties is described in U.S. Pat. No. 5,234,680, the disclosure of which is hereby incorporated by reference herein in its entirety. These methods generally involve the reaction of perfluoroalkyl carbanions with host molecules as follows: $(CF_3)_3C^- + R-X \rightarrow (CF_3)_3C-R$, where R is a host molecule and X is a good leaving group, such as bromine, chlorine, iodine or a sulfonato group. After adding a leaving group to the foregoing stabilizing material using methods well known in the art, perfluoro-t-butyl moieties can then be easily introduced to these derivatized stabilizing materials as described above. Additional methods are known in the art for the introduction of trifluoromethyl groups into various organic compounds. For example, trifluoromethyl groups may be introduced by nucleophilic perfluoroalkylation using perfluoroalkyl-trialkylsilanes.

Fluorine can be introduced into any of the aforementioned stabilizing materials or vesicles either in their monomeric or polymeric form. Preferably, fluorine moieties are introduced into monomers, such as fatty acids, amino acids or polymerizable synthetic organic compounds, which are then polymerized for subsequent use as stabilizing materials and/or vesicles.

The introduction of fluorine into stabilizing materials and/or vesicles may also be accomplished by forming vesicles in the presence of a perfluorocarbon gas. For example, when vesicles are formed from proteins, such as human serum albumin in the presence of a perfluorocarbon gas, such as perfluoropropane, using mechanical cavitation, fluorine from the gas phase becomes bound to the protein vesicles during formation. The presence of fluorine in the vesicles and/or stabilizing materials can be detected by NMR of vesicle debris which has been purified from disrupted vesicles. Fluorine can also be introduced into stabilizing materials and/or vesicles using other methods, such as sonication, spray-drying or emulsification techniques.

Another way in which fluorine can be introduced into the stabilizing material and/or vesicle is by using a fluorine-containing reactive compound. The term "reactive compound" refers to compounds which are capable of interacting with the stabilizing material and/or vesicle in such a manner that fluorine moieties become covalently attached to the stabilizing material and/or vesicle. When the stabilizing material is a protein, preferred reactive compounds are either alkyl esters or acyl halides which are capable of reacting with the protein's amino groups to form an amide linkage via an acylation reaction. The reactive compound can be introduced at any stage during vesicle formation, but is preferably added to the gas phase prior to vesicle formation. For example, when vesicles are to be made using mechanical or ultrasound cavitation techniques, the reactive compound can be added to the gas phase by bubbling the gas to be used in the formation of the vesicles (starting gas) through a solution of the reactive compound into the gas phase. The resultant gas mixture, which now contains the starting gas and the reactive compound, is then used to form vesicles. The vesicles are preferably formed by sonication of human serum albumin in the presence of a gas mixture, as described in U.S. Pat. No. 4,957,656, the disclosure of which is hereby incorporated herein by reference in its entirety.

Suitable fluorine containing alkyl esters and acyl halides for use as stabilizing materials and/or vesicle forming materials in the present invention include, for example, diethyl hexafluoroglutarate, diethyl tetrafluorosuccinate, methyl heptafluorobutyrate, ethyl heptafluorobutyrate, ethyl pentafluoropropionate, methyl pentafluoropropionate, ethyl perfluorooctanoate, methyl perfluorooctanoate, nonafluoropentanoyl chloride, perfluoropropionyl chloride, hexafluoroglutaryl chloride and heptafluorobutyryl chloride.

Other fluorine containing reactive compounds can also be synthesized and used as the stabilizing materials and/or vesicle forming materials in the present invention, including, for example, aldehydes, isocyanates, isothiocyanates, epoxides, sulfonyl halides, anhydrides, acid halides and alkyl sulfonates, which contain perfluorocarbon moieties, including $-CF_3$, $-C_2F_5$, $-C_3F_4$ and $-C(CF_3)_3$. These reactive compounds can be used to introduce fluorine moieties into any of the aforementioned stabilizing materials by choosing a combination which is appropriate to achieve covalent attachment of the fluorine moiety.

Sufficient fluorine should be introduced to decrease the permeability of the vesicle to the aqueous environment. This will result in a slower rate of gas exchange with the aqueous environment which is evidenced by enhanced pressure resistance. Although the specific amount of fluorine necessary to stabilize the vesicle will depend on the components of the vesicle and the gas contained therein, after introduction of fluorine the vesicle will preferably contain 0.01 to 20% by weight, and more preferably about 1 to 10% by weight fluorine.

It may be desirable to use a fluorinated liquid, especially a liquid perfluorocarbon or a liquid perfluoroether, which are liquids at the temperature of use, including, for example, the in vivo temperature of the human body, to assist or enhance the stability of the gaseous precursor filled compositions of the present invention. Suitable liquid perfluorocarbons and liquid perfluoroethers include, for example, perfluoroheptane, perfluorooctane, perfluorononane, perfluorodecane, perfluorodecalin, perfluorododecalin, perfluorooctyliodide, perfluorooctylbromide, perfluorotripropylamine, perfluorotributylamine, perfluorobutylethyl ether, bis(perfluoroisopropyl) ether and bis (perfluoropropyl) ether. Among these, perfluorooctylbromide is preferred. Although not intending to be bound by any theory of operation, in the case of vesicle compositions, the fluorinated liquid compound may be situated at the interface between the gas and the membrane or wall surface of the vesicle. Thus, an additional stabilizing layer of fluorinated liquid compound may be formed on the internal surface of the stabilizing composition, and this fluorinated liquid compound layer may also prevent the gas from diffusing through the vesicle membrane.

Preferred surfactants which may also be used in the compositions of the present invention are partially fluorinated phosphocholine surfactants. In these preferred fluorinated surfactants, the dual alkyl compounds may be fluorinated at the terminal alkyl chains and the proximal carbons may be hydrogenated. These fluorinated phosphocholine surfactants may be used for making the stabilizing materials and/or vesicles of the present invention.

Preferred embodiments of the present invention involve vesicles which comprise three components: (1) a neutral lipid, for example, a nonionic or zwitterionic lipid, (2) a negatively charged lipid, and (3) a lipid bearing a stabilizing material, for example, a hydrophilic polymer. Preferably, the amount of the negatively charged lipid will be greater than about 1 mole percent of the total lipid present, and the amount of lipid bearing a hydrophilic polymer will be greater than about 1 mole percent of the total lipid present. Exemplary and preferred negatively charged lipids include phosphatidic acids. The lipid bearing a hydrophilic polymer will desirably be a lipid covalently linked to the polymer, and the polymer will preferably have a weight average molecular weight of from about 400 to about 100,000. Suitable hydrophilic polymers are preferably selected from the group consisting of polyethylene glycol (PEG), polypropylene glycol, polyvinyl alcohol, and polyvinyl pyrrolidone and copolymers thereof, with PEG polymers being preferred. Preferably, the PEG polymer has a molecular weight of from about 1000 to about 7500, with molecular weights of from about 2000 to about 5000 being more preferred. The PEG or other polymer may be bound to the lipid, for example, DPPE, through a covalent bond, such as an amide, carbamate or amine linkage. In addition, the PEG or other polymer may be linked to a targeting ligand, or other phospholipids, with a covalent bond including, for example, amide, ester, ether, thioester, thioamide or disulfide bonds. Where the hydrophilic polymer is PEG, a lipid bearing such a polymer will be said to be "pegylated." In preferred form, the lipid bearing a hydrophilic polymer may be DPPE-PEG, including, for example, DPPE-PEG5000, which refers to DPPE having a polyethylene glycol polymer of a mean weight average molecular weight of about 5000 attached thereto (DPPE-PEG5000). Another suitable pegylated lipid is distearoylphosphatidylethanol-amine-polyethylene glycol 5000 (DSPE-PEG5000).

In preferred embodiments of the present invention, the lipid compositions may include about 77.5 mole % DPPC, 12.5 mole % of DPPA, and 10 mole % of DPPE-PEG5000. Also preferred are compositions which comprise about 80 to about 90 mole % DPPC, about 5 to about 15 mole % DPPA and about 5 to about 15 mole % DPPE-PEG5000. Especially preferred are compositions which comprise DPPC, DPPA and DPPE-PEG5000 in a mole % ratio of 82:10:8, respectively. DPPC is substantially neutral, since the phosphatidyl portion is negatively charged and the choline portion is positively charged. Consequently, DPPA, which is negatively charged, may be added to enhance stabilization in accordance with the mechanism described above. DPPE-PEG provides a pegylated material bound to the lipid membrane or skin of the vesicle by the DPPE moiety, with the PEG moiety free to surround the vesicle membrane or skin, and thereby form a physical barrier to various enzymatic and other endogenous agents in the body whose function is to degrade such foreign materials. The DPPE-PEG may provide more vesicles of a smaller size which are safe and stable to pressure when combined with other lipids, such as DPPC and DPPA, in the given ratios. It is also theorized that the pegylated material, because of its structural similarity to water, may be able to defeat the action of the macrophages of the human immune system, which would otherwise tend to surround and remove the foreign object. The result is an increase in the time during which the stabilized vesicles may function as diagnostic imaging contrast media.

The terms "stable" or "stabilized" mean that the vesicles may be substantially resistant to degradation, including, for example, loss of vesicle structure or encapsulated gas, gaseous precursor and/or bioactive agent, for a useful period of time. Typically, the vesicles employed in the present invention have a desirable shelf life, often retaining at least about 90% by volume of its original structure for a period of at least about two to three weeks under normal ambient conditions. In preferred form, the vesicles are desirably stable for a period of time of at least about 1 month, more preferably at least about 2 months, even more preferably at least about 6 months, still more preferably about eighteen months, and yet more preferably up to about 3 years. The vesicles described herein, including gas and/or gaseous precursor filled vesicles, may also be stable even under adverse conditions, such as temperatures and pressures which are above or below those experienced under normal ambient conditions.

The gas and/or gaseous precursor filled vesicles used in the present invention may be controlled according to size, solubility and heat stability by choosing from among the various additional or auxiliary stabilizing materials described herein. These materials can affect the parameters of the vesicles, especially vesicles formulated from lipids, not only by their physical interaction with the membranes, but also by their ability to modify the viscosity and surface tension of the surface of the gas and/or gaseous precursor filled vesicle. Accordingly, the gas and/or gaseous precursor filled vesicles used in the present invention may be favorably modified and further stabilized, for example, by the addition of one or more of a wide variety of (i) viscosity modifiers, including, for example, carbohydrates and their phosphorylated and sulfonated derivatives; polyethers, preferably with molecular weight ranges between 400 and 100,000; and di- and trihydroxy alkanes and their polymers, preferably with molecular weight ranges between 200 and 50,000; (ii) emulsifying and/or solubilizing agents including, for example, acacia, cholesterol, diethanolamine, glyceryl monostearate, lanolin alcohols, lecithin, mono- and di-glycerides, mono-ethanolamine, oleic acid, oleyl alcohol, poloxamer, for example, poloxamer 188, poloxamer 184, poloxamer 181, PLURONICS® (BASF, Parsippany, N.J.), polyoxyethylene 50 stearate, polyoxyl 35 castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan mono-laurate, sorbitan mono-oleate, sorbitan mono-palmitate, sorbitan monostearate, stearic acid, trolamine, and emulsifying wax; (iii) suspending and/or viscosity-increasing agents, including, for example, acacia, agar, alginic acid, aluminum mono-stearate, bentonite, magma, carbomer 934P, carboxymethyl-cellulose, calcium and sodium and sodium 12, carrageenan, cellulose, dextran, gelatin, guar gum, locust bean gum, veegum, hydroxyethyl cellulose, hydroxypropyl methyl-cellulose, magnesium-aluminum-silicate, ZEOLITES®, methylcellulose, pectin, polyethylene oxide, povidone, propylene glycol alginate, silicon dioxide, sodium alginate, tragacanth, xanthan gum, α-d-gluconolactone, glycerol and mannitol; (iv) synthetic suspending agents, such as polyethylene glycol (PEG), polyvinylpyrrolidone (PVP), polyvinylalcohol (PVA), polypropylene glycol (PPG), and polysorbate; and (v) tonicity raising agents which stabilize and add tonicity, including, for example, sorbitol, mannitol, trehalose, sucrose, propylene glycol and glycerol.

The present stabilizing materials and/or vesicles are desirably formulated in an aqueous environment which can induce the stabilizing material (e.g., a lipid, because of its hydrophobic-hydrophilic nature) to form vesicles, which may be the most stable configuration which can be achieved in such an environment. The diluents which can be employed to create such an aqueous environment include, for example, water, including deionized water, normal saline, physiological saline, or water containing one or more dissolved solutes, such as salts or sugars. Accordingly, when reference is made to heating the gaseous precursor filled compositions prior to administration to a patient, such heating preferably includes heating the aqueous environment or milieu in which the gaseous precursor filled compositions are contained.

The present invention describes methods of providing images of regions of a patient, diagnosing the presence of diseased tissue in a patient and delivering bioactive agents (with or without the use of a targeting ligand) to a patient by administering to the patient a composition comprising a gaseous precursor. Preferably, the gaseous precursor is a fluorinated compound, which includes compounds containing one or more fluorine atoms. Suitable fluorinated compounds for use as gaseous precursors in the present invention include, for example, perfluorocarbons, perfluoro ethers, hexafluoroacetone, 1,3-dichlorotetrafluoroacetone, tetrafluoroallene, boron trifluoride, 1,2,3-trichloro-2-fluoro-1,3-butadiene, hexafluoro-1,3-butadiene, 1-fluorobutane, perfluorobutane, decafluorobutane, perfluoro-1-butene, perfluoro-2-butene, 2-chloro-1,1,1,4,4,4-hexafluoro-butyne, 2-chloro-1,1,1,4,4,4-hexafluoro-2-butene, perfluoro-2-butyne, octafluorocyclobutane, perfluorocyclobutene, perfluorocyclobutane, perfluorocyclopentane, octafluorocyclopentene, perfluorocyclopropane, 1,1,1-trifluorodiazoethane, hexafluorodimethylamine, perfluoroethane, perfluoropropane, perfluorocyclopropane, perfluoropentane, perfluorocyclopentane, perfluorohexane, perfluorocyclohexane, hexafluoroethane, hexafluoropropylene, 1,1,2,2,3,3,4,4-octafluorobutane, 1,1,1,3,3-pentafluorobutane, octafluoropropane, octafluorocyclopentene, 1,1-dichlorofluoroethane, hexafluoro-2-butyne, octafluoro-2-butene, hexafluorobuta-1,3-diene, perfluorodimethylamine, 4-methyl-1,1,1,2-tetrafluoroethane, 1,1,1-trifluoroethane, 1,1,2,2-tetrafluoroethane, 1,1,2-trichloro-1,2,2-trifluoroethane, 1,1,1-trichloro-2,2,2-trifluoroethane, 1,1-dichloro-1,2-difluoroethylene, 1,1-dichloro-1,2,2,2-tetrafluoroethane, 1-chloro-1,1,2,2,2-pentafluoroethane, 1,1-difluoro-2-chloroethane, 1,1-dichloro-2-fluoroethane, dichloro-1,1,2,2-tetrafluoroethane, 1-chloro-1,1,2,2-tetrafluoroethane, 2-chloro-1,1-difluoroethane, 1,1,2-trifluoro-2-chloroethane, 1,2-difluorochloroethane, chloropentafluoroethane, dichlorotrifluoroethane, fluoroethane, nitropentafluoroethane, nitrosopentafluoroethane, perfluoroethylamine, 1,2-dichloro-2,2-difluoroethane, 1,1-dichloro-1,2-difluoroethane, 1,2-dichloro-1,1,3-trifluoropropane, 1,2-difluoroethane, 1,2-difluoroethylene, trifluoromethanesulfonylchloride, trifluoromethanesulfenylchloride, (pentafluorothio) trifluoromethane, trifluoromethanesulfonylfluoride, bromodifluoronitrosomethane, bromofluoromethane, bromochlorodifluoromethane, bromochlorofluoromethane, bromotrifluoromethane, bromotrifluoroethane, chlorodifluoronitromethane, chlorofluoromethane, chlorotrifluoromethane, chlorodifluoromethane, dibromofluoromethane, dibromodifluoromethane, dichlorodifluoromethane, dichlorofluoromethane, 1-bromoperfluorobutane, difluoromethane, difluoroiodomethane, fluoromethane, perfluoromethane, iodotrifluoromethane, iodotrifluoroethylene, nitrotrifluoromethane, nitrosotrifluoro-methane, tetrafluoromethane, trichlorofluoromethane, trifluoromethane, perfluoropent-1-ene, 1,1,1,2,2,3-hexafluoropropane, 2,2-difluoropropane, heptafluoro-1-nitropropane, heptafluoro-1-nitrosopropane, heptafluoro-2-iodopropane, perfluoropropane, hexafluoropropane, 1,1,1,2,3,3-hexafluoro-2,3-dichloropropane, 1-bromo-1,1,2,3,3,3-hexafluoropropane, 1-bromoperfluoropropane, 2-chloropentafluoro-1,3-butadiene, 3-fluoropropane, 3-fluoropropylene, perfluoropropylene, perfluorotetrahydropyran, perfluoromethyltetrahydrofuran, perfluorobutylmethyl ether, perfluoromethyl-n-butyl ether, perfluoromethylisopropyl ether, perfluoromethyl-t-butyl ether, perfluorobutylethyl ether, perfluoromethylpentyl ether, 3,3,3-trifluoropropyne, 3-fluorostyrene, sulfur (di)-decafluoride ($S_2F_{10}$), sulfur hexafluoride, selenium hexafluoride, trifluoroacetonitrile, trifluoromethylperoxide, trifluoromethylsulfide, tungsten hexafluoride, 1-bromononafluorobutane, 1-chloro-1-fluoro-1-bromomethane, 1-bromo-2,4-difluorobenzene, 2-iodo-1,1,1-trifluoroethane, bromine pentafluoride, perfluoro-2-methyl-2-pentene, 1,1,1,3,3-pentafluoropentane, 3-fluorobenzaldehyde, 2-fluoro-5-nitrotoluene, 3-fluorostyrene, 3,5-difluoroaniline, 2,2,2-trifluoroethylacrylate, 3-(trifluoromethoxy)acetophenone, bis(perfluoroisopropyl)ether, bis(perfluoropropyl)ether, perfluoroisobutylmethyl ether, perfluoro n-propylethyl ether, perfluorocyclobutylmethyl ether, perfluorocyclopropyl ethyl ether, perfluoroisopropylmethyl ether, perfluoro n-propyl methyl ether, perfluorodiethyl ether, perfluorocyclopropylmethyl ether, perfluoromethylethyl ether, perfluorodimethyl ether, and mixtures thereof.

More preferably, the gaseous precursors include, for example, fluorinated carbons, perfluorocarbons, sulfur hexafluoride, perfluoro ethers and combinations thereof. As the skilled artisan will appreciate, a particular fluorinated compound, such as sulfur hexafluoride, a perfluorocarbon or a perfluoro ether, may exist in the liquid state when the compositions are first made, and are thus used as a gaseous precursor. Whether the fluorinated compound is a liquid generally depends on its liquid/gas phase transition temperature, or boiling point. For example, a preferred perfluorocarbon, perfluoropentane, has a liquid/gas phase transition temperature (boiling point) of 29.5° C. This means that perfluoropentane is generally a liquid at room temperature (about 25° C.), but is converted to a gas within the human body, the normal temperature of which is about 37° C., which is above the transition temperature of perfluoropentane. Thus, under normal circumstances, perfluoropentane is a gaseous precursor.

As known to one skilled in the art, the effective boiling point of a substance may be related to the pressure to which that substance is exposed. This relationship is exemplified by the ideal gas law: PV=nRT, where P is pressure, V is volume, n is moles of substance, R is the gas constant, and T is temperature. The ideal gas law indicates that as pressure increases, the effective boiling point also increases. Conversely, as pressure decreases, the effective boiling point decreases.

Fluorocarbons for use as gaseous precursors in the compositions of the present invention include partially or fully fluorinated carbons, preferably perfluorocarbons that are saturated, unsaturated or cyclic. The preferred perfluorocarbons include, for example, perfluoromethane, perfluoroethane, perfluoropropane, perfluorocyclopropane, perfluorobutane, perfluorocyclobutane, perfluoropentane, perfluorocylcopentane, perfluorohexane, perfluorocyclohexane, and mixtures thereof. More preferably, the perfluorocarbon is perfluorohexane, perfluoropentane, perfluoropropane or perfluorobutane.

Preferred ethers include partially or fully fluorinated ethers, preferably perfluorinated ethers having a boiling point of from about 36° C. to about 60° C. Fluorinated ethers are ethers in which one or more hydrogen atoms is replaced by a fluorine atom. Fluorinated ethers have the general formula $CX_3(CX_2)_n$—O—$(CX_2)_nCX_3$, wherein X is a hydrogen atom, a fluorine atom or another halogen atom provided that at least one of X is a fluorine atom. More preferably, each X is a fluorine atom. Generally, fluorinated ethers containing about 4 to about 6 carbon atoms will have a boiling point within the preferred range for the invention, although smaller or larger chain fluorinated ethers may also be employed in appropriate circumstances. Preferred perfluorinated ethers for use as gaseous precursors in the present invention include, for example, perfluorotetrahydropyran, perfluoromethyltetrahydrofuran, perfluorobutylmethyl ether (e.g., perfluoro t-butylmethyl ether, perfluoro isobutyl methyl ether, perfluoro-n-butyl methyl ether), perfluoropropylethyl ether (e.g., perfluoro isopropyl ethyl ether, perfluoro n-propyl ethyl ether), perfluorocyclobutylmethyl ether, perfluorocyclopropylethyl ether, perfluoropropylmethyl ether (e.g., perfluoro isopropyl methyl ether, perfluoro n-propyl methyl ether), perfluorodiethyl ether, perfluorocyclopropylmethyl ether, perfluoromethylethyl ether and perfluorodimethyl ether.

Other preferred perfluoroether analogues contain between 4 and 6 carbon atoms, and optionally contain one halide ion, preferably $Br^{1-}$. For example, compounds having the structure $C_nF_yH_xOBr$, where n is an integer of from 1 to about 6, y is an integer of from 0 to about 13, and x is an integer of from 0 to about 13, are useful as gaseous precursors. Examples of useful gaseous precursors having this formula include perfluoropropyloxylbromide and 2-bromooxyperfluoropropane.

Other preferable fluorinated compounds for use as gaseous precursors in the present invention are sulfur hexafluoride and heptafluoropropane, including 1,1,1,2,3,3,3-heptafluoropropane and its isomer, 1,1,2,2,3,3,3-heptafluoropropane. Other fluorinated compounds that may be used as gaseous precursors in the present invention include compounds comprising a sulfur atom, including compounds of the formula $CF_3$—$(CF_2)_n$—SF, or $SF_5$—$(CF_2)_n$—$SF_5$, where n is an integer of from 1 to about 10.

Mixtures of different types of compounds, such as mixtures of a fluorinated compound (e.g., a perfluorocarbon or a perfluoroether) and another type of gas or gaseous precursor can also be used in the compositions of the present invention. Other gases and gaseous precursors are well known to one skilled in the art.

Generally, preferred gaseous precursors undergo phase transition to gas at a temperature up to about 60° C., preferably from about 25° C. to about 52° C., preferably from about 37° C., to about 50° C., more preferably from about 38° C. to about 48° C., even more preferably from about 38° C. to about 46° C., still even more preferably from about 38° C. to about 44° C., even still more preferably from about 38° C. to about 42° C. Most preferably, the gaseous precursors undergo a phase transition at a temperature of about less than 40° C. As will be recognized by one skilled in the art, the optimal phase transition temperature of a gaseous precursor for use in a particular application will depend upon considerations such as, for example, the particular patient, the tissue being targeted, the nature of the physiological stress state (i.e., disease, infection or inflammation, etc.) causing the increased temperature, the stabilizing material used, and/or the bioactive agent to be delivered.

Additionally, one skilled in the art will recognize that the phase transition temperature of a compound may be affected by local conditions within the tissue, such as, for example, local pressure (for example, interstitial, interfacial, or other pressures in the region). By way of example, if the pressure within the tissues is higher than ambient pressure, this will be expected to raise the phase transition temperature. The extent of such effects may be estimated using standard gas law predictions, such as Charles' Law and Boyle's Law. As an approximation, compounds having a liquid-to-gas phase transition temperature between about 30° C. and about 50° C. can be expected to exhibit about a 1° C. increase in the phase transition temperature for every 25 mm Hg increase in pressure. For example, the liquid-to-gas phase transition temperature (boiling point) of perfluoropentane is 29.5° C. at a standard pressure of about 760 mm Hg, but the boiling point is about 30.5° C. at an interstitial pressure of 795 mm Hg.

Materials used in stabilizing the gaseous precursor, discussed herein, may also affect the phase transition temperature of the gaseous precursor. In general, the stabilizing material is expected to increase the phase transition temperature of the gaseous precursor. In particular, a relatively rigid polymeric material, such as, for example, polycyanomethacrylate, may have a significant effect on the phase transition temperature of the gaseous precursor. Such an effect must be considered in the selection of the gaseous precursor and the stabilizing material.

The gaseous precursors and/or gases are preferably incorporated in the stabilizing materials and/or vesicles irrespective of the physical nature of the composition. Thus, it is contemplated that the gaseous precursors and/or gases may be incorporated, for example, in stabilizing materials in which the stabilizing materials are aggregated randomly, such as emulsions, dispersions or suspensions, as well as in vesicles, including vesicles which are formulated from lipids, such as micelles and liposomes. Incorporation of the gases and/or gaseous precursors in the stabilizing materials and/or vesicles may be achieved by using any of a number of methods.

In addition, a gas may be bubbled directly into an aqueous mixture of stabilizing materials and/or vesicle-forming compounds. Alternatively, a gas instillation method can be used as disclosed, for example, in U.S. Pat. Nos. 5,352,435 and 5,228,446, the disclosures of each of which are hereby incorporated herein by reference in their entirety. Suitable methods for incorporating the gas and/or gaseous precursor in cationic lipid compositions are disclosed also in U.S. Pat. No. 4,865,836, the disclosure of which is hereby incorporated herein by reference in its entirety. Other methods would be apparent to one skilled in the art based on the present disclosure. Preferably, the gas may be instilled in the stabilizing materials and/or vesicles after or during the addition of the stabilizing material and/or during formation of vesicles.

The compositions and stabilizing materials of the present invention may also comprise or be used in combination with a bioactive agent. Suitable bioactive agents include, for example, antineoplastic agents, blood products, biological response modifiers, anti-fungal agents, hormones, steroids, vitamins, peptides, peptide analogs, enzymes, anti-allergenic agents, anti-coagulation agents, circulatory agents, anti-tubercular agents, anti-viral agents, anti-anginal agents, antibiotics, anti-inflammatory agents, analgesics, anti-protozoan agents, anti-rheumatic agents, narcotics, cardiac glycoside agents, chelates, neuromuscular blocking agents, sedatives (hypnotics), local anesthetic agents, general anesthetic agents, radioactive particles, radioactive ions, X-ray contrast agents, monoclonal antibodies, polyclonal antibodies and genetic material.

Exemplary bioactive agents are listed below; however, the list is exemplary only and is not intended to limit the bioactive agents that may be used in the present invention.

Antineoplastic agents, include, for example, platinum compounds (e.g., spiroplatin, cisplatin, and carboplatin), methotrexate, adriamycin, mitomycin c, ansamitocin, bleomycin, bleomycin sulfate, cytosine arabinoside, arabinosyl adenine, mercaptopolylysine, vincristine, busulfan, chlorambucil, melphalan (e.g., PAM, L-PAM or phenylalanine mustard), mercaptopurine, mitotane, procarbazine hydrochloride, dactinomycin (actinomycin D), daunorubicin hydrochloride, doxorubicin hydrochloride, taxol, plicamycin (mithramycin), aminoglutethimide, estramustine phosphate sodium, flutamide, leuprolide acetate, megestrol acetate, tamoxifen citrate, testolactone, trilostane, amsacrine (m-AMSA), asparaginase (L-asparaginase), Erwina asparaginase, etoposide (VP-16), interferon α-2a, interferon α-2b, teniposide (VM-26), vinblastine sulfate (VLB), vincristine sulfate, and carzelesin.

Blood products, include, for example, erythropoietin, parenteral iron, hemin, and hematoporphyrins and their derivatives.

Biological response modifiers, include, for example, muramyldipeptide, muramyltripeptide, microbial cell wall components, lymphokines (e.g., bacterial endotoxin such as lipopolysaccharide, macrophage activation factor), subunits of bacteria (such as Mycobacteria, Corynebacteria), the synthetic dipeptide, N-acetyl-muramyl-L-alanyl-D-isoglutamine, and prostaglandins.

Anti-fungal agents, include, for example, ketoconazole, nystatin, griseofulvin, flucytosine (5-fc), miconazole, amphotericin B, ricin, and β-lactam antibiotics (e.g., sulfazecin).

Hormones and steroids, include, for example, growth hormone, melanocyte stimulating hormone, adrenocorticotropic hormone, dexamethasone, dexamethasone acetate, dexamethasone sodium phosphate, cortisone, cortisone acetate, hydrocortisone, hydrocortisone acetate, hydrocortisone cypionate, hydrocortisone sodium phosphate, hydrocortisone sodium succinate, prednisone, prednisolone, prednisolone acetate, prednisolone sodium phosphate, prednisolone tebutate, prednisolone pivalate, triamcinolone, triamcinolone acetonide, triamcinolone hexacetonide, triamcinolone diacetate, methylprednisolone, methylprednisolone acetate, methylprednisolone sodium succinate, flunsolide, beclomethasone dipropionate, betamethasone sodium phosphate, betamethasone, vetamethasone disodium phosphate, vetamethasone sodium phosphate, betamethasone acetate, betamethasone disodium phosphate, chloroprednisone acetate, corticosterone, desoxycorticosterone, desoxycorticosterone acetate, desoxycorticosterone pivalate, desoximethasone, estradiol, fludrocortisone, fludrocortisone acetate, dichlorisone acetate, fluorohydrocortisone, fluorometholone, fluprednisolone, paramethasone, paramethasone acetate, androsterone, fluoxymesterone, aldosterone, methandrostenolone, methylandrostenediol, methyl testosterone, norethandrolone, testosterone, testosterone enanthate, testosterone propionate, equilenin, equilin, estradiol benzoate, estradiol dipropionate, estriol, estrone, estrone benzoate, acetoxypregnenolone, anagestone acetate, chlormadinone acetate, flurogestone acetate, hydroxymethylprogesterone, hydroxymethylprogesterone acetate, hydroxyprogesterone, hydroxyprogesterone acetate, hydroxyprogesterone caproate, melengestrol acetate, normethisterone, pregnenolone, progesterone, ethynyl estradiol, mestranol, dimethisterone, ethisterone, ethynodiol diacetate, norethindrone, norethindrone acetate, norethisterone, fluocinolone acetonide, flurandrenolone, flunisolide, hydrocortisone sodium succinate, methylprednisolone sodium succinate, prednisolone phosphate sodium, triamcinolone acetonide, hydroxydione sodium, spironolactone, oxandrolone, oxymetholone, prometholone, testosterone cypionate, testosterone phenylacetate, estradiol cypionate, and norethynodrel.

Vitamins, include, for example, cyanocobalamin neinoic acid, retinoids and derivatives thereof such as retinol palmitate, α-tocopherol, naphthoquinone, cholecalciferol, folic acid and tetrahydrofolate.

Peptides and peptide analogs, include, for example, manganese super oxide dismutase, tissue plasminogen activator (t-PA), glutathione, insulin, dopamine, peptide ligands containing RGD, AGD, RGE, KGD, KGE or KQAGDV (Peptides with affinity for the GPIIBIIIa receptor), opiate peptides, enkephalins, endorphins and their analogs, human chorionic gonadotropin (HCG), corticotropin release factor (CRF), cholecystokinins and their analogs, bradykinins and their analogs and promoters and inhibitors, elastins, vasopressins, pepsins, glucagon, substance P, integrins, captopril, enalapril, lisinopril and other ACE inhibitors, adrenocorticotropic hormone (ACTH), oxytocin, calcitonins, IgG or fragments thereof, IgA or fragments thereof, IgM or fragments thereof, ligands for Effector Cell Protease Receptors (all subtypes), thrombin, streptokinase, urokinase, t-PA and all active fragments or analogs, Protein Kinase C and its binding ligands, interferons (α-interferon, β-interferon, γ-interferon), colony stimulating factors (CSF), granulocyte colony stimulating factors (GCSF), granulocyte-macrophage colony stimulating factors (GM-CSF), tumor necrosis factors (TNF), nerve growth factors (NGF), platelet derived growth factors, lymphotoxin, epidermal growth factors, fibroblast growth factors, vascular endothelial cell growth factors, erythropoietin, transforming growth factors, oncostatin M, interleukins (1, 2, 3, 4, 5, 6, 7, 8, 9, 10, 11 and 12), metalloprotein kinase ligands, collagenases and agonists and antagonists.

Enzymes, include, for example, alkaline phosphatase, cyclooxygenase type I and agonists and antagonists.

Anti-allergenic agents, include, for example, amelexanox.

Anti-coagulation agents, include, for example, phenprocoumon and heparin.

Circulatory drugs, include, for example, propranolol.

Anti-tubercular agents, include, for example, para-aminosalicylic acid, isoniazid, capreomycin sulfate cycloserine, ethambutol hydrochloride ethionamide, pyrazinamide, rifampin, and streptomycin sulfate.

Anti-viral agents, include, for example, acyclovir, amantadine azidothymidine (AZT or Zidovudine), ribavirin, and vidarabine monohydrate (adenine arabinoside, ara-A).

Anti-anginal agents, include, for example, diltiazem, nifedipine, verapamil, erythritol tetranitrate, isosorbide dinitrate, nitroglycerin (glyceryl trinitrate), and pentaerythritol tetranitrate.

Antibiotics, include, for example, dapsone, chloramphenicol, neomycin, cefaclor, cefadroxil, cephalexin, cephradine erythromycin, clindamycin, lincomycin, amoxicillin, ampicillin, bacampicillin, carbenicillin, dicloxacillin, cyclacillin, picloxacillin, hetacillin, methicillin, nafcillin, oxacillin, penicillin G, penicillin V, ticarcillin, rifampin, and tetracycline.

Anti-inflammatory agents and analgesics, include, for example, diflunisal, ibuprofen, indomethacin, meclofenamate, mefenamic acid, naproxen, oxyphenbutazone, phenylbutazone, piroxicam, sulindac, tolmetin, aspirin and salicylates.

Anti-protozoan agents, include, for example, chloroquine, metronidazole, hydroxychloroquine, quinine, and meglumine antimonate.

Anti-rheumatic agents, include, for example, penicillamine.

Narcotics, include, for example, paregoric and opiates, such as codeine, heroin, methadone, morphine and opium.

Cardiac glycoside agents, include, for example, deslanoside, digitoxin, digoxin, digitalin and digitalis.

Chelates, include, for example, diethylene triamine pentaacetic acid (DTPA) and 1,4,7,10-tetraazocyclododecane-N',N',N'',N''-tetraacetic acid (DOTA). Any chelate that is generally used in conjunction with paramagnetic or radioactive metal ions may be used.

Neuromuscular blocking agents, include, for example, atracurium mesylate, gallamine triethiodide, hexafluorenium bromide, metocurine iodide, pancuronium bromide, succinylcholine chloride (suxamethonium chloride), tubocurarine chloride, and vecuronium bromide.

Sedatives (hypnotics), include, for example, amobarbital, amobarbital sodium, aprobarbital, butabarbital sodium, chloral hydrate, ethchlorvynol, ethinamate, flurazepam hydrochloride, glutethimide, methotrimeprazine hydrochloride, methyprylon, midazolam hydrochloride paraldehyde, pentobarbital, pentobarbital sodium, phenobarbital sodium, secobarbital sodium, talbutal, temazepam, and triazolam.

Local anesthetic agents, include, for example, bupivacaine hydrochloride, chloroprocaine hydrochloride, etidocaine hydrochloride, lidocaine hydrochloride, mepivacaine hydrochloride, procaine hydrochloride, and tetracaine hydrochloride.

General anesthetic agents, include, for example, droperidol, etomidate, fentanyl citrate with droperidol, ketamine hydrochloride, methohexital sodium, and thiopental sodium.

Radioactive particles or radioactive ions, include, for example, strontium, rhenium, yttrium, technetium, and cobalt.

X-ray contrast agents, include, for example, X-ray contrast agents known in the art that contain heavy metals such as yttrium, ytterbium, lanthanides in chelates or other iodinated materials, such as iothalamate.

Genetic material, includes, for example, nucleic acids, RNA and DNA, of either natural or synthetic origin, including recombinant RNA and DNA and antisense RNA and DNA; hammerhead RNA, ribozymes, hammerhead ribozymes, antigene nucleic acids, both single and double stranded RNA and DNA and analogs thereof, ribooligonucleotides, antisense ribooligonucleotides, deoxyribooligonucleotides, and antisense deoxyribooligonucleotides. Other types of genetic material that may be used include, for example, genes carried on expression vectors such as plasmids, phagemids, cosmids, yeast artificial chromosomes (YACs), and defective or "helper" viruses, antigene nucleic acids, both single and double stranded RNA and DNA and analogs thereof, such as phosphorothioate and phosphorodithioate oligodeoxynucleotides. Additionally, the genetic material may be combined, for example, with proteins or other polymers. Other examples of genetic material include, for example, DNA encoding at least a portion of LFA-3, DNA encoding at least a portion of an HLA gene, DNA encoding at least a portion of dystrophin, DNA encoding at least a portion of CFTR, DNA encoding at least a portion of IL-2, DNA encoding at least a portion of TNF, and an antisense oligonucleotide capable of binding the DNA encoding at least a portion of Ras. DNA encoding certain proteins may be used in the treatment of many different types of diseases. For example, adenosine deaminase may be provided to treat ADA deficiency; tumor necrosis factor and/or interleukin-2 may be provided to treat advanced cancers; HDL receptor may be provided to treat liver disease; thymidine kinase may be provided to treat ovarian cancer, brain tumors, or HIV infection; HLA-B7 may be provided to treat malignant melanoma; interleukin-2 may be provided to treat neuroblastoma, malignant melanoma, or kidney cancer; interleukin-4 may be provided to treat cancer; HIV env may be provided to treat HIV infection; antisense ras/p53 may be provided to treat lung cancer; and Factor VIII may be provided to treat Hemophilia B. See, for example, *Science* 258:744–746.

The bioactive agents used in the present invention are preferably highly active in low concentrations. The targeting aspects of the invention further enable lower dosages to be used for therapy, since the effective concentration at the therapeutic site remains undiluted in the body. The amount of bioactive agent to be administered to a patient depends, for example, on the particular bioactive agent, the method in which the bioactive agent is being administered, and the age, sex, weight and physical condition of the patient. Generally, treatment is initiated with small dosages, which can then be increased by small increments, until the desired effect under the circumstances is achieved. Additionally, one skilled in the art may rely on reference materials, such as the *Physician's Desk Reference*, published by Medical Economics Company at Montvale, N.J. 07645-1742, to determine the appropriate amount of a particular bioactive agent that may be administered to a patient. In accordance with the present invention, the bioactive agent is delivered to the patient (e.g., in a region of the patient) for the purposes, for example, of treating a condition (i.e., a disease state, malady, disorder, etc.) in the patient.

The bioactive agent used in the present invention may be a prodrug, including the prodrugs described, for example, by Sinkula et al., *J. Pharm. Sci.*, 64:181–210 (1975) and in U.S. application Ser. No. 08/887,215 filed Jul. 2, 1997, the disclosures of each of which are hereby incorporated herein by reference in their entirety. For example, the prodrug may be a compound of the formula (XI):

R—(X)$_p$—D        (XI)

where R is a fluorinated amphiphilic moiety; X is a linking group; p is an integer of 0 or 1; and D is a bioactive agent.

In the compound of formula (XI), R is a fluorinated amphiphilic moiety, preferably a fluorinated lipid or a fluorinated surfactant. More preferably, R is a compound of the formula (IV), (V), (VI), (VII), (VIIa), (VIII), (VIIIa), (IX) or (X), which are described in detail above. The fluorinated amphiphilic moiety of formula (IV) may attach via the —COOH group to the linking group or bioactive agent. The fluorinated amphiphilic moiety of formula (V) may attach via the —OH group to the linking group or bioactive agent. The fluorinated amphiphilic moiety of formula (VI) may attach via the sugar moiety "A" to the linking group or bioactive agent. For example, the "—CHO" group on the sugar moiety may be converted to a —COOH group by methods known to one skilled in the art (e.g., reacting the sugar with $Br_2+H_2O$ or with $HNO_3$). Thereafter, the sugar moiety may be attached via the —COOH group to the linking group or bioactive agent. The fluorinated amphiphilic moiety of formula (VII) may attach via the Z group to the linking group or bioactive agent. As discussed below, the Z group may contain, for example, a reactive carboxyl, amine, hydroxyl or thiol group that can attach to the linking group or bioactive agent. Alternatively, if the Z group in formula (VII) is a saccharide residue, it may be attached to the linking group or bioactive agent following the method described for the fluorinated amphiphilic moiety of formula (VI). The fluorinated amphiphilic moiety of formula (VIIa) may attach via the —OH group (located on the phosphorous atom) to the linking group or bioactive agent. The fluorinated amphiphilic moiety of formula (VIII) may attach via the —COOH group to the linking group or bioactive agent. The fluorinated amphiphilic moiety of formula (VIIIa) may attach via the —COOH group to the linking group or bioactive agent. The fluorinated amphiphilic moiety of formula (IX) may attach via the —COOH group to the linking group or bioactive agent. The fluorinated amphiphilic moiety of formula (X) may attach via the —OH group (located on the phosphorous atom) to the linking group or bioactive agent.

In the compound of formula (XI), X is a linking group when p is 1. Preferably, X is a biodegradable linking group selected from the group consisting of an amide group, an ester group, an ether group, an anhydride group, a disulfide group, an $SO_2NH$ group, an amino group, a thio group and an alkyl group. More preferably, X is a linking group selected from the group consisting of —CONH—, —NCONH—, —C(=O)—O—, —O—, —C(=O)—O—C(=O)—, —S—S—, —$SO_2NH$—, —NH—, —S—, and —$(CH_2)_n$—, where n is an integer of from 1 to about 12, preferably from 1 to about 8, more preferably from 1 to about 4.

Alternatively, p is 0, such that no linking group, per se, is in the compound. Generally, p can be 0 if the bioactive agent contains an amide group, an ester group, an ether group, an anhydride group, a disulfide group, an $SO_2NH$ group, an amino group, a thio group or an alkyl group that can covalently bond to the fluorinated amphiphilic moiety. In view of the present disclosure and with knowledge of basic synthetic organic chemistry, one skilled in the art could readily determine whether any particular bioactive agent could be covalently bonded to a fluorinated amphiphilic moiety without using a linking group.

In the compound of formula (XI), D may be a wide variety of bioactive agents, including any of the bioactive agents described above. Preferably, the bioactive agent is an anti-neoplastic agent, a hormone, a steroid, an anti-fungal agent, a peptide or a peptide analog. More preferably, the bioactive agent is dexamethasone, amphotericin B, adriamycin, mitomycin c, taxol or tissue plasminogen activator (t-PA).

In view of the present disclosure, and with knowledge of basic synthetic organic chemistry, one skilled in the art would readily recognize the locations on any particular bioactive agent, linking group and fluorinated amphiphilic moiety where attachments may be made to covalently attach the bioactive agent to the linking group and to attach the linking group to the fluorinated amphiphilic moiety (when p is I in the compound of formula (XI)) or, alternatively, to covalently attach the bioactive agent to the fluorinated amphiphilic moiety (when p is 0 in the compound of formula (XI)). For example, —OH, —COOH, —NH or —SH groups which are present on a bioactive agent, a linking group or a fluorinated amphiphilic moiety are obvious points at which the bioactive agent, linking group and fluorinated amphiphilic moiety may be attached to each other. Bioactive agents generally have —OH, —COOH, —NH or —SH terminal groups at one or more locations, any of which may serve as the point of attachment to the linking group or bioactive agent. If the bioactive agent, linking group or fluorinated amphiphilic moiety does not have a —OH, —COOH, —NH or —SH terminal group, basic synthetic addition chemistry, which is well known to one skilled in the art, can be used to introduce an —OH group into the compound, which would then serve as a suitable point of attachment.

General schemes for synthesizing the prodrugs described herein are shown below. One skilled in the art will readily appreciate that certain modifications may be necessary, depending on the presence or absence of labile groups on the underivatized bioactive agents. As discussed above, the modifications may take the form, for example, of adding protecting or blocking groups to chemically reactive side groups or additions of reactive —COOH, —OH, —NH$_2$ or —SH groups for coupling.

Preliminarily, the fluorinated amphiphilic compounds are purified by dissolving in an appropriate organic solvent and heating in the presence of a small amount of activated charcoal. The solvents are then removed via vacuum evaporation. Appropriate organic solvents include, for example, ethyl acetate, acetonitrile, tetrahydrofuran, dichloroethane, acetone, toluene, methylene chloride or an alcohol having about 5 carbon atoms or less. If necessary to provide a reactive end, the fluorinated amphiphiles may then be exposed to an activating agent. Details of the various activations and coupling reactions are given by the following general schemes.

In all cases below, "R" designates a fluorinated amphiphilic moiety, including, for example, one or more of those of formulas (II), (III), (IV), (V), (VI), (VII) and/or (VIII) described herein. "BIOACTIVE" designates any suitable bioactive agent, including those described herein. The linkage between the R group and the BIOACTIVE agent may be a linking group "X" as defined herein (e.g., a compound of formula (XI) where p is 1) or may be a reactive moiety on the bioactive agent (e.g., a compound of formula (XI) where p is 0).

Amide linked prodrugs
R—COCl+BIOACTIVE-NH$_2$→R—CONH-BIOACTIVE
R—NCO+BIOACTIVE-NH$_2$→R—NCONH-BIOACTIVE
Ester linked prodrugs
R—COCl+BIOACTIVE-OH→R—COO-BIOACTIVE
R—COOH+BIOACTIVE-OH→R—COO-BIOACTIVE
Anhydride linked prodrugs
R—COOH+BIOACTIVE—COOH→R—COOC(O)-BIOACTIVE
Disulfide linked prodrugs
R—SH+BIOACTIVE-SH→R—S—S-BIOACTIVE
SONH$_2$ linked prodrugs
R—SOCl$_2$+BIOACTIVE-NH$_2$→R—SO$_2$NH-BIOACTIVE
Amino linked prodrugs
BIOACTIVE-CHO+R—NH$_2$+NaCNBH$_3$→R—NH-BIOACTIVE Thio linked prodrugs
BIOACTIVE-Br+R—SH→R—S-BIOACTIVE
Alkyl linked prodrugs
BIOACTIVE-Br+R—CH$_2$+Bu$_3$SnH→R—CH$_2$CH$_2$-BIOACTIVE Further details of experimental conditions and variations in the above schemes would be apparent to one skilled in the art in view of the present disclosure.

Alternatively, it is often useful to conjugate the bioactive agent through a modified sugar, such as glucosamine, or sugar acid derivative, such as succinate. An example of the synthesis of the fluorinated amphiphilic moiety attached to glucosamine can be generalized as follows:

R—OH+Cl$_3$CCOCOCCl$_3$→R—OCOCl
R—OCOCl+glucosamine-HCl+pyridine→R—OCONH-glucosamine As one skilled in the art will recognize, the glucosamine derivative is then available for reaction with the bioactive agent through either an amine group or a —OH group.

The bioactive agents of the present invention may also be the prodrugs described in U.S. application Ser. No. 08/851,780, filed May 6, 1997, the disclosure of which is hereby incorporated by reference herein in its entirety. For example, the prodrug may comprise a steroid covalently bonded to a lipid moiety via a linking group. For example, the prodrug may be a compound of the formula (XII):

$$D-X-L \qquad (XII)$$

where D is a steroid; X is a linking group comprising an ester group, a carbamate group, a carbonyl group, a thioester group, a disulfide group, an ether group, an anhydride group, or an amide group; and L is a lipid moiety comprising an acyl, alkyl, alkylaryl, fluoracyl, fluoroalkyl or fluoroalkylaryl group having from about 4 to about 40 carbon atoms.

Preferably, D is a steroid which may be a compound of the formula (XIV) or any of the steroids described herein. Most preferably, D is dexamethasone.

Preferably, X is a linking group that is sufficiently stable for storage but which is also biodegradable, such as, for example, an ester group. Most preferably, X is succinate.

Preferably, L is a lipid moiety comprising an acyl, alkyl, alkylaryl, fluoracyl, fluoroalkyl or fluoroalkylaryl moiety having from about 4 to about 40 carbon atoms and more preferably from about 6 to about 40 carbon atoms. The acyl or alkyl group may consist of one, two or three chains or an alkylaryl group. In a preferred embodiment, L may be a diacylated moiety in which two acyl chains are linked to glycerol. More preferably, L may be dipalmitoylglyceryl, dimyristoylglyceryl, distearoylglyceryl, or dioleoylglyceryl. Alternatively, L may be cholesterol. Thus, X-L is preferably dipalmitoylglycerylsuccinate, dimyristoylglycerylsuccinate, distearoylglycerylsuccinate, dioleoylglycerylsuccinate or cholesterol succinate.

In another embodiment, L may be a lipid moiety comprising a fluoroacyl, fluoroalkyl or fluoroalkylaryl group. The acyl, alkyl or alkylaryl group may comprise one or more fluorine atoms, preferably from about 3 to about 23 fluorine atoms, more preferably from about 5 to about 18 fluorine atoms. When the acyl, alkyl or alkylaryl group is part of a linear chain, the terminal carbon atoms are preferably fluorinated. Alternatively, the acyl, alkyl or alkylaryl group may be a perfluorinated group. Perfluorinated means that all the hydrogen atoms, except those whose replacement would affect the nature of the characteristic groups present, are replaced by fluorine atoms. For example, bipyridine moieties may be perfluoroalkylated as described in Garelli and Vierling, *Biochim. Biophys. Acta* (1992) 1127:41–48, the disclosure of which is hereby incorporated by reference herein in its entirety. Other fluorinated amphiphilic molecules which serve in this capacity are fluorosurfactants and the compounds disclosed in U.S. Pat. No. 5,562,893 and U.S. application Ser. No. 08/465,868, filed Jun. 6, 1995, the disclosures of which are hereby incorporated herein by reference in their entirety.

The stabilizing materials of the present invention may also comprise a bioactive agent that is a prodrug of the formula (XIII), which is encompassed within the scope of the compound of formula (XII):

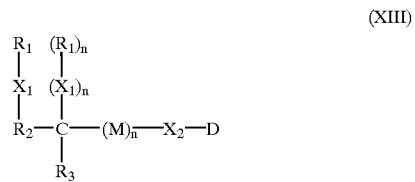

(XIII)

where each $X_1$ is independently a direct bond, —O—, —S—, —SO—, —SO$_2$—, —NR$_4$—, —X$_3$—C(=X$_4$)—, —C(=X$_4$)—X$_3$— or —C(=X$_4$)—; each n is independently an integer of 0 or 1; $X_2$ is a direct bond, —C(=X$_4$)—, —R$_5$—X$_3$—C(=X$_4$)—, —R$_5$—C(=X$_4$)—X$_3$, —X$_3$—C(=X$_4$)—R$_5$—, —C(=X$_4$)—X$_3$—R$_5$—, —X$_3$R$_5$—C(=X$_4$)—X$_3$—, —C(=X$_4$)—R$_5$—C(=X$_4$)—, —R$_5$—X$_3$C(=X$_4$)—R$_5$—C(=X$_4$)—, —C(=X$_4$)R$_5$—C(=X$_4$)—X$_3$— or —R$_5$—C(=X$_4$)—X$_3$—R$_5$—X$_3$—C(=X$_4$)—; each $X_3$ is independently —O—, —NR$_4$— or —S—; each $X_4$ is independently O or S; M is —R$_5$—X$_3$—, —R$_5$—X$_3$—C(=X$_4$)—, —R$_5$—C(=X$_4$)—X$_3$—, —R$_5$—X$_3$—(YX$_4$)P(=X$_4$)—X$_3$— or —X$_3$—(YX$_4$)P(=X$_4$)—X$_3$—R$_5$—; Y is hydrogen or a pharmaceutically acceptable counter ion; D is a steroid; each $R_1$ is independently an alkyl group of 1 to about 50 carbon atoms that is optionally substituted with one or more halogen atoms; each $R_2$ is independently an alkylene group of 1 to about 30 carbon atoms that is optionally substituted with one or more halogen atoms; each of $R_3$ and $R_4$ is independently =O, a hydrogen atom or an alkyl group of 1 to about 10 carbon atoms; and each $R_5$ is independently a direct bond or an alkylene group of 1 to about 30 carbon atoms.

In the above formula, when any symbol appears more than once in a particular formula or substituent, its meaning in each instance is independent of the other. Also, when each of two or more adjacent symbols is defined as being a "direct bond" to provide multiple, adjacent direct bonds, the multiple and adjacent direct bonds devolve into a single direct bond.

In preferred embodiments of formula (XIII), each $X_1$ is independently —X$_3$—C(=X$_4$)—, —C(=X$_4$)—X$_3$— or —C(=X$_4$)—. More preferably, each $X_1$ is independently —X$_3$—C(=X$_4$)— or —C(=X$_4$)—X$_3$—. Even more preferably, $X_1$ is —C(=X$_4$)—X$_3$—, for example, —C(=O)—O—.

In preferred embodiments of formula (XIII), $X_2$ is a direct bond, —C(=X$_4$)—, —C(=X$_4$)—R$_5$—C(=X$_4$)—, —C(=X$_4$)—R$_5$—C(=X$_4$)—X$_3$—, —R$_5$—X$_3$—C(=X$_4$)—, —R$_5$—C(=X$_4$)—X$_3$—, —X$_3$—C(=X$_4$)—R$_5$—, —R$_5$—C(=X$_4$)—X$_3$—, —X$_3$—C(=X$_4$)—R$_5$—, —C(=X$_4$)—X$_3$—R$_5$—, —X$_3$—R$_5$—C(=X$_4$)—X$_3$— or —R$_5$—X$_3$—C(=X$_4$)—R$_5$—C(=X$_4$)—X$_3$—. More preferably, $X_2$ is a direct bond, —C(=O)—CH$_2$CH$_2$—C(=O)—, —CH$_2$CH$_2$—C(=O)—NH—, or —CH$_2$CH$_2$NH—C(=O)—CH$_2$CH$_2$—C(=O)—NH—; most preferably —C(=O)—CH$_2$CH$_2$—C(=O)—.

In preferred embodiments, each $X_3$ is independently —O— or —NR$_4$—, preferably —O—.

Preferably, $X_4$ is O.

In certain preferred embodiments, M is —R$_5$—X$_3$—(YX$_4$)P(=X$_4$)—X$_3$—, —R$_5$—X$_3$— or —R$_5$—X$_3$—C(=X$_4$)—, with M more preferably being —CH$_2$O—(HO)P(=O)—O—, —CH$_2$O—C(=O)— or —CH$_2$—O—. In certain other preferred embodiments, M is —R$_5$—X$_3$—C(=X$_4$)— or —R$_5$—C(=X$_4$)—X$_3$—. In yet other preferred embodiments, M is —R$_5$—X$_3$—(YX$_4$)P(=X$_4$)—X$_3$— or —X$_3$—(YX$_4$)P(=X$_4$)—X$_3$—X$_3$—R$_5$— wherein at least one of $X_3$ or $X_4$ is S.

In formula (XIII), D is a steroid. Preferably, the steroid is a compound of the formula (XIV) or any of the steroids described herein. Most preferably, the steroid is dexamethasone.

In the above formula, each $R_1$ is independently an alkyl group which ranges from 1 to about 50 carbon atoms, and all combinations and subcombinations of ranges therein, or an alkenyl group of from about 2 to about 50 carbon atoms, and all combinations and subcombinations of ranges therein. Optionally, the alkyl group and/or alkenyl group can comprise one or more halogen atoms, including perhalogenated alkyl groups and/or alkenyl groups. The halogen atom may be chlorine, fluorine, bromine or iodine, with fluorine being preferred. Preferably, each $R_1$ is independently an alkyl group of greater than 1 to about 40 carbon atoms. More preferably, each $R_1$ is independently an alkyl group of about 5 to about 30 carbon atoms. Even more preferably, each $R_1$ is independently an alkyl group of about 10 to about 20 carbon atoms, with an alkyl group of about 13 to about 17 carbon atoms being more preferred, and with about 15 carbons being still more preferred. In certain preferred embodiments, $R_1$ is a shorter chain alkyl group of from 1 to about 20 carbon atoms. In certain other preferred embodiments, $R_1$ is a longer chain alkyl group of from about 20 to about 50 carbon atoms, or about 30 to about 50 carbon atoms.

In the above formula, each $R_2$ is independently an alkylene group which ranges from 1 to about 30 carbon atoms, and all combinations and subcombinations of ranges therein. Optionally, the alkylene group can comprise one or more halogen atoms, including perhalogenated alkylene groups. The halogen atom may be chlorine, fluorine, bromine or iodine, with fluorine being preferred. Preferably, each $R_2$ is independently an alkylene group of 1 to about 20 carbon atoms. More preferably, each $R_2$ is independently an alkylene group of 1 to about 10 carbon atoms. Even more preferably, each $R_2$ is independently an alkylene group of 1 to about 5 carbon atoms, more preferably about 1 or about 2 carbon atoms, with 2 carbon atoms being most preferred.

In the above formula, each of $R_3$ and $R_4$ is independently =O, a hydrogen atom or an alkyl group which ranges from 1 to about 10 carbon atoms, and all combinations and subcombinations of ranges therein. Preferably, each of $R_3$ and $R_4$ is =O, a hydrogen atom or alkyl of 1 to about 5 carbon atoms. More preferably, each of $R_3$ and $R_4$ is a hydrogen atom.

In the above formula, each $R_5$ is independently a direct bond or an alkylene group which ranges from 1 to about 30 carbon atoms, and all combinations and subcombinations of ranges therein. Preferably, each $R_5$ is independently a direct bond or an alkylene group of 1 to about 20 carbon atoms. More preferably, each $R_5$ is independently a direct bond or an alkylene group of 1 to about 10 carbon atoms. Even more preferably, each $R_5$ is independently a direct bond or an alkylene group of 1 to about 5 carbon atoms. Still more preferably, each $R_5$ is a direct bond or —(CH$_2$)$_x$—, where x is 1 or 2.

In other preferred embodiments for the compound of formula (XIII), $X_1$ is a direct bond; $X_2$ is a direct bond; n is 0; $R_3$ is =O; $R_2$ is an unsubstituted alkylene group having from 1 to about 20 carbon atoms, preferably from about 1 to about 12 carbon atoms, more preferably from about 2 to about 6 carbon atoms, even more preferably about 4 carbon atoms (e.g., —(CH$_2$)$_4$—); $R_1$ is a substituted alkyl group having from about 1 to about 30 carbon atoms; more preferably a fluorine substituted alkyl group having from about 1 to about 20 carbon atoms; more preferably a fluorine substituted alkyl group having from about 2 to about 18 carbon atoms; even more preferably a perfluorinated alkyl group having from about 4 to about 15 carbon atoms; still more preferably a perfluorinated alkyl group having from about 6 to about 12 carbon atoms; most preferably a perfluorinated alkyl group having about 9 carbon atoms (e.g., —(CF$_2$)$_8$—CF$_3$).

D in the compound of the formula (XII) and formula (XIII) may be any steroid, steroid hormone, steroid analog, sterol or compound having affinity to steroid or steroid-like receptors. In a preferred embodiment, the steroid in formula (XII) and (XIII) above, may be a compound of the formula (XIV):

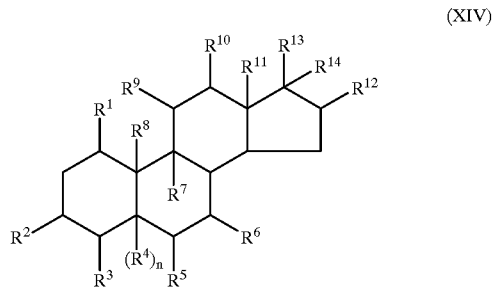

(XIV)

where $R^1$ is a saturated or unsaturated double bond; $R^2$ is R', =O, OR', R'—N—(R')$_2$, SR', C(=O)R', C(=O)OR', C(=S)OR', C(=O)SR', OC(=O)R', OOC(C$_6$H$_5$); R' is a hydrogen atom or a C$_1$ to C$_{60}$ saturated or unsaturated linear or branched hydrocarbon chain, optionally interrupted with O, S, P or N, and optionally substituted with halogen atoms; $R^3$ is a saturated or unsaturated double bond; $R^4$ is a halogen atom or R'; n is an integer of 0 or 1; $R^5$ is R' or a halogen atom; $R^6$ is R' or an unsaturated double bond; $R^7$ is R' or a halogen atom; R' is R' or an unsaturated double bond; $R^9$ is =O, OH, R' or a halogen atom; $R^{10}$ is R', a halogen atom or OH; $R^{11}$ is R' or C(=O)H; $R^{12}$ is R', OH, OCOR' or =CH$_2$; $R^{13}$ is R', =O, OH, OC(=O)R', C(=O)CH$_2$OR', C(=O)CH$_3$; C(=O)OR', CCH, or an alkyl halide group; and $R^{14}$ is R', OH, CCH, CCCH3, or OC(=O)R'.

The steroid may have an α or β stereochemistry. The halogen atoms in the compound of the formula (XIV) may be chlorine, bromine, fluorine or iodine; preferably fluorine or chlorine. R' is preferably a hydrogen atom, a methyl group, an ethyl group, a propyl group, a butyl group, a pentyl group, a hexyl group, —COCH$_2$OC(=O)C(CH$_3$), —C(=O)CH$_2$CH$_2$CO$_2$ or —COCH$_3$; more preferably R' is a hydrogen atom or a methyl group.

In addition to the steroids of formula (XIV) above, other steroids, known to those skilled in the art and described above, may be used in the present invention. Preferably, the steroid is dexamethasone. Additionally, steroids that can be used in formula (XII) and formula (XIII) include steroid hormones, sterols, steroid analogs or compounds with particular affinity to steroid or steroid-like receptors, such as diethylstilbestrol and analogs thereof; metyrapone and analogs thereof, and steroid analogs that maintain eutrogenic, androgenic, glucocorticoid, adrenocortoid, anabolic or birth control activity.

Preferably the steroid is particularly active, such that a low dose is required for a therapeutic effect. The amount of steroid to be administered depends, for example, on the particular steroid that is being administered, the method of administration of the steroid, and the age, sex, weight and physical condition of the patient. Generally, treatment is initiated with small dosages, which can then be increased by small increments until the optimum effect under the circumstances is reached. For example, the amount of steroid to be administered may variable range from about 0.1 mg to about 50 mg, preferably about 0.1 mg to about 25 mg, more preferably about 0.5 mg to about 5 mg.

Methods for synthesizing steroids are well-known to the skilled artisan and are set forth, for example, in *Organic Chemistry of Drug Synthesis*, Volume 1, Chapter 10 "Steroids" by Ledincer and Mitscher, the disclosure of which is hereby incorporated herein by reference in its entirety. The steroids of the present invention are also available from a wide variety of commercial suppliers, including, for example, *Sigma Chemical Company*, St. Louis, Mo.

In view of the present disclosure, and with knowledge of synthetic organic chemistry, one skilled in the art would readily recognize the locations on any particular steroid, linking group and lipid moiety where attachments may be made to covalently attach the steroid to the linking group and the linking group to the lipid moiety. For example, —OH, —COOH, —NH or —SH groups which are present on a steroid, a linking group or a lipid moiety are obvious points at which the steroid, linking group and lipid moiety may be attached to each other. Steroids generally have —OH, —COOH, —NH or —SH terminal groups at one or more locations, any of which may serve as the point of attachment to the linking group. If the steroid, linking group or lipid moiety does not have a —OH, —COOH, —NH or —SH terminal group, basic synthetic addition chemistry, which is well known to those skilled in the art, can be utilized to introduce an —OH group into the molecule, which would then be suitable as a point of attachment.

Although not intending to be bound by any particular theory of the invention, an example of the use of the prodrugs described herein includes attaching an acylated chemical group to the bioactive agent via an ester linkage which would readily cleave in vivo by enzymatic action in serum. The acylated prodrug may then be incorporated into the vesicle or stabilizing material. Thereafter, the prodrug may be delivered to the appropriate tissue or receptor via a targeting ligand. Upon reaching the desired tissue or receptor, the gas filled vesicle may be ruptured or popped by the sonic pulse from the ultrasound, and the prodrug encapsulated by the vesicle may then be exposed to the serum. The ester linkage may then be cleaved by esterases in the serum, thereby generating the bioactive agent. However, it is not necessary for the bioactive agent to be cleaved from the acylated chemical group and ester linkage in order for the bioactive agent to be therapeutically effective. In other words, the prodrug may retain the bioactivity of the drug or pharmaceutical agent.

Similarly, ultrasound may be utilized not only to rupture the gas filled vesicle, but also to cause thermal effects which may increase the rate of the chemical cleavage and the release of the active drug from the prodrug. The particular chemical structure of the bioactive agents may be selected or modified to achieve desired solubility such that the bioactive agent may either be encapsulated within the internal gas filled space of the vesicle, attached to the surface of the vesicle, embedded within the vesicle and/or any combination thereof. The surface-bound bioactive agent may bear one or more acyl chains such that, when the vesicle is ruptured or heated or ruptured via cavitation, the acylated bioactive agent may then leave the surface and/or the bioactive agent may be cleaved from the acyl chain chemical group. Similarly, other bioactive agents may be formulated with a hydrophobic group which is aromatic or sterol in structure to incorporate into the surface of the vesicle.

The compositions and stabilizing materials of the present invention may also comprise a targeting moiety, such as a targeting ligand. Targeting ligands are preferably associated with the stabilizing materials and/or vesicles covalently or non-covalently. In the case of stabilizing materials, the targeting ligahd may be bound, for example, via a covalent or non-covalent bond, to at least one of the lipids, proteins, polymers or surfactants incorporated in the stabilizing materials. Preferably, the targeting ligand is bound to the stabilizing materials and/or vesicles covalently. In the case of lipid compositions which comprise cholesterol, the targeting ligand is preferably bound to the cholesterol substantially only non-covalently, and/or the targeting ligand is bound covalently to a component of the composition, for example, another lipid, such as a phospholipid, other than the cholesterol.

If desired, the targeting ligands may also be bound to other stabilizing materials, for example, lipids, polymers, proteins or surfactants, which may be present in the compositions. The targeting ligands which are incorporated in the compositions of the present invention are preferably substances which are capable of targeting receptors and/or tissues in vivo or in vitro. With respect to the targeting of tissue, the targeting ligands are desirably capable of targeting heart tissue and membranous tissues, including endothelial and epithelial cells. In the case of receptors, the targeting ligands are desirably capable of targeting GPI-IbIIIa receptors or lymphocyte receptors, such as T-cells, B-cells or interleukin-2 receptors. Preferred targeting ligands for use in targeting tissues and/or receptors, including the tissues and receptors exemplified above, are selected from the group consisting of proteins, including antibodies, antibody fragments, hormones, hormone analogues, glycoproteins and lectins, peptides, polypeptides, amino acids, sugars, such as saccharides, including monosaccharides and polysaccharides, and carbohydrates, vitamins, steroids, steroid analogs, hormones, cofactors, and genetic material, including nucleosides, nucleotides, nucleotide acid constructs and polynucleotides, with peptides being particularly preferred.

An example of a protein which may be preferred for use as a targeting ligand is Protein A, which is protein that is produced by most strains of *Staphylococcus aureus*. Protein A is commercially available, for example, from Sigma Chemical Co. (St. Louis, Mo.). Protein A may then be used for binding a variety of IgG antibodies. Generally, peptides which are particularly useful as targeting ligands include natural, modified natural, or synthetic peptides that incorporate additional modes of resistance to degradation by vascularly circulating esterases, amidases, or peptidases. One very useful method of stabilization of peptide moieties incorporates the use of cyclization techniques. As an example, the end-to-end cyclization whereby the carboxy terminus is covalently linked to the amine terminus via an amide bond may be useful to inhibit peptide degradation and increase circulating half-life. Additionally, a side chain-to-side chain cyclization or an end-to-side chain cyclization is also particularly useful in inducing stability. In addition, the substitution of an L-amino acid for a D-amino acid in a strategic region of the peptide may offer resistance to biological degradation.

Preferred targeting ligands in the present invention include cell adhesion molecules (CAM), among which are, for example, cytokines, integrins, cadherins, immunoglobulins and selecting, all of which are discussed in detail below.

In connection with the targeting of endothelial cells, suitable targeting ligands include, for example, one or more of the following: growth factors, including, for example, basic fibroblast growth factor (bFGF), acidic fibroblast growth factor (aFGF), transforming growth factor-alpha (TGF-α), transforming growth factor-beta (TGF-β), platelet-derived endothelial cell growth factor (PD-ECGF) vascular endothelial growth factor (VEGF) and human growth factor (HGF); angiogenin; tumor necrosis factors, including tumor necrosis factor-alpha (TNF-α) and tumor necrosis factor-beta (TNF-β), and receptor antibodies and fragments thereof to tumor necrosis factor (TNF) receptor 1 or 2 family, including, for example, TNF-R1, TNF-R$_2$, FAS, TNFR-RP, NGF-R, CD30, CD40, CD27, OX40 and 4-1BB; copper-containing polyribonucleotide angiotropin with a molecular weight of about 4,500, as well as low molecular weight non-peptide angiogenic factors, such as 1-butyryl glycerol; the prostaglandins, including, for example, prostaglandin E$_1$ (PGE$_1$) and prostaglandin E$_2$ (PGE$_2$); nicotinamide; adenosine; dipyridamole; dobutamine; hyaluronic acid degradation products, such as, for example, degradation products resulting from hydrolysis of β linkages, including hyalobiuronic acid; angiogenesis inhibitors, including, for example, collagenase inhibitors; minocycline; medroxyprogesterone; chitin chemically modified with 6-O-sulfate and 6-O-carboxymethyl groups; angiostatic steroids, such as tetrahydrocortisol; and heparin, including fragments of heparin, such as, for example, fragments having a molecular weight of about 6,000, admixed with steroids, such as, for example, cortisone or hydrocortisone; angiogenesis inhibitors, including angioinhibin (AGM-1470—an angiostatic antibiotic); platelet factor 4; protamine; sulfated polysaccharide peptidoglycan complexes derived from the bacterial wall of an Arthobacter species; fungal-derived angiogenesis inhibitors, such as fumagillin derived from *Aspergillus fumigatus*; D-penicillamine; gold thiomalate; thrombospondin; vitamin D$_3$ analogues, including, for example, 1-α, 25-dihydroxy vitamin D$_3$ and a synthetic analogue 22-oxa-1-α, 25-dihydroxy-vitamin D$_3$; interferons, including, for example, α-interferon, β-interferon and γ-interferon; cytokines and cytokine fragments, such as the interleukins, including, for example, interleukin-1 (IL-1), interleukin-2 (IL-2), interleukin-3 (IL-3), interleukin-5 (IL-5) and interleukin-8 (IL-8); erythropoietin; a 20-mer peptide or smaller for binding to receptor or antagonists to native cytokines; granulocyte macrophage colony stimulating factor (GMCSF); LTB$_4$ leukocyte receptor antagonists; heparin, including low molecular weight fragments of heparin or analogues of heparin; simple sulfated polysaccharides, such as cyclodextrins, including α-cyclodextrin, β-cyclodextrin, and γ-cyclodextrin; tetradecasulfate; transferrin; ferritin; platelet factor 4; protamine; Gly-His-Lys complexed to copper; ceruloplasmin; (12R)-hydroxyeicosatrienoic acid; okadaic acid; lectins; antibodies; CD11a/CD18; and Very Late Activation Integrin-4 (VLA-4).

In another embodiment, small peptides which bind the interluekin-1 (IL-1) receptor may be used. For example, peptides generated by phage display core sequences of QPY have been shown to be essential for peptide binding, including, for example, AF12198, a 15-mer with a core sequence of WYQJY (SEQ ID NO: 1), where J is azetidine; and IL-1 antagonists with $K_d$ $10^{-10}$ to $10^{-12}$M, such as AcPhe-Glu, Trp-Pro-Gly-Trp-Tyr-Gln-Aze-Tyr-Ala-Leu-Pro-Leu-CONH$_2$ (SEQ ID NO: 2) or Ac-Phe-Glu-Trp-Pro-Gly-Trp-Tyr-Gln-Aze-Tyr-Ala-Leu-Pro-Leu-(SEQ ID NO: 3).

Endothelial-leukocyte adhesion molecules (ELAM's) are antigens which are expressed by endothelial cells under conditions of stress which then facilitate the migration of the leukocytes across the endothelium lining the vasculature into the surrounding tissues. These same endothelial-leukocyte adhesion molecules may be advantageously exploited as receptors for targeting of vesicles. These endothelial cell adhesion molecules belong to a family known as selectins in which the known members, such as GMP-140, all participate in endothelial-leukocyte adhesion and include ELAM-1, LAM-1 and the granule membrane protein 140 (GMP-140) also known as platelet activation-dependent granule-external membrane protein (PADGEM), VCAM-1/INCAM-110 (Vascular Adhesion Molecule/Inducible Adhesion Molecule) and ICAM-1 (Intercellular Adhesion Molecule).

The cadherin family of cell adhesion molecules may also be used as targeting ligands, including for example, the E-, N-, and P-cadherins, cadherin-4, cadherin-5, cadherin-6, cadherin-7, cadherin-8, cadherin-9, cadherin-10, and cadherin-11; and most preferably cadherin C-5. Further, antibodies directed to cadherins, such as, for example, the monoclonal antibody Ec6C10, may be used to recognize cadherins expressed locally by specific endothelial cells.

A wide variety of different targeting ligands can be selected to bind to the cytoplasmic domains of the ELAM molecules. Targeting ligands in this regard may include lectins, a wide variety of carbohydrate or sugar moieties, antibodies, antibody fragments, Fab fragments, such as, for example, Fab'2, and synthetic peptides, including, for example, Arginine-Glycine-Aspartic Acid (R-G-D) which may be targeted to wound healing. While many of these materials may be derived from natural sources, some may be synthesized by molecular biological recombinant techniques and others may be synthetic in origin. Peptides may be prepared by a variety of techniques known in the art. Targeting ligands derived or modified from human leukocyte origin, such as CD11a/CD18, and leukocyte cell surface glycoprotein (LFA-1), may also be used as these are known to bind to the endothelial cell receptor ICAM-1. The cytokine inducible member of the immunoglobulin superfamily, VCAM-1, which is mononuclear leukocyte-selective, may also be used as a targeting ligand. VLA-4, derived from human monocytes, may be used to target VCAM-1. Antibodies and other targeting ligands may be employed to target endoglin, which is an endothelial cell proliferation marker. Endoglin is upregulated on endothelial cells in miscellaneous solid tumors. A targeting ligand which may be used to target endoglin is the antibody TEC-11. Thorpe et al, *Breast Cancer Research and Treatment*, 36:237–51 (1995).

Endothelial cell activation in the setting of atherosclerosis is used in this invention to target the compositions to regions of arteriosclerosis including, for example, atherosclerotic plaque. One such target that can be used is the inducible mononuclear leukocyte endothelial adhesion molecule recognized by Rb1/9 as an ATHERO-ELAM. The monoclonal antibodies, H4/18 and H18/7, may be used to target endothelial cell surface antigens which are induced by cytokine mediators. As a preferred embodiment of this invention, gaseous precursor filled vesicles are targeted to atherosclerotic plaque to non-invasively detect diseased blood vessels before severe damage has occurred, for example, prior to stroke or myocardial infarction, so that appropriate medical or surgical intervention may be implemented. ATHERO-ELAM is a preferred target and ligands, such as antibodies, peptides, or lectins or combinations thereof may be used to target this cell surface epitope expressed on endothelial cells in the context of atherosclerosis. Alternatively, lipoproteins or lipoprotein fragments derived from low or high density lipoprotein proteins may be used as targeting ligands. Additionally, cholesterol may be used to target the endothelial cells and localize the lipids, vesicles, and the like, to regions of atherosclerotic plaque. In embodiments which involve the use of cholesterol as a targeting ligand, the cholesterol is preferably unmodified (non-derivatized) with other chemical groups, moieties, ligands, and the like.

A targeting ligand directed toward thrombotic material in the plaque may be used to differentiate between active and inactive regions of atherosclerotic plaque. Active plaques in the process of generating thrombi are more dangerous as these plaques may ultimately occlude a vessel or result in emboli. In this regard, in addition to low molecular weight heparin fragments, other targeting ligands, such as, for example, anti-fibrin antibody, tissue plasminogen activator (t-PA), anti-thrombin antibody and fibrin antibodies directed to platelet activation factions, may be used to target active plaque with evolving clots. Preferred targeting ligands are those which will target a plasma membrane associated GPIIbIIIa in activated platelets in addition to targeting P-selectin, and an antibody or associated antibody fragment directed to GPIIbIIIa. The present invention is also useful for detecting regions of acute myocardial infarction. By attaching anti-myosin (particularly cardiomyosin) antibody or anti-actin antibodies to the lipids, polymers or stabilizing materials, infarcted myocardium may be detected by the methods of the present invention. For targeting to granulation tissue (healing wounds), many of the above targeting ligands may be useful. The wound healing tripeptide, arginine-glycine-aspartic acid (RGD), may also be used as a targeting ligand in this regard.

As with the endothelial cells discussed above, a wide variety of peptides, proteins and antibodies may be employed as targeting ligands for targeting epithelial cells. Preferably, a peptide, including synthetic, semi-synthetic or naturally-occurring peptides, with high affinity to the epithelial cell target receptor may be selected, with synthetic peptides being more preferred. In connection with these preferred embodiments, peptides having from about 5 to about 15 amino acid residues are preferred. Antibodies may be used as whole antibody or antibody fragments, for example, Fab or Fab'2, either of natural or recombinant origin. The antibodies of natural origin may be of animal or human origin, or may be chimeric (mouse/human). Human recombinant or chimeric antibodies are preferred and fragments are preferred to whole antibody.

Examples of monoclonal antibodies which may be employed as targeting ligands in the present compositions include CALAM 27, which is formed by immunizing BALB/c mice with whole human squamous cell carcinoma of the tongue and forming hybridomas by crossing extracted spleen cells with those of an NS1 syngeneic myeloma cell line. Gioanni et al., *Cancer Research*, 47: 4417–4424 (1987). CALAM 27 is directed to surface epitopes of both normal and malignant epithelial cells. Normal lymph nodes generally do not contain cells expressing these epitopes. See *Cancer Research*, 47:4417–4424 (1987). Accordingly, lipid and/or vesicle compositions comprising this antibody can be used to target metastases in the lymph nodes. The monoclonal antibody 3C2 may be employed as a targeting ligand for targeting malignant epithelial cells of serious ovarian carcinoma and endometrioid carcinoma. Another exemplary targeting ligand is Mab 4C7 (see *Cancer Research*, 45:2358–2362 (1985)), which may be used to target mucinous carcinoma, endometriod carcinoma and mesonephroid carcinoma. For targeting squamous cell carcinoma in head and neck cancer, Mab E48 (*Biological Abstract*, Vol. 099 Issue. 066 Ref. 082748) may be used as a targeting ligand. For targeting malignant melanoma, the monoclonal antibody 225.28s (*Pathol. Biol.*, 38 (8):866–869 (1990)) may be employed. The monoclonal antibody mAb2E$_1$, which is targeted to EPR-1 (effector cell protease 1), may also be used.

Targeting ligands may be selected for targeting antigens, including antigens associated with breast cancer, such as epidermal growth factor receptor (EGFR), fibroblast growth factor receptor, erbB2/HER-2 and tumor associated carbohydrate antigens (*Cancer*, 74 (3):1006–12 (1994)). CTA 16.88, homologous to cytokeratins 8, 18 and 19, is expressed by most epithelial-derived tumors, including carcinomas of the colon, pancreas, breast, ovary and lung. Thus, antibodies directed to these cytokeratins, such as 16.88 (IgM) and 88BV59 (IgG3k), which recognize different epitopes on CTA 16.88 (*Semin. Nucl. Med.*, 23 (2):165–79 (1993)), maybe employed as targeting ligands. For targeting colon cancer, anti-CEA IgG Fab' fragments may be employed as targeting ligands. Chemically conjugated bispecific anti-cell surface antigen, anti-hapten Fab'-Fab antibodies may also be used as targeting ligands. The MG series monoclonal antibodies may be selected for targeting, for example, gastric cancer (*Chin. Med. Sci. J.*, 6 (1):56–59 (1991).

There are a variety of cell surface epitopes on epithelial cells for which targeting ligands may be selected. For example, the protein human papilloma virus (HPV) has been associated with benign and malignant epithelial proliferations in skin and mucosa. Two HPV oncogenic proteins, E6 and E7, may be targeted as these may be expressed in certain epithelial derived cancers, such as cervical carcinoma. See *Curr. Opin. Immunol.*, 6 (5):746–54 (1994). Membrane receptors for peptide growth factors (PGF-R), which are involved in cancer cell proliferation, may also be selected as tumor antigens. *Anticancer Drugs*, 5(4):379–93 (1994). Also, epidermal growth factor (EGF) and interleukin-2 may be targeted with suitable targeting ligands, including peptides, which bind these receptors. Certain melanoma associated antigens (MAA), such as epidermal growth factor receptor (EGFR) and adhesion molecules (*Tumor Biol.*, 15 (4):188–202 (1994)), which are expressed by malignant melanoma cells, can be targeted with the compositions provided herein. The tumor associated antigen FAB-72 on the surface of carcinoma cells may also be selected as a target.

A wide variety of targeting ligands may be selected for targeting myocardial cells. Exemplary targeting ligands include, for example, anticardiomyosin antibody, which may comprise polyclonal antibody, Fab'2 fragments, or be of human origin, animal origin, for example, mouse origin, or of chimeric origin. Additional targeting ligands include dipyridamole; digitalis; nifedipine; apolipoprotein; low density lipoproteins (LDL), including α-LDL, vLDL and methyl LDL; ryanodine; endothelin; complement receptor type 1; IgG Fc; beta 1-adrenergic; dihydropyridine; adenosine; mineralocorticoid; nicotinic acetylcholine and muscarinic acetylcholine; antibodies to the human alpha 1A-adrenergic receptor; bioactive agents, such as drugs, including the alpha 1-antagonist prazosin; antibodies to the anti-beta-receptor; drugs which bind to the anti-beta-receptor; anti-cardiac RyR antibodies; endothelin-1, which is an endothelial cell-derived vasoconstrictor peptide that exerts a potent positive inotropic effect on cardiac tissue (endothelin-1 binds to cardiac sarcolemmal vesicles); monoclonal antibodies which may be generated to the T-cell receptor α-β receptor and thereby employed to generate targeting ligands; the complement inhibitor sCR1; drugs, peptides or antibodies which are generated to the dihydropyridine receptor; monoclonal antibodies directed towards the anti-interleukin-2 receptor may be used as targeting ligands to direct the present compositions to areas of myocardial tissue which express this receptor and which may be up-regulated in conditions of inflammation; cyclosporine for directing similarly the compositions to areas of inflamed myocardial tissue; methylisobutyl isonitrile; lectins which bind to specific sugars on membranes of cardiac myocytes and cardiac endothelial cells; adrenomedullin (ADM), which is an endogenous hypotensive and vasorelaxing peptide; atrial natriuretic peptide (ANP); C-type natriuretic peptide (CNP), which is a 22 amino acid peptide of endothelial cell origin and is structurally related to atrial natriuretic peptide but genetically distinct, and possesses vasoactive and antimitogenic activity; vasonatrin peptide (VNP) which is a chimera of atrial natriuretic peptide (ANP) and C-type natriuretic peptide (CNP) and comprises 27 amino acids; thrombin; endothelium-derived relaxing factor (EDRF); neutral endopeptidase 1 (NEP-1); competitive inhibitors to EDRF, including, for example, NG-monomethyl-L-arginine (L-NMMA); potassium channel antagonists, such as charybdotoxin and glibenclamide; antiheart antibodies, which may be identified in patients with idiopathic dilated cardiomyopathy but which preferably do not elicit cytolysis in the myocardium; antibodies directed against the adenine nucleotide translocator, the branched-chain keto acid dehydrogenase or cardiac myosin; specific antagonists for the endothelin-A receptor, which may be referred to as BQ-123; and antibodies to the angiotensin II receptor.

Two of the major antigens of heart sarcolemmal are calcium binding glycoproteins which copurify with the dihydropyridine receptor. Antisera may be raised, including polyclonal or monoclonal antibodies, against purified sarcolemma. These antibodies may also be employed as targeted ligands. Purified fractions of the calcium binding glycoproteins may be isolated from the plasma membranes of the sarcolemma and then used to generate antibodies. ANP, which, as noted above, may be used as a targeting ligand, can be obtained from cultures of human aortic endothelial cells. ANP is generally localized in endothelium, but also may localize to the endothelial or myocardial tissue. ANP may be prepared, for example, using recombinant techniques, as well as by synthesis of the peptide using peptide synthesis techniques well known to one skilled in the art. It is also possible to use an antibody, either polyclonal or monoclonal, directed towards ANP. Similarly, a peptide directed to ANP may be used for targeting endothelial and/or myocardial cells. Both the β and α forms of atrial natriuretic factor may be used as potential targeting ligands for directing the present compositions to myocardial tissue.

A wide variety of targeting ligands may be employed to direct the present stabilizing materials, and particularly vesicle compositions, to the GPIIbIIIa receptor. Compositions which are directed to the GPIIbIIIa receptor are highly useful for targeting vascular thromboses or clots, and are useful for diagnosing, as well as treating such clots. Included among such targeting ligands are, for example, peptides, such as Arg-Gly-Asp-Ser (RGDS)(SEQ ID NO:4), Gly-Arg-Gly-Asp-Ser-Pro (GRGDSP) (SEQ ID NO: 5), and Gly-Pro-Arg-Pro (GPRP) (SEQ ID NO: 6). Pentapeptides containing the sequence Arg-Gly-Asp (RGD) are also useful including, for example, G4120, which is a cyclic peptide containing the amino acid sequence Arg-Gly-Asp (RGD). Also useful are peptides derived from human coagulation Factor XIIIA including, for example, fragments such as NKLIVRRGQS-FYVQIDFSRPYDPRR DLFRVEYVIGRYPQENKGTY-IPVPIVSELQSGKWGAKIVMREDRSVRL-SIQSSPKCIVGK FRMYVAVWTPYGVLRTSRNPETDTYIL-FNPWCEDDAVYLDNEKEREEYVLNDIGVIFY GEVNDIKTRSWSYGQF-R' (SEQ ID NO: 7) where R' is —CONH$_2$ or —NH$_2$. In addition, peptides which are fragments of the Factor XIIIA fragment, which include in their sequence the sequence NKLIVRRGOSFYVQIDFSRPYD-PRRD (SEQ ID NO: 8) or DDAVYLDNE KEREEYVLN-DIGVIFYGEVNDIKTRSWSYGQF (SEQ ID NO: 9).

Additional peptides which may be useful as targeting ligands for targeting the GPIIbIIIa receptor include, for example, peptides comprising the tripeptide sequence of arginine-tyrosine-aspartic acid (Arg-Tyr-Asp; also abbreviated RGD), linked from amino-to-carboxy-terminus and which may bind to the GPIIbIIIa binding region on activated platelets. Exemplary of such peptides include, for example, peptides of the general formula $R^1$-$(X^1)_n$-Arg-Tyr-Asp-$(Y)_o$-$(X^2)_m$-$R^2$, wherein each of $X^1$, $X^2$ and Y may independently be one or more amino acid residues while, in certain cases, it is preferred that Y is other than a serine or alanine residue, and each of m, n and o is independently 0 or 1, provided, in certain cases, that when m is 1, then o is 1, and R' is a protected or unprotected terminal amino group and $R^2$ is a protected or unprotected terminal carboxy group. In a preferred embodiment, $X^1$ is the peptide Ala-Arg-Arg-Ser-Ser-Pro-Ser-Tyr-Tyr (SEQ ID NO: 10) and $X^2$ is the peptide Gly-Ala-Gly-Pro-Tyr-Tyr-Ala-Met-Asp-Tyr (SEQ ID NO: 11). Useful peptides include Arg-Ser-Pro-Ser-Tyr-Tyr-Arg-Tyr-Asp-Gly-Ala-Gly-Pro-Tyr-Tyr-Ala-Met-Asp-Tyr (SEQ ID NO: 12) and Ala-Arg-Arg-Ser-Pro-Ser-Tyr-Tyr-Arg-Tyr-Asp-Gly-Ala-Gly-Pro-Tyr-Tyr-Ala-Met-Asp-Tyr (SEQ ID NO: 13).

Synthetic compounds which combine a natural amino acid sequence with synthetic amino acids can also be used as the targeting ligand, such as a fibrinogen receptor antagonist compound which comprises the sequence XX-Gly-Asp, wherein XX is a synthetic α-amino acid containing a linear side chain, such as

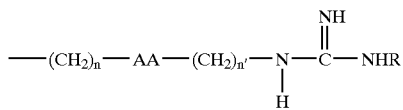

wherein n+n' is 3; AA is a single bond; and R is phenyl or benzyl; or —(CH$_2$)$_n$—AA—(CH$_2$)$_n$—NHR, wherein n is an integer of 1 to 4; n' is an integer of 2 to 4; AA is oxygen, sulfur or a single bond; and R is H, C$_{1-6}$ alkyl, optionally substituted aryl, optionally substituted arylmethyl or optionally substituted cycloalkyl, provided, in certain cases, that when AA is a single bond and R is H, then n+n' is other than 3 or 4.

Another such compound comprises a fibrinogen receptor antagonist of the formula:

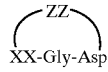

wherein XX is a synthetic α-amino acid containing a linear side chain having the formula

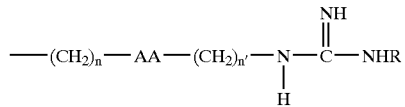

wherein n+n' is 3; AA is a single bond; and R is phenyl or benzyl; or —(CH$_2$)$_n$—AA—(CH$_2$)$_n$—NHR, wherein n is an integer of 1 to 4; n' is an integer of 2 to 4; AA is oxygen, sulfur or a single bond; and R is H, C$_{1-6}$ alkyl, optionally substituted cycloalkyl, provided that, in certain cases, when AA is a single bond and R is H, then n+n' is other than 3 or 4, and ZZ is a sequence of 1 to 4 optionally substituted amino acids.

Other useful peptides for use as targeting ligands include, for example, Elegantin, which has the following sequence: Gly-Glu-Glu-Cys-Asp-Cys-Gly-Ser-Pro-Glu-Asn-Pro-Cys-Cys-Asp-Ala-Ala-Thr-Cys-Lys-Leu-Arg-Pro-Gly-Ala-Gln-Cys-Ala-Asp-Gly-Leu-Cys-Cys-Asp-Gln-Cys-Arg-Phe-Lys-R-R'-Arg-Thr-Ile-Cys-Arg-Arg-Ala-Arg-Gly-Asp-Asn-Pro-Asp-Asp-Arg-Cys-Thr-Gly-Gln-Ser-Ala-Asp-Cys-Pro-Arg-Asn-Gly-Tyr (SEQ ID NO: 14), wherein each of R and R' is independently any amino acid; Albolabrin, which has the following sequence: Glu-Ala-Gly-Glu-Asp-Cys-Asp-Cys-Gly-Ser-Pro-Ala-Asn-Pro-Cys-Cys-Asp-Ala-Ala-Thr-Cys-Lys-Leu-Leu-Pro-Gly-Ala-Gln-Cys-Gly-Glu-Gly-Leu-Cys-Cys-Asp-Gln-Cys-Ser-Phe-Met-Lys-Lys-Gly-Thr-Ile-Cys-Arg-Arg-Ala-Arg-Gly-Asp-Asp-Leu-Asp-Asp-Tyr-Cys-Asn-Gly-Ile-Ser-Ala-Gly-Cys-Pro-Arg-Asn-Pro-Leu-His-Ala (SEQ ID NO: 15); Batroxostatin, which has the following sequence: Glu-Ala-Gly-Glu-Glu-Cys-Asp-Cys-Gly-Thr-Pro-Glu-Asn-Pro-Cys-Cys-Asp-Ala-Ala-Thr-Cys-Lys-Leu-Arg-Pro-Gly-Ala-Gln-Cys-Ala-Glu-Gly-Leu-Cys-Cys-Asp-Gln-Cys-Arg-Phe-Lys-Gly-Ala-Gly-Lys-Ile-Cys-Arg-Arg-Ala-Arg-Gly-Asp-Asn-Pro-Asp-Asp-Cys-Thr-Gly-Gln-Ser-Ala-Asp-Cys-Pro-Arg-Phe (SEQ ID NO: 16); and Flavoridin, which has the following sequence: Gly-Gly-Glu-Cys-Asp-Cys-Gly-Ser-Pro-Glu-Asn-Pro-Cys-Cys-Asp-Ala-Ala-Thr-Cys-Lys-Leu-Arg-Pro-Gly-Ala-Gln-Cys-Ala-Asp-Gly-Leu-Cys-Cys-Asp-Gln-Cys-Arg-Phe-Lys-R-R'-Arg-Thr-Ile-Cys-Arg-Ile-Ala-Arg-Gly-Asp-Phe-Pro-Asp-Asp-Arg-Cys-Thr-Gly-Leu-Ser-Ala-Asp-Cys-Pro-Arg-R-Asn-Asp-Leu (SEQ ID NO: 17), wherein each of R and R' is independently any amino acid.

Other ligands useful for targeting the GPIIbIIIa receptor include synthetic compounds, such as Ac-(D)Phe-Pro-boroArg and the cyclic peptidomimetic cyclo(D-2-aminobutyrate-N-Methyl-L-Arginyl-Glycyl-L-Aspartyl-3-amino-methyl-benzoic acid): methanesulfonate salt. Peptides that can also be used include a library of hexapeptides flanked by cysteine residues (capable of forming cyclic disulfides) and cyclic, disulfide-bonded forms of peptides with the sequence Arg-Gly-Asp or Lys-Gly-Asp, as well as the carboxyl-terminal derived peptide, REYVVMWK (SEQ ID NO: 18). Certain matrix glycoproteins such as Thrombospondin are also useful in this regard. Members of the serpin family of serine protease inhibitors, such as Plasminogen activator inhibitor type 1 (PAI-1) are other useful ligands.

Generally, it is preferred to employ as targeting ligands for the GPIIbIIIa receptor a peptide having from about 3 to about 20 amino acids, with peptides having from about 4 to about 15 amino acids being more preferred. Even more preferably, targeting ligands for the GPIIbIIIa receptor may comprise peptides having from about 4 to about 8 amino acids, with peptides having from about 4 to about 6 amino acids or about 5 amino acids being still more preferred. If desired, the peptides may be cyclized, for example, by (1) side chain-to-side chain covalent linkages, including, for example, by the formation of a disulfide linkage via the oxidation of two thiol containing amino acids or analogs thereof, including, for example, cysteine or penicillamine; (2) end-to-side chain covalent linkages, including, for example, by the use of the amino terminus of the amino acid sequence and a side chain carboxylate group, such as, for example, a non-critical glutamic acid or aspartic acid group. Alternatively, the end-to-side chain covalent linkage may involve the carboxylate terminus of the amino acid sequence and a side chain amino, amidine, guanidine, or other group in the sidechain which contains a nucleophilic nitrogen atom, such sidechain groups including, for example, lysine, arginine, homoarginine, homolysine, or the like; (3) end-to-end covalent linkages that are covalent amide linkages, or the like. Such processes are well known to those skilled in the art. In addition, "pseudocyclization" may be employed, in which cyclization occurs via non-covalent interactions, such as electrostatic interactions, which induces a folding of the secondary structure to form a type of cyclic moiety. It is contemplated that metal ions may aid the induction of a "pseudocyclic" formation. This type of pseudocyclic formation may be analogous to "zinc fingers." As known to one of ordinary skill in the art, zinc fingers involve the formation due to electrostatic interactions between a zinc ion ($Zn^{2+}$) and cysteine, penicillamine and/or homocysteine, of a region in the shape of a loop (the finger). In the case of homocysteine, the RGD sequence would reside at the tip of the finger. Of course, it is recognized that, in the context of the present invention, any type of stabilizing cyclization would be suitable as long the recognition and binding peptide ligand, such as, for example, RGD, maintains the proper conformation and/or topography to bind to the appropriate receptor in clots with a reasonable Michaelis-Menten constant ($k_m$) or binding constant. As used herein, the term "conformation" refers to the three-dimensional organization of the backbone of the peptide, peptoid, or pseudopeptide, and the term "topography" refers to the three-dimensional organization of the sidechain of the peptide, peptoid, or pseudopeptide.

Other suitable targeting ligands include the following compounds: Ac-Cys-Arg-Gly-Asp-Met-Phe-Gly-Cys-CONH$_2$ (SEQ ID NO: 19); Ac-Cys-Arg-Gly-Asp-Met-Leu-Arg-Cys-CONH$_2$ (SEQ ID NO: 20); Ac-Cys-Arg-Gly-Asp-Phe-Leu-Asn-Cys-CONH$_2$ (SEQ ID NO: 21); Ac-Cys-Asn-Thr-Leu-Lys-Gly-Asp-Cys-CONH$_2$ (SEQ ID NO: 22); Ac-Cys-Asn-Trp-Lys-Arg-Gly-Asp-Cys-CONH$_2$ (SEQ ID NO: 23); and Ac-Cys-N-methyl-Arg-Gly-Asp-Pen-CONH$_2$ (SEQ ID NO: 24), where "Pen" refers to penicillamine (β,β-dimethylcysteine).

Other compounds which may be used as targeting ligands include peptides, or derivatives thereof, represented by the formula A-B-Arg-Gly-Asp-C-D  (SEQ ID NO: 25)

wherein A is proline, thioproline, hydroxyproline, dehydroproline, 2-oxo-4-thiazolidine carboxylic acid, N-alkyl glycine or an amino acid derivative of the formula

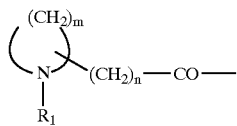

tryptophan, or a tryptophan derivative of the formula

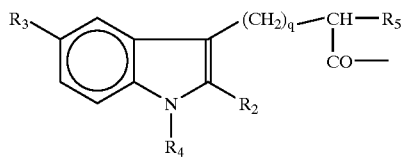

pyroglutamic acid or 2-azetidinone-4-carboxylic acid

B is serine, glycine, valine, alanine, threonine or β-alanine; C is an amino acid group having a hydrophobic functional group; and D is hydroxy or amino; wherein $R_1$ is hydrogen, —(CH$_2$)$_p$CH$_3$ or —CO—(CH$_2$)$_p$CH$_3$; $R_2$ is hydrogen or alkyl; $R_3$ is hydrogen or alkoxy; $R_4$ is hydrogen or alkyl; $R_5$ is hydrogen, amino or acylamino; m is an integer of 2 to 5; n is an integer of 0 to 2; p is an integer of 0 to 5; and q is an integer of 0 to 3.

Another targeting ligand which may be suitable for use in connection with the present compositions is a peptide, a peptide derivative, or a salt thereof having the formula A-B-Arg-Gly-Asp-C-D  (SEQ ID NO: 25)

where A is arotic acid or hydroorotic acid; B is an amino acid; C is an amino acid having a hydrophobic functional group; and D is hydroxy or amino. In the above compounds, examples of amino acids having hydrophobic functional groups in the definition of "C" are tryptophan and phenylalanine.

Various peptides which would be suitable for use as a targeting ligand in connection with the present invention, especially for targeting GPIIbIIIa, are disclosed, for example, in U.S. Pat. No. 5,498,601 and European Patent Applications: 0 368 486 A2, 0 382 451 A2, and 0 422 938 B1, the disclosures of which are hereby incorporated herein by reference, in their entirety. Other targeting ligands which may be used in the compositions of the present invention, in addition to those exemplified above, would be apparent to one of ordinary skill in the art in view of the present disclosure. Suitable targeting ligands include, for example, conjugated peptides, such as, for example, glycoconjugates and lectins, which are peptides attached to sugar moieties. The compositions may comprise a single targeting ligand, as well as two or more different targeting ligands.

The targeting ligand is preferably covalently bound to the surface of the stabilizing material or vesicle by a spacer including, for example, hydrophilic polymers, preferably polyethylene glycol. Preferred molecular weights of the polymers are from 1000 da to 10,000 da, with 500 da being most preferred. Preferably the polymer is bifunctional with the targeting ligand bound to a terminus of the polymer. Generally, the targeting ligand will range from about 0.1 to about 20 mole % of the exterior components of the vesicle. In the case of gas-filled lipid vesicles, this amount is preferably between about 0.5 and about 10 mole % with about 1 to about 10 mole % being most preferred. The exact ratio will depend upon the particular targeting ligand.

In one embodiment of the invention, the targeting ligands are directed toward lymphocytes which may be T-cells or B-cells, with T-cells being the preferred target. Depending on the targeting ligand, the composition may be targeted to one or more classes or clones of T-cells. To select a class of targeted lymphocytes, a targeting ligand having specific affinity for that class is employed. For example, an anti CD-4 antibody can be used for selecting the class of T-cells harboring CD-4 receptors, an anti CD-8 antibody can be used for selecting the class of T-cells harboring CD-8 receptors, an anti CD-34 antibody can be used for selecting the class of T-cells harboring CD-34 receptors, etc. A lower molecular weight ligand is preferably employed, e.g., Fab or a peptide fragment. For example, an OKT3 antibody or OKT3 antibody fragment may be used. When a receptor for a class of T-cells or clones of T-cells is selected, the composition will be delivered to that class of cells. Using HLA-derived peptides, for example, will allow selection of targeted clones of cells expressing reactivity to HLA proteins.

The ultimate purpose of the linkage between the targeting ligand and the target may be the delivery of a bioactive agent to the cell for endocytosis or fusion. Although not intending to be bound by any particular theory of operation, once the stabilizing material or vesicle has linked to its target, the bioactive agent may gain access to the interior of the target cell either through a fusion-initiated capping and patching mechanism, the intervention of clathrin-coated pits or through classical endocytosis, depending on the mechanisms for engulfnent peculiar to the target cell, or by other natural or induced means. A bioactive agent, such as dexamethasone, then stimulates programmed cell death (apoptosis) through its well-established cytotoxicity. One skilled in the art will recognize the potential for other such targeted uses of bioactive agents which gain access to the target cells or tissue via ligand-receptor binding.

The following table illustrate ligands from the major histocompatability complex (MHC) and their receptors in the class of T-cells for which they have affinity. All the ligands, T-cell receptors and peptide sequences in the table below may be used in the present invention.

TABLE 1

MHC LIGANDS AND T-CELL RECEPTORS

| T-Cell Receptor | Ligand | Peptide Sequence | SEQ ID NO. |
|---|---|---|---|
| HTB157.7 | $K^b$(Q10b hybrid) | Heterogeneous | |
| HTB157.7 | $pK^b$163–174 | NA | |
| 2C | $L^d$/p2Ca | LSPFPFDL* | 26 |
| 2C | $L^d$/p2Ca-A5 | LSPFAFDL | 27 |
| 2C | $L^d$/p2Ca-A3 | LSAFPFDL | 28 |
| 2C | $L^d$/p2Ca-A8 | LSPFPFDA | 29 |
| 2C | $L^d$/SL9 | SPFPFDLLL | 30 |
| 2C | $K^b$/p2Ca | LSPFPFDL | 26 |
| 2C | $L^d$/QL9 | QLSPSPDL | 31 |
| 4G3 | $K^b$/pOV8 | SIINFEKL | 32 |
| 2C | $L^d$/p2Ca-Y4 | LSPYPFDL | 33 |
| 2C | $L^d$/p2Ca-A1 | ASPFPFDL | 34 |
| Clone 30 | $K^b$/IgG (bivalent) | Heterogeneous | |
| 14.3d | 1-$E^d$/pHA | SSFGAFGIFPK | 35 |
| 5C.C7 | 1-$E^k$/MCC | ANERADLIAYLKQATK | 36 |
| 228.4 | 1-$E^k$/MCC-K99A | ANERADLIAYLKQATK | 36 |
| 2B4 | 1-$E^k$/MCC | ANERADLIAYLKQATK | 36 |
| 2B4 | 1-$E^k$/PCC | ANERADLIAYLKQATAK | 37 |
| 2B4 | 1-$E^k$/MCC-T102S | ANERADLIAYLKQASK | 38 |
| HA1.7 | SEB | | |
| 14.3d β | SEC1 | | |
| 14.3d β | SEC2 | | |
| 14.3d β | SEC3 | | |

TABLE 1-continued

MHC LIGANDS AND T-CELL RECEPTORS

| T-Cell Receptor | Ligand | Peptide Sequence | SEQ ID NO. |
|---|---|---|---|
| 14.3d β | SEB | | |
| 14.3d β | SPEA | | |

*Single-letter code for amino acids. Summarized from Fremont et al, Current Opinion In Immunology, (1996) 8:93–100, page 96, Table 2, the disclosure of which is hereby incorporated herein by reference in its entirety.

Another major area for targeted delivery involves the interlekin-2 (IL-2) system. IL-2 is a t-cell growth factor produced following antigen or mitogen induced stimulation of lymphoid cells. Among the cell types which produce IL-2 are $CD4^+$ and $CD8^+$ t-cells and large granular lymphocytes, as well as certain t-cell tumors. IL-2 receptors are glycoproteins expressed on responsive cells. They are notable in connection with the present invention because they are readily endocytosed into lysosomal inclusions when bound to IL-2. The ultimate effect of this endocytosis depends on the target cell, but among the notable in vivo effects are regression of transplantable murine tumors, human melanoma or renal cell cancer. IL-2 has also been implicated in antibacterial and antiviral therapies and plays a role in allograft rejection. In addition to IL-2 receptors, preferred targets include the anti-IL-2 receptor antibody, natural IL-2 and an IL-2 fragment of a 20-mer peptide or smaller generated by phage display which binds to the IL-2 receptor.

Although not intending to be bound by any particular theory of operation, IL-2 can be conjugated to the stabilizing materials and/or other delivery vehicles and thus mediate the targeting of cells bearing IL-2 receptors. Endocytosis of the ligand-receptor complex would then deliver a bioactive agent to the targeted cell, thereby inducing its death through apoptosis—independent and superceding any proliferative or activiating effect which IL-2 would promote alone.

Additionally, an IL-2 peptide fragment which has binding affinity for IL-2 receptors can be incorporated either by direct attachment to a reactive moiety on the bioactive agent or via a spacer or linker molecule with a reactive end such as an amine, hydroxyl, or carboxylic acid functional group. Such linkers are well known in the art and may comprise from 3 to 20 amino acid residues. Alternatively, D-amino acids or derivatized amino acids may be used which avoid proteolysis in the target tissue.

Still other systems which can be used in the present invention include IgM-mediated endocytosis in B-cells or a variant of the ligand-receptor interactions described above wherein the T-cell receptor is CD2 and the ligand is lymphocyte function-associated antigen 3 (LFA-3), as described, for example, by Wallner et al, *J. Experimental Med.*, 166:923–932 (1987), the disclosure of which is hereby incorporated by reference herein in its entirety.

The targeting ligand may be incorporated in the present stabilizing materials in a variety of ways. Generally speaking, the targeting ligand may be incorporated in the present stabilizing materials by being associated covalently or non-covalently with one or more of the stabilizing materials which are included in the compositions including, for example, the bioactive agents, lipids, proteins, polymers, surfactants, and/or auxiliary stabilizing materials. In preferred form, the targeting ligand may be associated covalently with one or more of the aforementioned materials contained in the present stabilizing materials. Preferred stabilizing materials of the present invention comprise bioactive agent, lipid, protein, polymer or surfactant compounds. In these compositions, the targeting ligands are preferably associated covalently with the bioactive agent, lipid, protein, polymer or surfactant compounds.

Exemplary covalent bonds by which the targeting ligands are associated with the stabilizing materials include, for example, amide (—CONH—); thioamide (—CSNH—); ether (ROR'), where R and R' may be the same or different and are other than hydrogen); ester (—COO—); thioester (—OS—); —O—; —S—; —S$_n$—, where n is greater than 1, preferably about 2 to about 8, and more preferably about 2; carbamates; —NH—; —NR—, where R is alkyl, for example, alkyl of from 1 to about 4 carbons; urethane; and substituted imidate; and combinations of two or more of these. Covalent bonds between targeting ligands and, for example, lipids, may be achieved through the use of molecules that may act as spacers to increase the conformational and topographical flexibility of the ligand. Examples of such spacers include, for example, succinic acid, 1,6-hexanedioic acid, 1,8-octanedioic acid, and the like, as well as modified amino acids, such as, for example, 6-aminohexanoic acid, 4-aminobutanoic acid, and the like. In addition, in the case of targeting ligands which comprise peptide moieties, side chain-to-side chain crosslinking may be complemented with side chain-to-end crosslinking and/or end-to-end crosslinking. Also, small spacer molecules, such as dimethylsuberimidate, may be used to accomplish similar objectives. The use of agents, including those used in Schiff's base-type reactions, such as gluteraldehyde, may also be employed. The Schiff's base linkages, which may be reversible linkages, can be rendered more permanent covalent linkages via the use of reductive amination procedures. This may involve, for example, chemical reducing agents, such as lithium aluminum hydride reducing agents or their milder analogs, including lithium aluminum diusobutyl hydride (DIBAL), sodium borohydride (NaBH$_4$) or sodium cyanoborohydride (NaBH$_3$CN).

The covalent linking of the targeting ligands to the stabilizing materials in the present compositions may be accomplished using synthetic organic techniques which would be apparent to one of ordinary skill in the art in view of the present disclosure. For example, the targeting ligands may be linked to the materials, including the lipids, via the use of well known coupling or activation agents. As known to the skilled artisan, activating agents are generally electrophilic, which can be employed to elicit the formation of a covalent bond. Suitable activating agents which may be used include, for example, carbonyldiimidazole (CDI), dicyclohexylcarbodiimide (DCC), diisopropylcarbodiimide (DIC), methyl sulfonyl chloride, Castro's Reagent, and diphenyl phosphoryl chloride.

The covalent bonds may involve crosslinking and/or polymerization. Cross-linking preferably refers to the attachment of two chains of polymer molecules by bridges, composed of either an element, a group, or a compound, which join certain carbon atoms of the chains by covalent chemical bonds. For example, crosslinking may occur in polypeptides which are joined by the disulfide bonds of the cystine residue. Crosslinking may be achieved, for example, by (1) adding a chemical substance (crosslinking agent) and exposing the mixture to heat, or (2) subjecting a polymer to high energy radiation. A variety of crosslinking agents, or "tethers", of different lengths and/or functionalities are described, for example, by Lunbland, *Techniques in Protein Modification*, CRC Press, Inc., Ann Arbor, Mich., pp. 249–68 (1995), the disclosures of which is hereby incorporated herein by reference in its entirety. Exemplary crosslinkers include, for example, 3,3'-dithiobis (succinimidylpropionate), dimethyl suberimidate, and its variations thereof, based on hydrocarbon length, and bis-N-maleimido-1,8-octane.

Additionally, the targeting ligands may be linked or attached to the bioactive agents, lipids, proteins, polymers, or surfactants or other stabilizing materials via a linking group. A variety of linking groups are available and would be apparent to one skilled in the art in view of the present disclosure. Preferably, the linking group comprises a hydrophilic polymer. Suitable hydrophilic polymers include, for example, polyalkyleneoxides such as, for example, polyethylene glycol (PEG) and poly-propylene glycol (PPG), polyvinylpyrrolidones, polyvinylmethylethers, polyacrylamides, such as, for example, polymethacrylamides, polydimethylacrylamides and polyhydroxypropyl-methacrylamides, polyhydroxyethyl acrylates, polyhydroxypropyl methacrylates, polymethyloxazolines, polyethyloxazolines, polyhydroxyethyloxazolines, polyhyhydroxypropyloxazolines, polyvinyl alcohols, polyphosphazenes, poly(hydroxyalkylcarboxylic acids), polyoxazolidines, polyaspartamide, and polymers of sialic acid (polysialics). The hydrophilic polymers are preferably selected from the group consisting of PEG, PPG, polyvinylalcohol and polyvinylpyrrolidone and copolymers thereof, with PEG and PPG polymers being more preferred and PEG polymers being even more prefered. Thus, in embodiments involving lipid compositions which comprise lipids bearing polymers including, for example, DPPE-PEG, the targeting ligand may be linked directly to the polymer which is attached to the lipid to provide, for example, a conjugate of DPPE-PEG-TL, where TL is a targeting ligand. Thus, using the example DPPE-PEG, such as, for example, DPPE-PEG5000, the aforementioned conjugate may be represented as DPPE-PEG5000-TL. The hydrophilic polymer used as a linking group is preferably a bifunctional polymer, for example, bifunctional PEG, such as diamino-PEG. In this case, one end of the PEG group is linked, for example, to a lipid compound, and is bound at the free end to the targeting ligand via an amide linkage. A hydrophilic polymer, for example, PEG, substituted with a terminal carboxylate group on one end and a terminal amino group on the other end, may also be used. These latter bifunctional hydrophilic polymer may be preferred since they possess various similarities to amino acids.

Standard peptide methodology may be used to link the targeting ligand to the lipid when utilizing linker groups having two unique terminal functional groups. Bifunctional hydrophilic polymers, and especially bifunctional PEGs, may be synthesized using standard organic synthetic methodologies. In addition, many of these materials are available commercially, such as, for example, α-amino-ω-carboxy-PEG which is commercially available from Shearwater Polymers (Huntsville, Ala.). An advantage of using a PEG material as the linking group is that the size of the PEG can be varied such that the number of monomeric subunits of ethylene glycol may be as few as, for example, about 5, or as many as, for example, about 500 or even greater. Accordingly, the "tether" or length of the linkage may be varied, as desired. This may be important depending, for example, on the particular targeting ligand employed. For example, a targeting ligand which comprises a large protein molecule may require a short tether, such that it will simulate a membrane bound protein. A short tether would also allow for a vesicle to maintain a close proximity to the cell. This can be used advantageously in connection with vesicles which also comprise a bioactive agent in that the concentration of bioactive agent which is delivered to the cell may be advantageously increased.

Another suitable linking group which may provide a short tether is glyceraldehyde. Glyceraldehyde may be bound, for example, to DPPE via a Schiff's base reaction. Subsequent Amadori rearrangement can provide a substantially short linking group. The β carbonyl of the Schiff's base may then react with a lysine or arginine of the targeting protein or peptide to form the targeted lipid.

More specifically, the compounds employed in the present stabilizing materials may contain various functional groups, such as, for example, hydroxy, thio and amine groups, which can react with a carboxylic acid or carboxylic acid derivative of the hydrophilic polymeric linker using suitable coupling conditions which would be apparent to one of ordinary skill in the art in view of the present disclosure. After the carboxylic acid group (or derivative thereof) reacts with the functional group, for example, hydroxy, thio or amine group to form an ester, thioester or amide group, any protected functional group may be deprotected utilizing procedures which would be well known to one skilled in the art. The term protecting group refers to any moiety which may be used to block the reaction of a functional group and which may be removed, as desired, to afford the unprotected functional group. Any of a variety of protecting groups may be employed and these will vary depending, for example, as to whether the group to be protected is an amine, hydroxyl or carboxyl moiety. If the functional group is a hydroxyl group, suitable protecting groups include, for example, certain ethers, esters and carbonates. Such protecting groups are described, for example, in Greene, T W and Wuts, P G M "Protective Groups in Organic Synthesis" John Wiley, New York, 2nd Edition (1991); the disclosure of which is hereby incorporated herein by reference in its entirety. Exemplary protecting groups for amine groups include, for example, t-butyloxycarbonyl (Boc), allyloxycarbonyl (Alloc), benzyloxycarbonyl(Cbz), o-nitrobenzyloxycarbonyl and and trifluoroacetate (TFA).

Amine groups which may be present, for example, on a backbone of a polymer which is included in the vesicles, may be coupled to amine groups on a hydrophilic linking polymer by forming a Schiff's base, for example, by using coupling agents, such as glutaraldehyde. An example of this coupling is described by Allcock et al, *Macromolecules*, 19(6):1502–1508 (1986), the disclosure of which is hereby incorporated herein by reference in its entirety. If, for example, vesicles are formulated from polylysine, free amino groups may be exposed on the surface of the vesicles, and these free amine groups may be activated as described above. The activated amine groups can be used, in turn, to couple to a functionalized hydrophilic polymer, such as, for example, α-amino-ω-hydroxy-PEG in which the ω-hydroxy group has been protected with a carbonate group. After the reaction is completed, the carbonate group can be cleaved, thereby enabling the terminal hydroxy group to be activated for reaction to a suitable targeting ligand. In certain embodiments, the surface of a vesicle may be activated, for example, by displacing chlorine atoms in chlorine-containing phosphazene residues, such as polydichlorophosphazene. Subsequent addition of a targeting ligand and quenching of the remaining chloride groups with water or aqueous methanol will yield the coupled product.

In addition, poly(diphenoxyphosphazene) can be synthesized (Allcock et al., *Macromolecules*, 19(6):1502–1508 (1986)) and immobilized, for example, on DPPE, followed by nitration of the phenoxy moieties by the addition of a mixture of nitric acid and acetic anhydride. The subsequent nitro groups may then be activated, for example, by (1) treatment with cyanogen bromide in 0.1 M phosphate buffer (pH 11), followed by addition of a targeting ligand containing a free amino moiety to generate a coupled urea analog, (2) formation of a diazonium salt using sodium nitrite/HCl, followed by addition of the targeting ligand to form a coupled ligand, and/or (3) the use of a dialdehyde, for example, glutaraldehyde as described above, to form a Schiff's base. After linking the DPPE to the hydrophilic polymer and the targeting ligand, the vesicles may be formulated utilizing the procedures described herein.

Aldehyde groups on polymers can be coupled with amines as described above by forming a Schiff's base. An example of this coupling procedure is described in Allcock and Austin, *Macromolecules*, 14:1616 (1981), the disclosure of which is hereby incorporated herein by reference in its entirety.

In the above procedures, the polymer or terminus of the lipid, for example, phosphatidylglycerol or phosphatidylethanolamine, is preferably activated and coupled to the hydrophilic polymeric linker, the terminus of which has been blocked in a suitable manner. As an example of this strategy, α-amino-ω-carboxy-PEG4000 having a t-Boc protected terminal amino group and a free carboxylate end, may be activated with 1,1'-carbonyldiimidazole in the presence of hydroxybenzotriazole in N-methylpyrollidone. After the addition of phosphatidylethanolamine, the t-Boc group may be removed by using trifluoroacetic acid (TFA), leaving the free amine. The amine may then be reacted with a targeting ligand which may comprise, for example, a peptide, protein, alkaloid, or other moiety, by similar activation of the ligand, to provide the lipid-linker-targeting ligand conjugate. Other strategies, in addition to those exemplified above, may be utilized to prepare the lipid-linker-targeting ligand conjugates. Generally, these methods employ synthetic strategies which are generally known to one skilled in the art of synthetic organic chemistry.

As known to one of ordinary skill in the art, immunoglobulins typically comprise a flexible region which is identified as the "hinge" region. See, e.g., "Concise Encyclopedia of Biochemistry", Second Edition, Walter de Gruyter & Co., pp. 282–283 (1988). Fab' fragments can be linked to the bioactive agents, lipids, polymers, proteins and/or vesicles using the well-defined sites of the thiols of the hinge region. This is a preferred region for coupling Fab' fragments as the potential binding site is remote from the antigen-recognition site. Generally, it may be difficult to utilize the thiols of the hinge group unless they are adequately prepared. In particular, as outlined by Shahinian and Salvias (*Biochimica et Biophysica Acta*, 1239:157–167 (1995)) it may be important to reduce the thiol groups so that they are available for coupling, for example, to maleimide derivatized linking groups. Examples of reducing agents commonly used are ethanedithiol, mercapto-ethanol, mercaptoethylamine or the more commonly used dithiothreitol, commonly referred to as Cleland's reagent. However, it should be noted that care should be exercised when utilizing certain reducing agents, such as dithiothreitol, as overreduction may result. Discriminating use of reducing agents may be necessary in connection with proteins whose activity or binding capacity may be compromised due to overreduction and subsequent denaturation or conformational change. See, Shahinian et al, *Biochim. Biophys. Acta*, 1239:157–167 (1995), the disclosure of which is hereby incorporated herein by reference in its entirety.

F(ab')$_2$ antibody fragments may be prepared by incubating the antibodies with pepsin (60 μg/ml) in 0.1 M sodium acetate (pH 4.2) for 4 h at 37° C. Digestion may be terminated by adding 2 M Tris (pH 8.8) to a final concentration of 80 mM. The F(ab')₂ fragments may then be obtained by centrifugation (10,000×g. 30 min. 4° C.). The supernatant may then be dialyzed at 4° C. against 150 mM NaCl, 20 mM phosphate at pH 7.0. This then may be chromatographed on a column of Protein A-Sepharose CL-4B to remove any undigested IgG. The Fab' fragments may then be prepared by extensively degassing the solutions and purging with nitrogen prior to use. The F(ab')₂ fragments may be provided at a concentration of 5 mg/ml and reduced under argon in 30 mM cysteine. Alternatively, cysteamine may be employed. 100 mM Tris, pH 7.6 may be used as a buffer for 15 min at 37° C. The solutions may then be diluted 2-fold with an equal volume of the appropriate experimental buffer and spun through a 0.4 ml spin column of Bio-Gel P-6DG. The resulting Fab' fragments may be more efficient in their coupling to maleimide linkers. Note also that the same procedure may be employed with other macromolecules containing cysteine residues for coupling, for example, to the maleimide spacers. Also, peptides may be utilized provided that they contain a cysteine residue. If the peptides have not been made fresh and there is a possibility of oxidation of cysteine residues within the peptide structure, it may be necessary to regenerate the thiol group using the approach outlined above.

Additional linkers would include other derivatives of lipids useful for coupling to a bifunctional spacer. For example, phosphatidylethanolamine (PE) may be coupled to a bifunctional agent. For example N-succinimidyl 4-(p-maleimido-phenyl)butyrate (SMPB) and N-succinimidyl 3-(2-pyridyldithiol) propionate (SPDP), N-succinimidyl trans-4-(N-maleimidylmethyl)cyclohexane-1-carboxylate (SMCC), and N-succinimidyl 3-maleimidylbenzoate (SMB) may be used among others, to produce, for example the functionalized lipids MPB-PE and PDP-PE.

The free end of the hydrophilic spacer, such as polyethylene glycol ethylamine, which contains a reactive group, such as an amine or hydroxyl group, could be used to bind a cofactor or other targeting ligand. For example, polyethylene glycol ethylamine may be reacted with N-succinimidylbiotin or p-nitrophenylbiotin to introduce onto the spacer a useful coupling group. For example, biotin may be coupled to the spacer and this will readily bind non-covalently proteins. As an example, MPB-PEG-DPPE may be synthesized as follows. DPPE-PEG with a free amino group at the terminus of the PEG will be provided as described previously. Synthesis of the SMPB:PEG-DPPE may then be carried out with 1 equivalent of triethylamine in chloroform at a molar ratio of 1:5 SMPB:DPPE-PEG. After 3 hours, the reaction mixture will be evaporated to dryness under argon. Excess unreacted SMPB and major by products will be removed by preparative thin layer chromatography (TLC, silica gel developed with 50% acetone in chloroform). The upper portion of the lipid band can be extracted from the silica with about 20–30% methanol in chloroform (V:V) resulting in the isolation of pure intact MPB-Peg-DPPE. Streptavidin may then be coupled to proteins so that the proteins in turn may then be coupled to the MPB-PEG-DPPE. Briefly SPDP would be incubated with streptavidin at room temperature for 30 minutes and chromatography employed to remove unreacted SPDP. Dithiothreitol (DTT) was added to the reaction mixture and 10 minutes later 2-thiopyridone at a concentration of 343 nM. The remainder of the reaction mixture is reduced with DTT (25 mM for 10 min.). The thiolated product is isolated by gel exclusion. The resulting streptavidin labeled proteins may then be used to bind to the biotinylated spacers affixed to the lipid moieties.

The targeted compounds of the present invention are incorporated in compositions which are used to form targeted emulsions and/or targeted vesicles, including, for example, targeted emulsions, targeted micelles, targeted liposomes, targeted albumin coated microspheres, targeted polymer coated microspheres, and/or targeted cochleates. The targeting ligand which is attached to the compounds from which the vesicles are prepared may be directed, for example, outwardly from the surface of the vesicle. Thus, there is provided a targeted vesicle which can be used to target receptors and tissues.

In certain embodiments, the targeting ligands may be incorporated in the present stabilizing materials via non-covalent associations. As known to one skilled in the art, non-covalent association is generally a function of a variety of factors, including, for example, the polarity of the involved molecules, the charge (positive or negative), if any, of the involved molecules, the extent of hydrogen bonding through the molecular network, and the like. Non-covalent bonds are preferably selected from the group consisting of ionic interaction, dipole-dipole interaction, hydrogen bonds, hydrophilic interactions, van der Waal's forces, and any combinations thereof. Non-covalent interactions may be employed to bind the targeting ligand to the lipid, or directly to the surface of a vesicle. For example, the amino acid sequence Gly-Gly-His may be bound to the surface of a vesicle, preferably by a linker, such as PEG, and copper, iron or vanadyl ion may then be added. Proteins, such as antibodies which contain histidine residues, may then bind to the vesicle via an ionic bridge with the copper ion, as described in U.S. Pat. No. 5,466,467, the disclosure of which is hereby incorporated herein by reference in its entirety. An example of hydrogen bonding involves cardiolipin lipids which can be incorporated into the lipid compositions.

In preferred embodiments of the present invention, which may involve vesicles, changes, for example, in pH and/or temperature in vivo, may be employed to promote a change in location in the targeting ligands, for example, from a location within the vesicle, to a location external to the outer wall of the vesicle. This may promote binding of the targeting ligands to targeting sites, for example, receptors, such as lymphocytes, and tissues, including myocardial, endothelial and epithelial cells, since the targeting ligand has a greater likelihood of exposure to such targeting sites. In addition, high energy ultrasound can be used to promote rupturing of the vesicles. This can also expose the targeting ligand to the desired binding site.

As an example, a targeting ligand incorporated into the compositions of the present invention may be of the formula (XV):

L-P-T                                                          (XV)

wherein L is a lipid, protein, polymer, carbohydrate, surfactant, bioactive agent or the like; P is a hydrophilic polymer; and T is a targeting ligand.

In a preferred embodiment, L is a lipid selected from the group consisting of lecithins, phosphatidylcholines, phosphatidylserines, phosphatidylinositols, cardiolipins, cholesterols, cholesterolamines, lysophosphatides, erythrosphingosines, sphingomyelins, ceramides, cerebrosides, saturated phospholipids, unsaturated phospholipids, and krill phospholipids. More preferably, L is a lipid is selected from the group consisting of lecithins, phosphatidylcholines, phosphatidylserines and phosphatidylinositols. In other preferred embodiments, L is a lipid selected from the group consisting of 1,2-diacyl-sn-glycero-3-phosphocholines, 1,2-diacyl-sn-glycero-3- phosphoethanolamines, 1,2-diacyl-sn-glycero-3-[phospho-rac-(1-glycerol)], 1,2-diacyl-sn-glycero-3-phosphates, 1,2-diacyl-sn-glycero-3-[phosphoserines], lysophosphatidylcholines, lysophosphatidylglycerols, 1,2-diacyl-sn-glycerols, 1,2-diacyl-ethylene glycols, N-(n-caproylamine)-1,2-diacyl-sn-glycero-3-phosphoethanolamines, N-dodecanylamine-1,2-diacyl-sn-glycero-3-phosphoethanolamines, N-succinyl-1,2-diacyl-sn-glycero-3-phosphoethanolamines, N-glutaryl-1,2-diacyl-sn-glycero-3-phosphoethanolamines and N-dodecanyl-1,2-diacyl-sn-glycero-3-phosphoethanolamines. More preferably, L is a lipid selected from the group consisting of 1,2-diacyl-sn-glycero-3-phosphocholines, 1,2-diacyl-sn-glycero-3-phosphoethanolamines, 1,2-diacyl-sn-glycero-3-[phospho-rac-(1-glycerol)], 1,2-diacyl-sn-glycero-3-phosphates, 1,2-diacyl-sn-glycero-3-[phosphoserines], lysophosphatidylcholines, lysophosphatidylglycerols and 1,2-diacyl-sn-glycerols.

In other preferred embodiments, L is a protein which comprises albumin.

In still other preferred embodiments, L is a polymer which comprises synthetic polymers or copolymers prepared from monomers selected from the group consisting of acrylic acid, methacrylic acid, ethyleneimine, crotonic acid, acrylamide, ethyl acrylate, methyl methacrylate, 2-hydroxyethyl methacrylate, lactic acid, glycolic acid, ε-caprolactone, acrolein, cyanoacrylate, bisphenol A, epichlorhydrin, hydroxyalkylacrylates, siloxane, dimethylsiloxane, ethylene oxide, propylene oxide, ethylene glycol, hydroxyalkylmethacrylates, N-substituted acrylamides, N-substituted methacrylamides, N-vinyl-2-pyrrolidone, 2,4-pentadiene-1-ol, vinyl acetate, acrylonitrile, styrene, p-aminostyrene, p-aminobenzylstyrene, sodium styrene sulfonate, sodium 2-sulfoxyethylmeth-acrylate, vinyl pyridine, aminoethyl methacrylates, 2-methacryloyloxytrimethylammonium chloride and polyphosphazene. Also preferred are compounds where L is a polymer which comprises synthetic polymers or copolymers selected from the group consisting of polyacrylic acid, polyethyleneimine, polymethacrylic acid, polymethylmethacrylate, polysiloxane, polydimethylsiloxane, polylactic acid, poly(ε-caprolactone), epoxy resin, poly(ethylene oxide), poly(propylene oxide), poly(ethylene glycol), polyamide, polyvinylidene-polyacrylonitrile, polyvinylidene-polyacrylonitrile-polymethylmethacrylate and polystyrene-polyacrylonitrile. Preferred among these polymers is polyvinylidene-polyacrylonitrile copolymer.

In other preferred embodiments, L is a surfactant, preferably a fluorosurfactant, and more preferably a fluorosurfactant having polyethylene glycol attached thereto.

In the above compounds, P is a hydrophilic polymer. Preferably, P is a hydrophilic polymer selected from the group consisting of polyalkyleneoxides, polyvinyl alcohol, polyvinylpyrrolidones, polyacrylamides, polymethacrylamides, polyphosphazenes, phosphazene, poly(hydroxyalkylcarboxylic acids) and polyoxazolidines. More preferably, P is a polyalkyleneoxide polymer, with polyethylene glycol and polypropylene glycol being even more preferred and polyethylene glycol being particularly preferred.

In the above formula, T is a targeting ligand. Preferably, T is a targeting ligand selected from the group consisting of proteins, peptides, saccharides, steroids, steroid analogs, and genetic material, with proteins, peptides and saccharides being more preferred.

In the case of targeting ligands which comprise saccharide groups, suitable saccharide moieties include, for example, monosaccharides, disaccharides and polysaccharides. Exemplary monosaccharides may have six carbon atoms and these saccharides include allose, altrose, glucose, dextrose, mannose, gulose, idose, galactose, talose, fructose, psicose, verbose and tagatose. Five carbon saccharides include ribose, arabinose, xylose, lyxose, ribulose and xylulose. Four carbon saccharides include erythrose, threose and erythrulose. Disaccharides include sucrose, lactose, maltose, isomaltose and cellobiose. Saccharide bearing targeting lipids may be synthesized through a multistep organic synthesis approach, as described more fully hereinafter. For example, lipids bearing targeting glucose moieties may be prepared by reacting, for example, α-glucopyranosyl bromide tetrabenzyl with ω-trifluoroacetylaminopoly-ethyleneglycol to obtain ω-glucopyranosyl tetrabenzyl-ω'-trifluoroacetylaminopoly-ethyleneglycol. This may then be hydrolyzed in a sodium carbonate or potassium carbonate solution and then hydrogenated to obtain ω-glucopyranpsyl-ω'amino-polyethyleneglycol. Aminoglyco-pyranosyl terminated polyethyleneglycol may then react with N-DPGS-succinimide to form the lipid bearing saccharide DPGS-NH-PEG-Glucose. In certain embodiments, the targeting ligands target cancer cells or tumor cells.

In another embodiment, the targeting ligand incorporated into the compositions of the present invention may be of the formula (XVI), which falls within the scope of the formula (XV):

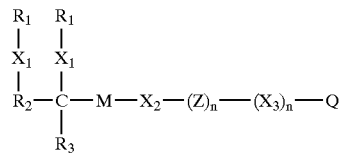

(XVI)

where each $X_1$ is independently —O—, —S—, —SO—, —SO$_2$—, —NR$_4$—, —X$_4$—C(=X$_5$)—, —C(=X$_5$)—X$_4$— or —C(=X$_5$)—; each of $X_2$ and $X_3$ is independently a direct bond, —R$_5$—X$_4$—C(=X$_5$)—, —R$_5$—C(=X$_5$)—X$_4$—, —X$_4$—C(=X$_5$)—R$_5$—, —C(=X$_5$)—X$_4$—R$_5$—, —X$_4$—R$_5$—C(=X$_5$)—X$_4$—, —R$_5$—X$_4$—C(=X$_5$)—R$_5$—C(=X$_5$)—X$_4$— or —R$_5$—C(=X$_5$)—X$_4$—R$_5$—X$_4$—C(=X$_5$)—; each $X_4$ is independently —O—, —NR$_4$— or —S—; each $X_5$ is independently O or S; M is —R$_5$—X$_4$—C(=X$_5$)—, —R$_5$—C(=X$_5$)—X$_4$—, —R$_5$—X$_4$—(YX$_5$)P(=X$_5$)—X$_4$— or —X$_4$—(YX$_5$)P(=X$_5$)—X$_4$—R$_5$—; each n is, independently, 0 or 1; Y is hydrogen or a pharmaceutically acceptable counter ion; Z is a hydrophilic polymer; Q is a targeting ligand or a precursor to a targeting ligand; each $R_1$ is independently an alkyl group of 1 to about 50 carbons that may optionally be substituted with one or more halogen atoms; each $R_2$ is independently an alkylene group of 1 to about 30 carbons that may optionally be substituted with one or more halogen atoms; each of $R_3$ and $R_4$ is independently hydrogen or alkyl of 1 to about 10 carbons; and each $R_5$ is independently a direct bond or alkylene of 1 to about 30 carbons.

In the above formula, when any symbol appears more than once in a particular formula or substituent, its meaning in each instance is independent of the other. Also in the above formula, it is intended that when each of two or more adjacent symbols is defined as being a "direct bond" to provide multiple, adjacent direct bonds, the multiple and adjacent direct bonds devolve into a single direct bond.

In preferred embodiments, each $X_1$ is independently —X$_4$—C(=X$_5$)—, —C(=X$_5$)—X$_4$— or —C(=X$_5$)—.

More preferably, each $X_1$ is independently —$X_4$—C(=$X_5$)— or —C(=$X_5$)—$X_4$—. Even more preferably, $X_1$ is —C(=$X_5$)—$X_4$—, for example, —C(=O)—O—.

In preferred embodiments, each of $X_2$ and $X_3$ is independently a direct bond, —$R_5$—$X_4$—C(=$X_5$)—, —$R_5$—C(=$X_5$)—$X_4$, —$X_4$—C(=$X_5$)—$R_5$—, —C(=$X_5$)—$X_4$— or $R_5$—$X_4$—C(=$X_5$)—$R_5$—C(=$X_5$)—$X_4$—. More preferably, $X_2$ is —$CH_2CH_2$—C(=O)—NH— or —$CH_2CH_2$NH—C(=O)—$CH_2CH_2$—C(=O)—NH— and $X_3$ is a direct bond, —C(=O)—NH—, —NH—C(=O)—, —NH—C(=O)—$CH_2$, —NHCH$_2$—C(=O)—NH— or —NH—C(=O)—$CH_2CH_2$.

Preferably, each $X_4$ is independently —O— or —N$R_4$—.

Preferably, $X_5$ is O.

In certain preferred embodiments, M is —$R_5$—$X_4$—C(=$X_5$)— or —$R_5$—$X_4$—(Y$X_5$)P(=$X_5$)—$X_4$—, with M more preferably being —$CH_2$O—C(=O) or —$CH_2$O—(HO)P(=O)—O—. In certain other preferred embodiments, M is —$R_5$—$X_4$—C(=$X_5$)— or —$R_5$—C(=$X_5$)—$X_4$—. In yet other preferred embodiments, M is —$R_5$—$X_4$—(Y$X_5$)P(=$X_5$)—$X_4$— or —$X_4$—(Y$X_5$)P(=$X_5$)—$X_4$—$R_5$—, wherein at least one of $X_4$ or $X_5$ is S.

In the above formula, Z is a hydrophilic polymer. Preferably, Z is selected from the group consisting of polyalkyleneoxides, polyvinyl alcohol, polyvinylpyrrolidones, polyacrylamides, polymethacrylamides, polyphosphazenes, poly(hydroxyalkylcarboxylic acids) and polyoxazolidines. More preferably, Z comprises a polyalkyleneoxide. Even more preferably, Z is a polyalkyleneoxide selected from the group consisting of polyethylene glycol and polypropylene glycol, with polyethylene glycol being still more preferred. In certain other preferred embodiments, Z is a hydrophilic polymer other than polyalkylene-oxides, including polyethylene glycol and polypropylene glycol. The molecular weight of Z may vary, depending, for example, on the particular end-use of the compounds. Preferably, Z is a polymer having a molecular weight which ranges from about 100 to about 10,000, and all combinations and subcombinations of ranges therein. More preferably, Z is a polymer having a molecular weight of from about 1,000 to about 5,000. Also preferred are polymers which exhibit polydispersities ranging from greater than about 1 to about 3, and all combinations and subcombinations of ranges therein. More preferably, Z is a polymer having a polydispersity of from greater than about 1 to about 2, with polydispersities of from greater than about 1 to about 1.5 being even more preferred, and polydispersities of from greater than about 1 to about 1.2 being still more preferred.

In the above formula, Q is a targeting ligand or a precursor thereto. In embodiments where Q is a targeting ligand, Q is preferably selected from the group consisting of proteins, peptides, saccharides, steroids, steroid analogs, and genetic material. In these latter embodiments, Q is preferably selected from the group consisting of proteins, peptides and saccharides.

In the above formula, each $R_1$ is independently alkyl which ranges from 1 to about 50 carbons, and all combinations and subcombinations of ranges therein, or alkenyl of from about 2 to about 50 carbons, and all combinations and subcombinations of ranges therein. Preferably, each $R_1$ is independently alkyl of greater than 1 to about 40 carbons. More preferably, each $R_1$ is independently alkyl of about 5 to about 30 carbons. Even more preferably, each $R_1$ is independently alkyl of about 10 to about 20 carbons, with alkyl of about carbons being still more preferred. In certain preferred embodiments, $R_1$ is a shorter chain alkyl of from 1 to about 20 carbons. In certain other preferred embodiments, $R_1$ is a longer chain alkyl of from about 20 to about 50 carbons, or about 30 to about 50 carbons. In other preferred embodiments, the alkyl group in $R_1$ may be substituted with one or more fluorine atoms, and may be perfluorinated.

In the above formula, each $R_2$ is independently alkylene which ranges from 1 to about 30 carbons, and all combinations and subcombinations of ranges therein. Preferably, each $R_2$ is independently alkylene of 1 to about 20 carbons. More preferably, each $R_2$ is independently alkylene of 1 to about 10 carbons. Even more preferably, each $R_2$ is independently alkylene of 1 to about 5 carbons, with methylene being especially preferred. In other preferred embodiments, the alkylene group in $R_2$ may be substituted with one or more fluorine atoms, and may be perfluorinated.

In the above formula, each of $R_3$ and $R_4$ is independently hydrogen or alkyl which ranges from 1 to about 10 carbons, and all combinations and subcombinations of ranges therein. Preferably, each of $R_3$ and $R_4$ is hydrogen or alkyl of 1 to about 5 carbons. More preferably, each of $R_3$ and $R_4$ is hydrogen.

In the above formula, each $R_5$ is independently a direct bond or alkylene which ranges from 1 to about 30 carbons, and all combinations and subcombinations of ranges therein. Preferably, each R, is independently a direct bond or alkylene of 1 to about 20 carbons. More preferably, each $R_5$ is independently a direct bond or alkylene of 1 to about 10 carbons. Even more preferably, each $R_5$ is independently a direct bond or alkylene of 1 to about 5 carbons. Still more preferably, each $R_5$ is a direct bond or —(CH$_2$)$_x$—, where x is 1 or 2.

The stabilizing materials and/or vesicles of the present invention may be prepared using any of a variety of suitable methods. These are described below separately for the embodiments involving stabilizing materials and a gas, including gas filled vesicles, and embodiments involving stabilizing materials and a gaseous precursor, including gaseous precursor filled vesicles, although stabilizing materials comprising both a gas and a gaseous precursor are a part of the present invention. A targeting ligand may be attached to the gas and/or gaseous precursor filled vesicle by bonding to one or more of the materials employed in the compositions from which they are made, including the bioactive agents, lipids, proteins, polymers, surfactants, carbohydrates and/or auxiliary stabilizing materials.

A wide variety of methods are available for the preparation of the stabilizing materials, including vesicles, such as micelles and/or liposomes. Included among these methods are, for example, shaking, drying, gas-installation, spray drying, and the like. Suitable methods for preparing vesicle compositions are described, for example, in U.S. Pat. No. 5,469,854, the disclosure of which is hereby incorporated herein by reference in its entirety. The vesicles are preferably prepared from lipids which remain in the gel state.

Micelles may be prepared using any one of a variety of conventional micellar preparatory methods which will be apparent to one skilled in the art. These methods typically involve suspension of the stabilizing material, such as a lipid compound, in an organic solvent, evaporation of the solvent, resuspension in an aqueous medium, sonication and centrifugation. The foregoing methods, as well as others, are discussed, for example, in Canfield et al., *Methods in Enzymology*, 189:418–422 (1990); El-Gorab et al, *Biochem. Biophys. Acta*, 306:58–66 (1973); Colloidal Surfactant, Shinoda, K., Nakagana, Tamamushi and Isejura, Academic Press, NY (1963) (especially "The Formation of Micelles", Shinoda, Chapter 1, pp. 1–88); *Catalysis in Micellar and Macromolecular Systems*, Fendler and Fendler, Academic Press, NY (1975). The disclosures of each of the foregoing publications are hereby incorporated herein by reference in their entirety.

In liposomes, the lipid compound(s) may be in the form of a monolayer or bilayer, and the monolayer or bilayer lipids may be used to form one or more monolayers or bilayers. In the case of more than one monolayer or bilayer, the monolayers or bilayers are generally concentric. Thus, lipids may be used to form unilamellar liposomes (comprised of one monolayer or bilayer), oligolamellar liposomes (comprised of two or three monolayers or bilayers) or multilamellar liposomes (comprised of more than three monolayers or bilayers).

A wide variety of methods are available in connection with the preparation of vesicles, including liposomes. Accordingly, liposomes may be prepared using any one of a variety of conventional liposomal preparatory techniques which will be apparent to one skilled in the art, including, for example, solvent dialysis, French press, extrusion (with or without freeze-thaw), reverse phase evaporation, simple freeze-thaw, sonication, chelate dialysis, homogenization, solvent infusion, microemulsification, spontaneous formation, solvent vaporization, solvent dialysis, French pressure cell technique, controlled detergent dialysis, and others, each involving the preparation of the vesicles in various fashions. See, e.g., Madden et al., *Chemistry and Physics of Lipids*, 53:37–46 (1990), the disclosure of which is hereby incorporated herein by reference in its entirety. Suitable freeze-thaw techniques are described, for example, in International Application Serial No. PCT/US89/05040, filed Nov. 8, 1989, the disclosure of which is hereby incorporated herein by reference in its entirety. Methods which involve freeze-thaw techniques are preferred in connection with the preparation of liposomes. Preparation of the liposomes may be carried out in a solution, such as an aqueous saline solution, aqueous phosphate buffer solution, or sterile water. The liposomes may also be prepared by various processes which involve shaking or vortexing, which may be achieved, for example, by the use of a mechanical shaking device, such as a Wig-L-Bug™ (Crescent Dental, Lyons, Ill.), a Mixomat (Degussa AG, Frankfurt, Germany), a Capmix (Espe Fabrik Pharmazeutischer Praeparate GMBH & Co., Seefeld, Oberay Germany), a Silamat Plus (Vivadent, Lechtenstein), or a Vibros (Quayle Dental, Sussex, England). Conventional microemulsification equipment, such as a Microfluidizerm (Microfluidics, Woburn, Mass.) may also be used.

Spray drying may be employed to prepare gas filled vesicles. Utilizing this procedure, the stabilizing materials, such as lipids, may be pre-mixed in an aqueous environment and then spray dried to produce gas filled vesicles. The vesicles may be stored under a headspace of a desired gas.

Many liposomal preparatory techniques which may be adapted for use in the preparation of vesicle compositions are discussed, for example, in U.S. Pat. Nos. 4,728,578, 4,728,575, 4,737,323, 4,533,254, 4,162,282, 4,310,505, and 4,921,706; U.K. Patent Application GB 2193095 A; International Application Serial No. PCT/US85/01161; Mayer et al., *Biochimica et Biophysica Acta*, 858:161–168 (1986); Hope et al., *Biochimica et Biophysica Acta*, 812:55–65 (1985); Mayhew et al., *Methods in Enzymology*, 149:64–77 (1987); Mayhew et al., *Biochimica et Biophysica Acta*, 755:169–74 (1984); Cheng et al, *Investigative Radiology*, 22:47–55 (1987); International Application Serial No. PCT/US89/05040; and *Liposome Technology*, Gregoriadis, ed., Vol. I, pp. 29–31, 51–67 and 79–108 (CRC Press Inc., Boca Raton, Fla. 1984), the disclosures of each of which are hereby incorporated by reference herein in their entirety.

In connection with stabilizing materials, and especially lipid compositions in the form of vesicles, it may be advantageous to prepare the lipid compositions at a temperature below the gel to liquid crystalline phase transition temperature of the lipids. This phase transition temperature is the temperature at which a lipid bilayer will convert from a gel state to a liquid crystalline state. See, for example, Chapman et al., *J. Biol. Chem.*, 249:2512–2521 (1974), the disclosure of which is hereby incorporated by reference herein in its entirety. It is generally believed that vesicles which are prepared from lipids that possess higher gel state to liquid crystalline state phase transition temperatures tend to have enhanced impermeability at any given temperature. See Derek Marsh, *CRC Handbook of Lipid Bilayers* (CRC Press, Boca Raton, Fla. 1990), at p. 139 for main chain melting transitions of saturated diacyl-sn-glycero-3-phosphocholines. The gel state to liquid crystalline state phase transition temperatures of various lipids will be readily apparent to one skilled in the art and are described, for example, in Gregoriadis, ed., *Liposome Technology*, Vol. I, 1–18 (CRC Press, 1984).

Stabilizing materials, such as lipids, comprising a gas can be prepared by agitating an aqueous solution containing, if desired, a stabilizing material, in the presence of a gas. The term "agitating" means any shaking motion of an aqueous solution such that gas is introduced from the local ambient environment into the aqueous solution. This agitation is preferably conducted at a temperature below the gel to liquid crystalline phase transition temperature of the lipid. The shaking involved in the agitation of the solutions is preferably of sufficient force to result in the formation of a lipid composition, including vesicle compositions, and particularly vesicle compositions comprising gas filled vesicles. The shaking may be by swirling, such as by vortexing, side-to-side, or up and down motion. Different types of motion may be combined. Also, the shaking may occur by shaking the container holding the aqueous lipid solution, or by shaking the aqueous solution within the container without shaking the container itself.

The shaking may occur manually or by machine. Mechanical shakers that may be used include, for example, a shaker table such as a VWR Scientific (Cerritos, Calif.) shaker table, as well as any of the shaking devices described hereinbefore, with the Capmix (Espe Fabrik Pharmazeutischer Praeparate GMBH & Co., Seefeld, Oberay, Germany) being preferred. It has been found that certain modes of shaking or vortexing can be used to make vesicles within a preferred size range. Shaking is preferred, and it is preferred that the shaking be carried out using the Espe Capmix mechanical shaker. In accordance with this preferred method, it is preferred that a reciprocating motion be utilized to generate the lipid compositions, and particularly vesicles. It is even more preferred that the motion be reciprocating in the form of an arc. It is contemplated that the rate of reciprocation, as well as the arc thereof, is particularly important in connection with the formation of vesicles. Preferably, the number of reciprocations or full cycle oscillations is from about 1000 to about 20,000 per minute. More preferably, the number of reciprocations or oscillations is from about 2500 to about 8000, with reciprocations or oscillations of from about 3300 to about 5000 being even more preferred. Of course, the number of oscillations can be dependent upon the mass of the contents being agitated. Generally speaking, a larger mass requires fewer oscillations. Another means for producing shaking includes the action of gas emitted under high velocity or pressure.

It will also be understood that preferably, with a larger volume of aqueous solution, the total amount of force will be correspondingly increased. Vigorous shaking is defined as at least about 60 shaking motions per minute, and is preferred. Vortexing at about 60 to about 300 revolutions per minute is more preferred. Vortexing at about 300 to about 1800 revolutions per minute is even more preferred.

In addition to the simple shaking methods described above, more elaborate methods can also be employed. Such elaborate methods include, for example, liquid crystalline shaking gas instillation processes and vacuum drying gas instillation processes, such as those described in U.S. Pat. Nos. 5,469,854, 5,580,575, 5,585,112, and 5,542,935, and U.S. application Ser. No. 08/307,305, filed Sep. 16, 1994, the disclosures of each of which are incorporated herein by reference in their entirety. Emulsion processes may also be employed in the preparation of compositions in accordance with the present invention. Such emulsification processes are described, for example, in Quay, U.S. Pat. Nos. 5,558,094, 5,558,853, 5,558,854, and 5,573,751, the disclosures of each of which are hereby incorporated herein by reference in their entirety. Spray drying may be also employed to prepare the gaseous precursor filled vesicles. Utilizing this procedure, the lipids may be pre-mixed in an aqueous environment and then spray dried to produce gaseous precursor filled vesicles. The vesicles may be stored under a headspace of a desired gas. Although any of a number of varying techniques can be used, the vesicle compositions employed in the present invention are preferably prepared using a shaking technique. Preferably, the shaking technique involves agitation with a mechanical shaking apparatus, such as an Espe Capmix (Seefeld, Oberay, Germany), using, for example, the techniques disclosed in U.S. application Ser. No. 160,232, filed Nov. 30, 1993, the disclosure of which is hereby incorporated by reference herein in its entirety. In addition, after extrusion and sterilization procedures, which are discussed in detail below, agitation or shaking may provide vesicle compositions which can contain substantially no or minimal residual anhydrous lipid phase in the remainder of the solution. (Bangham et al, *J. Mol. Biol.* 13:238–252 (1965)). Other preparatory techniques include those described in Unger, U.S. Pat. No. 5,205,290, the disclosure of which is hereby incorporated herein by reference in its entirety.

Foams comprise an additional embodiment of the invention. Foams find biomedical application in implants for local delivery of bioactive agents, tissue augmentation, wound healing, and prevention of peritoneal adhesions. Phospholipid foams can be created by increasing the concentration of the phospholipids as well as by mixing with materials such as cetyl alcohol, surfactants, simethicone or polymers, such as methylcellulose. Fluorinated phospholipids may also be used to create stable, long-lasting foams. The most stable foams are generally prepared from materials which are polymerized or cross-linked, such as polymerizable phospholipids. Since foaming is also a function of surface tension reduction, detergents are generally useful foaming agents.

Foams can also be produced by shaking gas filled vesicles, wherein the foam appears on the top of the aqueous solution, and is coupled with a decrease in the volume of the aqueous solution upon the formation of foam. Preferably, the final volume of the foam is at least about two times the initial volume of the aqueous stabilizing material solution; more preferably, the final volume of the foam is at least about three times the initial volume of the aqueous solution; even more preferably, the final volume of the foam is at least about four times the initial volume of the aqueous solution; and most preferably, all of the aqueous stabilizing material solution is converted to foam.

The required duration of shaking time may be determined by detection of the formation of foam. For example, 10 ml of lipid solution in a 50 ml centrifuge tube may be vortexed for approximately 15–20 minutes or until the viscosity of the gas filled liposomes becomes sufficiently thick so that it no longer clings to the side walls as it is swirled. At this time, the foam may cause the solution containing the gas filled liposomes to raise to a level of 30 to 35 ml.

The concentration of lipid required to form a preferred foam level will vary depending upon the type of lipid used, and may be readily determined by one skilled in the art, in view of the present disclosure. For example, in preferred embodiments, the concentration of 1,2-dipalmitoylphosphatidylcholine (DPPC) used to form gas filled liposomes according to the methods of the present invention is about 20 mg/ml to about 30 mg/ml saline solution. The concentration of distearoylphosphatidylcholine (DSPC) used in preferred embodiments is about 5 mg/ml to about 10 mg/ml saline solution. Specifically, DPPC in a concentration of 20 mg/ml to 30 mg/ml, upon shaking, yields a total suspension and entrapped gas volume four times greater than the suspension volume alone. DSPC in a concentration of 10 mg/ml, upon shaking, yields a total volume completely devoid of any liquid suspension volume and contains entirely foam.

Microemulsification is a common method of preparing an emulsion of a foam precursor. Temperature increases and/or lowered pressures will cause foaming as gas bubbles form in the liquid. As discussed above, the foam may be stabilized by, for example, surfactants, detergents or polymers.

The size of gas filled vesicles can be adjusted, if desired, by a variety of procedures, including, for example, microemulsification, vortexing, extrusion, filtration, sonication, homogenization, repeated freezing and thawing cycles, extrusion under pressure through pores of defined size, and similar methods. Gas filled vesicles prepared in accordance with the methods described herein can range in size from less than about 1 μm to greater than about 100 μm. In addition, after extrusion and sterilization procedures, which are discussed in detail below, agitation or shaking provides vesicle compositions which provide substantially no or minimal residual anhydrous lipid phase in the remainder of the solution. (Bangham, et al, *J. Mol. Biol.*, 13:238–252 (1965)). If desired, the vesicles of the present invention may be used as they are formed, without any attempt at further modification of the size thereof. For intravascular use, the vesicles preferably have diameters of less than about 30 μm, and more preferably, less than about 12 μm. For targeted intravascular use including, for example, binding to certain tissue, such as cancerous tissue, the vesicles can be significantly smaller, for example, less than about 100 nm in diameter. For enteric or gastrointestinal use, the vesicles can be significantly larger, for example, up to a millimeter in size. Preferably, the vesicles are sized to have diameters of from about 2 μm to about 100 μm.

The gas filled vesicles may be sized by a simple process of extrusion through filters wherein the filter pore sizes control the size distribution of the resulting gas filled vesicles. By using two or more cascaded or stacked sets of filters, for example, a 10 μm filter followed by an 8 μm filter, the gas filled vesicles can be selected to have a very narrow size distribution around 7 to 9 μm. After filtration, these gas filled vesicles can remain stable for over 24 hours.

The sizing or filtration step may be accomplished by the use, for example, of a filter assembly when the composition is removed from a sterile vial prior to use, or more preferably, the filter assembly may be incorporated into a syringe during use. The method of sizing the vesicles will then comprise using a syringe comprising a barrel, at least one filter, and a needle; and will be carried out by an extraction step which comprises extruding the vesicles from the barrel through the filter fitted to the syringe between the barrel and the needle, thereby sizing the vesicles before they are administered to a patient. The extraction step may also comprise drawing the vesicles into the syringe, where the filter will function in the same way to size the vesicles upon entrance into the syringe. Another alternative is to fill such a syringe with vesicles which have already been sized by some other means, in which case the filter now functions to ensure that only vesicles within the desired size range, or of the desired maximum size, are subsequently administered by extrusion from the syringe.

In other embodiments, the vesicle compositions may be heat sterilized or filter sterilized and extruded through a filter prior to shaking. Generally, vesicle compositions comprising a gas may be heat sterilized, and vesicle compositions comprising gaseous precursors may be filter sterilized. Once gas filled vesicles are formed, they may be filtered for sizing as described above. Performing these steps prior to the formation of gas and/or gaseous precursor filled vesicles provide sterile gas and/or gaseous precursor filled vesicles ready for administration to a patient. For example, a mixing vessel such as a vial or syringe may be filled with a filtered lipid composition, and the composition may be sterilized within the mixing vessel, for example, by autoclaving. Gas may be instilled into the composition to form gas filled vesicles by shaking the sterile vessel. Preferably, the sterile vessel is equipped with a filter positioned such that the gas filled vesicles pass through the filter before contacting a patient.

The step of extruding the solution of lipid compound through a filter decreases the amount of unhydrated material by breaking up any dried materials and exposing a greater surface area for hydration. Preferably, the filter has a pore size of about 0.1 to about 5 $\mu$m, more preferably, about 0.1 to about 4 $\mu$m, even more preferably, about 0.1 to about 2 $\mu$m, and still more preferably, about 1 $\mu$m. Unhydrated compound, which is generally undesirable, appears as amorphous clumps of non-uniform size.

The sterilization step provides a composition that may be readily administered to a patient for diagnostic imaging including, for example, ultrasound or CT. In certain embodiments, sterilization may be accomplished by heat sterilization, preferably, by autoclaving the solution at a temperature of at least about 100° C., and more preferably, by autoclaving at about 100° C. to about 130° C., even more preferably, about 110° C. to about 130° C., still more preferably, about 120° C. to about 130° C., and even more preferably, about 130° C. Preferably, heating occurs for at least about 1 minute, more preferably, about 1 to about 30 minutes, even more preferably, about 10 to about 20 minutes, and still more preferably, about 15 minutes. If desired, the extrusion and heating steps, as outlined above, may be reversed, or only one of the two steps can be used. Other modes of sterilization may be used, including, for example, exposure to gamma radiation.

In addition to the aforementioned embodiments, gaseous precursors contained in vesicles can be formulated which, upon activation, for example, by exposure to elevated temperature, varying pH, or light, undergo a phase transition from, for example, a liquid, including a liquid entrapped in a vesicle, to a gas, expanding to create the gas filled vesicles described herein. This technique is described in U.S. application Ser. No. 08/159,687, filed Nov. 30, 1993, and U.S. Pat. No. 5,542,935, the disclosures of which are hereby incorporated herein by reference in their entirety. The preferred method of activating the gaseous precursor is by exposure to elevated temperature. Activation or transition temperature, and like terms, refer to the boiling point of the gaseous precursor and is the temperature at which the liquid to gaseous phase transition of the gaseous precursor takes place. Useful gaseous precursors are those materials which have boiling points in the range of about −100° C. to about 70° C. The activation temperature is particular to each gaseous precursor.

The methods of preparing the gaseous precursor filled vesicles may be carried out below the boiling point of the gaseous precursor such that a liquid is incorporated, for example, into a vesicle. In addition, the methods may be conducted at the boiling point of the gaseous precursor, such that a gas is incorporated, for example, into a vesicle. For gaseous precursors having low temperature boiling points, liquid precursors may be emulsified using a microfluidizer device chilled to a low temperature. The boiling points may also be depressed using solvents in liquid media to utilize a precursor in liquid form. Further, the methods may be performed where the temperature is increased throughout the process, whereby the process starts with a gaseous precursor as a liquid and ends with a gas.

The methods of producing the temperature activated gaseous precursor filled vesicles may be carried out at a temperature below the boiling point of the gaseous precursor. In this embodiment, the gaseous precursor is entrapped within a vesicle such that the phase transition does not occur during manufacture. Instead, the gaseous precursor filled vesicles are manufactured in the liquid phase of the gaseous precursor. Activation of the phase transition may take place at any time as the temperature is allowed to exceed the boiling point of the precursor. Also, knowing the amount of liquid in a droplet of liquid gaseous precursor, the size of the vesicles upon attaining the gaseous state may be determined.

Alternatively, the gaseous precursors may be utilized to create stable gas filled vesicles which are pre-formed prior to use. In this embodiment, the gaseous precursor is added to a container housing a lipid composition at a temperature below the liquid-gaseous phase transition temperature of the respective gaseous precursor. As the temperature is increased, and an emulsion is formed between the gaseous precursor and liquid solution, the gaseous precursor undergoes transition from the liquid to the gaseous state. As a result of this heating and gas formation, the gas displaces the air in the head space above the liquid mixture so as to form gas filled vesicles which entrap the gas of the gaseous precursor, ambient gas (e.g. air), or coentrap gas state gaseous precursor and ambient air. This phase transition can be used for optimal mixing and formation of the contrast agent. For example, the gaseous precursor, perfluorobutane, can be entrapped in the lipid vesicles and as the temperature is raised beyond the boiling point of perfluorobutane (4° C.), perfluorobutane gas is entrapped in the vesicles. Accordingly, the gaseous precursors may be selected to form gas filled vesicles in vivo or may be designed to produce the gas filled vesicles in situ, during the manufacturing process, on storage, or at some time prior to use. A water bath, sonicator or hydrodynamic activation by pulling back the plunger of a syringe against a closed stopcock may be used to activate targeted gas filled vesicles from temperature-sensitive gaseous precursors prior to intravenous injection or infusion.

As a further embodiment of this invention, by preforming the gaseous precursor in the liquid state into an aqueous emulsion, the maximum size of the vesicle may be estimated by using the ideal gas law, once the transition to the gaseous state is effectuated. For the purpose of making gas filled vesicles from gaseous precursors, the gas phase is assumed to form instantaneously and substantially no gas in the newly formed vesicle has been depleted due to diffusion into the liquid, which is generally aqueous in nature. Hence, from a known liquid volume in the emulsion, one would be able to predict an upper limit to the size of the gas filled vesicle.

In embodiments of the present invention, a mixture of a lipid compound and a gaseous precursor, containing liquid droplets of defined size, may be formulated such that upon reaching a specific temperature, for example, the boiling point of the gaseous precursor, the droplets will expand into gas filled vesicles of defined size. The defined size represents an upper limit to the actual size because the ideal gas law cannot account for such factors as gas diffusion into solution, loss of gas to the atmosphere, and the effects of increased pressure.

The ideal gas law, which can be used for calculating the increase in the volume of the gas bubbles upon transitioning from liquid to gaseous states, is PV=nRT, where P is pressure in atmospheres (atm); V is volume in liters (L); n is moles of gas; T is temperature in degrees Kelvin (K); and R is the ideal gas constant (22.4 L-atm/K-mole). With knowledge of volume, density, and temperature of the liquid in the mixture of liquids, the amount, for example, in moles, and volume of liquid precursor may be calculated which, when converted to a gas, will expand into a vesicle of known volume. The calculated volume will reflect an upper limit to the size of the gas filled vesicle, assuming instantaneous expansion into a gas filled vesicle and negligible diffusion of the gas over the time of the expansion.

Thus, for stabilization of the precursor in the liquid state in a mixture wherein the precursor droplet is spherical, the volume of the precursor droplet may be determined by the equation: Volume (spherical vesicle)=4/3 $\pi r^3$, where r is the radius of the sphere.

Once the volume is predicted, and knowing the density of the liquid at the desired temperature, the amount of liquid gaseous precursor in the droplet may be determined. In more descriptive terms, the following can be applied: $V_{gas}=4/3\pi (r_{gas})^3$, by the ideal gas law, PV=nRT, substituting reveals, $V_{gas}=nRT/P_{gas}$, or, (A) $n=4/3[\pi r_{gas}^3]P/RT$, amount $n=4/3[\pi r_{gas}^3 P/RT]\cdot MW_n$. Converting back to a liquid volume (B) $V_{liq}=[4/3[\pi r_{gas}^3]P/RT]\cdot MW_n/D]$, where D is the density of the precursor. Solving for the diameter of the liquid droplet, (C) diameter/2=$[3/4\pi[4/3\cdot[\pi r_{gas}^3]P/RT]Mw_n/D]^{1/3}$, which reduces to Diameter=$2[[r_{gas}^3]P/RT[MW_n/D]]^{1/3}$.

As a further means of preparing vesicles of the desired size for use in the methods of the present invention, and with a knowledge of the volume and especially the radius of the liquid droplets, one can use appropriately sized filters to size the gaseous precursor droplets to the appropriate diameter sphere.

A representative gaseous precursor may be used to form a vesicle of defined size, for example, 10 $\mu$m diameter. In this example, the vesicle is formed in the bloodstream of a human being, thus the typical temperature would be 37° C. or 310 K. At a pressure of 1 atmosphere and using the equation in (A), $7.54\times10^{-17}$ moles of gaseous precursor would be required to fill the volume of a 10 $\mu$m diameter vesicle.

Using the above calculated amount of gaseous precursor and 1-fluorobutane, which possesses a molecular weight of 76.11, a boiling point of 32.5° C. and a density of 0.7789 g/mL at 20° C., further calculations predict that $5.74\times10^{-15}$ grams of this precursor would be required for a 10 $\mu$m vesicle. Extrapolating further, and with the knowledge of the density, equation (B) further predicts that $8.47\times10^{-16}$ mL of liquid precursor is necessary to form a vesicle with an upper limit of 10 $\mu$m.

Finally, using equation (C), a mixture, for example, an emulsion containing droplets with a radius of 0.0272 $\mu$m or a corresponding diameter of 0.0544 $\mu$m, is formed to make a gaseous precursor filled vesicle with an upper limit of a 10 $\mu$m vesicle.

An emulsion of this particular size could be easily achieved by the use of an appropriately sized filter. In addition, as seen by the size of the filter necessary to form gaseous precursor droplets of defined size, the size of the filter would also suffice to remove any possible bacterial contaminants and, hence, can be used as a sterile filtration as well.

This embodiment for preparing gas filled vesicles may be applied to all gaseous precursors activated by temperature. In fact, depression of the freezing point of the solvent system allows the use of gaseous precursors which would undergo liquid-to-gas phase transitions at temperatures below 0° C. The solvent system can be selected to provide a medium for suspension of the gaseous precursor. For example, 20% propylene glycol miscible in buffered saline exhibits a freezing point depression well below the freezing point of water alone. By increasing the amount of propylene glycol or adding materials such as sodium chloride, the freezing point can be depressed even further.

The selection of appropriate solvent systems may be determined by physical methods as well. When substances, solid or liquid, herein referred to as solutes, are dissolved in a solvent, such as water based buffers, the freezing point is lowered by an amount that is dependent upon the composition of the solution. Thus, as defined by Wall, one can express the freezing point depression of the solvent by the following equation: $\ln x_a = \ln(1-x_b) = \Delta H_{fus}/R(1/T_o - 1/T)$, where $x_a$ is the mole fraction of the solvent; $x_b$ is the mole fraction of the solute; $\Delta H_{fus}$ is the heat of fusion of the solvent; and $T_o$ is the normal freezing point of the solvent.

The normal freezing point of the solvent can be obtained by solving the equation. If $X_b$ is small relative to $x_a$, then the above equation may be rewritten as: $x_b = \Delta H_{fus}/R[T-T_o/T_oT] \approx \Delta H_{fus} \Delta T/RT_o^2$. The above equation assumes the change in temperature $\Delta T$ is small compared to $T_2$. This equation can be simplified further by expressing the concentration of the solute in terms of molality, m (moles of solute per thousand grams of solvent). Thus, the equation can be rewritten as $X_b = m/[m+1000/m_a] \approx mMa/1000$, where Ma is the molecular weight of the solvent. Thus, substituting for the fraction $x_b$: $\Delta T = [M_a RT_o^2/1000\Delta H_{fus}]m$ or $\Delta T = K_f m$, where $K_f M_a RT_o^2/1000\Delta H_{fus}$. $K_f$ is the molal freezing point and is equal to 1.86 degrees per unit of molal concentration for water at one atmosphere pressure. The above equation may be used to accurately determine the molal freezing point of solutions of gaseous-precursor filled vesicles. Accordingly, the above equation can be applied to estimate freezing point depressions and to determine the appropriate concentrations of liquid or solid solute necessary to depress the solvent freezing temperature to an appropriate value.

Methods of preparing the temperature activated gaseous precursor filled vesicles include:

(a) vortexing and/or shaking an aqueous mixture of gaseous precursor and additional materials as desired, including, for example, stabilizing materials, thickening agents and/or dispersing agents. Optional variations of this method include autoclaving before vortexing or shaking; heating an aqueous mixture of gaseous precursor; venting the vessel containing the mixture/suspension; shaking or permitting the gaseous precursor filled vesicle to form spontaneously and cooling down the suspension of gaseous precursor filled vesicles; and extruding an aqueous suspension of gaseous precursor through a filter of about 0.22 μm. Alternatively, filtering may be performed during in vivo administration of the vesicles such that a filter of about 0.22 μm is employed;

(b) microemulsification whereby an aqueous mixture of gaseous precursor is emulsified by agitation and heated to form, for example, vesicles prior to administration to a patient;

(c) heating a gaseous precursor in a mixture, with or without agitation, whereby the less dense gaseous precursor filled vesicles float to the top of the solution by expanding and displacing other vesicles in the vessel and venting the vessel to release air; and (d) utilizing in any of the above methods a sealed vessel to hold the aqueous suspension of gaseous precursor and maintaining the suspension at a temperature below the phase transition temperature of the gaseous precursor, followed by autoclaving to raise the temperature above the phase transition temperature, optionally with shaking, or permitting the gaseous precursor vesicle to form spontaneously, whereby the expanded gaseous precursor in the sealed vessel increases the pressure in the vessel, and cooling down the gas filled vesicle suspension, after which shaking may also take place.

Freeze drying is useful to remove water and organic materials prior to the shaking installation method. Drying installation methods may be used to remove water from vesicles. By pre-entrapping the gaseous precursor in the dried vesicles (i.e. prior to drying) after warming, the gaseous precursor may expand to fill the vesicle. Gaseous precursors can also be used to fill dried vesicles after they have been subjected to vacuum. As the dried vesicles are kept at a temperature below their gel state to liquid crystalline temperature, the drying chamber can be slowly filled with the gaseous precursor in its gaseous state.

Preferred methods for preparing the temperature activated gaseous precursor filled vesicles comprise shaking an aqueous solution having a lipid compound in the presence of a gaseous precursor at a temperature below the liquid state to gas state phase transition temperature of the gaseous precursor. This is preferably conducted at a temperature below the gel state to liquid crystalline state phase transition temperature of the lipid. The mixture is then heated to a temperature above the liquid state to gas state phase transition temperature of the gaseous precursor which causes the precursor to volatilize and expand. Heating is then discontinued, and the temperature of the mixture is then allowed to drop below the liquid state to gas state phase transition temperature of the gaseous precursor. Shaking of the mixture may take place during the heating step, or subsequently after the mixture is allowed to cool. Other methods for preparing gaseous precursor filled vesicles can involve shaking an aqueous solution of, for example, a lipid and a gaseous precursor, and separating the resulting gaseous precursor filled vesicles.

Conventional, aqueous-filled liposomes of the prior art are routinely formed at a temperature above the phase transition temperature of the lipids used to make them, since they are more flexible and thus useful in biological systems in the liquid crystalline state. See, for example, Szoka and Papahadjopoulos, *Proc. Natl. Acad. Sci.* (1978) 75:4194–4198. In contrast, the vesicles made according to certain preferred embodiments described herein are gaseous precursor filled, which imparts greater flexibility, since gaseous precursors after gas formation are more compressible and compliant than an aqueous solution.

The methods contemplated by the present invention provide for shaking an aqueous solution comprising a lipid, in the presence of a temperature activatable gaseous precursor. Preferably, the shaking is of sufficient force such that a foam is formed within a short period of time, such as about 30 minutes, and preferably within about 20 minutes, and more preferably, within about 10 minutes. The shaking may involve microemulsifying, microfluidizing, swirling (such as by vortexing), side-to-side, or up and down motion. In the case of the addition of gaseous precursor in the liquid state, sonication may be used in addition to the shaking methods set forth above. Further, different types of motion may be combined. Also, the shaking may occur by shaking the container holding the aqueous lipid solution, or by shaking the aqueous solution within the container without shaking the container itself. Further, the shaking may occur manually or by machine. Mechanical shakers that may be used include, for example, the mechanical shakers described hereinbefore, with an Espe Capmix (Seefeld, Oberay Germany) being preferred. Another means for producing shaking includes the action of gaseous precursor emitted under high velocity or pressure.

According to the methods described herein, in addition to a gaseous precursor, a gas may be provided by the local ambient atmosphere. The local ambient atmosphere can include the atmosphere within a sealed container, as well as the external environment. Alternatively, for example, a gas may be injected into or otherwise added to the container having the aqueous lipid solution or into the aqueous lipid solution itself to provide a gas other than air. Gases that are lighter than air are generally added to a sealed container, while gases heavier than air can be added to a sealed or an unsealed container. Accordingly, the present invention includes co-entrapment of air and/or other gases along with the gaseous precursors described herein.

Hence, the gaseous precursor filled vesicles can be used in substantially the same manner as the gas filled vesicles described herein, once activated by application to the tissues of a host, where such factors as temperature or pH may be used to cause generation of the gas. The gaseous precursors may undergo phase transitions from liquid to gaseous states at or near the normal body temperature of the host, and can be activated, for example, by the in vivo temperature of the host so as to undergo transition to the gaseous phase therein. In the preferred methods of the present invention, activation prior to administration to a patient is used, for example, by thermal, mechanical or optical means. This activation can occur where, for example, the host tissue is human tissue having a normal temperature of about 37° C. and the gaseous precursors undergo phase transitions from liquid to gaseous states up to about 60° C. or about 70° C.

In any of the techniques described above for the preparation of lipid-based vesicles, bioactive agents and/or targeting ligands may be incorporated with the lipids before, during or after formation of the vesicles, as would be apparent to one of ordinary skill in the art, in view of the present disclosure.

Conjugates of bioactive agents and fluorinated surfactants or conjugates of targeting ligands and fluorinated surfactants can be synthesized by variations on a theme suggested by the reaction sequence set forth in the present disclosure and according to methods known to one skilled in the art, as disclosed, for example, by Quay, et al, European Patent Publication EP 0 727 225 A2, the disclosure of which is hereby incorporated herein by reference in its entirety. If the bioactive agent of choice contains a fluorinated surfactant, such as ZONYL® FSN-100, the ZONYL® can be heated at reduced pressure to drive off volatile components, then the oily residue is reacted with a conjugation linker, the choice of which will ultimately depend on the chemistry of the functional groups on the steroid to be formulated into a prodrug. Alternatively, the bioactive agent could be activated by methods well-known in the art. For example, targeting ligand and fluorinated surfactant conjugates can be prepared by the reaction schemes below, where "LIG" refers to a targeting ligand or bioactive agent of the present invention and "$R_f$" refers to a fluorinated surfactant or fluorinated lipid of the present invention.

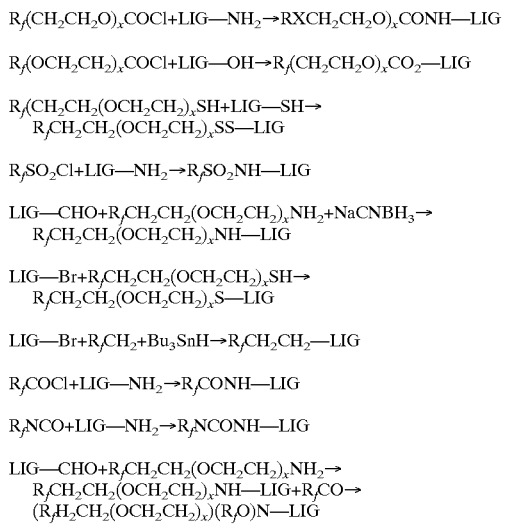

With respect to polyethylene glycol containing fragments, the following can be used, for example, PEG2-NHS ester, NHS-PEG-VS, NHS-PEG-MAL, methoxy-PEG-vinylsulfone, PEG-$(VS)_2$, methoxy-PEG-ald, PEG-$(ald)_2$, methoxy-PEG-epx, PEG-$(epx)_2$, methoxy-PEG-Tres, PEG-$(Tres)_2$, methoxy-PEG-NPC, PEG-$(NPC)_2$, methoxy-PEG-CDI, PEG-$(CDI)_2$, mPEG-Gly-OSu, mPEG-NLe-OSu, methoxy-SPA-PEG, $(SPA)_2$-PEG, methoxy-SS-PEG, $(SS)_2$-PEG all of which are available from Shearwater Polymers, Inc. (Huntsville, Ala.). Where these types of fragments are used, i.e., where the fragments may not themselves have surfactant properties adequate for a given ultrasound contrast formulation, or act only weakly as surfactants, the conjugate formed can be used in conjunction with other surfactants in the final formulation.

Vesicle compositions which comprise vesicles formulated from proteins, such as albumin vesicles, may be prepared by various processes, as will be apparent to one skilled in the art in view of the present disclosure. Suitable methods include those described, for example, in U.S. Pat. Nos. 4,572,203, 4,718,433, 4,774,958, and 4,957,656, the disclosures of each of which are hereby incorporated herein by reference in their entirety. Included among the methods are those which involve sonicating a solution of a protein. In preferred form, the starting material may be an aqueous solution of a heat-denaturable, water-soluble biocompatible protein. The encapsulating protein is preferably heat-sensitive so that it can be partially insolubilized by heating during sonication. Suitable heat-sensitive proteins include, for example, albumin, hemoglobin, and collagen, preferably, the protein is a human protein, with human serum albumin (HSA) being more preferred. HSA is available commercially as a sterile 5% aqueous solution, which is suitable for use in the preparation of protein-based vesicles. As would be apparent to one of ordinary skill in the art, other concentrations of albumin, as well as other proteins which are heat-denaturable, can be used to prepare the vesicles. Generally speaking, the concentration of HSA can vary and may range from about 0.1 to about 25% by weight, and all combinations and subcombinations of ranges therein. It may be preferable, in connection with certain methods for the preparation of protein-based vesicles, to utilize the protein in the form of a dilute aqueous solution. For albumin, it may be preferred to utilize an aqueous solution containing from about 0.5 to about 7.5% by weight albumin, with concentrations of less than about 5% by weight being preferred, for example, from about 0.5 to about 3% by weight.

Protein-based vesicles may be prepared using equipment which is commercially available. For example, in connection with a feed perparation operation as disclosed, for example, in U.S. Pat. No. 4,957,656, stainless steel tanks which are commercially available from Walker Stainless Equipment Co. (New Lisbon, Wis.), and process filters which are commercially available from Millipore (Bedford, Mass.), may be utilized.

The sonication operation may utilize both a heat exchanger and a flow through sonciating vessel, in series. Heat exhanger equipment of this type may be obtained from ITT Standard (Buffalo, N.Y.). The heat exchanger maintains operating temperature for the sonciation process, with temperature controls ranging from about 65° C. to about 80° C., depending on the makeup of the media. The vibration frequency of the sonication equipment may vary over a wide range, for example, from about 5 to about 40 kilohertz (kHz), with a majority of the commerically available sonicators operating at about 10 or 20 kHz. Suitable sonicating equipment include, for example, a Sonics & Materials Vibra-Cell, equipped with a flat-tipped sonicator horn, commercially available from Sonics & Materials, Inc. (Danbury, Conn.). The power applied to the sonicator horn can be varied over power settings scaled from 1 to 10 by the manufacturer, as with Sonics & Materials Vibra-Cell Model VL1500. An intermediate power setting, for example, from 5 to 9, can be used. It is preferred that the vibrational frequency and the power supplied be sufficeint to produce cavitation in the liquid being sonicated. Feed flow rates may range from about 50 mL/min to about 1000 mL/min, and all combinations and subcombinations of ranges therein. Residence times in the sonication vessel can range from about 1 second to about 4 minutes, and gaseous fluid addition rates may range from about 10 cubic centimeters (cc) per minute to about 100 cc/min, or 5% to 25% of the feed flow rate, and all combinations and subcombinations of ranges therein.

It may be preferable to carry out the sonication in such a manner to produce foaming, and especially intense foaming, of the solution. Generally, intense foaming and aerosolating are important for obtaining a contrast agent having enhanced concentration and stability. To promote foaming, the power input to the sonicator horn may be increased, and the process may be operated under mild pressure, for example, about 1 to about 5 psi. Foaming may be easily detected by the cloudy appearance of the solution, and by the foam produced.

Suitable methods for the preparation of protein-based vesicles may also involve physically or chemically altering the protein or protein derivative in aqueous solution to denature or fix the material. For example, protein-based vesicles may be prepared from a 5% aqueous solution of HSA by heating after formation or during formation of the contrast agent via sonication. Chemical alteration may involve chemically denaturing or fixing by binding the protein with a difunctional aldehyde, such as gluteraldehyde. For example, the vesicles may be reacted with 0.25 grams of 50% aqueous gluteradehyde per gram of protein at pH 4.5 for 6 hours. The unreacted gluteraldehyde may then be washed away from the protein.

In any of the techniques described above for the preparation of protein-based stabilizing materials and/or vesicles, bioactive agents and/or targeting ligands may be incorporated with the proteins before, during or after formation of the vesicles, as would be apparent to one of ordinary skill in the art, based on the present disclosure.

Vesicle compositions which comprise vesicles formulated from polymers may be prepared by various processes, as will be readily apparent to one skilled in the art in view of the present disclosure. Exemplary processes include, for example, interfacial polymerization, phase separation and coacervation, multiorifice centrifugal preparation, and solvent evaporation. Suitable procedures which may be employed or modified in accordance with the present disclosure to prepare vesicles from polymers include those procedures disclosed in U.S. Pat. Nos. 4,179,546, 3,945,956, 4,108,806, 3,293,114, 3,401,475, 3,479,811, 3,488,714, 3,615,972, 4,549,892, 4,540,629, 4,421,562, 4,420,442, 4,898,734, 4,822,534, 3,732,172, 3,594,326, and 3,015,128; Japan Kokai Tokkyo Koho 62 286534, British Patent No. 1,044,680, Deasy, *Microencapsulation and Related Drug Processes*, 20:195–240 (Marcel Dekker, Inc., N.Y., 1984), Chang et al., *Canadian J. of Physiology and Pharmacology*, 44:115–129 (1966), and Chang, *Science*, 146:524–525 (1964), the disclosures of each of which are hereby incorporated herein by reference in their entirety.

In accordance with a preferred synthesis protocol, the vesicles may be prepared using a heat expansion process, such as, for example, the process described in U.S. Pat. Nos. 4,179,546, 3,945,956, and 4,108,806, British Patent No. 1,044,680, and Japan Kokai Tokkyo Koho 62 286534. In general terms, the heat expansion process may be carried out by preparing vesicles of an expandable polymer or copolymer which may contain in their void (cavity) a volatile liquid (including the gaseous precursors described herein). The vesicle is then heated, plasticising the vesicle and converting the volatile liquid into a gas, causing the vesicle to expand to up to about several times its original size. When the heat is removed, the thermoplastic polymer retains at least some of its expanded shape. Vesicles produced by this process tend to be of particularly low density, and are thus preferred. The foregoing described process is well known in the art, and may be referred to as the heat expansion process for preparing low density vesicles. Polymers and volatile liquids (including gaseous precursors of the present invention) useful in the heat expansion process will be readily apparent to one skilled in the art.

In certain preferred embodiments, the vesicles which are formulated from synthetic polymers and which may be employed in the methods of the present invention are commercially available from Expancel, Nobel Industries (Sundsvall, Sweden), including EXPANCEL 551 DE™ microspheres. The EXPANCEL 551 DE™ microspheres are composed of a copolymer of vinylidene and acrylonitrile which have encapsulated therein isobutane liquid. Such microspheres are sold as a dry composition and are approximately 50 microns in size. The EXPANCEL 551 DE™ microspheres have a specific gravity of only 0.02 to 0.05, which is between one-fiftieth and one-twentieth the density of water.

In any of the techniques described above for the preparation of polymer-based stabilizing materials and/or vesicles, bioactive agents and/or targeting ligands may be incorporated with the polymers before, during or after formation of the vesicles, as would be apparent to one of ordinary skill in the art, based on the present disclosure.

As with the preparation of stabilizing materials and/or vesicles, a wide variety of techniques are available for the preparation of stabilizing materials comprising bioactive agents and/or targeting ligands. For example, the stabilizing materials and/or vesicle compositions may be prepared from a mixture of lipid compounds, bioactive agents and/or targeting ligands and gases and/or gaseous precursors. In this case, lipid compositions are prepared as described above in which the compositions also comprise bioactive agents and/or targeting ligands. Thus, for example, micelles can be prepared in the presence of a bioactive agent and/or targeting ligand. In connection with lipid compositions which comprise a gas, the preparation can involve, for example, bubbling a gas directly into a mixture of the lipid compounds and one or more additional materials. Alternatively, the lipid compositions may be pre-formed from lipid compounds and gas and/or gaseous precursors. In the latter case, the bioactive agent and/or targeting ligand is then added to the lipid composition prior to use. For example, an aqueous mixture of liposomes and gas may be prepared to which the bioactive agent and/or targeting ligand is added and which is agitated to provide the liposome composition. The liposome composition can be readily isolated since the gas and/or bioactive agent and/or targeting ligand filled liposome vesicles generally float to the top of the aqueous solution. Excess bioactive agent and/or targeting ligand can be recovered from the remaining aqueous solution.

As one skilled in the art will recognize, any of the stabilizing materials and/or vesicle compositions may be lyophilized for storage, and reconstituted or rehydrated, for example, with an aqueous medium (such as sterile water, phosphate buffered solution, or aqueous saline solution), with the aid of vigorous agitation. Lyophilized preparations generally have the advantage of greater shelf life. To prevent agglutination or fusion of the lipids and/or vesicles as a result of lyophilization, it may be useful to include additives which prevent such fusion or agglutination from occurring. Additives which may be useful include sorbitol, mannitol, sodium chloride, glucose, dextrose, trehalose, polyvinylpyrrolidone and poly(ethylene glycol) (PEG), for example, PEG 400. These and other additives are described in the literature, such as in the U.S. Pharmacopeia, USP XXII, NF XVII, The United States Pharmacopeia, The National Formulary, United States Pharmacopeial Convention Inc., 12601 Twinbrook Parkway, Rockville, Md. 20852, the disclosure of which is hereby incorporated herein by reference in its entirety.

The concentration of lipid required to form a desired stabilized vesicle level will vary depending upon the type of lipid used, and may be readily determined by routine experimentation. For example, in preferred embodiments, the concentration of 1,2-dipalmitoylphosphatidylcholine (DPPC) used to form stabilized vesicles according to the methods of the present invention is about 0.1 mg/ml to about 30 mg/ml of saline solution, more preferably from about 0.5 mg/ml to about 20 mg/ml of saline solution, and most preferably from about 1 mg/ml to about 10 mg/ml of saline solution. The concentration of distearoylphosphatidylcholine (DSPC) used in preferred embodiments is about 0.1 mg/ml to about 30 mg/ml of saline solution, more preferably from about 0.5 mg/ml to about 20 mg/ml of saline solution, and most preferably from about I mg/ml to about 10 mg/ml of saline solution. The amount of composition which is administered to a patient can vary. Typically, the intravenous dose may be less than about 10 ml for a 70 kg patient, with lower doses being preferred.

Another embodiment of preparing a targeted therapeutic composition comprises combining at least one lipid and a gaseous precursor; agitating until gas filled vesicles are formed; adding a bioactive agent and/or targeting ligand to the gas filled vesicles such that the bioactive agent and/or targeting ligand binds to the gas filled vesicle by a covalent bond or non-covalent bond; and agitating until a delivery vehicle comprising gas filled vesicles and a bioactive agent and/or targeting ligand result. Rather than agitating until gas filled vesicles are formed before adding the bioactive agent and/or targeting ligand, the gaseous precursor may remain a gaseous precursor until the time of use.

Alternatively, a method of preparing targeted therapeutic compositions may comprise combining at least one lipid and a bioactive agent and/or targeting ligand such that the bioactive agent and/or targeting ligand binds to the lipid by a covalent bond or non-covalent bond, adding a gaseous precursor and agitating until a delivery vehicle comprising gas-filled vesicles and a bioactive agent and/or targeting ligand result. In addition, the gaseous precursor may be added and remain a gaseous precursor until the time of use.

Alternatively, the gaseous precursors may be utilized to create stable gas filled vesicles with bioactive agents and/or targeting ligands which are pre-formed prior to use. In this embodiment, the gaseous precursor and bioactive agent and/or targeting ligand are added to a container housing a suspending and/or stabilizing medium at a temperature below the liquid-gaseous phase transition temperature of the respective gaseous precursor. As the temperature is then exceeded, and an emulsion is formed between the gaseous precursor and liquid solution, the gaseous precursor undergoes transition from the liquid to the gaseous state. As a result of this heating and gas formation, the gas displaces the air in the head space above the liquid suspension so as to form gas filled lipid spheres which entrap the gas of the gaseous precursor, ambient gas for example, air, or coentrap gas state gaseous precursor and ambient air. This phase transition can be used for optimal mixing and stabilization of the delivery vehicle. For example, the gaseous precursor, perfluorobutane, can be entrapped in the lipid or other stabilizing compound, and as the temperature is raised, beyond 4° C. (boiling point of perfluorobutane) stabilizing compound entrapped fluorobutane gas results. As an additional example, the gaseous precursor fluorobutane, can be suspended in an aqueous suspension containing emulsifying and stabilizing agents such as glycerol or propylene glycol and vortexed on a commercial vortexer. Vortexing is commenced at a temperature low enough that the gaseous precursor is liquid and is continued as the temperature of the sample is raised past the phase transition temperature from the liquid to gaseous state. In so doing, the precursor converts to the gaseous state during the microemulsification process. In the presence of the appropriate stabilizing agents, surprisingly stable gas filled vesicles and bioactive agents and/or targeting ligand result.

All of the above embodiments involving preparations of the stabilized gas filled vesicles used in the present invention, may be sterilized by autoclave or sterile filtration if these processes are performed before either the gas instillation step or prior to temperature mediated gas conversion of the temperature sensitive gaseous precursors within the suspension. Alternatively, one or more antibactericidal agents and/or preservatives may be included in the formulation of the compositions including, for example, sodium benzoate, all quaternary ammonium salts, sodium azide, methyl paraben, propyl paraben, sorbic acid, ascorbylpalmitate, butylated hydroxyanisole, butylated hydroxytoluene, chlorobutanol, dehydroacetic acid, ethylenediamine, monothioglycerol, potassium benzoate, potassium metabisulfite, potassium sorbate, sodium bisulfite, sulfur dioxide, and organic mercurial salts. Such sterilization, which may also be achieved by other conventional means, such as by irradiation, will be necessary where the stabilized microspheres are used for imaging under invasive circumstances, for example, intravascularly or intraperitoneally. The appropriate means of sterilization will be apparent to the artisan instructed by the present description of the stabilized gas filled vesicles and their use. The compositions are generally stored as an aqueous suspension but in the case of dried or lyophilized vesicles or dried or lyophilized lipidic spheres the compositions may be stored as a dried or lyophilized powder ready to be reconstituted or rehydrated prior to use.

The gaseous precursor filled compositions of the present invention are particularly useful as contrast media in diagnostic imaging, and for use in all areas where diagnostic imaging is employed, when they are heated to a temperature at or above the phase transition temperature of the gaseous precursor instilled in the composition prior to administration to a patient. Diagnostic imaging is a means to visualize internal body regions of a patient, and includes, for example, ultrasound imaging, magnetic resonance imaging (MRI), nuclear magnetic resonance (NMR), computed tomography (CT), electron spin resonance (ESR); nuclear medicine when the contrast medium includes radioactive material; optical imaging, particularly with a fluorescent contrast medium, elastography, radiofrequency (RF), microwave laser and the like. Diagnostic imaging also includes therapeutic imaging, such as promoting the rupture of vesicles via the methods of the present invention. For example, ultrasound may be used to visualize the vesicles and verify the localization of the vesicles in certain tissue. In addition, ultrasound may be used to promote rupture of the vesicles once the vesicles reach the intended target, including tissue and/or receptor destinations, thus releasing a bioactive agent.

In accordance with the present invention, there are provided methods of imaging a patient, diagnosing the presence of diseased tissue in a patient, delivering (with or without a targeting ligand) a bioactive agent to a patient and/or treating a condition or disease in a patient. The methods of the present invention achieve unexpectedly superior results (e.g., unexpectedly superior contrast and contrast enhancement) when gaseous precursor filled compositions are used as contrast agents, and when the gaseous precursor filled compositions are thermally preactivated by heating to temperatures at or above the boiling point of the instilled gaseous precursor prior to the in vivo administration of the compositions to a patient. In particular, thermally preactivating gaseous precursor filled compositions prior to in vivo administration of the compositions to a patient profoundly enhances the acoustic activity of the compositions when diagnostic or therapeutic imaging is applied.

The methods of the present invention may be carried out by heating a composition comprising a gaseous precursor to a temperature at or above the boiling point of the instilled gaseous precursor, administering the thermally preactivated gaseous precursor filled composition to a patient, and then scanning the patient using, for example, ultrasound, computed tomography, magnetic resonance imaging and/or other forms of diagnostic imaging described herein or known in the art, to obtain visible images of an internal region of a patient and/or of any diseased tissue in that region. The contrast medium may be particularly useful in providing images of tissue, such as myocardial, endothelial, and/or epithelial tissue, as well as the gastrointestinal, pulmonary and cardiovascular regions, but can also be employed more broadly, such as in imaging the vasculature, or in other ways as will be readily apparent to one skilled in the art.

The present invention also provides a method of diagnosing the presence of diseased tissue in a patient. Diseased tissue includes, for example, endothelial tissue which results from vasculature that supports diseased tissue. As a result, the localization and visualization of endothelial tissue to a region of a patient which under normal circumstances is not associated with endothelial tissue provides an indication of diseased tissue in the region. The present methods can also be used in connection with delivery of bioactive agents and/or targeting ligands to internal regions of a patient.

The amount of the gaseous precursor filled compositions of the present invention to be administered to a patient depends, for example, on the method in which the compositions are being administered, and the age, sex, weight and physical condition of the patient. Generally, treatment is initiated with small dosages, which can then be increased by small increments, until the desired effect under the circumstances is achieved. For example, following the thermal preactivation methods of the present invention, the gaseous precursor filled compositions may be administered to a patient at a dose of about 0.005 cc/Kg of body weight to about 0.2 cc/Kg of body weight, preferably from about 0.005 cc/Kg of body weight to less than about 0.1 cc/Kg of body weight, more preferably from about 0.005 cc/Kg of body weight to about 0.05 cc/Kg of body weight. The targeting aspects of the invention further enable lower dosages of the gaseous precursor filled compositions to be used for therapy, since the effective concentration of the compositions at the therapeutic site remains undiluted in the body.

The gaseous precursor filled compositions of the invention may be administered to the patient by a variety of different means. The means of administration will vary depending upon the intended application. As one skilled in the art would recognize, administration of the compositions, stabilizing materials and/or vesicles of the present invention can be carried out in various fashions, for example, topically, including ophthalmic, dermal, ocular and rectal, intrarectally, transdermally, orally, intraperitoneally, parenterally, intravenously, intralymphatically, intratumorly, intramuscularly, interstitially, intra-arterially, subcutaneously, intraocularly, intrasynovially, transepithelially, pulmonarily via inhalation, ophthalmically, sublingually, buccally, or via nasal inhalation via insufflation or nebulization.

The stabilizing materials and/or vesicles of the present invention are preferably administered as an infusion. "Infusion" refers to intravascular or intra-arterial administration at a rate of, for example, less than about 1 cc/second, more preferably less than about 0.5 cc/second or less than about 30 cc/minute, even more preferably at about 0.1 cc/minute to about 30 cc/minute, most preferably at about 0.1 cc/minute to about 5.0 cc/minute. Varying the rate of infusion is also desirable. For example, infusion may initially be started at a rate of about 1.0 to about 4.0 cc/second, followed by a more sustained infusion rate of about 0.1 cc/second. The fast infusion rate initially achieves the optimal level of the stabilizing material and/or vesicle in the blood, while the slow infusion rate is better tolerated hemodynamically.

Ultrasound mediated targeting and drug release and activation using the contrast agents, bioactive agents and/or targeting ligands of the present invention is advantageous for treating a variety of different diseases and medical conditions, such as autoimmune diseases, organ transplants, arthritis, and myasthenia gravis. Following the systemic administration of the delivery vehicles to a patient, ultrasound may then be applied to the affected tissue. For arthritis, including synovial-based inflammation arthritis, such as rheumatoid arthritis, ultrasound may be applied to the joints affected by the disease. For myasthenia gravis, ultrasound may be applied to the thymus. For transplant rejection, ultrasound may be applied to the organ transplant, such as in a kidney transplant.

For topical applications, the compositions may be used alone, may be mixed with one or more solubilizing agents or may be used with a delivery vehicle, and applied to the skin or mucosal membranes. Penetrating and/or solubilizing agents useful for topical application include, for example, pyrrolidones such as 2-pyrrolidone, N-methyl-2-pyrrolidone, 1-methyl-2-pyrrolidone, 5-methyl-2-pyrrolidone, 1-ethyl-2-pyrrolidone, 2-pyrrolidone-5-carboxylic acid, N-hydroxyethylpyrrolidone, N-cyclohexylpyrrolidone, N-dimethylaminopropylpyrrolidone, N-cocalyklpyrrolidone, N-tallowalkylpyrrolidone, 1-lauryl-2-pyrrolidone, and 1-hyxyl-2-pyrrolidone; fatty acids such as oleic acid, linoleic acid, heptanoic acid, caproic acid, lauric acid, stearic acid, octadecenoic acid, palmitoleic acid, myristic acid and palmitelaidic acid; sulfoxides such as dimethylsulfoxide, dimethylacetamide, dimethylformamide, N-methylformamide and decylmethylsulfoxide; amines and derivatives such as N,N-diethyl-m-toluamide, dodecylamine, ethoxylated amine, N,N-bis(2-hydroxyethyl) oleylamine, dodecyl-N,N-dimethylamino acetate, sodium pryoglutaminate and N-hydroxylethalacetamide; terpenes and terpenoids such as a-pinenes, d-limonene, 3-carene, a-terpineol, terpinen-4-ol, careol, abisabolol, carvone, pulegone, piperitone, menthone, fenchone, cyclohexene oxide, limonene oxide, pinene oxide, cyclopentene oxide, ascaridol, 7-oxabicyclo(2.2.1)heptane, 1,8-cineole, safrole, 1-carvone, terpenoid cyclohexanone derivatives, acyclic terpenehydrocarbon chains, hydrocarbon terpenes, cyclic ether terpenes, cardamon seed extract, monoterpene terpineol and acetyl terpineol; essential oils of eucalyptus, chenopodium and yang ylang; surfactants such as anionic-sodiumlaurylsulfate, phenylsulfurate CA, calciumdodecylbenzene sulfonate, empicol ML26/F and magnesiumlaurylsulfate; cationic-cetyltrimethylammonium bromide; nonionic-synperonic NP series and PE series and the polysorbates; zwiterionic-N-dodecyl-N,N-dimethylbetaine; alcohols such as ethanol, lauryl alcohol, linolenyl alcohol, 1-octanol, 1-propanol and 1-butanol; urea, cyclic unsaturated urea analogs, glycols, azone, n-alkanols, n-alkanes, orgelase, alphaderm cream and water. The penetrating/solubilizing agents may or may not be in a base which can be composed of various substances known to one skilled in the art, including, for example, glycerol, propylene glycol, isopropyl myristate, urea in propylene glycol, ethanol and water, and polyethylene glycol (PEG).

Compositions formulated with penetration enhancing agents, known to one skilled in the art and described above, may be administered transdermally in a patch or reservoir with a permeable membrane applied to the skin. The use of rupturing ultrasound may increase transdermal delivery of therapeutic compounds. Further, an imaging mechanism may be used to monitor and modulate delivery of the compositions. For example, diagnostic ultrasound may be used to visually monitor the bursting of the gas filled vesicles and modulate drug delivery and/or a hydrophone may be used to detect the sound of the. bursting of the gas filled vesicles and modulate drug delivery.

The delivery of bioactive agents from the stabilizing materials of the present invention using ultrasound is best accomplished for tissues which have a good acoustic window for the transmission of ultrasonic energy. This is the case for most tissues in the body such as muscle, the heart, the lungs, the liver and most other vital structures. In the brain, in order to direct the ultrasonic energy past the skull, a surgical window may be necessary.

The gaseous precursor filled vesicles of the present invention are especially useful for bioactive agents and/or targeting ligands that may be degraded in aqueous media or upon exposure to oxygen and/or atmospheric air. For example, the vesicles may be filled with an inert gas for use with labile bioactive agents. Additionally, the gaseous precursor filled vesicles may be filled with an inert gas and used to encapsulate a labile bioactive agent and/or targeting ligand for use in a region of a patient that would normally cause the therapeutic to be exposed to atmospheric air, such as cutaneous and ophthalmic applications.

The invention is useful in delivering bioactive agents to a patient's lungs. For pulmonary applications, dried or lyophilized powdered compositions may be administered via inhaler. Aqueous suspensions of liposomes, micelles or other vesicles, preferably gas/gaseous precursor filled, may be administered via nebulization. The thermally preactivated gaseous precursor filled compositions of the present invention are lighter than, for example, conventional liquid filled liposomes which generally deposit in the central proximal airway rather than reaching the periphery of the lungs. Therefore, the gaseous precursor filled compositions of the present invention may improve delivery of a bioactive agent to the periphery of the lungs, including the terminal airways and the alveoli. For application to the lungs, the compositions may be applied through nebulization.

In applications such as the targeting of the lungs, which are lined with lipids, the bioactive agent may be released upon aggregation of the compositions of the present invention with the lipids lining the targeted tissue. Additionally, the compositions may burst after administration without the use of ultrasound. Thus, ultrasound need not be applied to release the drug in the above type of administration.

It is a further embodiment of this invention in which ultrasound activation affords site specific delivery of the bioactive agents. The gas and/or gaseous precursor filled stabilizing materials or vesicles are echogenic and visible on ultrasound. Ultrasound can be used to image the target tissue and to monitor the drug carrying vehicles as they pass through the treatment region. As increasing levels of ultrasound are applied to the treatment region, this breaks apart the delivery vehicles and/or releases the drug within the treatment region. With particular reference to prodrugs, "release of the drug" includes: (1) the release of the prodrug from the delivery vehicle but not the release of the drug from the linking group and lipid or fluorinated moiety; (2) the release of the drug from the covalently bonded lipid or fluorinated moiety and/or the linking group, but not from the delivery vehicle; and (3) the release of the drug from both the delivery vehicle and from the covalently bonded lipid or fluorinated moiety and/or the linking group.

Drug release and/or vesicle rupture can be monitored ultrasonically by several different mechanisms. Bubble or vesicle destruction results in the eventual dissolution of the ultrasound signal. However, prior to signal dissolution, the delivery vehicles/vesicles provide an initial burst of signal. In other words, as increasing levels of ultrasound energy are applied to the treatment zone containing the delivery vehicles or vesicles, there is a transient increase in signal. This transient increase in signal may be recorded at the fundamental frequency, the harmonic, odd harmonic or ultraharmonic frequency.

Generally, the gaseous precursor filled compositions of the invention are administered in the form of an aqueous suspension such as in water or a saline solution (e.g., phosphate buffered saline). Preferably, the water is sterile. Also, preferably the saline solution is an isotonic saline solution, although, if desired, the saline solution may be hypotonic (e.g., about 0.3 to about 0.5% NaCl). The solution may be buffered, if desired, to provide a pH range of about 5 to about 7.4. Preferably, dextrose or glucose is included in the media. Other solutions that may be used for administration of the compositions of the present invention include oils, such as, for example, almond oil, corn oil, cottonseed oil, ethyl oleate, isopropyl myristate, isopropyl palmitate, mineral oil, myristyl alcohol, octyldodecanol, olive oil, peanut oil, persic oil, sesame oil, soybean oil, squalene and fluorinated oils. Accordingly, when reference is made to heating the gaseous precursor filled compositions prior to administration to a patient, such heating preferably includes heating the aqueous suspension, solution or milieu in which the gaseous precursor filled compositions are contained.

The size of the stabilizing materials and/or vesicles of the present invention will depend upon the intended use. With smaller liposomes, resonant frequency ultrasound will generally be higher than for the larger liposomes. Sizing also serves to modulate resultant liposomal biodistribution and clearance. In addition to filtration, the size of the liposomes can be adjusted, if desired, by procedures known to one skilled in the art, such as shaking, microemulsification, vortexing, filtration, repeated freezing and thawing cycles, extrusion, extrusion under pressure through pores of a defined size, sonication, homogenization, the use of a laminar stream of a core of liquid introduced into an immiscible sheath of liquid. Extrusion under pressure through pores of defined size is a preferred method of adjusting the size of the liposomes. See, for example, U.S. Pat. Nos. 4,728,578, 4,728,575, 4,737,323, 4,533,254, 4,162,282, 4,310,505 and 4,921,706; U.K. Patent Application GB 2193095 A; International Applications PCT/US85/01161 and PCT/US89/05040; Mayer et al., *Biochimica et Biophysica Acta*, 858:161–168 (1986); Hope et al., *Biochimica et Biophysica Acta*, 812:55–65 (1985); Mayhew et al., *Methods in Enzymology*, 149:64–77 (1987); Mayhew et al., *Biochimica et Biophysica Acta*, 755:169–74 (1984); Cheng et al, *Investigative Radiology*, 22:47–55 (1987); and *Liposomes Technology*, Gregoriadis, ed., Vol. I, pp. 29–37, 51–67 and 79–108 (CRC Press Inc, Boca Raton, Fla., 1984). The disclosures of each of the foregoing patents, publications and patent applications are hereby incorporated by reference herein in their entirety.

Since vesicle size influences biodistribution, different size vesicles may be selected for various purposes. For example, for intravascular application, the preferred size range is a mean outside diameter between about 30 nm and about 10 $\mu$m, with the preferable mean outside diameter being about 5 μm. More specifically, for intravascular application, the size of the vesicles is preferably about 10 μm or less in mean outside diameter, and preferably less than about 7 μm, and more preferably less than about 5 μm in mean outside diameter. Preferably, the vesicles are no smaller than about 30 nm in mean outside diameter. To provide therapeutic delivery to organs such as the liver and to allow differentiation of tumor from normal tissue, smaller vesicles, between about 30 nm and about 100 nm in mean outside diameter, are preferred. For embolization of a tissue such as the kidney or the lung, the vesicles are preferably less than about 200 μm in mean outside diameter. For intranasal, intrarectal or topical administration, the vesicles are preferably less than about 100 μm in mean outside diameter. Large vesicles, between 1 and about 10 μm in size, will generally be confined to the intravascular space until they are cleared by phagocytic elements lining the vessels, such as the macrophages and Kupffer cells lining capillary sinusoids. For passage to the cells beyond the sinusoids, smaller vesicles, for example, less than about 1 μm in mean outside diameter, e.g., less than about 300 nm in size, may be utilized. In preferred embodiments, the vesicles are administered individually, rather than embedded in a matrix, for example.

For in vitro use, such as cell culture applications, the gas filled vesicles may be added to the cells in cultures and then incubated. Subsequently sonic energy can be applied to the culture media containing the cells and liposomes.

In carrying out the imaging methods of the present invention, the stabilizing materials and vesicle compositions can be used alone, or in combination with diagnostic agents, bioactive agents, targeting ligands or other agents, including excipients such as flavoring or coloring materials, which are well known to one skilled in the art.

In the case of diagnostic applications, such as ultrasound and CT, energy, such as ultrasonic energy, is applied to at least a portion of the patient to image the target tissue. A visible image of an internal region of the patient is then obtained, such that the presence or absence of diseased tissue can be ascertained. With respect to ultrasound, ultrasonic imaging techniques, including second harmonic imaging, and gated imaging, are well known in the art, and are described, for example, in Uhlendorf, *IEEE Transactions on Ultrasonics, Ferroelectrics, and Frequency Control*, 14(1):70–79 (1994) and Sutherland, et al., *Journal of the American Society of Echocardiography*, 7(5):441–458 (1994), the disclosures of each of which are hereby incorporated herein by reference in their entirety. CT imaging techniques which are employed are conventional and are described, for example, in *Computed Body Tomography*, Lee, Sagel, and Stanley, eds., 1983, Ravens Press, New York, N.Y., the disclosure of which is hereby incorporated by reference herein in its entirety.

Ultrasound can be used for both diagnostic and therapeutic purposes. In diagnostic ultrasound, ultrasound waves or a train of pulses of ultrasound may be applied with a transducer. The ultrasound is generally pulsed rather than continuous, although it may be continuous, if desired. Thus, diagnostic ultrasound generally involves the application of a pulse of echoes, after which, during a listening period, the ultrasound transducer receives reflected signals. Harmonics, ultraharmonics or subharmonics may be used. The second harmonic mode may be beneficially employed, in which the 2x frequency is received, where x is the incidental frequency. This may serve to decrease the signal from the background material and enhance the signal from the transducer using the targeted contrast media of the present invention which may be targeted to the desired site, for example, blood clots. Other harmonic signals, such as odd harmonics signals, for example, 3x or 5x, would be similarly received using this method. Subharmonic signals, for example, x/2 and x/3, may also be received and processed so as to form an image.

In addition to the pulsed method, continuous wave ultrasound, for example, Power Doppler, may be applied. This may be particularly useful where rigid vesicles, for example, vesicles formulated from polymethyl methacrylate, are employed. In this case, the relatively higher energy of the Power Doppler may be made to resonate the vesicles and thereby promote their rupture. This can create acoustic emissions which may be in the subharmonic or ultraharmonic range or, in some cases, in the same frequency as the applied ultrasound. It is contemplated that there will be a spectrum of acoustic signatures released in this process and the transducer so employed may receive the acoustic emissions to detect, for example, the presence of a clot. In addition, the process of vesicle rupture may be employed to transfer kinetic energy to the surface, for example of a clot to promote clot lysis. Thus, therapeutic thrombolysis may be achieved during a combination of diagnostic and therapeutic ultrasound. Spectral Doppler may also be employed. In general, the levels of energy from diagnostic ultrasound are insufficient to promote the rupture of vesicles and to facilitate release and cellular uptake of the bioactive agents. As noted above, diagnostic ultrasound may involve the application of one or more pulses of sound. Pauses between pulses permits the reflected sonic signals to be received and analyzed. The limited number of pulses used in diagnostic ultrasound limits the effective energy which is delivered to the tissue that is being studied.

Higher energy ultrasound, for example, ultrasound which is generated by therapeutic ultrasound equipment, is generally capable of causing rupture of the vesicle composition. In general, devices for therapeutic ultrasound employ from about 10 to about 100% duty cycles, depending on the area of tissue to be treated with the ultrasound. Areas of the body which are generally characterized by larger amounts of muscle mass, for example, the back and thighs, as well as highly vascularized tissues, such as heart tissue, may require a larger duty cycle, for example, up to about 100%.

In therapeutic ultrasound, continuous wave ultrasound is used to deliver higher energy levels. For the rupture of vesicles, continuous wave ultrasound is preferred, although the sound energy may also be pulsed. If pulsed sound energy is used, the sound will generally be pulsed in echo train lengths of from about 8 to about 20 or more pulses at a time. Preferably, the echo train lengths are about 20 pulses at a time. In addition, the frequency of the sound used may vary from about 0.025 to about 100 megahertz (MHz). In general, frequency for therapeutic ultrasound preferably ranges between about 0.75 and about 3 MHz, with from about 1 and about 2 MHz being more preferred. In addition, energy levels may vary from about 0.5 Watt (W) per square centimeter ($cm^2$) to about 5.0 W/$cm^2$, with energy levels of from about 0.5 to about 2.5 W/$cm^2$ being preferred. Energy levels for therapeutic ultrasound involving hyperthermia are generally from about 5 W/$cm^2$ to about 50 W/$cm^2$. For very small vesicles, for example, vesicles having a diameter of less than about 0.5 μm, higher frequencies of sound are generally preferred because smaller vesicles are capable of absorbing sonic energy more effectively at higher frequencies of sound. When very high frequencies are used, for example, greater than about 10 MHz, the sonic energy will generally penetrate fluids and tissues to a limited depth only.

Thus, external application of the sonic energy may be suitable for skin and other superficial tissues. However, it is generally necessary for deep structures to focus the ultrasonic energy so that it is preferentially directed within a focal zone. Alternatively, the ultrasonic energy may be applied via interstitial probes, intravascular ultrasound catheters or endoluminal catheters. In addition to the therapeutic uses discussed above, the present compositions can be employed in connection with esophageal carcinoma or in the coronary arteries for the treatment of atherosclerosis, as well as the therapeutic uses described, for example, in U.S. Pat. No. 5,149,319, the disclosure of which is hereby incorporated by reference herein in its entirety.

A therapeutic ultrasound device may be used which employs two frequencies of ultrasound. The first frequency may be x, and the second frequency may be 2x. In preferred form, the device would be designed such that the focal zones of the first and second frequencies converge to a single focal zone. The focal zone of the device may then be directed to the targeted compositions, for example, targeted vesicle compositions, within the targeted tissue. This ultrasound device may provide second harmonic therapy with simultaneous application of the x and 2x frequencies of ultrasound energy. It is contemplated that, in the case of ultrasound involving vesicles, this second harmonic therapy may provide improved rupturing of vesicles as compared to ultrasound energy involving a single frequency. Also, it is contemplated that the preferred frequency range may reside within the fundamental harmonic frequencies of the vesicles. Lower energy may also be used with this device. An ultrasound device which may be employed in connection with the aforementioned second harmonic therapy is described, for example, in Kawabata, et al., *Ultrasonics Sonochemistry*, 3:1–5 (1996), the disclosure of which is hereby incorporated by reference herein in its entirety.

For use in ultrasonic imaging, preferably, the vesicles of the invention possess a reflectivity of greater than 2 dB, more preferably between about 4 dB and about 20 dB. Within these ranges, the highest reflectivity for the vesicles of the invention is exhibited by the larger vesicles, by higher concentrations of vesicles, and/or when higher ultrasound frequencies are employed.

For therapeutic drug delivery, the rupturing of the bioactive agent containing vesicle compositions and/or liposomes of the invention is carried out by applying ultrasound of a certain frequency to the region of the patient where therapy is desired, after the compositions have been administered to or have otherwise reached that region, e.g., via delivery with targeting ligands. Specifically, it has been found that when ultrasound is applied at a frequency corresponding to the peak resonant frequency of the bioactive agent containing gas filled vesicles, the vesicles will rupture and release their contents. The peak resonant frequency can be determined either in vivo or in vitro, but preferably in vivo, by exposing the compositions to ultrasound, receiving the reflected resonant frequency signals and analyzing the spectrum of signals received to determine the peak, using conventional means. The peak, as so determined, corresponds to the peak resonant frequency, or second harmonic, as it is sometimes termed.

Preferably, the compositions of the present invention have a peak resonant frequency of between about 0.5 and about 10 MHz. Of course, the peak resonant frequency of the gaseous precursor filled vesicles of the invention will vary depending on the outside diameter and, to some extent, the elasticity or flexibility of the liposomes, with the larger and more elastic or flexible liposomes having a lower resonant frequency than the smaller and less elastic or flexible vesicles.

The bioactive agent containing gas filled vesicles will also rupture when exposed to non-peak resonant frequency ultrasound in combination with a higher intensity (wattage) and duration (time). This higher energy, however, results in greatly increased heating, which may not be desirable. By adjusting the frequency of the energy to match the peak resonant frequency, the efficiency of rupture and release is improved, appreciable tissue heating does not generally occur (frequently no increase in temperature above about 2° C.), and less overall energy is required. Thus, application of ultrasound at the peak resonant frequency, while not required, is most preferred.

For diagnostic or therapeutic ultrasound, any of the various types of diagnostic ultrasound imaging devices may be employed in the practice of the invention, the particular type or model of the device not being critical to the method of the invention. Also suitable are devices designed for administering ultrasonic hyperthermia, such devices being described in U.S. Pat. Nos. 4,620,546, 4,658,828, and 4,586,512, the disclosures of each of which are hereby incorporated herein by reference in their entirety. Preferably, the device employs a resonant frequency (RF) spectral analyzer. The transducer probes may be applied externally or may be implanted. Ultrasound is generally initiated at lower intensity and duration, and then intensity, time, and/or resonant frequency increased until the vesicle is visualized on ultrasound (for diagnostic ultrasound applications) or ruptures (for therapeutic ultrasound applications).

Although application of the various principles will be readily apparent to one skilled in the art, in view of the present disclosure, by way of general guidance, for gas filled vesicles of about 1.5 to about 10 μm in mean outside diameter, the resonant frequency will generally be in the range of about 1 to about 10 MHz. By adjusting the focal zone to the center of the target tissue (e.g., the tumor) the gas filled vesicles can be visualized under real time ultrasound as they accumulate within the target tissue. Using the 7.5 MHz curved array transducer as an example, adjusting the power delivered to the transducer to maximum and adjusting the focal zone within the target tissue, the spatial peak temporal average (SPTA) power will then be a maximum of approximately 5.31 mW/cm² in water. This power will cause some release of bioactive agents from the gas filled vesicles, but much greater release can be accomplished by using a higher power.

By switching the transducer to the doppler mode, higher power outputs are available, up to 2.5 W/cm² from the same transducer. With the machine operating in doppler mode, the power can be delivered to a selected focal zone within the target tissue and the gas filled vesicles can be made to release their contents, including bioactive agents. Selecting the transducer to match the resonant frequency of the gas filled vesicles will make this process of release even more efficient.

For larger diameter gas filled vesicles, e.g., greater than 3 μm in mean outside diameter, a lower frequency transducer may be more effective in accomplishing therapeutic release. For example, a lower frequency transducer of 3.5 MHz (20 mm curved array model) may be selected to correspond to the resonant frequency of the gas filled vesicles. Using this transducer, 101.6 mW/cm² may be delivered to the focal spot, and switching to doppler mode will increase the power output (SPTA) to 1.02 W/cm².

To use the phenomenon of cavitation to release and/or activate the bioactive agents within the gas filled stabilizing materials and/or vesicles, lower frequency energies may be used, as cavitation occurs more effectively at lower frequencies. Using a 0.757 MHz transducer driven with higher voltages (as high as 300 volts) cavitation of solutions of gas-filled liposomes will occur at thresholds of about 5.2 atmospheres.

The ranges of energies transmitted to tissues from diagnostic ultrasound on commonly used instruments is known to one skilled in the art and described, for example, by Carson et al, *Ultrasound in Med. & Biol.*, 3:341–350 (1978), the disclosure of which is hereby incorporated herein by reference in its entirety. Commonly used instruments for diagnostic ultrasound include the Piconics Inc. (Tyngsboro, Mass.) Portascan general purpose scanner with receiver pulser 1966 Model 661; the Picker (Cleveland, Ohio) Echoview 8L Scanner including 80C System or the Medisonics (Mountain View, Calif.) Model D-9 Versatone Bidirectional Doppler. In general, these ranges of energies employed in pulse repetition are useful for diagnosis and monitoring compositions but are insufficient to rupture the compositions of the present invention.

Either fixed frequency or modulated frequency ultrasound may be used in diagnostic and therapeutic applications. Fixed frequency is defined wherein the frequency of the sound wave is constant over time. A modulated frequency is one in which the wave frequency changes over time, for example, from high to low (PRICH) or from low to high (CHIRP). For example, a PRICH pulse with an initial frequency of 10 MHz of sonic energy is swept to 1 MHz with increasing power from 1 to 5 watts. Focused, frequency modulated, high energy ultrasound may increase the rate of local gaseous expansion within the compositions and rupturing to provide local delivery of therapeutics.

Where the gas or gaseous precursor filled stabilizing materials and/or vesicles are used for drug delivery, the bioactive agent to be delivered may be embedded within the wall of the vesicle, encapsulated in the vesicle and/or attached to the surface of the vesicle. The phrase "attached to" or variations thereof means that the bioactive agent is linked in some manner to the inside and/or the outside wall of the microsphere, such as through a covalent or ionic bond or other means of chemical or electrochemical linkage or interaction. The phrase "encapsulated in" or variations thereof means that the bioactive agent is located in the internal microsphere void. The phrase "embedded within" or variations thereof signifies the positioning of the bioactive agent within the vesicle wall(s) or layer(s). The phrase "comprising a bioactive agent" denotes all of the varying types of positioning in connection with the vesicle. Thus, the bioactive agent can be positioned variably, such as, for example, entrapped within the internal void of the gas filled vesicle, situated between the gas and the internal wall of the gas filled vesicle, incorporated onto the external surface of the gas filled vesicle, enmeshed within the vesicle structure itself and/or any combination thereof. The delivery vehicles may also be designed so that there is a symmetric or an asymmetric distribution of the drug both inside and outside of the stabilizing material and/or vesicle.

Any of a variety of bioactive agents, including those described herein, may be encapsulated in, attached to and/or embedded in the vesicles. If desired, more than one bioactive agent may be applied using the vesicles. For example, a single vesicle may contain more than one bioactive agent or vesicles containing different bioactive agents may be co-administered. In a preferred embodiment, the compositions of the present invention comprise a bioactive agent and a targeting ligand. By way of example, a monoclonal antibody capable of binding to melanoma antigen and an oligonucleotide encoding at least a portion of EL-2 may be administered at the same time. The phrase "at least a portion of" means that the entire gene need not be represented by the oligonucleotide, so long as the portion of the gene represented provides an effective block to gene expression.

Genetic materials and bioactive agents may be incorporated into the internal gas filled space of these vesicles during the gas installation process or into or onto the vesicle membranes of these particles. Incorporation onto the surface of these particles is preferred. Genetic materials and bioactive agents with a high octanol/water partition coefficient may be incorporated directly into the layer or wall surrounding the gas or incorporated onto the surface of the gas filled vesicles is more preferred. To accomplish this, groups capable of binding genetic materials or bioactive agents are generally incorporated into the stabilizing material layers which will then bind these materials. In the case of genetic materials, this is readily accomplished through the use of cationic lipids or cationic polymers which may be incorporated into the dried lipid starting materials.

As discussed above, the gaseous precursor filled compositions of the present invention may be used in connection with diagnostic imaging, therapeutic imaging and drug delivery, including, for example, ultrasound (US), magnetic resonance imaging (MRI), nuclear magnetic resonance (NMR), computed tomography (CT), electron spin resonance (ESR), nuclear medical imaging, optical imaging, elastography, drug delivery with ultrasound, radiofrequency (RF), microwave laser and the like. The gaseous precursor filled compositions of the present invention may be used in combination with various contrast agents, including conventional contrast agents, which may serve to further increase their effectiveness as contrast agents for diagnostic and therapeutic imaging.

Examples of suitable contrast agents for use in combination with the present compositions include, for example, stable free radicals, such as, stable nitroxides, as well as compounds comprising transition, lanthanide and actinide elements, which may, if desired, be in the form of a salt or may be covalently or non-covalently bound to complexing agents, including lipophilic derivatives thereof, or to proteinaceous macromolecules. Preferable transition, lanthanide and actinide elements include, for example, Gd(III), Mn(II), Cu(II), Cr(III), Fe(II), Fe(III), Co(II), Er(II), Ni(II), Eu(III) and Dy(III). More preferably, the elements may be Gd(III), Mn(II), Cu(II), Fe(II), Fe(III), Eu(III) and Dy(III), most preferably Mn(II) and Gd(III). The foregoing elements may be in the form of a salt, including inorganic salts, such as a manganese salt, for example, manganese chloride, manganese carbonate, manganese acetate, and organic salts, such as manganese gluconate and manganese hydroxylapatite. Other exemplary salts include salts of iron, such as iron sulfides, and ferric salts, such as ferric chloride.

The above elements may also be bound, for example, through covalent or noncovalent association, to complexing agents, including lipophilic derivatives thereof, or to proteinaceous macromolecules. Preferable complexing agents include, for example, diethylenetriaminepentaacetic acid (DTPA), ethylenediaminetetraacetic acid (EDTA), 1,4,7,10-tetraazacyclododecane-N,N',N',N'"-tetraacetic acid (DOTA), 1,4,7,10-tetraazacyclododecane-N,N',N"-triacetic acid (DOTA), 3,6,9-triaza-12-oxa-3,6,9-tricarboxymethylene-10-carboxy-13-phenyltridecanoic acid (B-19036), hydroxybenzylethylenediamine diacetic acid (HBED), N,N'-bis(pyridoxyl-5-phosphate)ethylene diamine, N,N'-diacetate (DPDP), 1,4,7-triazacyclononane-N,N',N"-triacetic acid (NOTA), 1,4,8,11-tetraazacyclotetradecane-N,N',N",N'"-tetraacetic acid (TETA), kryptands (macrocyclic complexes), and desferrioxamine. More preferably, the complexing agents are EDTA, DTPA, DOTA, DO3A and kryptands, most preferably DTPA. Preferable lipophilic complexes include alkylated derivatives of the complexing agents EDTA, DOTA, for example, N,N'-bis-(carboxydecylamidomethyl-N-2,3-dihydroxypropyl)ethylenediamine-N,N'-diacetate (EDTA-DDP); N,N'-bis-(carboxyoctadecylamidomethyl-N-2,3-dihydroxypropyl)ethylenediamine-N,N'-diacetate (EDTA-ODP); and N,N'-Bis(carboxylaurylamidomethyl-N-2,3-dihydroxypropyl)ethylenediamine-N,N'-diacetate (EDTA-LDP); including those described in U.S. Pat. No. 5,312,617, the disclosure of which is hereby incorporated herein by reference in its entirety. Preferable proteinaceous macromolecules include, for example, albumin, collagen, polyarginine, polylysine, polyhistidine, γ-globulin and β-globulin, with albumin, polyarginine, polylysine, and polyhistidine being more preferred. Suitable complexes therefore include Mn(II)-DTPA, Mn(II)-EDTA, Mn(II)-DOTA, Mn(II)-DO3A, Mn(II)-kryptands, Gd(III)-DTPA, Gd(III)-DOTA, Gd(III)-DO3A, Gd(III)-kryptands, Cr(III)-EDTA, Cu(II)-EDTA, or iron-desferrioxamine, more preferably Mn(II)-DTPA or Gd(III)-DTPA.

Nitroxides are paramagnetic contrast agents which increase both T1 and T2 relaxation rates on MRI by virtue of the presence of an unpaired electron in the nitroxide molecule. As known to one of ordinary skill in the art, the paramagnetic effectiveness of a given compound as an MRI contrast agent may be related, at least in part, to the number of unpaired electrons in the paramagnetic nucleus or molecule, and specifically, to the square of the number of unpaired electrons. For example, gadolinium has seven unpaired electrons whereas a nitroxide molecule has one unpaired electron. Thus, gadolinium is generally a much stronger MRI contrast agent than a nitroxide. However, effective correlation time, another important parameter for assessing the effectiveness of contrast agents, confers potential increased relaxivity to the nitroxides. When the tumbling rate is slowed, for example, by attaching the paramagnetic contrast agent to a large molecule, it will tumble more slowly and thereby more effectively transfer energy to hasten relaxation of the water protons. In gadolinium, however, the electron spin relaxation time is rapid and will limit the extent to which slow rotational correlation times can increase relaxivity. For nitroxides, however, the electron spin correlation times are more favorable and tremendous increases in relaxivity may be attained by slowing the rotational correlation time of these molecules. The gaseous precursor filled compositions of the present invention are ideal for attaining the goals of slowed rotational correlation times and resultant improvement in relaxivity. Although not intending to be bound by any particular theory of operation, since the nitroxides may be designed to coat the perimeters of the vesicles, for example, by making alkyl derivatives thereof, the resulting correlation times can be optimized. Moreover, the resulting contrast medium of the present invention may be viewed as a magnetic sphere, a geometric configuration which maximizes relaxivity.

Exemplary superparamagnetic contrast agents suitable for use in the compositions of the present invention include metal oxides and sulfides which experience a magnetic domain, ferro- or ferrimagnetic compounds, such as pure iron, magnetic iron oxide, such as magnetite, $\gamma$-$Fe_2O_3$, $Fe_3O_4$, manganese ferrite, cobalt ferrite and nickel ferrite. Along with the gaseous precursors described herein, paramagnetic gases can be employed in the present compositions, such as oxygen 17 gas ($^{17}O_2$), hyperpolarized xenon, neon, or helium. MR whole body imaging may then be employed to rapidly screen the body, for example, for thrombosis, and ultrasound may be applied, if desired, to aid in thrombolysis.

The contrast agents, such as the paramagnetic and superparamagnetic contrast agents described above, may be employed as a component within the compositions of the present invention. With respect to vesicles, the contrast agents may be entrapped within the internal void thereof, administered as a solution with the vesicles, incorporated with any additional stabilizing materials, or coated onto the surface or membrane of the vesicle. Mixtures of any one or more of the paramagnetic agents and/or superparamagnetic agents in the present compositions may be used. The paramagnetic and superparamagnetic agents may also be coadministered separately, if desired.

If desired, the paramagnetic or superparamagnetic agents may be delivered as alkylated or other derivatives incorporated into the compositions, especially the lipidic walls of the vesicles. In particular, the nitroxides 2,2,5,5-tetramethyl-1-pyrrolidinyloxy, free radical and 2,2,6,6-tetramethyl-1-piperidinyloxy, free radical, can form adducts with long chain fatty acids at the positions of the ring which are not occupied by the methyl groups via a variety of linkages, including, for example, an acetyloxy linkage. Such adducts are very amenable to incorporation into the lipid and/or vesicle compositions of the present invention.

The stabilizing materials and/or vesicles of the present invention, and especially the vesicles, may serve not only as effective carriers of the superparamagnetic agents described above, but also may improve the effect of the susceptibility contrast agents. Superparamagnetic contrast agents include metal oxides, particularly iron oxides but including manganese oxides, and as iron oxides, containing varying amounts of manganese, cobalt and nickel which experience a magnetic domain. These agents are nanoparticles or microparticles land have very high bulk susceptibilities and transverse relaxation rates. The larger particles, for example, particles having diameters of about 100 nm, have much higher R2 relaxivities as compared to R1 relaxivities. The smaller particles, for example, particles having diameters of about 10 to about 15 nm, have somewhat lower R2 relaxivities, but much more balanced R1 and R2 values. Much smaller particles, for example, monocrystalline iron oxide particles having diameters of about 3 to about 5 nm, have lower R2 relaxivities, but probably the most balanced R1 and R2 relaxation rates. Ferritin can also be formulated to encapsulate a core of very high relaxation rate superparamagnetic iron. It has been discovered that the compositions of the present invention, especially vesicle compositions, including gaseous precursor filled vesicles, can increase the efficacy and safety of these conventional iron oxide based MRI contrast agents.

The iron oxides may simply be incorporated into the compositions of the present invention. Preferably, in the case of vesicles formulated from lipids, the iron oxides may be incorporated into the walls of the vesicles, for example, by being adsorbed onto the surfaces of the vesicles, or entrapped within the interior of the vesicles.

Without being bound to any particular theory of operation, the compositions of the present invention increase the efficacy of the superparamagnetic contrast agents by several mechanisms. First, the compositions function to increase the apparent magnetic concentration of the iron oxide particles. Also, the compositions increase the apparent rotational correlation time of the MRI contrast agents, including paramagnetic and superparamagnetic agents, so that relaxation rates are increased. In addition, the compositions appear to increase the apparent magnetic domain of the contrast medium according to the manner described hereinafter.

Certain of the compositions of the present invention, and especially compositions formulated from lipids, may be visualized as flexible spherical domains of differing susceptibility from the suspending medium, including, for example, the aqueous suspension of the contrast medium or blood or other body fluids, for example, in the case of intravascular injection or injection into other body locations. In the case of ferrites or iron oxide particles, the contrast provided by these agents is dependent on particle size. This phenomenon is common and is often referred to as the "secular" relaxation of the water molecules. Described in more physical terms, this relaxation mechanism is dependent upon the effective size of the molecular complex in which a paramagnetic atom, or paramagnetic molecule, or molecules, may reside. One physical explanation may be described in the following Solomon-Bloembergen equations which define the paramagnetic contributions as a function of the $T_1$ and $T_2$ relaxation times of a spin ½ nucleus with gyromagnetic ratio g perturbed by a paramagnetic ion:

$$1/T_1 M = (2/15)S(S+1)\gamma^2 g^2 \beta^2/r^6[3\tau_c/(1+\omega_I^2\tau_c^2)+7\tau_c/(1+\omega_s^2\tau_c^2)]+(2/3)S(S+1)A^2/h^2[\tau_e/(1+\omega_s 2\tau_e^2)]$$

and $$1/T_2 M = (1/15)S(S+1)\gamma^2 g^2 \beta^2/r^6[3\tau_c/(1+\omega_I^2\tau_c^2)+7\tau_c/(1+\omega_s^2\tau_c^2)]+(1/3)S(S+1)A^2/h^2[\tau_e/(1+\omega_s^2\tau_e^2)]$$

where S is the electron spin quantum number; g is the electronic g factor; β is the Bohr magneton; $\omega_I$ and $\omega_s$ (657 $w_I$) is the Larmor angular precession frequencies for the nuclear spins and electron spins; r is the ion-nucleus distance; A is the hyperfine coupling constant; $\tau_c$ and $\tau_e$ are the correlation times for the dipolar and scalar interactions, respectively; and h is Planck's constant.

A few large particles may have a much greater effect than a larger number of much smaller particles, primarily due to a larger correlation time. If one were to make the iron oxide particles very large however, increased toxicity may result, and the lungs may be embolized or the complement cascade system may be activated. Furthermore, the total size of the particle is not as important as the diameter of the particle at its edge or outer surface. The domain of magnetization or susceptibility effect falls off exponentially from the surface of the particle. Generally, in the case of dipolar (through space) relaxation mechanisms, this exponential fall off exhibits an $r^6$ dependence for a paramagnetic dipole-dipole interaction. Interpreted literally, a water molecule that is 4 Å away from a paramagnetic surface will be influenced 64 times less than a water molecule that is 2 Å away from the same paramagnetic surface. The ideal situation in terms of maximizing the contrast effect would be to make the iron oxide particles hollow, flexible and as large as possible. It has not been possible to achieve this heretofore and the benefits have been unrecognized heretofore. By coating the inner or outer surfaces of the compositions, particularly vesicles, with the contrast agents, even though the individual contrast agents, for example, iron oxide nanoparticles or paramagnetic ions, are relatively small structures, the effectiveness of the contrast agents may be even further enhanced. In so doing, the contrast agents may function as an effectively much larger sphere wherein the effective domain of magnetization is determined by the diameter of the vesicle and is maximal at the surface of the vesicle. These agents afford the advantage of flexibility, namely, compliance. While rigid vesicles might lodge in the lungs or other organs and cause toxic reactions, these flexible vesicles slide through the capillaries much more easily.

In contrast to the flexible compositions described above, it may be desirable, in certain circumstances, to formulate compositions from substantially impermeable polymeric materials including, for example, polymethyl methacrylate. This would generally result in the formation of compositions which may be substantially impermeable and relatively inelastic and brittle. In embodiments involving diagnostic imaging, for example, ultrasound, contrast media which comprise such brittle compositions would generally not provide the desirable reflectivity that the flexible compositions may provide. However, by increasing the power output on ultrasound, the brittle compositions, such as microspheres, can be made to rupture, thereby causing acoustic emissions which can be detected by an ultrasound transducer.

Nuclear Medicine Imaging (NMI) may also be used in connection with the diagnostic and therapeutic method aspects of the present invention. For example, NMI may be used to detect radioactive gases, such as $Xe^{133}$, which may be incorporated in the gaseous precursor filled compositions. Such radioactive gases may be entrapped within vesicles for use in detecting, for example, thrombosis. Preferably, bifunctional chelate derivatives are incorporated in the walls of vesicles, and the resulting vesicles may be employed in both NMI and ultrasound. In this case, high energy, high quality nuclear medicine imaging isotopes, such as technetium$^{99m}$ or indium$^{111}$ can be incorporated in the walls of vesicles. Whole body gamma scanning cameras can then be employed to rapidly localize regions of vesicle uptake in vivo. If desired, ultrasound may also be used to confirm the presence, for example, of a clot within the blood vessels, since ultrasound generally provides improved resolution as compared to nuclear medicine techniques. NMI may also be used to screen the entire body of the patient to detect areas of vascular thrombosis, and ultrasound can be applied to these areas locally to promote rupture of the vesicles and treat the clot.

For optical imaging, optically active gases, such as argon or neon, may also be incorporated in the gaseous precursor filled compositions of the present invention. In addition, optically active materials, for example, fluorescent materials, including porphyrin derivatives, may also be used. Elastography is an imaging technique which generally employs much lower frequency sound, for example, about 60 kHz, as compared to ultrasound which can involve frequencies of over 1 MHz. In elastography, the sound energy or vibratory energy is generally applied to the tissue and the elasticity of the tissue may then be determined. In connection with preferred embodiments of the invention, which involve highly elastic vesicles, the deposition of such vesicles onto, for example, a clot, increases the local elasticity of the tissue and/or the space surrounding the clot. This increased elasticity may then be detected with elastography. If desired, elastography can be used in conjunction with other imaging techniques, such as MRI and ultrasound.

EXAMPLES

The invention is further demonstrated in the following examples. Examples 1–3 are actual examples, and Examples 4 and 5 are prophetic examples. The examples are for purposes of illustration only and are not intended to limit the scope of the present invention.

Example 1

Several vials were filled with 1.5 ml of a lipid mixture comprising 82 mol % dipalmitoylphosphatidylcholine (DPPC), 10 mol % dipalmitoylphosphatidic acid (DPPA) and 8 mol % dipalmitoylphosphatidylethanolamine-polyethylene glycol 5,000 (DPPE-PEG-5000). The headspace was removed with a vacuum pump and 10 $\mu$l of perfluoromethylbutyl ether was injected into the vial. Perfluoromethylbutyl ether has a boiling point of about 35–36° C. The vials were shaken for 60 seconds on an ESPE Capmix.

Imaging was conducted on an anesthetized dog (hereafter "the patient"). The perfluoromethyl-butyl ether filled lipid vesicles were diluted at 3 ml into a 100 ml saline bag at room temperature (about 25° C.). The dilution was infused into the patient's cephalic vein using a BioRad Econo-pump microprocessor controlled peristaltic pump. The infusion was injected into the patient at a rate of 2 ml/min. Imaging of the patient's heart was conducted using an Acoustic Imaging 5200S ultrasound machine. No contrast was visible.

The experiment was repeated, except that the perfluoromethylbutyl ether filled lipid vesicles were diluted at 3 ml into a 100 ml saline bag that was placed in an incubator at a temperature of about 40° C. The dilution was infused into the patient's cephalic vein using a BioRad Econo-pump microprocessor controlled peristaltic pump. The infusion was injected into the patient at a rate of 2 ml/min. Imaging of the patient's heart was conducted using an Acoustic Imaging 5200S ultrasound machine. Excellent dense contrast imaging was observed.

Example 2

Several vials were filled with 1.5 ml of a lipid mixture comprising 82 mol % dipalmitoylphosphatidylcholine (DPPC), 10 mol % dipalmitoylphosphatidic acid (DPPA) and 8 mol % dipalmitoylphosphatidylethanolamine-polyethylene glycol 5,000 (DPPE-PEG-5000). The headspace was removed with a vacuum pump and 10 $\mu$l of perfluoropentane was injected into the vial. Perfluoropentane has a boiling point of about 29.5° C. The vials were shaken for 60 seconds with a Wig-L-Bug.

Imaging was conducted on an anesthetized dog. The perfluoropentane filled lipid vesicles were diluted at 3 ml into a 100 ml saline bag at room temperature (about 25° C.). The dilution was infused into the patient's cephalic vein using a BioRad Econo-pump microprocessor controlled peristaltic pump. The infusion was injected into the patient at a rate of 2 ml/min. Imaging of the patient's heart was conducted using an Acoustic Imaging 5200S ultrasound machine. No contrast was visible.

The experiment was repeated, except that the perfluoropentane filled lipid vesicles were diluted at 3 ml into a 100 ml saline bag that was placed in an incubator at a temperature of about 40° C. The dilution was infused into the patient's cephalic vein using a BioRad Econo-pump microprocessor controlled peristaltic pump. The infusion was injected into the patient at a rate of 2 ml/min. Imaging of the patient's heart was conducted using an Acoustic Imaging 5200S ultrasound machine. Excellent dense contrast imaging was observed.

Example 3

GPIIbIIIa binding peptide (Integrated Biomolecule Corporation, Tucson, Ariz.) was covalently bonded to DPPE-PEG 3400 to produce DPPE-PEG-Lys-Gln-Ala-Gly-Asp-Val (SEQ ID NO: 39), as follows. To a cooled (0 to 5° C.) solution of chlorosulfonyl isocyanate (14.2 mg) in $CHCl_3$ (5 mL) was added a solution of $\omega,\omega'$-dimethylenecarboxypolyethylene glycol (0.34 g) and triethylamine (20 mg) in $CHCl_3$ (20 mL). The reaction mixture was stirred overnight and poured into ice water. The organic layer was isolated and dried ($NaSO_4$). Filtration and concentration of the organic layer in vacuo yielded the title anhydride compound as a white solid (0.2 g).

To a cooled (0 to 10° C.) solution of the above anhydride compound (0.3 g) in $CH_2Cl_2$ (10 mL) was added a solution of DPPE (0.07 g) and triethylamine (0.05 g) in $CH_2Cl_2$ (15 mL). The resulting reaction mixture was stirred overnight, poured into ice water and neutralized with 10% HCl to a pH of less than 3. The organic layer was isolated and dried ($NaSO_4$). Filtration and concentration of the organic layer in vacuo provided 0.45 g of DPPE-$\omega$-carboxy-PEG as a dark white solid.

To a cooled (0 to 5° C.) solution of DCC (3 mg) in acetonitrile (2 mL) was added a solution of DPPE-$\omega$-carboxy-PEG from Step B (60 mg), N-hydroxy-succinimide (1.8 mg) and dimethylaminopyridine (0.2 mg) in acetonitrile (6 mL). The resulting mixture was stirred for 3 hours at 0 to 5° C. and then overnight at room temperature. The solid which formed was removed by filtration and the filtrate was concentrated in vacuo to provide 60 mg of DPPE-$\omega$-carboxy-PEG-succinimide.

To a cooled (0 to 5° C.) solution of Lys-Gln-Ala-Gly-Asp-Val (SEQ ID NO: 39) (5 mg) in a buffer solution at pH 8.5 was added dropwise DPPE-$\omega$-carboxy-PEG-succinimide (40 mg) in acetonitrile (10 mL). The resulting mixture was stirred at room temperature for about 48 hours. The acetonitrile was removed in vacuo, and the mineral salt was dialyzed out through a membrane having a molecular weight cutoff of 1000. Lyophilization afforded 35 mg-of DPPE-PEG-Lys-Gln-Ala-Gly-Asp-Val (SEQ ID NO: 39) as a white solid.

This peptide conjugate (DPPE-PEG-Lys-Gln-Ala-Gly-Asp-Val) was then combined with a dried lipid mixture of 82 mole % DPPC, 8 mol % DPPE-PEG5000 and 10 mol % DPPA. This mixture was hydrated and lyophilized on a Labconco Lyph-Lock 12 lyophilizer (Kansas City, Mo.). The lyophilized material was resuspended in 8:1:1 normal saline:propylene glycol:glycerol at a concentration of 1 mg/mL. Aliquots of this mixture were placed into 2 ml Wheaton vials (Millville, N.J.), capped and the headspace replaced with perfluoromethylbutyl ether (Flura, Newport, Tenn.). The vials were agitated to provide a vesicle composition targeted to the GPIIbIIIa receptor (hereafter "thrombus-targeting contrast agent").

A thrombus was created by placing a guidewire into the femoral artery of a dog. Thrombin-soaked cotton threads were attached to the guidewire to serve as a structure for clot formation. The threads were left in place for 30 minutes before the thrombin-targeting contrast agent was injected. 3 ml of the thrombus-targeting contrast agent containing perfluoromethylbutyl ether was added to 100 ml of 40° C. pre-heated saline and infused into the dog at a rate of about 2.0 cc/minute. Using ultrasound imaging, a brilliant contrast illuminated the region around the clot.

The experiment was repeated, except that the saline was maintained at room temperature (e.g., about 25° C.). Using ultrasound imaging, no clot binding could be observed.

Example 4

The material of Example 1 is placed into a heated saline bas as described in Example 1. The tubing exiting the bag is placed beneath a sonication horn (Heat Systems Probe, Farmingdale, N.Y.) at 60 kHz, power level setting #1, and infused into a patient, as described herein. An acoustical couplant gel is used to ensure good coupling of the sonicator horn with the tubing. The purpose of the sonication is to more completely activate the gaseous precursor, as well as to evenly size the bubbles. Particle sizing of the bubbles after passage through the in-line sonicator shows increased bubble count and descreased mean diameter with no appreciable bubbles over 10 microns in diameter.

Example 5

The material of Example 2 is used as described in Example 2 except that a continuous wave ultrasound transducer, 1 MHz at 0.5 watts/cm$^2$, is applied to the tubing just proximal to the angiocath which enters the patient. The tubing infusing the contrast agent into the patient is embedded in agar gel and the transducer is applied to the top of the gel containing the tubing. Ultrasound is applied continuously during the infusion. The result is better activation of the precursor and uniform bubble size, with no appreciable bubbles over 10 microns in diameter.

The disclosure of each patent, patent application and publication cited or described in this document is hereby incorporated by reference herein in its entirety.

Various modifications of the invention, in addition to those described herein, will be apparent to one skilled in the art from the foregoing description. Such modifications are also intended to fall within the spirit and scope of the appended claims.

---

What is claimed is:

1. A method for lysing an intravascular blood clot in the brain of a patient, said method comprising: (i) heating a composition comprising lipid vesicles encapsulating a gaseous precursor to a temperature at or above the boiling point of the gaseous precursor, wherein said gaseous precursor is a fluorinated compound, said lipid vesicles comprise at least one phosphatidylcholine, at least one phosphatidylethanolamine, and at least one phosphatidic acid, wherein said phosphatidylcholine is selected from the group consisting of dioleoylphosphatidylcholine, dimyristoylphosphatidylcholine, dipalmitoylphosphatidylcholine, and distearoylphosphatidylcholine; said phosphatidylethanolamine is selected from the group consisting of dipalmitoylphosphatidylethanolamine, dioleoylphosphatidylethanolamine, and N-succinyl-dioleoylphosphatidylethanolamine; and said phosphatidic acid is dipalmatoylphosphatidic acid, (ii) administering said composition to a patient, and (iii) applying ultrasonic energy to the brain of the patient in an amount sufficient to cavitate or rupture at least a portion of said vesicles.

2. A method according to claim 1, wherein said vesicle composition is administered as an intravascular infusion.

3. A method according to claim 2, wherein said vesicle composition is administered as an intra-arterial infusion.

4. A method according to claim 1, wherein said gas or gaseous precursor comprises a perfluorocarbon.

5. A method according to claim 4, wherein said perfluorocarbon is selected from the group consisting of perfluoromethane, perfluoroethane, perfluoropropane, perfluorocyclopropane, perfluorobutane, perfluorocyclobutane, perfluoropentane, perfluorocyclopentane, perfluorohexane and perfluorocyclohexane.

6. A method according to claim 5, wherein said perfluorocarbon is selected from the group consisting of perfluoropropane, perfluorocyclopropane, perfluorobutane, and perfluorocyclobutane.

7. A method according to claim 1 wherein said vesicles further comprise a hydrophilic polymer.

8. A method according to claim 7, wherein said hydrophilic polymer comprises polyethylene glycol.

9. A method according to claim 1, wherein said vesicles further comprise a targeting ligand.

10. A method according to claim 9, wherein said targeting ligand is covalently bound to said vesicles via a hydrophilic polymer linking group.

11. A method according to claim 9, wherein said targeting ligand targets cells or receptors selected from the group consisting of endothelial cells and the glycoprotein GPI-IbIIIa receptor.

12. A method according to claim 11, wherein said targeting ligand is selected from the group consisting of proteins, peptides, saccharides, steroids, steroid analogs, bioactive agents and genetic material.

13. A method according to claim 12, wherein said targeting ligand is selected from the group consisting of proteins, peptides and saccharides.

14. A method according to claim 13, wherein said targeting ligand is selected from the group consisting of proteins and peptides.

15. A method according to claim 14, wherein said targeting ligand comprises a peptide.

16. A method according to claim 15, wherein said peptide comprises the sequence Arg-Gly-Asp.

17. A method according to claim 1, wherein said ultrasound is applied through a surgically created window in the skull.

18. A method according to claim 1, wherein said ultrasound is applied in a pulsed and focused mode.

19. A method according to claim 1, wherein said vesicles further comprise a bioactive agent.

20. A method according to claim 18, wherein said bioactive agent is selected from the group consisting of anti-coagulation agents, circulatory agents, anti-inflammatories, corticosteroids, tissue plasminogen activator, streptokinase, and urokinase.

21. A method according to claim 1 further comprising scanning the patient with diagnostic imaging to identify the location of said blood clot in the brain.

22. A method according to claim 21, wherein said scanning is performed after initiating administration of said vesicle composition.

23. A method according to claim 21, wherein said diagnostic imaging comprises nuclear medicine imaging.

24. A method according to claim 21, wherein said diagnostic imaging comprises ultrasound imaging.

25. A method according to claim 15, wherein said peptide has the sequene Lys-Gln-Ala-Gly-Asp-Val.

* * * * *

UNITED STATES PATENT AND TRADEMARK OFFICE
CERTIFICATE OF CORRECTION

PATENT NO.    : 6,716,412 B2
DATED         : April 6, 2004
INVENTOR(S)   : Evan C. Unger It is certified that error appears in the above-identified patent and that said Letters Patent is hereby corrected as shown below:

Title page,
Item [56], References Cited, U.S. PATENT DOCUMENTS, please add:
-- 4,303,736        12/1981      Torobin         428/403
   4,582,756        4/1986       Niinuma et al.  428/327
   4,229,360 B1     11/1991      Schneider et al. 260/403 --
FOREIGN PATENT DOCUMENTS, please delete "WO 84/02909" and insert
-- WO 94/02909 -- therefor.
please add:
-- WO 91/18612            12/1991
   WO 95/32006            11/1995
   WO 98/04292      2/1998 --
OTHER PUBLICATIONS,
"Mattrey et al.," reference, please delete "39-343" and insert -- 339-343 -- therefor.
"Shiina et al.," reference, please delete "Hyperthermiaby" and insert -- Hyperthermia by -- therefor.
"Kost et al.," reference, please delete "Plenum de Gier et" and insert -- Plenum Press, New York and London), pp. 387-396 (1985) -- therefor.
"Relations Between ...," reference, please insert -- de Gier et.,-- at the beginning of the line before "al."
"Poznansky et al.," reference, please delete "Biologica" and insert -- Biological -- therefor.
"Ter-Pogossia," reference, please delete "Ter-Pogossia" and insert -- Ter-Pogossian -- therefor.
"Kee, et al.," reference, please delete "Kee" and insert -- Lee -- therefor.
"Villanueva et al.," reference, please delete "Patters" and insert -- Patterns -- therefor.
"Yang et al.," reference, please delete "Facture" and insert -- Fracture -- therefor.
Please add:
-- Jain, et al., *Introduction to Biological Membranes*, Ch. 9, pp. 192-231 (J. Wiley and Sons, NY 1980) --
-- Deamer et al., "Permeability of Lipid Bilayers to Water and Ionic Solutes", *Chemistry and Physics of Lipids*, Vol. 40, pp. 167-188 (1986) --
-- Fukuda et al., "Polymer-Encased Vesicles Derived from Dioctadecyldimethylammonium Methacrylate", *J. Am. Chem. Soc., Vol.* 108, pp. 2321-2327 (1986) --
-- Pieterson, "A New Warning System for Fires of Electrical Origin," *CERN European Organization for Nuclear Research, Health and Safety Division*, March, 1977, 1-5 --
-- Broomley, et al., "Microbubble contrast agents: a new era in ultrasound." Clinical *Review, BMJ*, May 19, 2001, XP008001399, 1222-1225 --

UNITED STATES PATENT AND TRADEMARK OFFICE
CERTIFICATE OF CORRECTION

PATENT NO. : 6,716,412 B2
DATED : April 6, 2004
INVENTOR(S) : Evan C. Unger

It is certified that error appears in the above-identified patent and that said Letters Patent is hereby corrected as shown below:

Column 7,
Line 48, please delete "ore" and insert -- or -- therefor.

Column 11,
Line 25, please delete "($-C_6HRO-$)" and insert -- ($-C_6H_{10}-$) -- therefor.

Column 15,
Formula I, please delete " 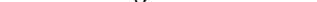 I "

and insert -- 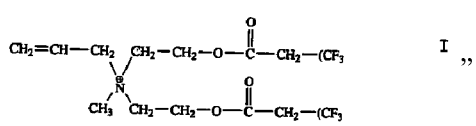 I -- therefor.

Formula K, please delete "  K "

and insert --  K -- therefor.

Formula M, please delete " $CH_3-(CH_2)_{12}-C\equiv C-C\equiv C-(CH_2)_8-COO-(CH_2)_2$  H
                                                                                    \N/
                                                        $CH_3-(CH_2)_{12}-C\equiv C-C\equiv C-(CH_2)_8-COO-(CH_2)_2$  $CH_2-Cl$   M "

and insert --  M -- therefor.

Formula O, please delete " $CH_3-(CH_2)_{14}-CH_2$  CH
                                                    \N/
                                    $CH_2=(H_3C)C-COO-(CH_2)_{10}-CH_2$  CH   O "

and insert -- $CH_3-(CH_2)_{14}-CH_2$ \N/ $CH_3$ $Br^-$
              $CH_2=(H_3C)C-COO-(CH_2)_{10}-CH_2$ $CH_3$  O -- therefor.

UNITED STATES PATENT AND TRADEMARK OFFICE
CERTIFICATE OF CORRECTION

PATENT NO. : 6,716,412 B2
DATED : April 6, 2004
INVENTOR(S) : Evan C. Unger

It is certified that error appears in the above-identified patent and that said Letters Patent is hereby corrected as shown below:

Column 17,
Formula Q, please delete "  "

and insert -- 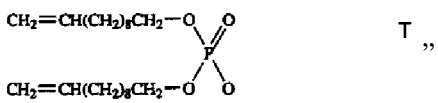 Q -- therefor.

Line 60, please delete "–X$_2$–R5X$_2$) ..." and insert -- –X$_2$–(R$_5$X$_2$) ... -- therefor.

Column 18,
Formula T, please delete " (formula) T "

and insert -- (formula) T -- therefor.

Line 39, please delete "(=X$_2$–(R$_5$X$_2$)P(=X$_{2)}$–X$_2$–" and insert -- (=X$_2$– or –X$_2$–(R$_5$X$_2$)P(=X$_{2)}$–X$_2$–" -- therefor.
Line 62, please delete "each X," and insert -- each X$_1$ -- therefor.

Column 20,
Line 26, please delete "each or S" and insert -- each X$_2$ is independently O or S -- therefor.
Line 39, please delete "each Y," and insert -- each Y$_1$ -- therefor.
Line 65, please delete "Preferably, X," and insert -- Preferably, X$_1$ -- therefor.

Column 21,
Line 45, please delete "each X," and insert -- each X$_1$ -- therefor.

Column 22,
Line 4, please delete "–N(R$_{12}$), –S(R$_{12}$), –P(R$_{12}$)" and insert -- –N(R$_{12}$)$_w$, –S(R$_{12}$)$_w$, –P(R$_{12}$)$_w$ -- therefor.
Line 18, please delete "each X," and insert -- each X$_1$ -- therefor.
Line 21, please delete "–X$_2$–Preferably" and insert -- –X$_2$–(R$_5$X$_2$)P(=X$_2$)–X$_2$–. Preferably -- therefor.
Line 59, please delete "0 or I" and insert -- 0 or 1 -- therefor.

Column 24,
Line 67, please delete "bis(dodecyaminocarbonyl..." and insert -- bis(dodecylaminocarbonyl... -- therefor.

UNITED STATES PATENT AND TRADEMARK OFFICE
CERTIFICATE OF CORRECTION

PATENT NO. : 6,716,412 B2
DATED : April 6, 2004
INVENTOR(S) : Evan C. Unger

It is certified that error appears in the above-identified patent and that said Letters Patent is hereby corrected as shown below:

Column 30,
Line 13, please delete "T is" and insert -- Y is --; and, also, please delete "... $(ORS)_q–$... " and insert -- ... $(OR_5)_q–$... -- therefor.
Line 16, please delete "$–N(R_6),$" and insert -- $–N(R_6)_r,$ -- therefor.
Line 35, please delete "Each X," and insert -- Each $X_1$ -- therefor.

Column 33,
Line 53, please delete "p1l" and insert -- p1 -- therefor.

Column 40,
Line 46, please delete "$CF_3–(CF_2)_n–SF$" and insert -- $CF_3–(CF_2)_n–SF_5$ -- therefor.

Column 49,
Line 29, please delete "$(=X_4)–$... $(=X_4)–$" and insert -- $(=X_4)–$...$(=X_4)–X_3–$ -- therefor.

Column 50,
Line 10, please delete "$–X_3–$...$(=X_4) –X_4)–X_3–R_5–$" and insert -- $–X_3–$...$(=X_4)–X_3–R_5–$ -- therefor.

Column 51,
Line 46, please delete "R' is" and insert -- $R^8$ is -- therefor.
Line 52, please delete "an α or β" and insert -- an ∝ or β -- therefor.

Column 52,
Line 13, please delete "variable" and insert -- variably -- therefor.

Column 53,
Line 16, please delete "ligahd" and insert -- ligand -- therefor.

Column 54,
Line 54, please delete "$TNF-R_2$" and insert -- TNF-R2 -- therefor.

Column 57,
Line 28, please delete "maybe" and insert -- may be -- therefor.

Column 63,
Line 30, please delete "engulfnent" and insert -- engulfment -- therefor.

UNITED STATES PATENT AND TRADEMARK OFFICE
CERTIFICATE OF CORRECTION

PATENT NO. : 6,716,412 B2
DATED : April 6, 2004
INVENTOR(S) : Evan C. Unger

It is certified that error appears in the above-identified patent and that said Letters Patent is hereby corrected as shown below:

Column 65,
Line 10, please delete "(–OS–)" and insert -- (–COS–) -- therefor.
Line 35, please delete "diusobutyl" and insert -- diisobutyl -- therefor.

Column 66,
Line 20, please delete "polyhyhydroxy" and insert -- polyhydroxy -- therefor.

Column 67,
Line 39, please delete the second occurrence of "and".

Column 72,
Line 18, please delete "ω-glucopyranpsyl-" and insert -- ω-glucopyranosyl- -- therefor.
Line 37, please delete "each X," and insert -- each $X_1$ -- therefor.

Column 73,
Line 6, please delete "–C(=$X_5$)–$X_4$– or" and insert -- –C(=$X_5$)–$X_4$–$R_5$, –$X_4$–$R_5$–C(=$X_5$)–$X_4$–or -- therefor.
Line 66, please delete "about carbons" and insert -- about 15 carbons -- therefor.

Column 74,
Line 26, please delete "R," and insert -- $R_5$ -- therefor.
Line 32, please delete "I or 2" and insert -- 1 or 2 -- therefor.

Column 75,
Line 48, please delete "Microfluidizerm" and insert -- Microfluidizer$^{TM}$ -- therefor.

Column 82,
Line 44, please delete "$X_b$" and insert -- $x_b$ -- therefor.
Line 45, please delete "$x_b$," and insert -- $x^b$ -- therefor.

Column 85,
Line 20, please delete "→RXCH$_2$CH$_2$O)$_x$ ..." and insert -- →R$_f$(CH$_2$CH$_2$O)$_x$ ... -- therefor.
Line 39, please delete "(R$_f$H$_2$CH$_2$ ... (R$_f$O)N–LIG" and insert -- (R$_f$CH$_2$CH$_2$... (R$_f$CO)N–LIG -- therefor.

Column 86,
Line 23, please delete "perparation" and insert -- preparation -- therefor.
Line 30, pleae delete "sonciating" and insert -- sonicating -- therefor.
Line 33, please delete "sonciation" and insert -- sonication -- therefor.
Line 48, please delete "sufficeint" and insert -- sufficient -- therefor.

UNITED STATES PATENT AND TRADEMARK OFFICE
CERTIFICATE OF CORRECTION

PATENT NO. : 6,716,412 B2
DATED : April 6, 2004
INVENTOR(S) : Evan C. Unger

It is certified that error appears in the above-identified patent and that said Letters Patent is hereby corrected as shown below:

Column 87,
Line 9, please delete "gluteradehyde" and insert -- gluteraldehyde -- therefor.

Column 92,
Line 41, please delete "N-hydroxylethalacetamide" and insert
-- N-hydroxylethylacetamide -- therefor.

Column 102,
Line 37, please delete "land" and insert -- and -- therefor.

Column 103,
Line 29, please delete

"$1/T_2M=(1/15)S(S + 1)\gamma^2g^2\beta^2/r^6[3\tau_c/(1 + \omega_i^2\tau_c^2) + 7\tau_c/(1 + \omega_x^2\tau_c^2] + (2/3)S(S + 1)A^2/h^2[\tau_c/(1 + \omega_s2\tau_e^2)]$"

and insert

-- $-1/T_2M=(1/15)S(S + 1)\gamma^2g^2\beta^2/r^6[4\tau_c + 3\ \tau_c/(1+\omega_i^2\tau_c^2) + 13\tau_c/(1+\omega_x^2\tau_c^2] + (2/3)S(S + 1)A^2/h^2\ [\tau_c/(1+ \omega_s2\tau_e^2)]$" -- therefor.

Column 107,
Line 2, please delete "bas" and insert -- base -- therefor.

Column 123,
Line 50, please delete "dipalmatoylphosphatidic" and insert -- dipalmitoylphosphatidic --
therefor.

Signed and Sealed this

Twenty-first Day of December, 2004

JON W. DUDAS
*Director of the United States Patent and Trademark Office*